United States Patent

Tseng

[19]

[11] Patent Number: 5,985,799
[45] Date of Patent: Nov. 16, 1999

[54] TRICYCLIC HERBICIDAL HETEROCYCLES

[75] Inventor: Chi-Ping Tseng, Wilmington, Del.

[73] Assignee: E.I. du Pont de Nemours and Company, Wilmington, Del.

[21] Appl. No.: 09/068,485

[22] PCT Filed: Nov. 13, 1996

[86] PCT No.: PCT/US96/18381

§ 371 Date: May 12, 1998

§ 102(e) Date: May 12, 1998

[87] PCT Pub. No.: WO97/19087

PCT Pub. Date: May 29, 1997

Related U.S. Application Data

[60] Provisional application No. 60/006,876, Nov. 17, 1995.

[51] Int. Cl.$^6$ .......................... A01N 43/90; A01N 43/56; C07D 231/00; C07D 495/04

[52] U.S. Cl. .......................... 504/281; 504/241; 504/246; 504/253; 504/271; 504/280; 504/282; 504/288; 504/289; 544/250; 546/80; 546/275.7; 548/242; 548/247; 548/248; 548/359.1; 548/259.5; 548/364.4; 549/26; 549/27

[58] Field of Search .............................. 548/359.1, 359.5; 549/26, 27; 504/281, 288, 253; 546/275.7

[56] References Cited

U.S. PATENT DOCUMENTS 3,341,552   9/1967   Cornell ................................. 260/329.3

*Primary Examiner*—Laura L. Stockton

[57] ABSTRACT

Compounds of Formula (I), and their N-oxides and agriculturally-suitable salts, are disclosed which are useful in controlling undesired vegetation, wherein J is Formula (II), Q is represented by Q-1 through Q-4 and X, Y, Z, $R^{1-19}$, m, n, p, q, and r are as defined in the disclosure. Also disclosed are compositions containing the compounds of Formula (I) and a method for controlling undesired vegetation which involves contacting the vegetation or its environment with an effective amount of a compound of Formula (I).

J is

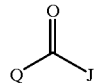

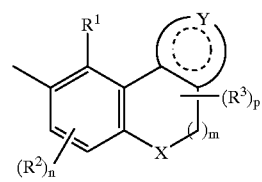

I

Q is

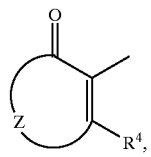

Q-1

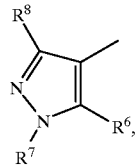

Q-2

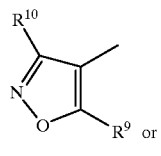

Q-3

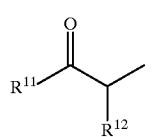

or

Q-4

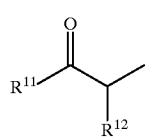

13 Claims, No Drawings

TRICYCLIC HERBICIDAL HETEROCYCLES

This application benefit of Provisional Appl. 60/006876, filed Nov. 17, 1995. This application is a 371 of PCT/US96/18381 filed Nov. 13, 1996.

BACKGROUND OF THE INVENTION

This invention relates to certain tricyclic heterocycles, their N-oxides, agriculturally-suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumers. The control of undesired vegetation in noncrop areas is also important. Many products are commercially available for these purposes, but the need continues for new compounds which are more effective, less costly and environmentally safe.

SUMMARY OF THE INVENTION

This invention is directed to compounds of Formula I including all geometric and stereoisomers, N-oxides, and agriculturally suitable salts thereof, agricultural compositions containing them and their use for controlling undesirable vegetation:

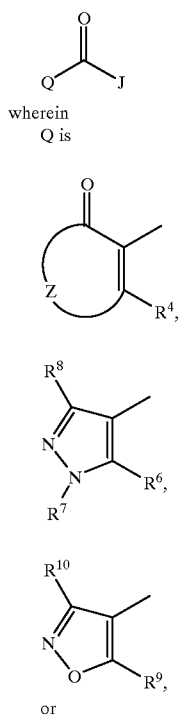

wherein
Q is

Q-1

Q-2

Q-3 or

Q-4

J is

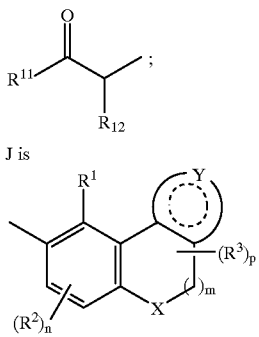

X is O, S(O)$_r$, N(C$_1$–C$_2$ alkyl) or CH$_2$ optionally substituted with 1–2 C$_1$–C$_2$ alkyl; Y together with the carbons to which it is attached form a phenyl ring or a fused five or six-membered heterocyclic ring, which may be fully aromatic or partially or fully saturated, containing 1 to 3 heteroatoms independently selected from the group nitrogen, oxygen, and sulfur, provided that the heterocyclic ring contains no more than 2 oxygens and no more than 2 sulfurs, and the ring is optionally substituted with one to three groups independently selected from the group C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, aminosulfonyl, C$_1$–C$_2$ alkylaminosulfonyl, C$_2$–C$_4$ dialkylaminosulfonyl, NR$^{15}$R$^{16}$, C$_2$–C$_6$ alkoxyalkyl, C$_2$–C$_6$ alkoxycarbonyl, C$_2$–C$_6$ alkylcarbonyl, halogen, cyano, nitro, phenyl optionally substituted with C$_1$–C$_3$ alkyl, halogen, cyano or nitro, and pyridyl optionally substituted with C$_1$–C$_3$ alkyl, halogen, cyano or nitro, provided that when a nitrogen atom of the fused heterocyclic ring is substituted, then the nitrogen substituent is other than halogen;

Z is selected from the group —CH$_2$CH$_2$CH$_2$—, —OCH$_2$CH$_2$—, —O—CH═CH—, —NR$^{13}$CH$_2$CH$_2$—, —NR$^{13}$CH═CH—, —N═CHCH$_2$—, —OCH$_2$O—, —NR$^{13}$CH$_2$NR$^{13}$—, —N═CHNR$^{13}$—, —CH$_2$OCH$_2$—, —CH$_2$NR$^{13}$CH$_2$—, —CH$_2$S(O)$_r$CH$_2$—, —CH$_2$C(O)CH$_2$—, —CH═NCH$_2$—, —CH$_2$CH$_2$—, —OCH$_2$—, —SCH$_2$—, and —NR$^{13}$CH$_2$—, each group optionally substituted with one to four R$^5$, and the directionality of the Z linkage is defined such that the moiety depicted on the left side of the linkage is bonded to the carbonyl carbon of Q-1;

R$^1$ and R$^2$ are independently H, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, aminosulfonyl, C$_1$–C$_2$ alkylaminosulfonyl, C$_2$–C$_4$ dialkylaminosulfonyl, halogen, cyano or nitro;

each R$^3$ is C$_1$–C$_2$ alkyl;

R$^4$ is OR$^{14}$, SH, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, halogen or NR$^{15}$R$^{16}$; or R$^4$ is phenylthio, phenylsulfonyl or —SCH$_2$C(O)Ph, each optionally substituted with C$_1$–C$_3$ alkyl, halogen, cyano or nitro;

each R$^5$ is independently H, C$_1$–C$_3$ alkyl, C$_3$–C$_6$ alkenyl, C$_3$–C$_6$ alkynyl, C$_1$–C$_3$ alkoxy, formyl, C$_2$–C$_6$ alkoxycarbonyl, —CH($C_1$–$C_3$ alkoxy)$_2$, $C_1$–$C_3$ alkylthio, $C_2$–$C_4$ alkylthioalkyl, cyano or halogen; or when two $R^5$ are attached to the same carbon atom, then said $R^5$ pair can be taken together to form —OCH$_2$CH$_2$O—, —OCH$_2$CH$_2$CH$_2$O—, —SCH$_2$CH$_2$S— or —SCH$_2$CH$_2$CH$_2$S—, each group optionally substituted with 1–4 CH$_3$;

$R^6$ is OR$^{14}$, SH, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, halogen or NR$^{15}$R$^{16}$; or $R^6$ is phenylthio, phenylsulfonyl or —SCH$_2$C(O)Ph, each optionally substituted with $C_1$–$C_3$ alkyl, halogen, cyano or nitro;

$R^7$ is H, $C_1$–$C_6$ alkyl, $C_1$–$C_6$ haloalkyl, $C_3$–$C_6$ alkenyl, $C_3$–$C_6$ alkynyl or —CH$_2$CH$_2$OR$^{13}$; or $R^7$ is phenyl or benzyl, each optionally substituted on the phenyl ring with $C_1$–$C_3$ alkyl, halogen, cyano or nitro;

$R^8$ is H, $C_1$–$C_6$ alkyl, $C_1$–$C_6$ haloalkyl, $C_1$–$C_6$ alkoxy, $C_1$–$C_6$ haloalkoxy, halogen, cyano or nitro;

$R^9$ is H, $C_1$–$C_6$ alkyl, $C_1$–$C_6$ haloalkyl, $C_3$–$C_6$ cycloalkyl or $C_3$–$C_6$ halocycloalkyl;

$R^{10}$ is H, $C_2$–$C_6$ alkoxycarbonyl, $C_2$–$C_6$ haloalkoxycarbonyl, CO$_2$H or cyano;

$R^{11}$ is $C_1$–$C_6$ alkyl, $C_1$–$C_6$ haloalkyl, $C_3$–$C_6$ cycloalkyl optionally substituted with 1–4 $C_1$–$C_3$ alkyl or $C_3$–$C_6$ halocycloalkyl;

$R^{12}$ is cyano, $C_2$–$C_6$ alkoxycarbonyl, $C_2$–$C_6$ alkylcarbonyl, S(O)$_r$R$^{16}$ or C(O)NR$^{15}$R$^{16}$;

$R^{13}$ is H or $C_1$–$C_6$ alkyl;

$R^{14}$ is H, $C_1$–$C_6$ alkyl, $C_1$–$C_6$ haloalkyl, $C_2$–$C_6$ alkoxyalkyl, formyl, $C_2$–$C_6$ alkylcarbonyl, $C_2$–$C_6$ alkoxycarbonyl, C(O)NR$^{15}$R$^{16}$, $C_1$–$C_6$ alkylsulfonyl or $C_1$–$C_6$ haloalkylsulfonyl; or $R^{14}$ is phenyl, benzyl, benzoyl, —CH$_2$C(O)phenyl or phenylsulfonyl, each optionally substituted on the phenyl ring with $C_1$–$C_3$ alkyl, halogen, cyano or nitro;

$R^{15}$ is H or $C_1$–$C_6$ alkyl;

$R^{16}$ is $C_1$–$C_6$ alkyl or $C_1$–$C_6$ alkoxy; or $R^{15}$ and $R^{16}$ can be taken together as —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$OCH$_2$CH$_2$;

m is 0, 1 or 2;

n is 1 or 2;

p is 0, 1, or 2; and r is 0, 1 or 2.

The dotted line in the ring containing Y in J of Formula I indicates that the ring may be unsaturated, or may be partially or fully saturated as further defined in the above recitation of Y.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include CH$_3$S(O), CH$_3$CH$_2$S(O), CH$_3$CH$_2$CH$_2$S(O), (CH$_3$)$_2$CHS(O) and the different butylsulfinyl, pentylsulfinyl and hexylsulfinyl isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. "Alkylamino", "dialkylamino", and the like, are defined analogously to the above examples. "Cycloalkyl" includes, for example, cyclopropyl, cyclobutyl, cyclopentyl, and cyclohexyl.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. Examples of "haloalkoxy" include CF$_3$O, CCl$_3$CH$_2$O, HCF$_2$CH$_2$CH$_2$O and CF$_3$CH$_2$O. Examples of "haloalkylthio" include CCl$_3$S, CF$_3$S, CCl$_3$CH$_2$S and ClCH$_2$CH$_2$CH$_2$S. Examples of "haloalkylsulfonyl" include CF$_3$S(O)$_2$, CCl$_3$S(O)$_2$, CF$_3$CH$_2$S(O)$_2$ and CF$_3$CF$_2$S(O)$_2$.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; $C_2$ alkoxyalkyl designates CH$_3$OCH$_2$; $C_3$ alkoxyalkyl designates, for example, CH$_3$CH(OCH$_3$), CH$_3$OCH$_2$CH$_2$ or CH$_3$CH$_2$OCH$_2$; and $C_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$. Examples of "alkylcarbonyl" include C(O)CH$_3$, C(O)CH$_2$CH$_2$CH$_3$ and C(O)CH(CH$_3$)$_2$. Examples of "alkoxycarbonyl" include CH$_3$OC(=O), CH$_3$CH$_2$OC(=O), CH$_3$CH$_2$CH$_2$OC(=O), (CH$_3$)$_2$CHOC(=O) and the different butoxy- or pentoxycarbonyl isomers. In the above recitations, when a compound of Formula I includes a six-membered aromatic ring which contains a nitrogen atom, then all substituents on the heterocyclic ring are attached through the carbon atom(s) of that ring.

When a group contains a substituent which can be hydrogen, for example $R^1$ or $R^{14}$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

Some compounds of this invention can exist as one or more tautomers. One skilled in the art will recognize, for example, that compounds of Formula Ia (Formula I where Q is Q-1, $R^4$ is $OR^{14}$, and $R^{14}$ is H) can also exist as the tautomers of Formulae Ib and Ic as shown below. One skilled in the art will recognize that said tautomers often exist in equilibrium with each other. As these tautomers interconvert under environmental and physiological conditions, they provide the same useful biological effects. The present invention includes mixtures of such tautomers as well as the individual tautomers of compounds of Formula I.

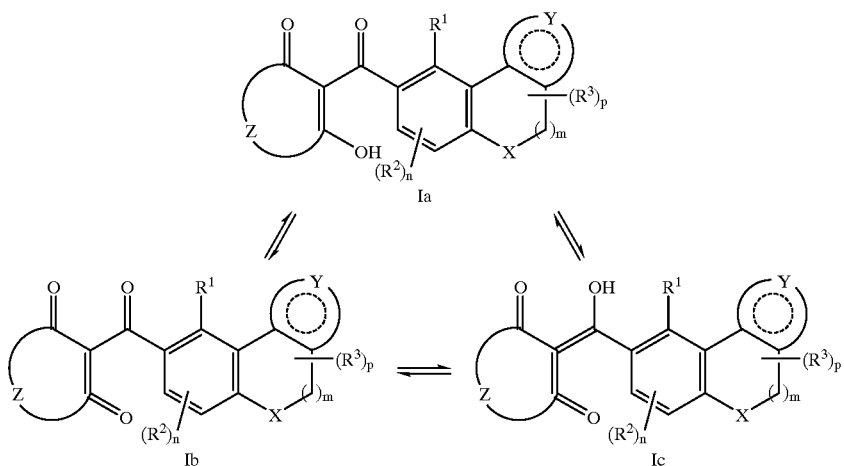

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or enol. Preferred salts include the lithium, sodium, potassium, triethylammonium, and quaternary ammonium salts of the compounds of the invention.

Preferred compounds for reasons of better activity and/or ease of synthesis are:

Preferred 1. Compounds of Formula I, and N-oxides and agriculturally-suitable salts thereof, wherein J is selected from the group

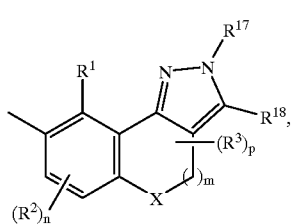

J-1

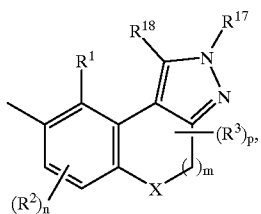

J-2

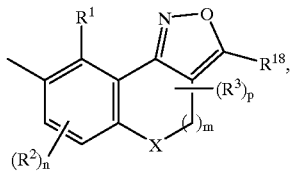

J-3

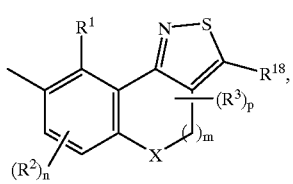

J-4

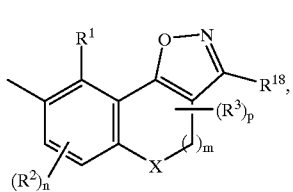

J-5

J-6 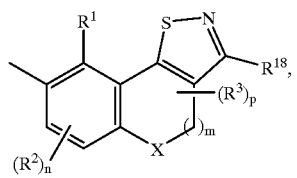
J-7 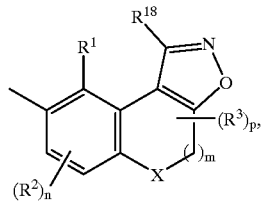
J-8 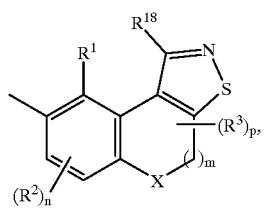
J-9 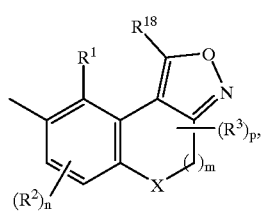
J-10 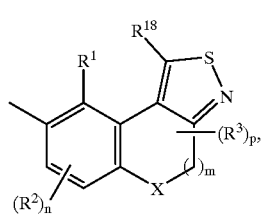
J-11 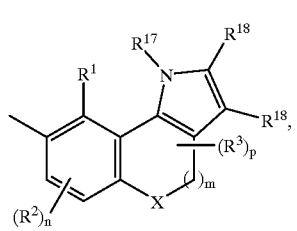
J-12 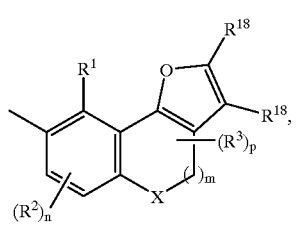
J-13 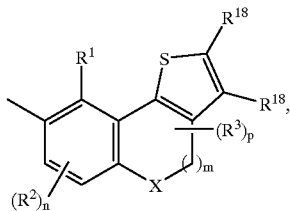
J-14 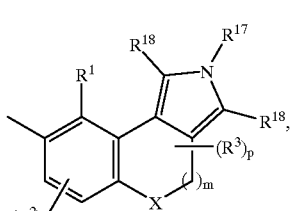
J-15 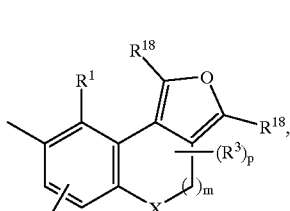
J-16 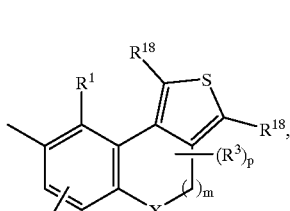
J-17 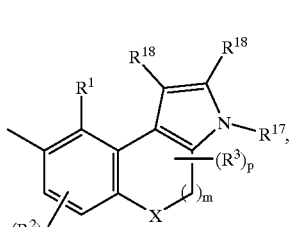
J-18 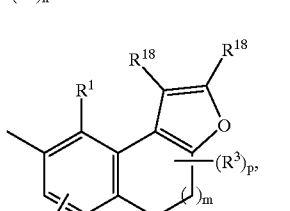
J-19 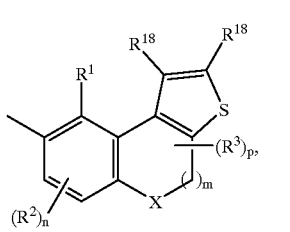

-continued
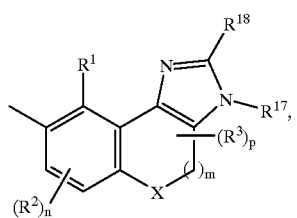
J-20
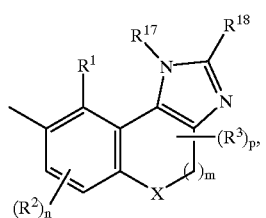
J-21
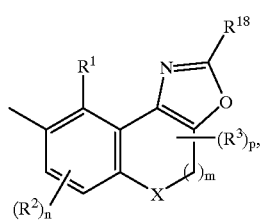
J-22
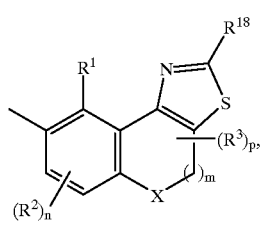
J-23
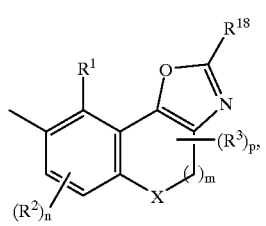
J-24
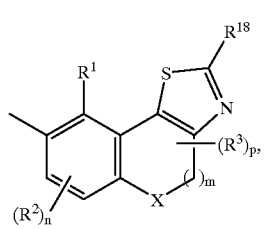
J-25
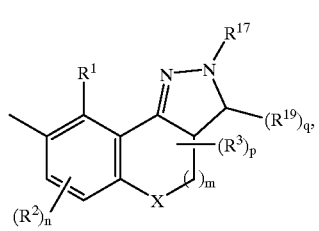
J-26
-continued
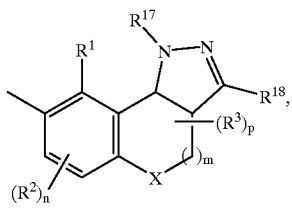
J-27
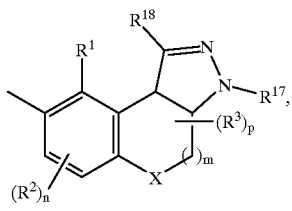
J-28
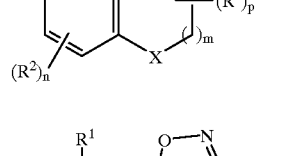
J-29
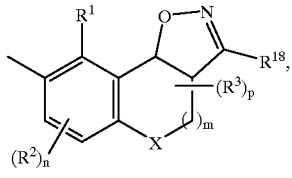
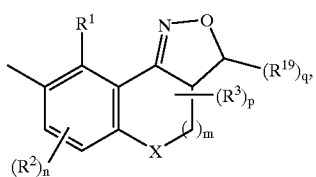
J-30
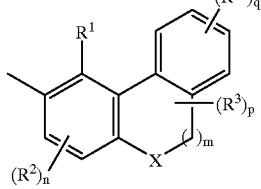
J-31
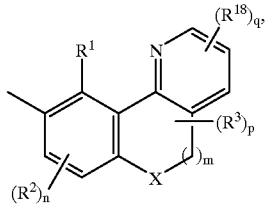
J-32
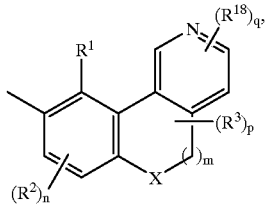
J-33

$R^{17}$ is H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylsulfonyl, $C_1$–$C_6$ haloalkylsulfonyl, aminosulfonyl, $C_1$–$C_2$ alkylaminosulfonyl, $C_2$–$C_4$ dialkylaminosulfonyl, $C_2$–$C_6$ alkoxyalkyl, $C_2$–$C_6$ alkoxycarbonyl or $C_2$–$C_6$ alkylcarbonyl; or $R^{17}$ is phenyl or pyridyl, each optionally substituted with $C_1$–$C_3$ alkyl, halogen, cyano or nitro;

each $R^{18}$ is independently H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, aminosulfonyl, $C_1$–$C_2$ alkylaminosulfonyl, $C_2$–$C_4$ dialkylaminosulfonyl, $NR^{15}R^{16}$, $C_2$–$C_6$ alkoxyalkyl, $C_2$–$C_6$ alkoxycarbonyl, $C_2$–$C_6$ alkylcarbonyl, halogen, cyano or nitro;

each $R^{19}$ is independently H, $C_1$–$C_6$ alkyl, $C_1$–$C_6$ haloalkyl, $C_2$–$C_6$ alkoxyalkyl, $C_2$–$C_6$ alkoxycarbonyl or $C_2$–$C_6$ alkylcarbonyl; and q is 0, 1 or 2.

Preferred 2. Compounds of Preferred 1 wherein:

Q is Q-1.

Preferred 3. Compounds of Preferred 2 wherein:

Z is $CH_2CH_2CH_2$ optionally substituted with one to four $R^5$; $R^1$ and $R^2$ are independently H, $C_1$–$C_3$ alkyl, $C_1$–$C_3$ alkoxy, halogen or nitro;

$R^4$ is $OR^{14}$; and $R^{14}$ is H or $C_1$–$C_4$ alkylsulfonyl; or $R^{14}$ is benzoyl or phenylsulfonyl, each optionally substituted with $C_1$–$C_3$ alkyl, halogen, cyano or nitro.

Preferred 4. Compounds of Preferred 3 wherein:

X is $S(O)_r$;

m is 1 or 2; and r is 2.

Preferred 5. Compounds of Preferred 1 wherein:

Q is Q-2;

Preferred 6. Compounds of Preferred 5 wherein:

$R^1$ and $R^2$ are independently H, $C_1$–$C_3$, alkyl, $C_1$–$C_3$ alkoxy, halogen or nitro;

$R^6$ is SH or $C_1$–$C_4$ alkylsulfonyl; or $R^6$ is benzoyl or phenylsulfonyl, each optionally substituted with $C_1$–$C_3$ alkyl, halogen, cyano, or nitro;

$R^7$ is H, $C_1$–$C_6$ alkyl, or $C_3$–$C_6$ alkenyl; and $R^8$ is H;

Preferred 7. Compounds of Preferred 6 wherein:
X is $S(O)_r$;
m is 1 or 2; and
r is 2.
Preferred 8. Compounds of Preferred 1 wherein:
Q is Q-3.
Preferred 9. Compounds of Preferred 8 wherein:
$R^1$ and $R^2$ are independently H, $C_1$–$C_3$ alkyl, $C_1$–$C_3$ alkoxy, halogen or nitro;
$R^9$ is H, $C_1$–$C_3$ alkyl, or cyclopropyl; and
$R^{10}$ is H or $C_2$–$C_3$ alkoxycarbonyl.
Preferred 10. Compounds of Preferred 9 wherein:
X is $S(O)_r$;
m is 1 or 2; and
r is 2.
Preferred 11. Compounds of Preferred 1 wherein:
Q is Q-4.
Preferred 12. Compounds of Preferred 11 wherein:
$R^1$ and $R^2$ are independently H, $C_1$–$C_3$ alkyl, $C_1$–$C_3$ alkoxy, halogen or nitro;
$R^{11}$ is $C_3$–$C_6$ cycloalkyl or $C_3$–$C_6$ halocycloalkyl, each optionally substituted with 1–4 $C_1$–$C_3$ alkyl; and
$R^{12}$ is cyano or $C_2$–$C_6$ alkoxycarbonyl.
Preferred 13. Compounds of Preferred 12 wherein:
X is $S(O)_r$;
m is 1 or 2; and
r is 2.
Most preferred are compounds of Formula Ia above, and sodium, potassium, and quaternary ammonium salts thereof, selected from the group:
  a) 2-[(2,4-dihydro-2,6,9-trimethyl[1]benzothiopyrano[4,3-c]pyrazol-8-yl)carbonyl]-1,3-cyclohexanedione S,S-dioxide;
  b) 2-[(2-ethyl-2,4-dihydro-6,9-dimethyl[1]benzothiopyrano[4,3-c]pyrazol-8-yl)carbonyl]-1,3-cyclohexanedione S,S-dioxide;
  c) 2-[(2,4-dihydro-2,6,9-trimethyl[1]benzothiopyrano[4,3-c]pyrazol-8-yl)carbonyl]-5-methyl-1,3-cyclohexanedione S,S-dioxide;
  d) (2,4-dihydro-2,6,9-trimethyl[1]benzothiopyrano[4,3-c]pyrazol-8-yl)(1-ethyl-5-hydroxy-1H-pyrazol-4-yl)methanone S,S-dioxide;
  e) 2-[(3-chloro-2-ethyl-2,4-dihydro-6,9-dimethyl[1]benzothiopyrano[4,3-c]pyrazol-8-yl)carbonyl]-1,3-cyclohexanedione S,S-dioxide; and
  f) 2-[(4,5-dihydro-2,7,10-trimethyl-2H[1]benzothiepino[5,4-c]pyrazol-9-yl)carbonyl]-5-methyl-1,3-cyclohexanedione S,S-dioxide.

This invention also relates to herbicidal compositions comprising herbicidally effective amounts of the compounds of Formula I and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of Formula I (e.g., as a composition described herein). The preferred methods of use are those involving the above preferred compounds.

DETAILS OF THE INVENTION

The compounds of Formula I can be prepared by one or more of the following methods and variations as described in Schemes 1–24. The definitions of Q, X, Y, Z, $R^1$–$R^{19}$, m, n, p and r in the compounds of Formulae 1–27 below are as defined above in the Summary of the Invention. Compounds of Formulae Ia–Ig are various subsets of the compounds of Formula I, and all substituents for Formulae Ia–Ig are as defined above for Formula I.

Compounds of General Formula Id can be readily prepared by one skilled in the art by using the reactions and techniques described in Schemes 1–16 of this section as well as by following the specific procedures given in Examples 1, 2 and 4.

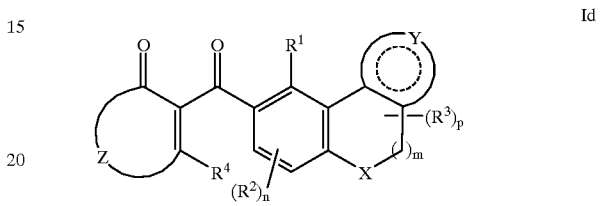

Id

Scheme 1 illustrates the preparation of compounds of Formula Id ($R^4$=$OR^{14a}$ and $R^{14a}$ is the same as $R^{14}$ as described in the Summary of the Invention excluding H) whereby a compound of Formula Id ($R^4$=OH) is reacted with a reagent of Formula 1 in the presence of a base wherein $X^1$ is chlorine, bromine, fluorine, trifluorosulfonyloxy (OTf), or acetyloxy (OAc) and $R^{14a}$ is as previously defined. The coupling is carried out by methods known in the art (or by slight modification of these methods): for example, see K. Nakamura, et al., WO 95/04054.

Scheme 1

Id ($R^4$ = OH) + $R^{14a}X^1$ $\xrightarrow{\text{base}}$ Id ($R^4$ = $OR^{14a}$)

1

Compounds of Formula Id ($R^4$=Nu; Nu=$SR^{14b}$ or $OR^{14c}$; $R^{14b}$ is H, $C_1$–$C_6$ alkyl or $C_1$–$C_6$ haloalkyl; $R^{14c}$ is $C_1$–$C_6$ alkyl, $C_1$–$C_6$ haloalkyl or $C_2$–$C_6$ alkoxyalkyl) can be prepared by one skilled in the art from a compound of Formula Id ($R^4$=halogen) by treatment with a nucleophile of Formula 2 (Nu=$SR^{14b}$ or $OR^{14c}$; M=Na, K, or Li) as shown in Scheme 2 using methods well documented in the literature (or slight modification of these methods): for example, see S. Miyano, et al., *J. Chem. Soc., Perkin Trans. 1* (1976), 1146.

Scheme 2

Id ($R^4$ = halogen) + $MSR^{14b}$ or $MOR^{14c}$ ⟶

2

Id ($R^4$ = $SR^{14b}$ or $OR^{14c}$)

Compounds of Formula Id ($R^4$=halogen) can be prepared by reacting a compound of Formula Id ($R^4$=OH) with a halogenating reagent such as oxalyl bromide or oxalyl chloride (Scheme 3). This conversion is carried out by methods known in the art (or by slight modification of these methods): for example see S. Muller, et al., WO 94/13619; S. Muller, et al., DE 4,241,999.

Scheme 3

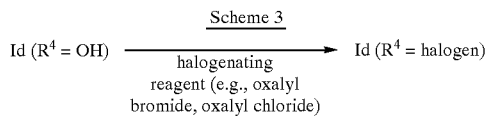

Scheme 4 illustrates the preparation of compounds of Formula Id ($R^4$=OH), whereby an enol ester of Formula 3 is reacted with a base such as triethylamine in the presence of a catalytic amount of cyanide source (e.g., acetone cyanohydrin or potassium cyanide). This rearrangement is carried out by methods known in the art (or by slight modification of these methods): for example see W. J. Michaely, EP 369,803.

Scheme 4

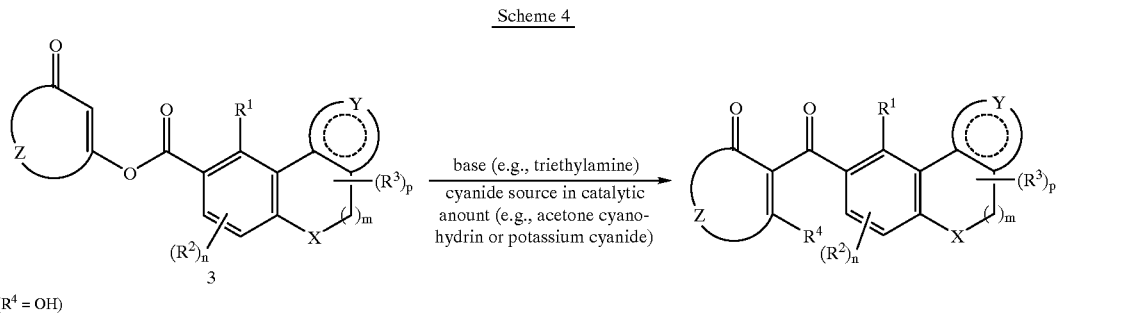

Enol esters of Formula 3 can be prepared by reacting a dione of Formula 4 with an acid chloride of Formula 5 in the presence of a slight mole excess of a base such as triethylamine in an inert organic solvent such as acetonitrile, methylene chloride or toluene at temperatures between 0° C. and 110° C. (Scheme 5). This type of coupling is known in the art: for example, see W. J. Michaely, EP 369,803.

Scheme 5

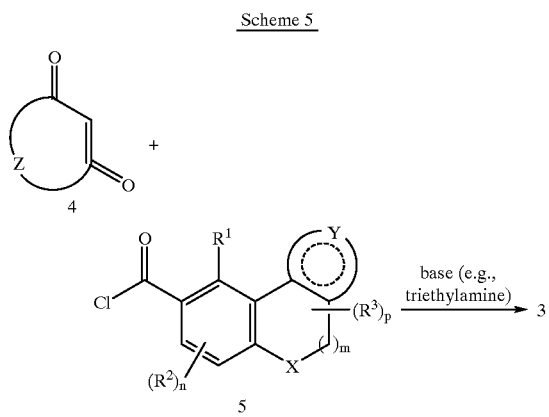

The acid chlorides of Formula 5 can be prepared by one skilled in the art by reacting an acid of Formula 6 with chlorinating agents such as oxalyl chloride or thionyl chloride and a catalytic amount of dimethylformamide (Scheme 6). This chlorination is well known in the art: for example, see W. J. Michaely, EP 369,803.

Scheme 6

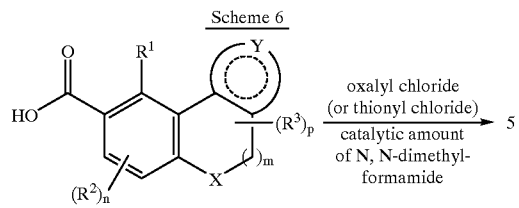

Scheme 7 illustrates the preparation of acids of Formula 6 (X=S(O)$_r$; r=1 or 2) whereby an acid of Formula 6 (X=S) is reacted with an oxidizing reagent such as peroxyacetic acid, m-chloroperoxybenzoic acid, Oxone®, or hydrogen peroxide (the reaction may be buffered with a base such as sodium acetate or sodium carbonate). The oxidation is carried out by methods known in the art (or by slight modification of these methods): for example, see B. M. Trost, et al., *J. Org. Chem.* (1988), 53, 532; B. M. Trost, et al., *Tetrahedron Lett.* (1981), 21, 1287; S. Patai, et al., *The Chemistry of Sulphones and Sulphoxides*, John Wiley & Sons. For some acids of Formula 6 (X=S) with a functional group not compatible with the reaction conditions, the functional group may be protected before the oxidation and then be deprotected after the oxidation. The protecting and deprotecting procedures are well known in the literature: for example see T. W. Greene, et al., *Protective Groups in Organic Synthesis* (Second Edition), John Wiley & Sons, Inc.

Scheme 7

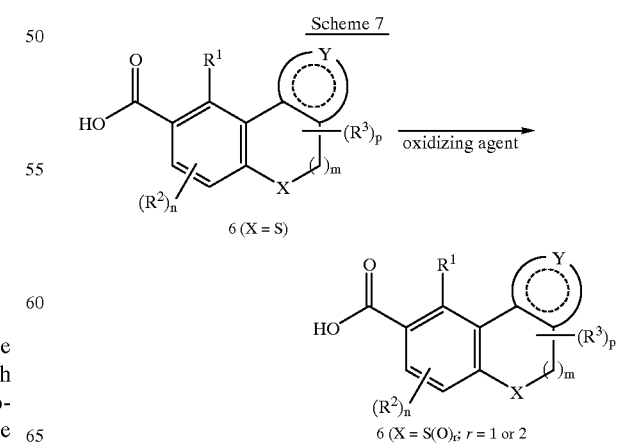

Scheme 8 illustrates the preparation of acids of Formula 6 (r=0 if X=S(O)$_r$) whereby a phenyl bromide of Formula 7 (r=0 if X=S(O)$_r$) is treated with n-butyllithium (or magnesium) and the lithium salt (or the Grignard reagent) generated in situ is then reacted with carbon dioxide followed by acidification with an acid such as hydrochloric acid. This conversion is carried out by methods known in the art (or by slight modification of these methods): for example, see M. A. Ogliaruso, et al., *Synthesis of Carboxylic Acids, Esters and Their Derivatives*, pp 27–28, John Wiley & Sons; A. J. Bridges, et al., *J. Org. Chem.* (1990), 55, 773; C. Franke, et al., *Angew. Chem. Int. Ed.* (1969), 8, 68. Protecting and deprotecting functional groups not compatible with the reaction conditions may be necessary for compounds with such a functional group.

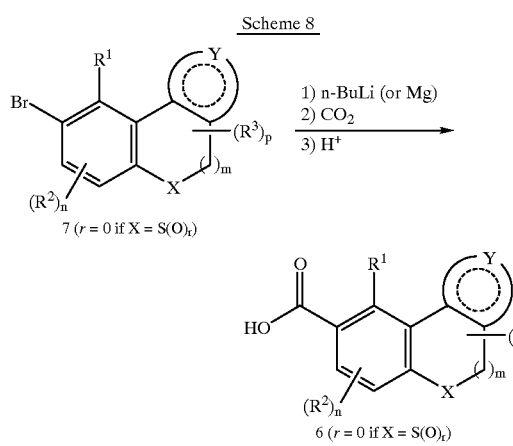

Scheme 8a illustrates the preferred method for the preparation of acids of Formula 6 (r=2 if X=S(O)$_r$) whereby a phenyl bromide of Formula 7 (r=2 if X=S(O)$_r$) is treated with copper cyanide followed by hydrolysis of the intermediate nitrile to the carboxylic acid. This conversion is carried out by methods known in the art (or by slight modification of these methods): for example, see L. Friedman and H. Shechter *J. Org. Chem.* (1961), 26, 2522. Protecting and deprotecting functional groups not compatible with the reaction conditions may be necessary for compounds with such a functional group.

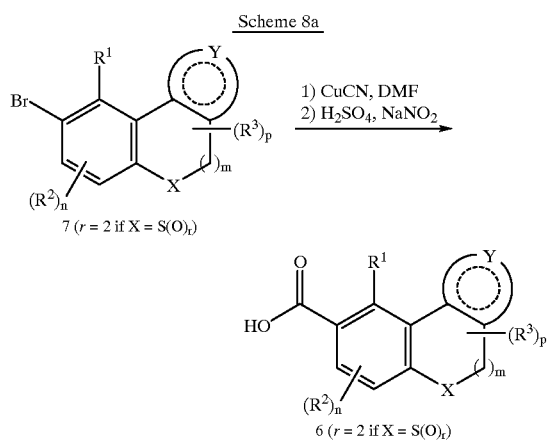

Phenyl bromides of Formula 7 (r=0 if X=S(O)$_r$) can be readily prepared by one skilled in the art by using the reactions and techniques described in Schemes 9–14 (or by slight modification of these methods). Scheme 9 illustrates the preparation of phenyl bromides of Formula 7a (r=0 if X=S(O)$_r$) and Formula 7b (r=0 if X=S(O)$_r$) whereby a ketone of Formula 8 is reacted with a hydrazine of Formula 9. Some of the immediate products from the reactions of Scheme 9 may be further modified (e.g., conversion of OH on the pyrazole ring to Cl by treatment with POCl$_3$ or N-alkylation of the 1-H-pyrazole with an alkylating reagent such as ethyl bromide or ethyl sulfate) to give the desired phenyl bromides of Formula 7a (r=0 if X=S(O)$_r$) and Formula 7b (r=0 if X=S(O)$_r$) The above-mentioned reactions are carried out by methods known in the art (or by slight modification of these methods): for example, see A. R. Katritzky, et al., *Comprehensive Heterocyclic Chemistry*, Volume 5, p 121 and pp 277–280, (1984) Pergamon Press; M. Hauser, et al., *J. Org. Chem.* (1961), 26, 451; E. F. M. Stephenson, *Org. Synth.* (1949), 29, 54.

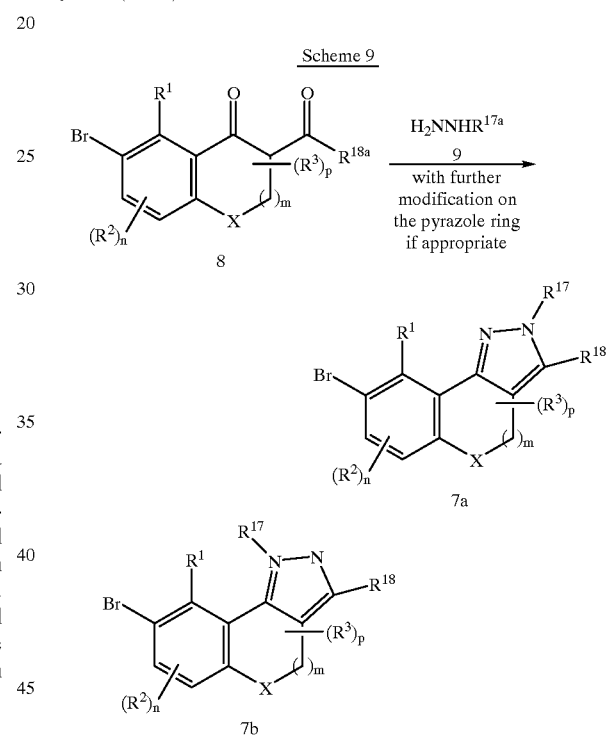

$R^{17a}$ = H or $C_1$–$C_4$ alkyl
$R^{18a}$ = $R^{18}$ excluding halogen, cyano, and nitro Alternatively, many phenyl bromides of Formula 7a (r=0 if X=S(O)$_r$) and Formula 7b (r=0 if X=S(O)$_r$) can also be prepared by reacting a ketone of Formula 10 with a hydrazine of Formula 9 (Scheme 10) in an inert organic solvent such as acetonitrile, ethanol or toluene at temperatures between 0° C. and 110° C. for a period of time ranging from 1 hour to 3 days. The reaction mixture is then concentrated and the resulting residue is flash column chromatographed over silica gel with eluents such as mixtures of ethyl acetate and hexanes to give the phenyl bromides of Formula 7a (r=0 if X=S(O)$_r$) and Formula 7b (r=0 if X=S(O)$_r$). Phenyl bromides of Formula 7a ($R^{17}$=H; r=0 if X=S(O)$_r$) or Formula 7b ($R^{17}$=H; r=0 if X=S(O)$_r$) may be further N-alkylated with an alkylating reagent such as ethyl bromide or ethyl sulfate to give the phenyl bromides of Formula 7a ($R^{17}$=$C_1$–$C_6$ alkyl; r=0 if X=S(O)$_r$) and Formula 7b ($R^{17}$=$C_1$–$C_6$ alkyl; r=0 if X=S(O)$_r$).

Phenyl bromides of Formula 7a (X=S(O)$_r$ and r=0) and Formula 7b (X=S(O)$_r$ and r=0) can also be oxidized to compounds of Formula 7a (X=S(O)$_r$ and r=1 or 2) and Formula 7b (X=S(O)$_r$ and r=1 or 2) by employing similar methods as described for Scheme 7.

Scheme 10

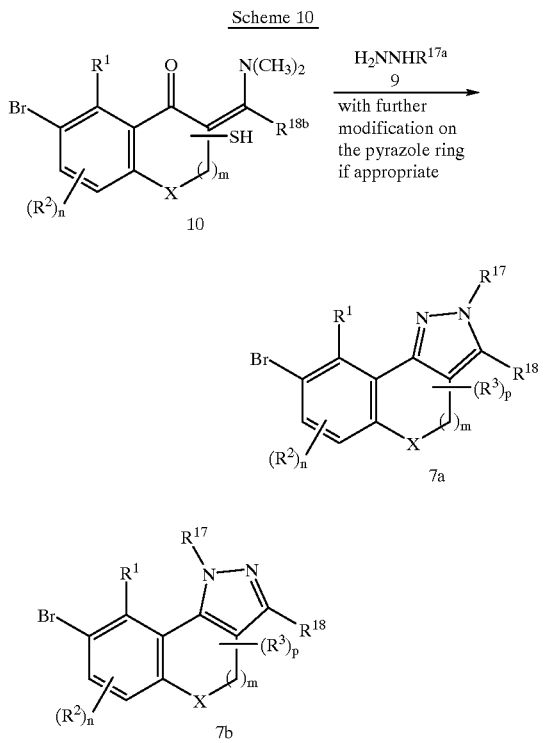

R$^{18b}$ = H or C$_1$–C$_6$ alkyl

Similarly, phenyl bromides of Formula 7c (r=0 if X=S(O)$_r$) and Formula 7d (r=0 if X=S(O)$_r$) can also be prepared by reacting a ketone of Formula 8 or Formula 10 with hydroxylamine or hydroxylamine hydrochloride (Scheme 11). Some of the immediate products from the reactions of Scheme 11 may be further modified (e.g., conversion of OH on the isoxazole ring to Cl by treatment with POCl$_3$) to give the desired phenyl bromides of Formula 7a (r=0 if X=S(O)$_r$) and Formula 7b (r=0 if X=S(O)$_r$) The above-mentioned conversions are carried out by methods known in the art (or by slight modification of these methods): for example, see A. R. Katritzky, et al., *Comprehensive Heterocyclic Chemistry*, Volume 6, pp 61–64 and p 118, (1984) Pergamon Press; H. Boshagen, *Chem. Ber.*, (1967), 100, 3326.

Scheme 11

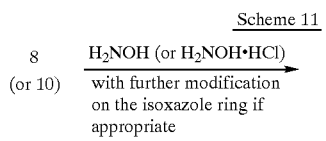

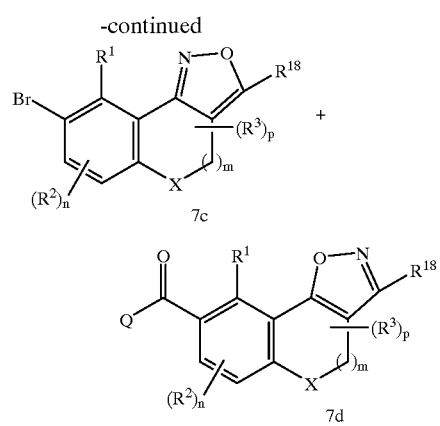

Scheme 12 illustrates the preparation of phenyl bromides of Formula 7e (r=0 if X=S(O)$_r$) whereby a ketone of Formula 8 or Formula 10 is reacted with an amidine of Formula 11. Some of the immediate products from the reactions of Scheme 12 may be further modified (e.g., conversion of OH on the pyrimidine ring to Cl by treatment with POCl$_3$ or conversion of NH$_2$ on the pyrimidine ring to Cl by treatment with NaNO$_2$/HCl/H$_2$O). The above-mentioned reactions are carried out by methods known in the art (or by slight modification of these methods): for example, see A. R. Katritzky, et al., *Comprehensive Heterocyclic Chemistry*, Volume 3, p 112–114, (1984) Pergamon Press; D. J. Brown, et al., *J. Chem. Soc. C.* (1967), 1922; I. Kogon, et al., *Org. Synth.* (1963), IV, 182.

Scheme 12

R$^{18c}$ = H, C$_1$–C$_4$ alkyl, OH or NH$_2$

Scheme 13 illustrates the preparation of phenyl bromides of Formula 7f (r=0 if X=S(O)$_r$) whereby a ketone of Formula 12 is reacted with a hydrazine of Formula 9. This conversion is carried out by methods known in the art (or by slight modification of these methods): for example, see A. R. Katritzky, et al., *Comprehensive Heterocyclic Chemistry*, Volume 5, pp 278–279, (1984) Pergamon Press.

Scheme 13

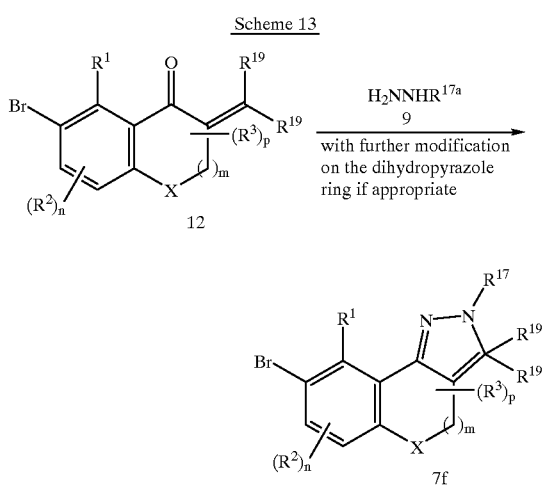

Other phenyl bromides of Formula 7 can be prepared in an analogous manner using methods known in the art (or by slight modification of these methods): for example, see A. R. Katritzky, et al., *Comprehensive Heterocyclic Chemistry*, Volumes 2–6, (1984) Pergamon Press; E. Campaigne, et al., *J. Heterocycl. Chem.,* (1969), 553; A. N. Fujiwara, *J. Heterocycl. Chem.*, (1968), 853.

The ketones of Formula 8 can be prepared by one skilled in the art by reacting a ketone of Formula 13 with an anhydride of Formula 14 (or an acyl chloride of Formula 15) and a catalytic amount of a Lewis acid such as boron trifluoride (Scheme 14). This conversion is well known in the art: for example, see A. Philipp, et al., *Can. J. Chem.*, (1979), 57, 3292; B. M. Perfetti, et al., *J. Am. Chem. Soc.*, (1953), 75, 626.

Scheme 14

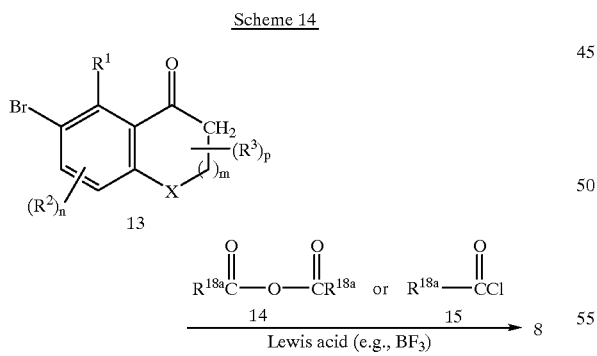

The ketones of Formula 10 can be prepared by one skilled in the art by reacting a ketone of Formula 13 with an amide dimethyl acetal of Formula 16 (Scheme 15). This conversion is well known in the art: for example, see G. Litkei, et al., *Org. Prep. Proced. Int.*, (1990), 22, 47–56; N. Dereu, et al., *J. Organomet. Chem.*, (1981), 208, 11; B. Gammill., *Synthesis*, (1979), 901.

Scheme 15

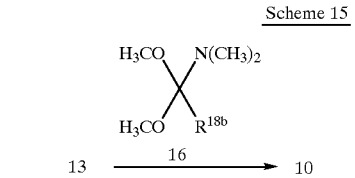

The ketones of Formula 12 can be prepared by one skilled in the art by reacting a ketone of Formula 13 with an aldehyde or a ketone of Formula 17 (or its equivalent) in the presence of an acid or a base as shown in Scheme 16. This conversion is well known in the art: for example, see J. L. Gras., *Tetrahedron Lett.*, (1978), 2111; L. Engman, et al., *Tetrahedron Lett.*, (1981), 5251; A. Roedig, et al., *Chem. Ber.*, (1960), 2294; T. Girija, et al., *J. Chem. Soc., Perk. Trans. 1*, (1991), 1467; A. J. Laurent, et al., *Tetrahedron Lett.*, (1992) 8091.

Scheme 16

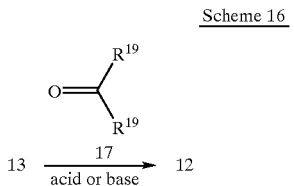

The ketones of Formula 13 can be prepared by methods known in the art (or by slight modification of these methods): for example, see W. Flemming, et al., *Chem. Ber.*, (1925), 58, 1612; I. W. J. Still, et al., *Can. J. Chem.*, (1976), 54. 453–470; V. J. Traynelis, et al., *J. Org. Chem.*, (1961), 26, 2728; 1. Nasuno, et al., WO 94/08988.

Compounds of General Formula Ie can be readily prepared by one skilled in the art by using the reactions and techniques described in Schemes 17–19 of this section as well as by following the specific procedures given in Examples 3, 5, and 6.

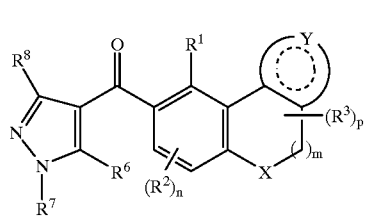

Ie

Scheme 17 illustrates the preparation of compounds of Formula Ie ($R_{6a}$ is $OR^{14}$ as described in the Summary of the Invention excluding OH) whereby a compound of Formula Ie ($R^6$=OH) is reacted with a reagent of Formula 18 in the presence of a base wherein $X^2$ is chlorine, bromine, fluorine, OTf, or OAc and $R^{6a}$ is as previously defined. This coupling is carried out by methods known in the art (or by slight modification of these methods): for example, see K. Nakamura, et al., WO 95/04054.

Scheme 17

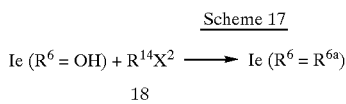

Scheme 18 illustrates the preparation of compounds of Formula Ie ($R^6$=OH), whereby an ester of Formula 19 or its isomer 19a is reacted with a base such as triethylamine in the presence of a catalytic amount of cyanide source (e.g., acetone cyanohydrin or potassium cyanide). This rearrangement is carried out by methods known in the art (or by slight modification of these methods): for example, see W. J. Michaely, EP 369,803.

Scheme 18

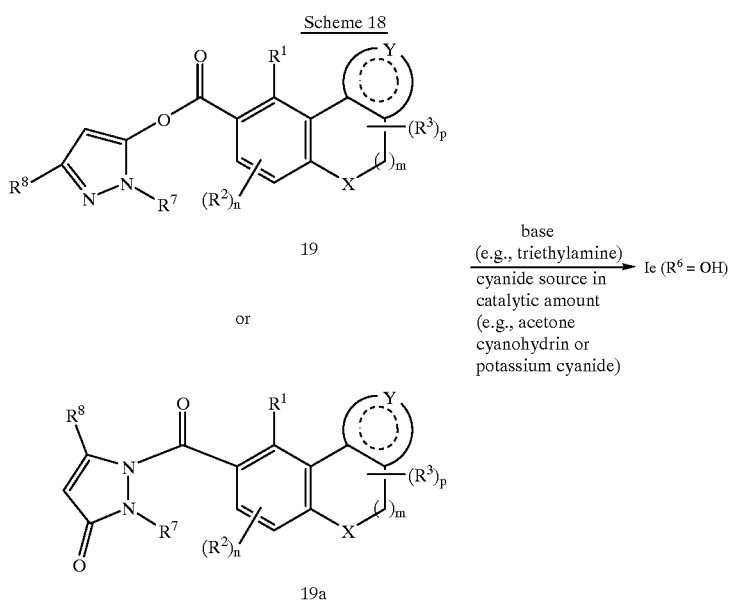

Esters of Formula 19 or amides of Formula 19a can be prepared by reacting a hydroxypyrazole of Formula 20 with an acid chloride of Formula 5 in the presence of a slight mole excess of a base such as triethylamine in an inert organic solvent such as acetonitrile, methylene chloride or toluene at temperatures between 0° C. and 110° C. (Scheme 19). This type of coupling is carried out by methods known in the art (or by slight modification of these methods): for example, see W. J. Michaely, EP 369,803.

Scheme 19

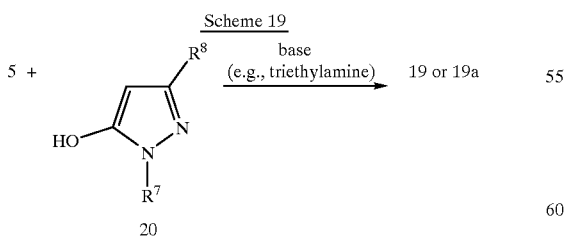

Compounds of General Formula If can be readily prepared by one skilled in the art by using the reactions and techniques described in Schemes 20–23 of this section.

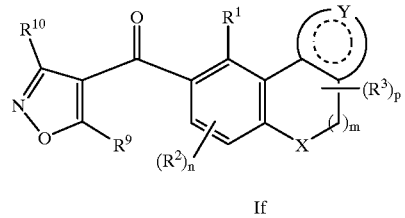

If

Scheme 20 illustrates the preparation of compounds of Formula If whereby a compound of Formula 21 is reacted with a salt of hydroxylamine such as hydroxylamine hydrochloride in the presence of a base or acid acceptor such as triethylamine or sodium acetate. The substituents of the immediate products may be further modified if appropriate. This cyclization is carried out by methods known in the art (or by slight modification of these methods): for example, see P. A. Cain, et al., EP 560,483; C. J. Pearson, et al., EP 636,622.

Scheme 20

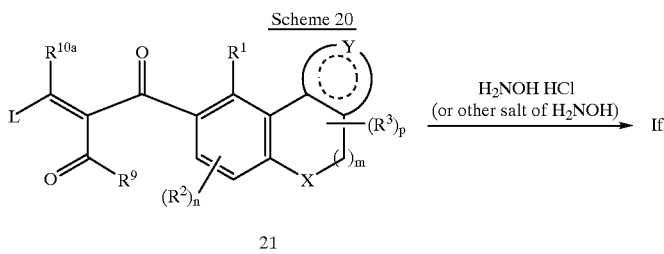

wherein

L is a leaving group such as $C_1$–$C_4$alkoxy (e.g. $OC_2H_5$)
or N,N-dialkylamino (e.g. dimethyl amino)
$R^{10a}$ is H, $C_2$–$C_6$ alkoxycarbonyl, $C_2$–$C_6$ haloalkoxycarbonyl or $CONH_2$ Scheme 21 illustrates the preparation of compounds of Formula 21 whereby a compound of Formula 22 is reacted with a reagent of Formula 23 or Formula 24. This conversion is carried out by methods known in the art (or by slight modification of these methods): for example, see P. A. Cain, et al., EP 560,483; C. J. Pearson, et al., EP 636,622.

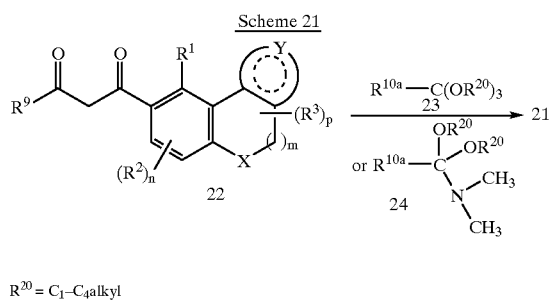

$R^{20}$ = $C_1$–$C_4$alkyl

Scheme 22 illustrates the preparation of compounds of Formula 22 whereby a ester of Formula 25 is decarboxylated in the presence of a catalyst, such as p-toluenesulfonic acid, in an inert solvent such as toluene. This conversion is carried out by methods known in the art (or by slight modification of these methods): for example, see P. A. Cain, et al., EP 560,483; C. J. Pearson, et al., EP 636,622.

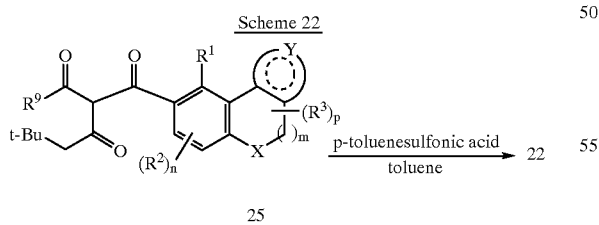

Esters of Formula 25 can be prepared by reacting the metal salt of a compound of Formula 26 with an acid chloride of Formula 5 (Scheme 23). This type of coupling is known in the art: for example see P. A. Cain, et al., EP 560,483; C. J. Pearson, et al., EP 636,622.

Scheme 23

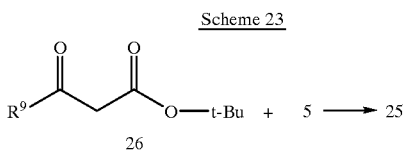

Scheme 24 illustrates the preparation of compounds of Formula Ig whereby a compound of Formula 5 is reacted with a compound of Formula 27 in the presence of a base such as triethylamine, potassium carbonate, sodium hydride or $Mg(OEt)_2$ in an inert organic solvent such as diethyl ether, tetrahydrofuran, N,N-dimethylformamide, dichloromethane or acetonitrile.

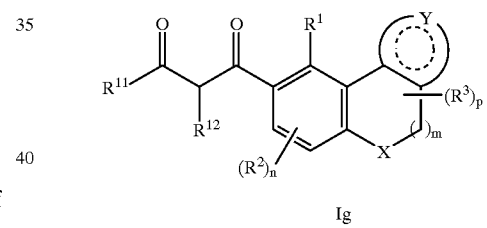

This conversion is carried out by methods known in the art (or slight modification of these methods); for example, see J. W. Ashmore, EP 213,892 and P. A. Caln, EP 496,631 A1.

Scheme 24

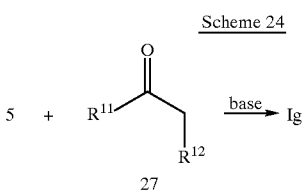

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective*

Groups in Organic Synthesis, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet.

EXAMPLE 1

Step A: Preparation of 3-[(2,5-dimethylphenyl)thio] propanoic acid 43.4 g (1.086 mol) of sodium hydroxide was added to 230 mL of water, 75.0 g (0.543 mol) of 2,5-dimethylthiophenol (purchased from Aldrich Chemical Company) was then added and the mixture was cooled to about 10° C. 91.30 g (0.597 mol) of 3-bromopropionic acid (purchased from Aldrich Chemical Company) was added in portions keeping the temperature below 25° C. The mixture was warmed to room temperature, stirred for 2 hr under nitrogen, and was then washed with diethyl ether (3×500 mL). The aqueous layer was acidified with 1N HCl and filtered to yield 112.79 g of the title compound of Step A as a solid melting at 97–98° C. $^1$H NMR (CDCl$_3$): δ2.3 (s,3H), 2.34 (s,3H), 2.68 (t,2H), 3.1 (t,2H), 6.9 (d,1H), 7.06–7.14 (m,2H).

Step B: Preparation of 2,3-dihydro-5,8-dimethyl-4H-1-benzothiopyran-4-one 530 mL of concentrated sulfuric acid was added to 24.91 g (0.119 mol) of the title compound of Step A while being cooled with an acetone/ice bath. The ice bath was removed, the mixture stirred for 1 hr and was then poured over crushed ice. The aqueous layer was extracted with a 1:9 mixture of diethyl ether:hexane (6×500 mL), dried (MgSO$_4$), filtered, and evaporated to dryness to yield 11.75 g of the title compound of Step B as an oil. $^1$H NMR (CDCl$_3$): δ2.3 (s,3H), 2.6 (s,3H), 2.97 (m,2H), 3.2 (m,2H), 6.9–7.1 (m,2H).

Step C: Preparation of 6-bromo-2,3-dihydro-5,8-dimethyl-4H-1-benzothiopyran-4-one A solution of 4.07 g (0.021 mol) of the title compound of Step B in 25 mL of methylene chloride was added dropwise to a mixture of 7.07 g (0.053 mol) of aluminum chloride (purchased from Aldrich Chemical Company) and 25 mL of methylene chloride. The suspension was stirred for approximately 15 minutes, 1.14 mL (0.022 mol) of bromine (purchased from Janssen) was added dropwise and the mixture was refluxed for 10 minutes. The hot mixture was poured into 10 mL of concentrated hydrochloric acid containing 75 g of ice, stirred for 10 minutes, diluted with 50 mL of water, and extracted with diethyl ether (2×200 mL). The organic layer was washed with water (2×200 mL), dried (Na$_2$SO$_4$), filtered and evaporated to dryness. The crude product was chromatographed over silica gel eluting with ethyl acetate:hexane (5% 95%) to yield 2.62 g of the title compound of Step C as a solid melting at 87–88° C. $^1$H NMR (CDCl$_3$): δ2.3 (s,3H), 2.6 (s,3H), 3.0 (m,2H), 3.2 (m,2H), 7.45 (s,1H).

Step D: Preparation of 6-bromo-3-[(dimethylamino) methylene]-2,3-dihydro-5,8-dimethyl-4H-1-benzothiopyran-4-one 20.0 g (0.074 mole) of the title compound of Step C and 100 mL of N,N-dimethylformamide dimethyl acetal (purchased from Aldrich Chemical Company) were stirred under nitrogen at reflux overnight. The mixture was concentrated, the residue was stirred in water, and filtered. The solid was dissolved in methylene chloride, dried (MgSO$_4$), filtered, and evaporated to dryness to yield 21.54 g of the title compound of Step D as an oil. $^1$H NMR (CDCl$_3$): δ2.49 (s,3H), 2.56 (s,3H), 3.16 (s,6H), 3.86 (s,2H), 7.34 (s,1H), 7.57 (s,1H).

Step E: Preparation of 8-bromo-2,4-dihydro-2,6,9-trimethyl[1]benzothiopyrano[4,3-c]pyrazole 4.53 mL (0.085 mol) of methyl hydrazine (purchased from Aldrich Chemical Company) was added dropwise to a mixture of 21.54 g (0.066 mol) of the title compound of Step D in 115 mL of ethanol. The mixture was stirred at reflux under nitrogen for 5 hr and was then evaporated to dryness. The crude product was chromatographed over silica gel eluting with a mixture of (1:9) ethyl acetate:hexane to yield two components. Concentration of the major fraction yielded 14.72 g of the title compound of Step E as an oil; $^1$H NMR (CDCl$_3$): δ2.3 (s,3H), 2.82 (s,3H), 3.76 (s,2H), 3.9 (s,3H), 7.2 (s, 1H), 7.3 (s,1H). Concentration of the minor fraction yielded 3.87 g of the isomer 8-bromo-1,4-dihydro-1,6,9-trimethyl[1]benzothiopyrano[4,3-c]pyrazole as an oil; $^1$H NMR (CDCl$_3$): δ2.3 (s,3H), 2.46 (s,3H), 3.75 (s,3H), 3.59 and 3.81 (2d,2H), 7.4 (s,1H), 7.45 (s,1H).

Step F: Preparation of 2,4-dihydro-2,6,9-trimethyl[1]benzothiopryano[4,3-c]pyrazole-8-carboxylic acid 3.73 mL (0.050 mol) of bromoethane (purchased from Aldrich Chemical Company) was added dropwise to a mixture of 2.11 g (0.088 mol) of magnesium in 70 mL of tetrahydrofuran. After stirring for 10 minutes, a solution of 7.77 g (0.025 mol) of the title compound of Step E in 100 mL of tetrahydrofuran was added dropwise and the mixture stirred at reflux under nitrogen overnight. After cooling to room temperature, carbon dioxide was bubbled into the mixture for 1 hr keeping the temperature below 20° C. 55 mL of 10% hydrochloric acid was added dropwise and the resulting mixture was allowed to stir for 5 hr at room temperature. The mixture was evaporated to dryness, extracted with ethyl acetate (3×250 mL), dried (Na$_2$SO$_4$), filtered, and evaporated to dryness. The residue was triturated in hexane, the hexane was decanted, and the residue was dissolved in 1M sodium carbonate. The aqueous solution was extracted with diethyl ether (3×200 mL), acidified with concentrated hydrochloric acid, and extracted with diethyl ether (3×300 mL). The combined organic layers were dried (MgSO$_4$), filtered, and evaporated to dryness to yield 2.55 g of the title compound of Step F as a solid melting at 195° C. (decomposed). $^1$H NMR (Me$_2$SO-d$_6$): δ2.3 (s, 3H), 2.77 (s,3H), 3.89 (m,5H), 7.4 (s,1H), 7.6 (s,1H).

Step G: Preparation of 2,4-dihydro-2,6,9-trimethyl[1]benzothiopyran[4,3-c]pyrazole-8-carboxylic acid 5,5-dioxide 6.70 mL (0.066 mol) of hydrogen peroxide (35%) was added to 50 mL of trifluoroacetic acid, and allowed to stir under nitrogen for 30 minutes. The solution was cooled to about 0° C., and 4.46 g (0.016 mol) of the title compound of Step F was added in portions while keeping the temperature below 15° C. The mixture stirred at room temperature overnight and then 2 mL of methyl sulfide was added to the mixture. The resulting mixture was allowed to stir for 15 minutes and was then evaporated to dryness. The residue was triturated in a mixture of diethyl ether:hexane (8:2), allowed to stand overnight, and the organic mixture was decanted. The residue was triturated in water, and an orange solid was removed. The orange solid was dissolved in 250 mL of chloroform, dried (MgSO$_4$), filtered, and evaporated to dryness to yield a portion of the title compound of Step G. The diethyl ether:hexane (8:2) decant was concentrated, the residue was triturated in water, and the water was decanted. The residue was dissolved in chloroform, dried (MgSO$_4$), filtered, and evaporated to dryness to yield the title compound of Step G. The two products were combined to yield 3.62 g of the title compound of Step G as a semi-solid. $^1$H NMR (Me$_2$SO-d$_6$): δ2.63 (s,3H), 2.7 (s,3H), 3.9 (s,3H), 4.7 (s,2H), 7.5 (s,1H), 7.8 (s,1H).

Step H: Preparation of 3-oxo-1-cylcohexen-1-yl 2,4-dihydro-2,6,9-trimethyl[1]benzothiopyrano[4,3-c]pyrazole-8-carboxylate 5.5-dioxide 3.62 g (0.0118 mol) of the title compound of Step G, 3.09 mL (0.035 mol) of oxalyl chloride (purchase from Janssen), and 2 drops of N,N-dimethylformamide were added to 50 mL of methylene chloride. The mixture was refluxed under nitrogen for 2 hr, and was then evaporated to dryness. 50 mL of methylene chloride was added to the residue and was then evaporated to dryness. Another 50 mL of methylene chloride was added to the residue, and the solution was cooled to about 0° C. 1.46 g (0.013 mol) of 1,3-cyclohexanedione (purchased from Aldrich Chemical Company) was added followed by 5.1 mL (0.0366 mol) of triethylamine, and the mixture was stirred overnight while warming to room temperature. The mixture was evaporated to dryness, and the crude product was chromatographed over silica gel eluting with a mixture of methylene chloride:diethyl ether (9:1) to yield 1.53 g of the title compound of Step H as a solid melting at 158–160° C. $^1$H NMR (CDCl$_3$): δ2.2 (m,2H), 2.5 (m,2H), 2.7 (m,2H), 2.78 (s,3H), 2.9 (s,3H), 3.99 (s,3H), 4.39 (s,2H), 6.1 (s,1H), 7.5 (s,1H), 7.6 (s,1H).

Step I: Preparation of 2-[(2,4-dihydro-2,6,9-trimethyl[1]benzothiopyrano[4,3-c]pyrazol-8-yl)carbonyl]-1,3-cyclohexanedione S,S-dioxide 1.44 g (0.0036 mol) of the title compound of Step H, 2 drops of acetone cyanohydrin (purchased from Aldrich Chemical Company), and 0.88 mL (0.0063 mol) of triethylamine were added to 100 mL of acetonitrile and the mixture was allowed to stir overnight at room temperature under nitrogen. About 0.10 g of potassium cyanide was added to the mixture, and the mixture was stirred for 1 hr. The mixture was evaporated to dryness and water was added to the residue. The mixture was acidified to pH 1 with concentrated hydrochloric acid and then filtered to provide the crude product. The crude product was dissolved in methylene chloride and the solution was dried (MgSO$_4$), filtered, and evaporated to dryness to yield 0.79 g of the title compound of Step I, a compound of the invention, as a solid melting at 228° C. (dec.). $^1$H NMR (CDCl$_3$): δ1.96 (m,2H), 2.4 (m,2H), 2.48 (s,3H), 2.6 (s,3H), 2.7 (m,2H), 3.8 (s,3H), 4.27 (s,2H), 6.8 (s,1H), 7.3 (s,1H).

EXAMPLE 2

Step A: Preparation of 1,4-dihydro-1,6,9-trimethyl[1]benzothiopyrano[4,3-c]pyrazole-8-carboxylic acid 6.74 g (0.021 mol) of 8-bromo-1,4-dihydro-1,6,9-trimethyl[1]benzothiopyrano[4,3-c]pyrazole (from Example 1, Step E) was added to 150 mL of tetrahydrofuran and cooled to −70° C. 10.4 mL (0.026 mol) of 2.5 M n-butyllithium in hexanes (purchased from Aldrich Chemical Company) was added dropwise keeping the temperature below −60° C. After stirring for 10 minutes, carbon dioxide was bubbled into the mixture for 1 hr. The mixture warmed to room temperature, 200 mL of hexane was added, and then the mixture was filtered. The solid was added to 300 mL of water, acidified to about pH 1 with concentrated hydrochloric acid and then filtered. The filtered residue was dissolved in chloroform and the solution was dried (MgSO$_4$), filtered and evaporated to dryness to yield 4.02 g of the title compound of Step A as a solid melting at >230° C. $^1$H NMR (CDCl$_3$): δ2.4 (s,3H), 2.7 (s,3H), 3.77 (s,3H), 3.67 and 3.88 (2d,2H), 7.48 (s,1H), 7.88 (s,1H).

Step B: Preparation of 1,4-dihydro-1,6,9-trimethyl[1]benzothiopyrano[4,3-c]pyrazole-8-carboxylic acid 5,5-dioxide 5.8 mL (0.0598 mol) of 35% hydrogen peroxide was added to 50 mL of trifluoroacetic acid and the mixture was allowed to stir under nitrogen for 30 minutes. The solution was cooled to about 0° C., 4.0 g (0.0145 mol) of the title compound of Step A was added in portions while keeping the temperature below 15° C., the mixture was then stirred at room temperature for 2 days. 2 mL of methyl sulfide was added to the mixture. The mixture was allowed to stir for 15 minutes and was then evaporated to dryness. The residue was stirred in a diethyl ether:hexane (8:2) mixture for 30 minutes and filtered to yield approximately 6.0 g of the title compound of Step B as a solid melting at >210° C. $^1$H NMR (Me$_2$SO-d$_6$): δ2.5(s,3H), 2.63 (s, 3H), 3.7 (s, 3H), 4.7 (m, 2H), 7.68 (s,1H), 7.8 (s,1H).

Step C: Preparation of 3-oxo-1-cyclohexen-1-yl 1,4-dihydro-1,6,9-trimethyl[1]benzothiopyrano[4,3-c]pyrazole-8-carboxylate 5,5-dioxide 2.0 g (0.0065 mol) of the title compound of Step B, 1.71 mL (0.0196 mol) of oxalyl chloride (purchase from Janssen), and 2 drops of N,N-dimethylformamide were added to 50 mL of methylene chloride. The mixture was refluxed under nitrogen for 2 h and was then evaporated to dryness. 50 mL of methylene chloride was added to the residue and it was then evaporated to dryness. Another 50 mL of methylene chloride was added to the residue and the solution was cooled to about 0° C. 0.80 g (0.0071 mol) of 1,3-cyclohexanedione (purchased from Aldrich Chemical Company) was added followed by 2.8 mL (0.020 mol) of triethylamine, and the mixture was stirred for 3 days while warming to room temperature. The mixture was evaporated to dryness and the crude product was chromatographed over silica gel eluting with a mixture of ethyl acetate:hexane (6:4) to yield 0.86 g of the title compound of Step C as a solid melting at 196° C. (decomposed). $^1$H NMR (CDCl$_3$): δ2.2 (m,2H), 2.5 (m,2H), 2.64 (s,3H), 2.7 (m,2H), 2.8 (s,3H), 3.8 (s,3H), 4.3 and 4.4 (2d, 2H), 6.06 (s,1H), 7.65 (s,1H), 7.94 (s,1H).

Step D: Preparation of 2-[(1,4-dihydro-1,6,9-trimethyl[1]benzothiopyrano[4,3-c]pyrazol-8-yl)carbonyl]-1,3-cyclohexanedione S,S-dioxide 0.80 g (0.0020 mol) of the title compound of Step C, 2 drops of acetone cyanohydrin (purchased from Aldrich Chemical Company), and 0.49 mL (0.0035 mol) of triethylamine were added to 100 mL of acetonitrile and the mixture was allowed to stir overnight at room temperature under nitrogen. The mixture was evaporated to dryness and water was added to the residue. The resulting mixture was acidified to pH 1 with concentrated hydrochloric acid and filtered to provide the crude product. The crude product was dissolved in methylene chloride and the solution was dried (MgSO$_4$), filtered and evaporated to dryness to yield 0.47 g of the title compound of Step D, a compound of the invention, as a solid melting at >220° C. $^1$H NMR (CDCl$_3$): δ2.1 (m,2H), 2.3 (s,3H), 2.6–2.76 (m,7H), 3.8 (s,3H), 4.2–4.4 (m,2H), 6.98–7.6 (2H).

EXAMPLE 3

Step A: Preparation of 1-ethyl-1H-pyrazol-5-yl 1,4-dihydro-1,6,9-trimethyl[1]benzothiopyrano[4,3-c]pyrazole-8-carboxylate 5,5-dioxide 2.0 g (0.0065 mol) of the title compound of Step B in Example 2, 1.71 mL (0.0196 mol) of oxalyl chloride (purchase from Janssen), and 2 drops of N,N-dimethylformamide were added to 50 mL of methylene chloride. The mixture was refluxed under nitrogen for 2 h and was then evaporated to dryness. 50 mL of methylene chloride was added to the residue and it was evaporated to dryness. Another 50 mL of methylene chloride was added to the residue and the solution was cooled to about 0° C. 0.80 g (0.0071 mol) of 1-ethyl-1H-pyrazol-5-ol was added followed by 2.8 mL (0.020 mol) of triethylamine, and the mixture was stirred for 3 days while warming to room temperature. The mixture was evaporated to dryness and the crude product was chromatographed over silica gel eluting with a mixture of ethyl acetate: hexane (6:4) to yield 0.40 g of the title compound of Step A as a solid melting at 173–175° C. $^1$H NMR (CDCl$_3$): δ1.5 (t,3H), 2.7 (s,3H), 2.8 (s,3H), 3.8 (s,3H), 4.1 (q,2H), 4.3 and 4.4 (2d,2H), 6.2–8.0 (4H).

Step B: Preparation of (1,4-dihydro-1,6,9-trimethyl[1]benzothiopyrano[4,3-c]pyrazol-8-yl)(1-ethyl-5-hydroxy-1H-pyrazol-4-yl)methanone S,S-dioxide 0.38 g (0.95 mmol) of the title compound of Step A, 1 drop of acetone cyanohydrin (purchased from Aldrich Chemical Company), and 0.23 mL (1.66 mmol) of triethylamine were added to 50 mL of acetonitrile and the mixture was allowed to stir at room temperature under nitrogen overnight. The mixture was evaporated to dryness and water was added to the residue. The resulting mixture was acidified to pH 1 with concentrated hydrochloric acid and filtered to yield 0.12 g of the title compound of Step B, a compound of the invention, as a solid melting at 96° C. (decomposed). $^1$H NMR (CDCl$_3$): δ1.5 (t,3H), 2.60 (s,3H), 2.76 (s,3H), 3.83 (s,3H), 4.0–4.4 (m,4H), 7.4–7.8 (m,3H).

EXAMPLE 4

Step A: Preparation of 3-[(4-bromo-2,5-dimethylphenyl)thio]propanoic acid 25.23 g (0.12 mol) of the title compound of Example 1, Step A was dissolved in 250 mL of dichloromethane and cooled to 5° C. A solution of 19.12 g (0.12 mol) of bromine in 25 mL of dichloromethane was added dropwise over 45 minutes, keeping the reaction temperature at 5° C. The reaction was then allowed to warm to room temperature, diluted with 200 mL of dichloromethane and washed twice with 400 mL of water. The organice layer was separated, dried over magnesium sulfate, filtered, and concentrated under reduced pressure to yield 34.35 g of the title compound of step A as a white solid melting at 105–107° C. $^1$H NMR (CDCl$_3$): δ2.33 (s,3H), 2.34 (s, 3H), 2.67 (t, 2H), 3.10 (t, 2H), 7.18 (s, 1H), 7.36 (s, 1H).

Step B: Preparation of 6-bromo-2,3-dihydro-5,8-dimethyl-4H-1-benzothiopyran-4-one 19.50 g (67.4 mmol) of the title compound of Step A was dissolved in 156 mL of dichloromethan and cooled to 5° C. 78 mL of concentrated sulfuric acid was added dropwise over 45 minutes with vigorous stirring and the reaction was then allowed to stir at 5° C. for 1.5 hours. The reaction was poured into 500 mL of ice water, the layers were separated and the aqueous phase extracted twice with 300 mL of dichloromethane. The combined organic layers were washed twice with 1.0 N NaOH, once with water. dried over magnesium sulfate and concentrated under reduced pressure to yield 16.04 g of the title compound of Step B as a yellow solid melting at 86–87° C. $^1$H NMR (CDCl$_3$): δ2.26 (s, 3H), 2.59 (s, 3H), 3.00 (t, 2H), 3.19 (t, 2H), 7.45 (s, 1H).

Step C: Preparation of 8-bromo-2,4-dihydro-6,9-dimethyl[1]benzothiopyrano[4,3-c]pyrazole 2.80 g (10 mmol) of the title compound of Step B and 1.79 g(15 mmol) of N,N-dimethylformamide dimethyl acetal were dissolved in 16 mL of ethyl acetate and heated to reflux. The methanol/ethyl acetate mixture was removed via a Dean Stark trap and was replaced with fresh ethyl acetate. After heating to reflux for 4 hours, the reaction was cooled to room temperature and allowed to stand overnight. It was then reluxed further for 2 hours, cooled to 60° C., and 0.75 g (15 mmol) of hydrazine monohydrate was added. The reaction was reheated to reflux for 1 hour, cooled to room temperature, and diluted to 100 mL with ethyl acetate. The organic phase was washed twice with 100 mL of water, dried over magnesium sulfate, and concentrated under reduced pressure to yield 3.10 g of an oily yellow solid. This solide was triturated with hexanes, collected by filtration, washed further with hexanes, and dried to yield 2.79 g of the title compound of Step C as a pale yellow solid melting at 162–164° C. $^1$H NMR (CDCl$_3$): δ2.34 (s, 3H), 2.79 (s, 3H), 3.84 (s, 2H), 7.35 (s, 1H), 7.46 (s, 1H), 10.4 (br s).

Step D: Preparation of 8-bromo-2-ethyl-2,4-dihydro-6,9-dimethyl[1]benzothiopyrano[4,3-c]pyrazole A mixture of 6.09 g (20 mmol) of the title compound of Step C, 1.52 g (23 mmol) of potassium hydroxide, 0.31 g (5% by weight of the title compound of Step C) of tetrabutylammonium hydrogen sulfate, 25 mL of toluene, and 25 mL of water was stirred for 15 minutes at room temperature. 3.85 g (25 mmol) of diethyl sulfate was added and the reaction stirred vigorously for 6.5 hours. The reaction was then diluted with 250 mL of ethyl acetate, washed twice with 100 mL of 1.0 N HCl, once with brine, dried over magnesium sulfate and concentrated under reduced pressure. The crude oil was dissolved in 300 mL of methanol, 3 mL of a 25% sodium methoxide/methanol solution was added and the resulting solution was concentrated at 60° C. under reduced pressure. The mixture was then redissolved in diethyl ether and 1.0 N HCl, the layers were separated, and the organic phase was washed with brine, dried over magnesium sulfate, and concentrated under reduced pressure to yield 6.50 g of a reddish oil. GC analysis showed a ratio of approximately 10:1 of the title compound of Step D to the 1-ethyl isomer. $^1$H NMR (CDCl$_3$): δ1.52 (t, 3H), 2.32 (s, 3H), 2.83 (s, 3H), 3.77 (s, 2H), 4.18 (q, 2H), 7.23 (s, 1H), 7.30 (s, 1H).

Step E: Preparation of 8-bromo-2-ethyl-2,4-dihydro-6,9-dimethyl[1]benzothiopyrano[4,3-c]pyrazole 5,5-dioxide 6.42 g (approximately 17 mmol) of the crude title compound of Step D, 32 mL of glacial acetic acid, and 12 drops of concentrated sulfuric acid were heated to 70° C. The heat source was removed and 7.76 g (80 mmol) of 35% aqueous hydrogen peroxide was added dropwise over 15 minutes, keeping the reaction temperature at about 70° C. After 1 hour at 73–74° C., the reaction was cooled to room temperature, poured into 400 mL of ethyl acetate, washed with 400 mL of water, 400 mL of aqueous sodium metabisulfite, aqueous sodium bicarbonate, and brine. A check for peroxides with starch-iodide paper was negative. The organic phase was dried over magnesium sulfate and concentrated under reduced pressure to yield 6.90 g of a yellow solid. This solid was dissolved in 100 mL of dichloromethane and rinsed through a one inch bed of silica gel which was further rinsed with one liter of dichloromethane. The combined rinses were concentrated under reduced pressure to yield 5.70 g of the title compound of Step E as an off-white solid melting at 138–141° C. $^1$H NMR (CDCl$_3$): δ1.54 (t, 3H), 2.70 (s, 3H), 2.85 (s, 3H), 4.22 (q, 2H), 4.35 (s, 2H), 7.44 (s, 1H), 7.50 (s, 1H).

Step F: Preparation of 2-ethyl-2,4-dihydro-6,9-dimethyl[1]benzothiopyrano[4,3-c]pyrazole-8-carbonitrile 5,5-dioxide 3.00 g (8 mmol) of the title compound of Step E, 1.07 g (12 mmol) of copper (I) cyanide, and 50 mL of N,N-dimethylformamide were heated to reflux for 5.5 hours and then let stir at room temperature overnight. The reaction was then diluted with 300 mL of ethyl acetate, washed twice with 200 mL of a solution of 50% saturated ammonium chloride in water with 20 mL of 35% ammonium hydroxide added, washed twice with 300 mL of water, dried over magnesium sulfate and concentrated under reduced pressure to yield 2.50 g of a tan solid. This solid was dissolved in 50 mL of dichloromethane and rinsed through a one inch bed of silica gel, which was further rinsed with 500 mL of dichloromethane and then 200 mL of 10% ethyl acetate:dichloromethane. The rinses were separately concentrated under reduced pressure. The dichloromethane rinse yielded 2.31 g of the title compound of Step F as an off-white solid melting at 185–187° C. $^1$H NMR (CDCl$_3$): δ1.53 (t, 3H), 2.35 (s, 3H), 2.92 (s, 3H), 3.86 (s, 2H), 4.20 (q, 2H), 7.26 (s, 1H), 7.27 (s, 1H).

Step G: Preparation of 2-ethyl-2,4-dihydro-6,9-dimethyl[1]benzothiopyrano[4,3-c]pyrazole-8-carboxylic acid 5,5-dioxide 1.00 g (3.2 mmol) of the title compound of Step F, 2 mL of water, and 6 mL of sulfuric acid were heated to 140° C. for one hour. The reaction was allowed to cool to 60° C. and 0.25 g of sodium nitrite in 1 mL of water was added dropwise over 30 minutes and stirring was continued for another 30 minutes. The reaction was allowed to cool to room temperature, poured into 25 mL of ice water and the resulting solid was isolated by filtration and washed with 5 mL of cold water. Drying overnight yielded 1.02 g of a tan solid. The aqueous filtrate was extracted three times with 50 mL of dichloromethane and the organic phases were combined, dried over magnesium sulfate and concentrated under reduced pressure to yield 0.36 g of a brown oil. This oil and the isolated solid were dissolved in 50 mL of 1.0 N sodium hydroxide, washed with 25 mL of diethyl ether, acidified with concentrated HCl, and extracted four times with 50 mL of ethyl acetate. The combined organic layers were dried over magnesium sulfate and concentrated under reduced pressure to yield 0.98 g of the title compound of Step G as a tan solid melting at 204–206° C. $^1$H NMR (CDCl$_3$): δ1.53 (t, 3H), 2.38 (s, 3H), (2.99 (s, 3H), 3.83 (s, 2H), 4.21 (q, 2H), 7.26 (s, 1H), 7.68 (s, 1H).

Step H: Preparation of 3-oxo-1-cyclohexen-1-yl 2-ethyl-2,4-dihydro-6,9-dimethyl[1]benzothiopyrano[4,3-c]pyrazole-8-carboxylate 5,5-dioxide 6.0 g (0.019 mol) of the title compound of Step G, 4.9 mL (0.056 mol) of oxalyl chloride (purchase from Janssen), and 2 drops of N,N-dimethylformamide were added to 50 mL of methylene chloride. The mixture was refluxed under nitrogen for 2 hr and was evaporated to dryness. 50 mL of methylene chloride was added to the residue and it was evaporated to dryness. Another 50 mL of methylene chloride was added to the residue and the solution was cooled to about 0° C. 2.31 g (0.021 mol) of 1,3-cyclohexanedione (purchased from Aldrich Chemical Company) was added followed by 8.1 mL (0.058 mol) of triethylamine and the mixture was stirred overnight while warming to room temperature. The mixture was evaporated to dryness and the crude product was chromatographed over silica gel eluting with a mixture of ethyl acetate:hexane (6:4) to yield 1.78 g of the title compound of Step H as a solid melting at 160–162° C. $^1$H NMR (CDCl$_3$): δ1.6 (t,3H), 2.2 (m,2H), 2.5 (m,2H), 2.7 (m,2H), 2.8 (s,3H), 2.9 (s,3H), 4.2 (q,2H), 4.4 (m,2H), 6.07 (s,1H), 7.46–7.6 (m,2H).

Step I: Preparation of 2-[(2-ethyl-2,4-dihydro-6,9-dimethyl[1]benzothiopyrano[4,3-c]pyrazol-8-yl)carbonyl]-1,3-cyclohexanedione S,S-dioxide 1.70 g (0.0041 mol) of the title compound of Step H, 2 drops of acetone cyanohydrin (purchased from Aldrich Chemical Company), and 1.0 mL (0.0072 mol) of triethylamine were added to 100 mL of acetonitrile and the mixture was allowed to stir at room temperature under nitrogen overnight. About 0.05 g of potassium cyanide was then added to the mixture and it was stirred for 4 h. The mixture was evaporated to dryness and water was added to the residue. The resulting mixture was acidified to pH 1 with concentrated hydrochloric acid and filtered to yield 1.51 g of the title compound of Step I, a compound of the invention, as a solid melting at 205° C. (decomposed). 1H NMR (CDCl$_3$): δ1.5 (t,3H), 2.06 (m,2H), 2.5 (m,2H), 2.6 (m,2H), 2.7 (s,3H), 2.8 (m,2H), 4.2 (q,2H), 4.4 (m,2H), 6.9–7.4 (m,2H).

EXAMPLE 5

Step A: Preparation of 1-ethyl-1H-pyrazol-5-yl 2-ethyl-2,4-dihydro-6,9-dimethyl[1]benzothiopyrano[4,3-c]pyrazole-8-carboxylate 5,5-dioxide 5.9 g (0.018 mol) of the title compound of Step G in Example 4, 4.8 mL (0.055 mol) of oxalyl chloride (purchase from Janssen), and 2 drops of N,N-dimethylformamide were added to 50 mL of methylene chloride. The mixture was refluxed under nitrogen for 2 h and was then evaporated to dryness. 50 mL of methylene chloride was added to the residue and it was evaporated to dryness. Another 50 mL of methylene chloride was added to the residue and the solution was cooled to about 0° C. 2.48 g (0.022 mol) of 1-ethyl-1H-pyrazol-5-ol was added followed by 7.97 mL (0.057 mol) of triethylamine, and the mixture was stirred overnight while warming to room temperature. The mixture was evaporated to dryness and the crude product was chromatographed over silica gel eluting with a mixture of ethyl acetate: hexane (6:4) to yield 0.18 g of the title compound of Step A as a solid melting at 137° C. (decomposed). $^1$H NMR (CDCl$_3$): δ1.45 (t,3H), 1.56 (t,3H), 2.8 (s,3H), 2.9 (s,3H), 4.1 (m,2H), 4.3 (m,2H), 4.4 (m,2H), 6.3–7.7 (m,4H).

Step B: Preparation of (2-ethyl-2,4-dihydro-6,9-dimethyl[1]benzothiopyrano[4,3-c]pyrazol-8-yl)(1-ethyl-5-hydroxy-1H-pyrazol-4-yl)methanone S,S-dioxide 0.18 g (0.43 mmol) of the title compound of Step A, 0.50 drops of acetone cyanohydrin (purchased from Aldrich Chemical Company), and 0.11 mL (0.76 mmol) of triethylamine were added to 25 mL of acetonitrile and the mixture was allowed to stir at room temperature under nitrogen overnight. About 0.05 g of potassium cyanide was added to the mixture and it was stirred for 4 h. About 0.03 g of potassium cyanide was then added and the mixture was allowed to stir for 1 h. The mixture was evaporated to dryness and water was added to the residue. The resulting mixture was then acidified to pH 1 with concentrated hydrochloric acid, and filtered to yield 0.11 g of the title compound of Step B, a compound of the invention, as a solid melting at 97° C. (decomposed). $^1$H NMR (CDCl$_3$): δ1.47 (t, 3H), 1.54 (t, 3H), 2.7 (s, 3H), 2.8 (s, 3H), 4.1 (q, 2H), 4.2 (q, 2H), 4.4 (m, 2H), 7.2–7.45 (m,3H).

EXAMPLE 6

Step A: Preparation of 1-[(2,4-dihydro-2,6,9-trimethyl[1]benzothiopyrano[4,3-c]pyrazol-8-yl)carbonyl]-2-ethyl-1,2-dihydro-3H-pyrazol-3-one S,S-dioxide 4.0 g (0.013 mol) of the title compound of Step G in Example 1, 3.42 mL (0.039 mol) of oxalyl chloride (purchased from Janssen) and 2 drops of N,N-dimethylformamide were added to 50 mL of methylene chloride. The mixture was refluxed for 2 h and was then evaporated to dryness. 50 mL of methylene chloride was added to the residue and it was evaporated to dryness. Another 50 mL of methylene chloride was added to the residue and the solution was cooled to about 0° C. 1.60 g (0.014 mol) of 1-ethyl-1H-pyrazol-5-ol was added followed by 5.62 mL (0.040 mol) of triethylamine, and the mixture was stirred under nitrogen overnight while warming to room temperature. The mixture was evaporated to dryness and the crude product was chromatographed over silica gel eluting first with a mixture of ethyl acetate:hexane (7:3) and then with ethyl acetate to yield 1.35 g of the title compound of Step A as a solid melting at >210° C. $^1$H NMR (CDCl$_3$): δ7.45 (s, 1H), 7.2–7.35 (m, 2H), 5.74 (d, 1H), 4.4 (m, 4H), 3.98 (s, 3H), 2.78 (s, 3H), 2.7 (s, 3H), 1.3 (t, 3H).

Step B: Preparation of (2.4-dihydro-2,6,9-trimethyl[1]benzothiopyrano[4,3-c]pyrazol-8-yl)(1-ethyl-5-hydroxy-1H-pyrazol-4-yl)methanone S,S-dioxide 1.3 g (3.25 mmol) of the title compound of Step A, 1 drop of acetone cyanohydrin (purchased from Aldrich Chemical Company), and 0.79 mL (5.69 mmol) of triethylamine were added to 25 mL of acetonitrile and the mixture was allowed to stir at room temperature under nitrogen for 15 min. 0.06 g of potassium cyanide was then added and the mixture was allowed to stir at room temperature under nitrogen overnight. Another 0.03 g of potassium cyanide was added and the reaction mixture was allowed to stir at room temperature under nitrogen for another 3 days. The mixture was evaporated to dryness and water was added to the residue. The resulting mixture was acidified to pH 1 with concentrated hydrochloric acid and filtered. The solid collected was dissolved in methylene chloride and the resulting solution was dried over MgSO$_4$ and then concentrated to yield 0.48 g of the title compound of Step B, a compound of the invention, as a solid melting at 133° C. (decomposed). $^1$H NMR (Me$_2$SO-d$_6$): δ7.86 (s, 1H), 7.32 (s, 1H), 7.25 (s, 1H), 4.72 (s, 2H), 3.9–4.0 (m, 5H), 2.64 (s, 3H), 2.57 (s, 3H), 1.28 (t, 3H).

By the procedures described herein together with methods known in the art, the following compounds of Tables 1 to 18 can be prepared. The following abbreviation is used in the Tables which follow: Ph=phenyl.

TABLE 1

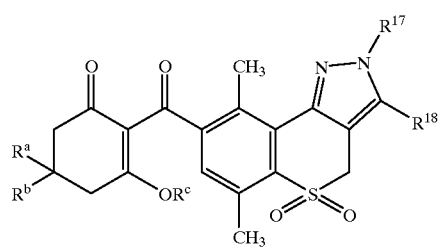

| R$^a$ | R$^b$ | R$^c$ | R$^{17}$ | R$^{18}$ |
|---|---|---|---|---|
| H | H | PhC(=O) | H | H |
| H | CH$_3$ | PhC(=O) | H | H |
| CH$_3$ | CH$_3$ | PhC(=O) | H | H |
| H | H | PhC(=O)CH$_2$ | H | H |
| H | CH$_3$ | PhC(=O)CH$_2$ | H | H |
| CH$_3$ | CH$_3$ | PhC(=O)CH$_2$ | H | H |
| H | H | 4-CH$_3$PhC(=O) | H | H |
| H | CH$_3$ | 4-CH$_3$PhC(=O) | H | H |
| CH$_3$ | CH$_3$ | 4-CH$_3$PhC(=O) | H | H |
| H | H | CH$_3$S(O)$_2$ | H | H |
| H | CH$_3$ | CH$_3$S(O)$_2$ | H | H |
| CH$_3$ | CH$_3$ | CH$_3$S(O)$_2$ | H | H |
| H | H | CH$_3$CH$_2$S(O)$_2$ | H | H |
| H | CH$_3$ | CH$_3$CH$_2$S(O)$_2$ | H | H |
| CH$_3$ | CH$_3$ | CH$_3$CH$_2$S(O)$_2$ | H | H |
| H | H | CH$_3$CH$_2$CH$_2$S(O)$_2$ | H | H |
| H | CH$_3$ | CH$_3$CH$_2$CH$_2$S(O)$_2$ | H | H |
| CH$_3$ | CH$_3$ | CH$_3$CH$_2$CH$_2$S(O)$_2$ | H | H |
| H | H | PhS(O)$_2$ | H | H |
| H | CH$_3$ | PhS(O)$_2$ | H | H |
| CH$_3$ | CH$_3$ | PhS(O)$_2$ | H | H |
| H | H | 4-CH$_3$PhS(O)$_2$ | H | H |
| H | CH$_3$ | 4-CH$_3$PhS(O)$_2$ | H | H |
| CH$_3$ | CH$_3$ | 4-CH$_3$PhS(O)$_2$ | H | H |
| H | H | PhC(=O) | CH$_3$ | H |
| H | CH$_3$ | PhC(=O) | CH$_3$ | H |
| CH$_3$ | CH$_3$ | PhC(=O) | CH$_3$ | H |
| H | H | PhC(=O)CH$_2$ | CH$_3$ | H |
| H | CH$_3$ | PhC(=O)CH$_2$ | CH$_3$ | H |
| CH$_3$ | CH$_3$ | PhC(=O)CH$_2$ | CH$_3$ | H |
| H | H | 4-CH$_3$PhC(=O) | CH$_3$ | H |
| H | CH$_3$ | 4-CH$_3$PhC(=O) | CH$_3$ | H |
| CH$_3$ | CH$_3$ | 4-CH$_3$PhC(=O) | CH$_3$ | H |
| H | H | CH$_3$S(O)$_2$ | CH$_3$ | H |
| H | CH$_3$ | CH$_3$S(O)$_2$ | CH$_3$ | H |
| CH$_3$ | CH$_3$ | CH$_3$S(O)$_2$ | CH$_3$ | H |
| H | H | CH$_3$CH$_2$S(O)$_2$ | CH$_3$ | H |
| H | CH$_3$ | CH$_3$CH$_2$S(O)$_2$ | CH$_3$ | H |
| CH$_3$ | CH$_3$ | CH$_3$CH$_2$S(O)$_2$ | CH$_3$ | H |
| H | H | CH$_3$CH$_2$CH$_2$S(O)$_2$ | CH$_3$ | H |
| H | CH$_3$ | CH$_3$CH$_2$CH$_2$S(O)$_2$ | CH$_3$ | H |
| CH$_3$ | CH$_3$ | CH$_3$CH$_2$CH$_2$S(O)$_2$ | CH$_3$ | H |
| H | H | PhS(O)$_2$ | CH$_3$ | H |
| H | CH$_3$ | PhS(O)$_2$ | CH$_3$ | H |
| CH$_3$ | CH$_3$ | PhS(O)$_2$ | CH$_3$ | H |
| H | H | 4-CH$_3$PhS(O)$_2$ | CH$_3$ | H |
| H | CH$_3$ | 4-CH$_3$PhS(O)$_2$ | CH$_3$ | H |
| CH$_3$ | CH$_3$ | 4-CH$_3$PhS(O)$_2$ | CH$_3$ | H |
| H | H | PhC(=O) | CH$_3$CH$_2$ | H |
| H | CH$_3$ | PhC(=O) | CH$_3$CH$_2$ | H |
| CH$_3$ | CH$_3$ | PhC(=O) | CH$_3$CH$_2$ | H |
| H | H | PhC(=O)CH$_2$ | CH$_3$CH$_2$ | H |
| H | CH$_3$ | PhC(=O)CH$_2$ | CH$_3$CH$_2$ | H |
| CH$_3$ | CH$_3$ | PhC(=O)CH$_2$ | CH$_3$CH$_2$ | H |
| H | H | 4-CH$_3$PhC(=O) | CH$_3$CH$_2$ | H |
| H | CH$_3$ | 4-CH$_3$PhC(=O) | CH$_3$CH$_2$ | H |
| CH$_3$ | CH$_3$ | 4-CH$_3$PhC(=O) | CH$_3$CH$_2$ | H |
| H | H | CH$_3$S(O)$_2$ | CH$_3$CH$_2$ | H |
| H | CH$_3$ | CH$_3$S(O)$_2$ | CH$_3$CH$_2$ | H |
| CH$_3$ | CH$_3$ | CH$_3$S(O)$_2$ | CH$_3$CH$_2$ | H |
| H | H | CH$_3$CH$_2$S(O)$_2$ | CH$_3$CH$_2$ | H |
| H | CH$_3$ | CH$_3$CH$_2$S(O)$_2$ | CH$_3$CH$_2$ | H |
| CH$_3$ | CH$_3$ | CH$_3$CH$_2$S(O)$_2$ | CH$_3$CH$_2$ | H |
| H | H | CH$_3$CH$_2$CH$_2$S(O)$_2$ | CH$_3$CH$_2$ | H |
| H | CH$_3$ | CH$_3$CH$_2$CH$_2$S(O)$_2$ | CH$_3$CH$_2$ | H |
| CH$_3$ | CH$_3$ | CH$_3$CH$_2$CH$_2$S(O)$_2$ | CH$_3$CH$_2$ | H |
| H | H | PhS(O)$_2$ | CH$_3$CH$_2$ | H |
| H | CH$_3$ | PhS(O)$_2$ | CH$_3$CH$_2$ | H |

TABLE 1-continued

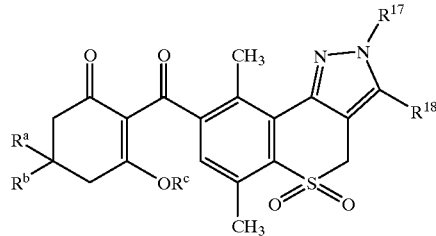

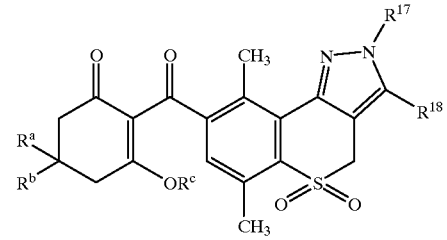

| $R^a$ | $R^b$ | $R^c$ | $R^{17}$ | $R^{18}$ |
|---|---|---|---|---|
| CH₃ | CH₃ | PhS(O)₂ | CH₃CH₂ | H |
| H | H | 4-CH₃PhS(O)₂ | CH₃CH₂ | H |
| H | CH₃ | 4-CH₃PhS(O)₂ | CH₃CH₂ | H |
| CH₃ | CH₃ | 4-CH₃PhS(O)₂ | CH₃CH₂ | H |
| H | H | PhC(=O) | CH₃CH₂CH₂ | H |
| H | CH₃ | PhC(=O) | CH₃CH₂CH₂ | H |
| CH₃ | CH₃ | PhC(=O) | CH₃CH₂CH₂ | H |
| H | H | PhC(=O)CH₂ | CH₃CH₂CH₂ | H |
| H | CH₃ | PhC(=O)CH₂ | CH₃CH₂CH₂ | H |
| CH₃ | CH₃ | PhC(=O)CH₂ | CH₃CH₂CH₂ | H |
| H | H | 4-CH₃PhC(=O) | CH₃CH₂CH₂ | H |
| H | CH₃ | 4-CH₃PhC(=O) | CH₃CH₂CH₂ | H |
| CH₃ | CH₃ | 4-CH₃PhC(=O) | CH₃CH₂CH₂ | H |
| H | H | CH₃S(O)₂ | CH₃CH₂CH₂ | H |
| H | CH₃ | CH₃S(O)₂ | CH₃CH₂CH₂ | H |
| CH₃ | CH₃ | CH₃S(O)₂ | CH₃CH₂CH₂ | H |
| H | H | CH₃CH₂S(O)₂ | CH₃CH₂CH₂ | H |
| H | CH₃ | CH₃CH₂S(O)₂ | CH₃CH₂CH₂ | H |
| CH₃ | CH₃ | CH₃CH₂S(O)₂ | CH₃CH₂CH₂ | H |
| H | H | CH₃CH₂CH₂S(O)₂ | CH₃CH₂CH₂ | H |
| H | CH₃ | CH₃CH₂CH₂S(O)₂ | CH₃CH₂CH₂ | H |
| CH₃ | CH₃ | CH₃CH₂CH₂S(O)₂ | CH₃CH₂CH₂ | H |
| H | H | PhS(O)₂ | CH₃CH₂CH₂ | H |
| H | CH₃ | PhS(O)₂ | CH₃CH₂CH₂ | H |
| CH₃ | CH₃ | PhS(O)₂ | CH₃CH₂CH₂ | H |
| H | H | 4-CH₃PhS(O)₂ | CH₃CH₂CH₂ | H |
| H | CH₃ | 4-CH₃PhS(O)₂ | CH₃CH₂CH₂ | H |
| CH₃ | CH₃ | 4-CH₃PhS(O)₂ | CH₃CH₂CH₂ | H |
| H | H | PhC(=O) | H | CH₃ |
| H | CH₃ | PhC(=O) | H | CH₃ |
| CH₃ | CH₃ | PhC(=O) | H | CH₃ |
| H | H | PhC(=O)CH₂ | H | CH₃ |
| H | CH₃ | PhC(=O)CH₂ | H | CH₃ |
| CH₃ | CH₃ | PhC(=O)CH₂ | H | CH₃ |
| H | H | 4-CH₃PhC(=O) | H | CH₃ |
| H | CH₃ | 4-CH₃PhC(=O) | H | CH₃ |
| CH₃ | CH₃ | 4-CH₃PhC(=O) | H | CH₃ |
| H | H | CH₃S(O)₂ | H | CH₃ |
| H | CH₃ | CH₃S(O)₂ | H | CH₃ |
| CH₃ | CH₃ | CH₃S(O)₂ | H | CH₃ |
| H | H | CH₃CH₂S(O)₂ | H | CH₃ |
| H | CH₃ | CH₃CH₂S(O)₂ | H | CH₃ |
| CH₃ | CH₃ | CH₃CH₂S(O)₂ | H | CH₃ |
| H | H | CH₃CH₂CH₂S(O)₂ | H | CH₃ |
| H | CH₃ | CH₃CH₂CH₂S(O)₂ | H | CH₃ |
| CH₃ | CH₃ | CH₃CH₂CH₂S(O)₂ | H | CH₃ |
| H | H | PhS(O)₂ | H | CH₃ |
| H | CH₃ | PhS(O)₂ | H | CH₃ |
| CH₃ | CH₃ | PhS(O)₂ | H | CH₃ |
| H | H | 4-CH₃PhS(O)₂ | H | CH₃ |
| H | CH₃ | 4-CH₃PhS(O)₂ | H | CH₃ |
| CH₃ | CH₃ | 4-CH₃PhS(O)₂ | H | CH₃ |
| H | H | PhC(=O) | CH₃ | CH₃ |
| H | CH₃ | PhC(=O) | CH₃ | CH₃ |
| CH₃ | CH₃ | PhC(=O) | CH₃ | CH₃ |
| H | H | PhC(=O)CH₂ | CH₃ | CH₃ |
| H | CH₃ | PhC(=O)CH₂ | CH₃ | CH₃ |
| CH₃ | CH₃ | PhC(=O)CH₂ | CH₃ | CH₃ |
| H | H | 4-CH₃PhC(=O) | CH₃ | CH₃ |
| H | CH₃ | 4-CH₃PhC(=O) | CH₃ | CH₃ |
| CH₃ | CH₃ | 4-CH₃PhC(=O) | CH₃ | CH₃ |
| H | H | CH₃S(O)₂ | CH₃ | CH₃ |
| H | CH₃ | CH₃S(O)₂ | CH₃ | CH₃ |
| CH₃ | CH₃ | CH₃S(O)₂ | CH₃ | CH₃ |
| H | H | CH₃CH₂S(O)₂ | CH₃ | CH₃ |
| H | CH₃ | CH₃CH₂S(O)₂ | CH₃ | CH₃ |
| CH₃ | CH₃ | CH₃CH₂S(O)₂ | CH₃ | CH₃ |
| H | H | CH₃CH₂CH₂S(O)₂ | CH₃ | CH₃ |
| H | CH₃ | CH₃CH₂CH₂S(O)₂ | CH₃ | CH₃ |
| CH₃ | CH₃ | CH₃CH₂CH₂S(O)₂ | CH₃ | CH₃ |
| H | H | PhS(O)₂ | CH₃ | CH₃ |
| H | CH₃ | PhS(O)₂ | CH₃ | CH₃ |
| CH₃ | CH₃ | PhS(O)₂ | CH₃ | CH₃ |
| H | H | 4-CH₃PhS(O)₂ | CH₃ | CH₃ |
| H | CH₃ | 4-CH₃PhS(O)₂ | CH₃ | CH₃ |
| CH₃ | CH₃ | 4-CH₃PhS(O)₂ | CH₃ | CH₃ |
| H | H | PhC(=O) | CH₃CH₂ | CH₃ |
| H | CH₃ | PhC(=O) | CH₃CH₂ | CH₃ |
| CH₃ | CH₃ | PhC(=O) | CH₃CH₂ | CH₃ |
| H | H | PhC(=O)CH₂ | CH₃CH₂ | CH₃ |
| H | CH₃ | PhC(=O)CH₂ | CH₃CH₂ | CH₃ |
| CH₃ | CH₃ | PhC(=O)CH₂ | CH₃CH₂ | CH₃ |
| H | H | 4-CH₃PhC(=O) | CH₃CH₂ | CH₃ |
| H | CH₃ | 4-CH₃PhC(=O) | CH₃CH₂ | CH₃ |
| CH₃ | CH₃ | 4-CH₃PhC(=O) | CH₃CH₂ | CH₃ |
| H | H | CH₃S(O)₂ | CH₃CH₂ | CH₃ |
| H | CH₃ | CH₃S(O)₂ | CH₃CH₂ | CH₃ |
| CH₃ | CH₃ | CH₃S(O)₂ | CH₃CH₂ | CH₃ |
| H | H | CH₃CH₂S(O)₂ | CH₃CH₂ | CH₃ |
| H | CH₃ | CH₃CH₂S(O)₂ | CH₃CH₂ | CH₃ |
| CH₃ | CH₃ | CH₃CH₂S(O)₂ | CH₃CH₂ | CH₃ |
| H | H | CH₃CH₂CH₂S(O)₂ | CH₃CH₂ | CH₃ |
| H | CH₃ | CH₃CH₂CH₂S(O)₂ | CH₃CH₂ | CH₃ |
| CH₃ | CH₃ | CH₃CH₂CH₂S(O)₂ | CH₃CH₂ | CH₃ |
| H | H | PhS(O)₂ | CH₃CH₂ | CH₃ |
| H | CH₃ | PhS(O)₂ | CH₃CH₂ | CH₃ |
| CH₃ | CH₃ | PhS(O)₂ | CH₃CH₂ | CH₃ |
| H | H | 4-CH₃PhS(O)₂ | CH₃CH₂ | CH₃ |
| H | CH₃ | 4-CH₃PhS(O)₂ | CH₃CH₂ | CH₃ |
| CH₃ | CH₃ | 4-CH₃PhS(O)₂ | CH₃CH₂ | CH₃ |
| H | H | PhC(=O) | CH₃CH₂CH₂ | CH₃ |
| H | CH₃ | PhC(=O) | CH₃CH₂CH₂ | CH₃ |
| CH₃ | CH₃ | PhC(=O) | CH₃CH₂CH₂ | CH₃ |
| H | H | PhC(=O)CH₂ | CH₃CH₂CH₂ | CH₃ |
| H | CH₃ | PhC(=O)CH₂ | CH₃CH₂CH₂ | CH₃ |
| CH₃ | CH₃ | PhC(=O)CH₂ | CH₃CH₂CH₂ | CH₃ |
| H | H | 4-CH₃PhC(=O) | CH₃CH₂CH₂ | CH₃ |
| H | CH₃ | 4-CH₃PhC(=O) | CH₃CH₂CH₂ | CH₃ |
| CH₃ | CH₃ | 4-CH₃PhC(=O) | CH₃CH₂CH₂ | CH₃ |
| H | H | CH₃S(O)₂ | CH₃CH₂CH₂ | CH₃ |
| H | CH₃ | CH₃S(O)₂ | CH₃CH₂CH₂ | CH₃ |
| CH₃ | CH₃ | CH₃S(O)₂ | CH₃CH₂CH₂ | CH₃ |
| H | H | CH₃CH₂S(O)₂ | CH₃CH₂CH₂ | CH₃ |
| H | CH₃ | CH₃CH₂S(O)₂ | CH₃CH₂CH₂ | CH₃ |
| CH₃ | CH₃ | CH₃CH₂S(O)₂ | CH₃CH₂CH₂ | CH₃ |
| H | H | CH₃CH₂CH₂S(O)₂ | CH₃CH₂CH₂ | CH₃ |
| H | CH₃ | CH₃CH₂CH₂S(O)₂ | CH₃CH₂CH₂ | CH₃ |
| CH₃ | CH₃ | CH₃CH₂CH₂S(O)₂ | CH₃CH₂CH₂ | CH₃ |
| H | H | PhS(O)₂ | CH₃CH₂CH₂ | CH₃ |
| H | CH₃ | PhS(O)₂ | CH₃CH₂CH₂ | CH₃ |
| CH₃ | CH₃ | PhS(O)₂ | CH₃CH₂CH₂ | CH₃ |
| H | H | 4-CH₃PhS(O)₂ | CH₃CH₂CH₂ | CH₃ |
| H | CH₃ | 4-CH₃PhS(O)₂ | CH₃CH₂CH₂ | CH₃ |
| CH₃ | CH₃ | 4-CH₃PhS(O)₂ | CH₃CH₂CH₂ | CH₃ |
| H | H | PhC(=O) | H | Cl |
| H | CH₃ | PhC(=O) | H | Cl |
| CH₃ | CH₃ | PhC(=O) | H | Cl |
| H | H | PhC(=O)CH₂ | H | Cl |

TABLE 1-continued

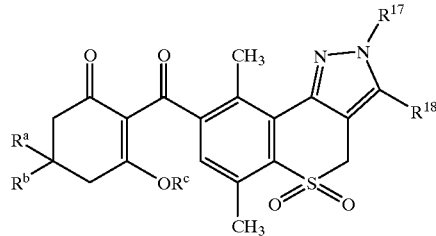

| $R^a$ | $R^b$ | $R^c$ | $R^{17}$ | $R^{18}$ |
|---|---|---|---|---|
| H | H | PhC(=O)CH$_2$ | H | Cl |
| CH$_3$ | CH$_3$ | PhC(=O)CH$_2$ | H | Cl |
| H | H | 4-CH$_3$PhC(=O) | H | Cl |
| H | CH$_3$ | 4-CH$_3$PhC(=O) | H | Cl |
| CH$_3$ | CH$_3$ | 4-CH$_3$PhC(=O) | H | Cl |
| H | H | CH$_3$S(O)$_2$ | H | Cl |
| H | CH$_3$ | CH$_3$S(O)$_2$ | H | Cl |
| CH$_3$ | CH$_3$ | CH$_3$S(O)$_2$ | H | Cl |
| H | H | CH$_3$CH$_2$S(O)$_2$ | H | Cl |
| H | CH$_3$ | CH$_3$CH$_2$S(O)$_2$ | H | Cl |
| CH$_3$ | CH$_3$ | CH$_3$CH$_2$S(O)$_2$ | H | Cl |
| H | H | CH$_3$CH$_2$CH$_2$S(O)$_2$ | H | Cl |
| H | CH$_3$ | CH$_3$CH$_2$CH$_2$S(O)$_2$ | H | Cl |
| CH$_3$ | CH$_3$ | CH$_3$CH$_2$CH$_2$S(O)$_2$ | H | Cl |
| H | H | PhS(O)$_2$ | H | Cl |
| H | CH$_3$ | PhS(O)$_2$ | H | Cl |
| CH$_3$ | CH$_3$ | PhS(O)$_2$ | H | Cl |
| H | H | 4-CH$_3$PhS(O)$_2$ | H | Cl |
| H | CH$_3$ | 4-CH$_3$PhS(O)$_2$ | H | Cl |
| CH$_3$ | CH$_3$ | 4-CH$_3$PhS(O)$_2$ | H | Cl |
| H | H | PhC(=O) | CH$_3$ | Cl |
| H | CH$_3$ | PhC(=O) | CH$_3$ | Cl |
| CH$_3$ | CH$_3$ | PhC(=O) | CH$_3$ | Cl |
| H | H | PhC(=O)CH$_2$ | CH$_3$ | Cl |
| H | CH$_3$ | PhC(=O)CH$_2$ | CH$_3$ | Cl |
| CH$_3$ | CH$_3$ | PhC(=O)CH$_2$ | CH$_3$ | Cl |
| H | H | 4-CH$_3$PhC(=O) | CH$_3$ | Cl |
| H | CH$_3$ | 4-CH$_3$PhC(=O) | CH$_3$ | Cl |
| CH$_3$ | CH$_3$ | 4-CH$_3$PhC(=O) | CH$_3$ | Cl |
| H | H | CH$_3$S(O)$_2$ | CH$_3$ | Cl |
| H | CH$_3$ | CH$_3$S(O)$_2$ | CH$_3$ | Cl |
| CH$_3$ | CH$_3$ | CH$_3$S(O)$_2$ | CH$_3$ | Cl |
| H | H | CH$_3$CH$_2$S(O)$_2$ | CH$_3$ | Cl |
| H | CH$_3$ | CH$_3$CH$_2$S(O)$_2$ | CH$_3$ | Cl |
| CH$_3$ | CH$_3$ | CH$_3$CH$_2$S(O)$_2$ | CH$_3$ | Cl |
| H | H | CH$_3$CH$_2$CH$_2$S(O)$_2$ | CH$_3$ | Cl |
| H | CH$_3$ | CH$_3$CH$_2$CH$_2$S(O)$_2$ | CH$_3$ | Cl |
| CH$_3$ | CH$_3$ | CH$_3$CH$_2$CH$_2$S(O)$_2$ | CH$_3$ | Cl |
| H | H | PhS(O)$_2$ | CH$_3$ | Cl |
| H | CH$_3$ | PhS(O)$_2$ | CH$_3$ | Cl |
| CH$_3$ | CH$_3$ | PhS(O)$_2$ | CH$_3$ | Cl |
| H | H | 4-CH$_3$PhS(O)$_2$ | CH$_3$ | Cl |
| H | CH$_3$ | 4-CH$_3$PhS(O)$_2$ | CH$_3$ | Cl |
| CH$_3$ | CH$_3$ | 4-CH$_3$PhS(O)$_2$ | CH$_3$ | Cl |
| H | H | PhC(=O) | CH$_3$CH$_2$ | Cl |
| H | CH$_3$ | PhC(=O) | CH$_3$CH$_2$ | Cl |
| CH$_3$ | CH$_3$ | PhC(=O) | CH$_3$CH$_2$ | Cl |
| H | H | PhC(=O)CH$_2$ | CH$_3$CH$_2$ | Cl |
| H | CH$_3$ | PhC(=O)CH$_2$ | CH$_3$CH$_2$ | Cl |
| CH$_3$ | CH$_3$ | PhC(=O)CH$_2$ | CH$_3$CH$_2$ | Cl |
| H | H | 4-CH$_3$PhC(=O) | CH$_3$CH$_2$ | Cl |
| H | CH$_3$ | 4-CH$_3$PhC(=O) | CH$_3$CH$_2$ | Cl |
| CH$_3$ | CH$_3$ | 4-CH$_3$PhC(=O) | CH$_3$CH$_2$ | Cl |
| H | H | CH$_3$S(O)$_2$ | CH$_3$CH$_2$ | Cl |
| H | CH$_3$ | CH$_3$S(O)$_2$ | CH$_3$CH$_2$ | Cl |
| CH$_3$ | CH$_3$ | CH$_3$S(O)$_2$ | CH$_3$CH$_2$ | Cl |
| H | H | CH$_3$CH$_2$S(O)$_2$ | CH$_3$CH$_2$ | Cl |
| H | CH$_3$ | CH$_3$CH$_2$S(O)$_2$ | CH$_3$CH$_2$ | Cl |
| CH$_3$ | CH$_3$ | CH$_3$CH$_2$S(O)$_2$ | CH$_3$CH$_2$ | Cl |
| H | H | CH$_3$CH$_2$CH$_2$S(O)$_2$ | CH$_3$CH$_2$ | Cl |
| H | CH$_3$ | CH$_3$CH$_2$CH$_2$S(O)$_2$ | CH$_3$CH$_2$ | Cl |
| CH$_3$ | CH$_3$ | CH$_3$CH$_2$CH$_2$S(O)$_2$ | CH$_3$CH$_2$ | Cl |
| H | H | PhS(O)$_2$ | CH$_3$CH$_2$ | Cl |
| H | CH$_3$ | PhS(O)$_2$ | CH$_3$CH$_2$ | Cl |

TABLE 1-continued

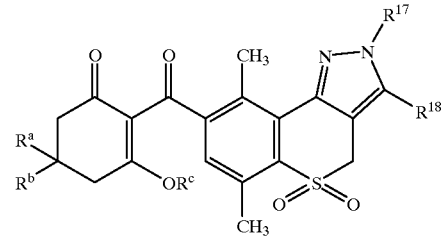

| $R^a$ | $R^b$ | $R^c$ | $R^{17}$ | $R^{18}$ |
|---|---|---|---|---|
| CH$_3$ | CH$_3$ | PhS(O)$_2$ | CH$_3$CH$_2$ | Cl |
| H | H | 4-CH$_3$PhS(O)$_2$ | CH$_3$CH$_2$ | Cl |
| H | CH$_3$ | 4-CH$_3$PhS(O)$_2$ | CH$_3$CH$_2$ | Cl |
| CH$_3$ | CH$_3$ | 4-CH$_3$PhS(O)$_2$ | CH$_3$CH$_2$ | Cl |
| H | H | PhC(=O) | CH$_3$CH$_2$CH$_2$ | Cl |
| H | CH$_3$ | PhC(=O) | CH$_3$CH$_2$CH$_2$ | Cl |
| CH$_3$ | CH$_3$ | PhC(=O) | CH$_3$CH$_2$CH$_2$ | Cl |
| H | H | PhC(=O)CH$_2$ | CH$_3$CH$_2$CH$_2$ | Cl |
| H | CH$_3$ | PhC(=O)CH$_2$ | CH$_3$CH$_2$CH$_2$ | Cl |
| CH$_3$ | CH$_3$ | PhC(=O)CH$_2$ | CH$_3$CH$_2$CH$_2$ | Cl |
| H | H | 4-CH$_3$PhC(=O) | CH$_3$CH$_2$CH$_2$ | Cl |
| H | CH$_3$ | 4-CH$_3$PhC(=O) | CH$_3$CH$_2$CH$_2$ | Cl |
| CH$_3$ | CH$_3$ | 4-CH$_3$PhC(=O) | CH$_3$CH$_2$CH$_2$ | Cl |
| H | H | CH$_3$S(O)$_2$ | CH$_3$CH$_2$CH$_2$ | Cl |
| H | CH$_3$ | CH$_3$S(O)$_2$ | CH$_3$CH$_2$CH$_2$ | Cl |
| CH$_3$ | CH$_3$ | CH$_3$S(O)$_2$ | CH$_3$CH$_2$CH$_2$ | Cl |
| H | H | CH$_3$CH$_2$S(O)$_2$ | CH$_3$CH$_2$CH$_2$ | Cl |
| H | CH$_3$ | CH$_3$CH$_2$S(O)$_2$ | CH$_3$CH$_2$CH$_2$ | Cl |
| CH$_3$ | CH$_3$ | CH$_3$CH$_2$S(O)$_2$ | CH$_3$CH$_2$CH$_2$ | Cl |
| H | H | CH$_3$CH$_2$CH$_2$S(O)$_2$ | CH$_3$CH$_2$CH$_2$ | Cl |
| H | CH$_3$ | CH$_3$CH$_2$CH$_2$S(O)$_2$ | CH$_3$CH$_2$CH$_2$ | Cl |
| CH$_3$ | CH$_3$ | CH$_3$CH$_2$CH$_2$S(O)$_2$ | CH$_3$CH$_2$CH$_2$ | Cl |
| H | H | PhS(O)$_2$ | CH$_3$CH$_2$CH$_2$ | Cl |
| H | CH$_3$ | PhS(O)$_2$ | CH$_3$CH$_2$CH$_2$ | Cl |
| CH$_3$ | CH$_3$ | PhS(O)$_2$ | CH$_3$CH$_2$CH$_2$ | Cl |
| H | H | 4-CH$_3$PhS(O)$_2$ | CH$_3$CH$_2$CH$_2$ | Cl |
| H | CH$_3$ | 4-CH$_3$PhS(O)$_2$ | CH$_3$CH$_2$CH$_2$ | Cl |
| CH$_3$ | CH$_3$ | 4-CH$_3$PhS(O)$_2$ | CH$_3$CH$_2$CH$_2$ | Cl |

TABLE 2

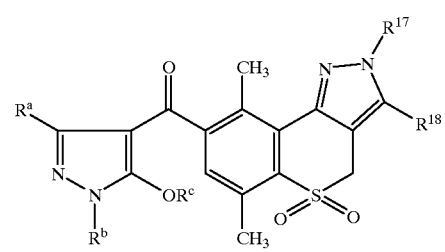

| $R^a$ | $R^b$ | $R^c$ | $R^{17}$ | $R^{18}$ |
|---|---|---|---|---|
| H | CH$_3$CH$_2$ | PhC(=O) | H | H |
| CH$_3$ | CH$_3$ | PhC(=O) | H | H |
| H | CH$_3$CH$_2$ | 4-CH$_3$PhC(=O) | H | H |
| CH$_3$ | CH$_3$ | 4-CH$_3$PhC(=O) | H | H |
| H | CH$_3$CH$_2$ | CH$_3$S(O)$_2$ | H | H |
| CH$_3$ | CH$_3$ | CH$_3$S(O)$_2$ | H | H |
| H | CH$_3$CH$_2$ | CH$_3$CH$_2$S(O)$_2$ | H | H |
| CH$_3$ | CH$_3$ | CH$_3$CH$_2$S(O)$_2$ | H | H |
| H | CH$_3$CH$_2$ | CH$_3$CH$_2$CH$_2$S(O)$_2$ | H | H |
| CH$_3$ | CH$_3$ | CH$_3$CH$_2$CH$_2$S(O)$_2$ | H | H |
| H | CH$_3$CH$_2$ | PhS(O)$_2$ | H | H |
| CH$_3$ | CH$_3$ | PhS(O)$_2$ | H | H |
| H | CH$_3$CH$_2$ | 4-CH$_3$PhS(O)$_2$ | H | H |
| CH$_3$ | CH$_3$ | 4-CH$_3$PhS(O)$_2$ | H | H |
| H | CH$_3$CH$_2$ | PhC(=O) | CH$_3$ | H |
| CH$_3$ | CH$_3$ | PhC(=O) | CH$_3$ | H |

TABLE 2-continued

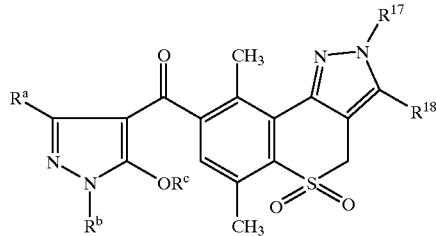

| $R^a$ | $R^b$ | $R^c$ | $R^{17}$ | $R^{18}$ |
|---|---|---|---|---|
| H | $CH_3CH_2$ | $4\text{-}CH_3PhC(=O)$ | $CH_3$ | H |
| $CH_3$ | $CH_3$ | $4\text{-}CH_3PhC(=O)$ | $CH_3$ | H |
| H | $CH_3CH_2$ | $CH_3S(O)_2$ | $CH_3$ | H |
| $CH_3$ | $CH_3$ | $CH_3S(O)_2$ | $CH_3$ | H |
| H | $CH_3CH_2$ | $CH_3CH_2S(O)_2$ | $CH_3$ | H |
| $CH_3$ | $CH_3$ | $CH_3CH_2S(O)_2$ | $CH_3$ | H |
| H | $CH_3CH_2$ | $CH_3CH_2CH_2S(O)_2$ | $CH_3$ | H |
| $CH_3$ | $CH_3$ | $CH_3CH_2CH_2S(O)_2$ | $CH_3$ | H |
| H | $CH_3CH_2$ | $PhS(O)_2$ | $CH_3$ | H |
| $CH_3$ | $CH_3$ | $PhS(O)_2$ | $CH_3$ | H |
| H | $CH_3CH_2$ | $4\text{-}CH_3PhS(O)_2$ | $CH_3$ | H |
| $CH_3$ | $CH_3$ | $4\text{-}CH_3PhS(O)_2$ | $CH_3$ | H |
| H | $CH_3CH_2$ | $PhC(=O)$ | $CH_3CH_2$ | H |
| $CH_3$ | $CH_3$ | $PhC(=O)$ | $CH_3CH_2$ | H |
| H | $CH_3CH_2$ | $4\text{-}CH_3PhC(=O)$ | $CH_3CH_2$ | H |
| $CH_3$ | $CH_3$ | $4\text{-}CH_3PhC(=O)$ | $CH_3CH_2$ | H |
| H | $CH_3CH_2$ | $CH_3S(O)_2$ | $CH_3CH_2$ | H |
| $CH_3$ | $CH_3$ | $CH_3S(O)_2$ | $CH_3CH_2$ | H |
| H | $CH_3CH_2$ | $CH_3CH_2S(O)_2$ | $CH_3CH_2$ | H |
| $CH_3$ | $CH_3$ | $CH_3CH_2S(O)_2$ | $CH_3CH_2$ | H |
| H | $CH_3CH_2$ | $CH_3CH_2CH_2S(O)_2$ | $CH_3CH_2$ | H |
| $CH_3$ | $CH_3$ | $CH_3CH_2CH_2S(O)_2$ | $CH_3CH_2$ | H |
| H | $CH_3CH_2$ | $PhS(O)_2$ | $CH_3CH_2$ | H |
| $CH_3$ | $CH_3$ | $PhS(O)_2$ | $CH_3CH_2$ | H |
| H | $CH_3CH_2$ | $4\text{-}CH_3PhS(O)_2$ | $CH_3CH_2$ | H |
| $CH_3$ | $CH_3$ | $4\text{-}CH_3PhS(O)_2$ | $CH_3CH_2$ | H |
| H | $CH_3CH_2$ | $PhC(=O)$ | $CH_3CH_2CH_2$ | H |
| $CH_3$ | $CH_3$ | $PhC(=O)$ | $CH_3CH_2CH_2$ | H |
| H | $CH_3CH_2$ | $4\text{-}CH_3PhC(=O)$ | $CH_3CH_2CH_2$ | H |
| $CH_3$ | $CH_3$ | $4\text{-}CH_3PhC(=O)$ | $CH_3CH_2CH_2$ | H |
| H | $CH_3CH_2$ | $CH_3S(O)_2$ | $CH_3CH_2CH_2$ | H |
| $CH_3$ | $CH_3$ | $CH_3S(O)_2$ | $CH_3CH_2CH_2$ | H |
| H | $CH_3CH_2$ | $CH_3CH_2S(O)_2$ | $CH_3CH_2CH_2$ | H |
| $CH_3$ | $CH_3$ | $CH_3CH_2S(O)_2$ | $CH_3CH_2CH_2$ | H |
| H | $CH_3CH_2$ | $CH_3CH_2CH_2S(O)_2$ | $CH_3CH_2CH_2$ | H |
| $CH_3$ | $CH_3$ | $CH_3CH_2CH_2S(O)_2$ | $CH_3CH_2CH_2$ | H |
| H | $CH_3CH_2$ | $PhS(O)_2$ | $CH_3CH_2CH_2$ | H |
| $CH_3$ | $CH_3$ | $PhS(O)_2$ | $CH_3CH_2CH_2$ | H |
| H | $CH_3CH_2$ | $4\text{-}CH_3PhS(O)_2$ | $CH_3CH_2CH_2$ | H |
| $CH_3$ | $CH_3$ | $4\text{-}CH_3PhS(O)_2$ | $CH_3CH_2CH_2$ | H |
| H | $CH_3CH_2$ | $PhC(=O)$ | H | $CH_3$ |
| $CH_3$ | $CH_3$ | $PhC(=O)$ | H | $CH_3$ |
| H | $CH_3CH_2$ | $4\text{-}CH_3PhC(=O)$ | H | $CH_3$ |
| $CH_3$ | $CH_3$ | $4\text{-}CH_3PhC(=O)$ | H | $CH_3$ |
| H | $CH_3CH_2$ | $CH_3S(O)_2$ | H | $CH_3$ |
| $CH_3$ | $CH_3$ | $CH_3S(O)_2$ | H | $CH_3$ |
| H | $CH_3CH_2$ | $CH_3CH_2S(O)_2$ | H | $CH_3$ |
| $CH_3$ | $CH_3$ | $CH_3CH_2S(O)_2$ | H | $CH_3$ |
| H | $CH_3CH_2$ | $CH_3CH_2CH_2S(O)_2$ | H | $CH_3$ |
| $CH_3$ | $CH_3$ | $CH_3CH_2CH_2S(O)_2$ | H | $CH_3$ |
| H | $CH_3CH_2$ | $PhS(O)_2$ | H | $CH_3$ |
| $CH_3$ | $CH_3$ | $PhS(O)_2$ | H | $CH_3$ |
| H | $CH_3CH_2$ | $4\text{-}CH_3PhS(O)_2$ | H | $CH_3$ |
| $CH_3$ | $CH_3$ | $4\text{-}CH_3PhS(O)_2$ | H | $CH_3$ |
| H | $CH_3CH_2$ | $PhC(=O)$ | $CH_3$ | $CH_3$ |
| $CH_3$ | $CH_3$ | $PhC(=O)$ | $CH_3$ | $CH_3$ |
| H | $CH_3CH_2$ | $4\text{-}CH_3PhC(=O)$ | $CH_3$ | $CH_3$ |
| $CH_3$ | $CH_3$ | $4\text{-}CH_3PhC(=O)$ | $CH_3$ | $CH_3$ |
| H | $CH_3CH_2$ | $CH_3S(O)_2$ | $CH_3$ | $CH_3$ |
| $CH_3$ | $CH_3$ | $CH_3S(O)_2$ | $CH_3$ | $CH_3$ |
| H | $CH_3CH_2$ | $CH_3CH_2S(O)_2$ | $CH_3$ | $CH_3$ |
| $CH_3$ | $CH_3$ | $CH_3CH_2S(O)_2$ | $CH_3$ | $CH_3$ |
| H | $CH_3CH_2$ | $CH_3CH_2CH_2S(O)_2$ | $CH_3$ | $CH_3$ |
| $CH_3$ | $CH_3$ | $CH_3CH_2CH_2S(O)_2$ | $CH_3$ | $CH_3$ |

TABLE 2-continued

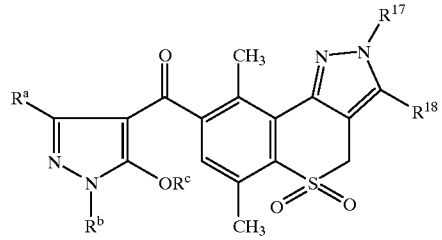

| $R^a$ | $R^b$ | $R^c$ | $R^{17}$ | $R^{18}$ |
|---|---|---|---|---|
| H | $CH_3CH_2$ | $PhS(O)_2$ | $CH_3$ | $CH_3$ |
| $CH_3$ | $CH_3$ | $PhS(O)_2$ | $CH_3$ | $CH_3$ |
| H | $CH_3CH_2$ | $4\text{-}CH_3PhS(O)_2$ | $CH_3$ | $CH_3$ |
| $CH_3$ | $CH_3$ | $4\text{-}CH_3PhS(O)_2$ | $CH_3$ | $CH_3$ |
| H | $CH_3CH_2$ | $PhC(=O)$ | $CH_3CH_2$ | $CH_3$ |
| $CH_3$ | $CH_3$ | $PhC(=O)$ | $CH_3CH_2$ | $CH_3$ |
| H | $CH_3CH_2$ | $4\text{-}CH_3PhC(=O)$ | $CH_3CH_2$ | $CH_3$ |
| $CH_3$ | $CH_3$ | $4\text{-}CH_3PhC(=O)$ | $CH_3CH_2$ | $CH_3$ |
| H | $CH_3CH_2$ | $CH_3S(O)_2$ | $CH_3CH_2$ | $CH_3$ |
| $CH_3$ | $CH_3$ | $CH_3S(O)_2$ | $CH_3CH_2$ | $CH_3$ |
| H | $CH_3CH_2$ | $CH_3CH_2S(O)_2$ | $CH_3CH_2$ | $CH_3$ |
| $CH_3$ | $CH_3$ | $CH_3CH_2S(O)_2$ | $CH_3CH_2$ | $CH_3$ |
| H | $CH_3CH_2$ | $CH_3CH_2CH_2S(O)_2$ | $CH_3CH_2$ | $CH_3$ |
| $CH_3$ | $CH_3$ | $CH_3CH_2CH_2S(O)_2$ | $CH_3CH_2$ | $CH_3$ |
| H | $CH_3CH_2$ | $PhS(O)_2$ | $CH_3CH_2$ | $CH_3$ |
| $CH_3$ | $CH_3$ | $PhS(O)_2$ | $CH_3CH_2$ | $CH_3$ |
| H | $CH_3CH_2$ | $4\text{-}CH_3PhS(O)_2$ | $CH_3CH_2$ | $CH_3$ |
| $CH_3$ | $CH_3$ | $4\text{-}CH_3PhS(O)_2$ | $CH_3CH_2$ | $CH_3$ |
| H | $CH_3CH_2$ | $PhC(=O)$ | $CH_3CH_2CH_2$ | $CH_3$ |
| $CH_3$ | $CH_3$ | $PhC(=O)$ | $CH_3CH_2CH_2$ | $CH_3$ |
| H | $CH_3CH_2$ | $4\text{-}CH_3PhC(=O)$ | $CH_3CH_2CH_2$ | $CH_3$ |
| $CH_3$ | $CH_3$ | $4\text{-}CH_3PhC(=O)$ | $CH_3CH_2CH_2$ | $CH_3$ |
| H | $CH_3CH_2$ | $CH_3S(O)_2$ | $CH_3CH_2CH_2$ | $CH_3$ |
| $CH_3$ | $CH_3$ | $CH_3S(O)_2$ | $CH_3CH_2CH_2$ | $CH_3$ |
| H | $CH_3CH_2$ | $CH_3CH_2S(O)_2$ | $CH_3CH_2CH_2$ | $CH_3$ |
| $CH_3$ | $CH_3$ | $CH_3CH_2S(O)_2$ | $CH_3CH_2CH_2$ | $CH_3$ |
| H | $CH_3CH_2$ | $CH_3CH_2CH_2S(O)_2$ | $CH_3CH_2CH_2$ | $CH_3$ |
| $CH_3$ | $CH_3$ | $CH_3CH_2CH_2S(O)_2$ | $CH_3CH_2CH_2$ | $CH_3$ |
| H | $CH_3CH_2$ | $PhS(O)_2$ | $CH_3CH_2CH_2$ | $CH_3$ |
| $CH_3$ | $CH_3$ | $PhS(O)_2$ | $CH_3CH_2CH_2$ | $CH_3$ |
| H | $CH_3CH_2$ | $4\text{-}CH_3PhS(O)_2$ | $CH_3CH_2CH_2$ | $CH_3$ |
| $CH_3$ | $CH_3$ | $4\text{-}CH_3PhS(O)_2$ | $CH_3CH_2CH_2$ | $CH_3$ |
| H | $CH_3CH_2$ | $PhC(=O)$ | H | Cl |
| $CH_3$ | $CH_3$ | $PhC(=O)$ | H | Cl |
| H | $CH_3CH_2$ | $4\text{-}CH_3PhC(=O)$ | H | Cl |
| $CH_3$ | $CH_3$ | $4\text{-}CH_3PhC(=O)$ | H | Cl |
| H | $CH_3CH_2$ | $CH_3S(O)_2$ | H | Cl |
| $CH_3$ | $CH_3$ | $CH_3S(O)_2$ | H | Cl |
| H | $CH_3CH_2$ | $CH_3CH_2S(O)_2$ | H | Cl |
| $CH_3$ | $CH_3$ | $CH_3CH_2S(O)_2$ | H | Cl |
| H | $CH_3CH_2$ | $CH_3CH_2CH_2S(O)_2$ | H | Cl |
| $CH_3$ | $CH_3$ | $CH_3CH_2CH_2S(O)_2$ | H | Cl |
| H | $CH_3CH_2$ | $PhS(O)_2$ | H | Cl |
| $CH_3$ | $CH_3$ | $PhS(O)_2$ | H | Cl |
| H | $CH_3CH_2$ | $4\text{-}CH_3PhS(O)_2$ | H | Cl |
| $CH_3$ | $CH_3$ | $4\text{-}CH_3PhS(O)_2$ | H | Cl |
| H | $CH_3CH_2$ | $PhC(=O)$ | $CH_3$ | Cl |
| $CH_3$ | $CH_3$ | $PhC(=O)$ | $CH_3$ | Cl |
| H | $CH_3CH_2$ | $4\text{-}CH_3PhC(=O)$ | $CH_3$ | Cl |
| $CH_3$ | $CH_3$ | $4\text{-}CH_3PhC(=O)$ | $CH_3$ | Cl |
| H | $CH_3CH_2$ | $CH_3S(O)_2$ | $CH_3$ | Cl |
| $CH_3$ | $CH_3$ | $CH_3S(O)_2$ | $CH_3$ | Cl |
| H | $CH_3CH_2$ | $CH_3CH_2S(O)_2$ | $CH_3$ | Cl |
| $CH_3$ | $CH_3$ | $CH_3CH_2S(O)_2$ | $CH_3$ | Cl |
| H | $CH_3CH_2$ | $CH_3CH_2CH_2S(O)_2$ | $CH_3$ | Cl |
| $CH_3$ | $CH_3$ | $CH_3CH_2CH_2S(O)_2$ | $CH_3$ | Cl |
| H | $CH_3CH_2$ | $PhS(O)_2$ | $CH_3$ | Cl |
| $CH_3$ | $CH_3$ | $PhS(O)_2$ | $CH_3$ | Cl |
| H | $CH_3CH_2$ | $4\text{-}CH_3PhS(O)_2$ | $CH_3$ | Cl |
| $CH_3$ | $CH_3$ | $4\text{-}CH_3PhS(O)_2$ | $CH_3$ | Cl |
| H | $CH_3CH_2$ | $PhC(=O)$ | $CH_3CH_2$ | Cl |
| $CH_3$ | $CH_3$ | $PhC(=O)$ | $CH_3CH_2$ | Cl |
| H | $CH_3CH_2$ | $4\text{-}CH_3PhC(=O)$ | $CH_3CH_2$ | Cl |
| $CH_3$ | $CH_3$ | $4\text{-}CH_3PhC(=O)$ | $CH_3CH_2$ | Cl |

TABLE 2-continued

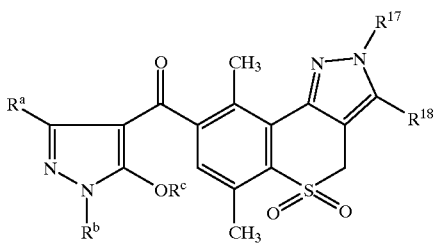

| $R^a$ | $R^b$ | $R^c$ | $R^{17}$ | $R^{18}$ |
|---|---|---|---|---|
| H | $CH_3CH_2$ | $CH_3S(O)_2$ | $CH_3CH_2$ | Cl |
| $CH_3$ | $CH_3$ | $CH_3S(O)_2$ | $CH_3CH_2$ | Cl |
| H | $CH_3CH_2$ | $CH_3CH_2S(O)_2$ | $CH_3CH_2$ | Cl |
| $CH_3$ | $CH_3$ | $CH_3CH_2S(O)_2$ | $CH_3CH_2$ | Cl |
| H | $CH_3CH_2$ | $CH_3CH_2CH_2S(O)_2$ | $CH_3CH_2$ | Cl |
| $CH_3$ | $CH_3$ | $CH_3CH_2CH_2S(O)_2$ | $CH_3CH_2$ | Cl |
| H | $CH_3CH_2$ | $PhS(O)_2$ | $CH_3CH_2$ | Cl |
| $CH_3$ | $CH_3$ | $PhS(O)_2$ | $CH_3CH_2$ | Cl |
| H | $CH_3CH_2$ | $4\text{-}CH_3PhS(O)_2$ | $CH_3CH_2$ | Cl |
| $CH_3$ | $CH_3$ | $4\text{-}CH_3PhS(O)_2$ | $CH_3CH_2$ | Cl |
| H | $CH_3CH_2$ | $PhC(=O)$ | $CH_3CH_2CH_2$ | Cl |
| $CH_3$ | $CH_3$ | $PhC(=O)$ | $CH_3CH_2CH_2$ | Cl |
| H | $CH_3CH_2$ | $4\text{-}CH_3PhC(=O)$ | $CH_3CH_2CH_2$ | Cl |
| $CH_3$ | $CH_3$ | $4\text{-}CH_3PhC(=O)$ | $CH_3CH_2CH_2$ | Cl |
| H | $CH_3CH_2$ | $CH_3S(O)_2$ | $CH_3CH_2CH_2$ | Cl |
| $CH_3$ | $CH_3$ | $CH_3S(O)_2$ | $CH_3CH_2CH_2$ | Cl |
| H | $CH_3CH_2$ | $CH_3CH_2S(O)_2$ | $CH_3CH_2CH_2$ | Cl |
| $CH_3$ | $CH_3$ | $CH_3CH_2S(O)_2$ | $CH_3CH_2CH_2$ | Cl |
| H | $CH_3CH_2$ | $CH_3CH_2CH_2S(O)_2$ | $CH_3CH_2CH_2$ | Cl |
| $CH_3$ | $CH_3$ | $CH_3CH_2CH_2S(O)_2$ | $CH_3CH_2CH_2$ | Cl |
| H | $CH_3CH_2$ | $PhS(O)_2$ | $CH_3CH_2CH_2$ | Cl |
| $CH_3$ | $CH_3$ | $PhS(O)_2$ | $CH_3CH_2CH_2$ | Cl |
| H | $CH_3CH_2$ | $4\text{-}CH_3PhS(O)_2$ | $CH_3CH_2CH_2$ | Cl |
| $CH_3$ | $CH_3$ | $4\text{-}CH_3PhS(O)_2$ | $CH_3CH_2CH_2$ | Cl |
| H | $CH_3CH_2$ | $PhC(=O)CH_2$ | H | H |
| $CH_3$ | $CH_3$ | $PhC(=O)CH_2$ | H | H |
| H | $CH_3CH_2$ | $PhC(=O)CH_2$ | $CH_3$ | H |
| $CH_3$ | $CH_3$ | $PhC(=O)CH_2$ | $CH_3$ | H |
| H | $CH_3CH_2$ | $PhC(=O)CH_2$ | $CH_3CH_2$ | H |
| $CH_3$ | $CH_3$ | $PhC(=O)CH_2$ | $CH_3CH_2$ | H |
| H | $CH_3CH_2$ | $PhC(=O)CH_2$ | $CH_3CH_2CH_2$ | H |
| $CH_3$ | $CH_3$ | $PhC(=O)CH_2$ | $CH_3CH_2CH_2$ | H |
| H | $CH_3CH_2$ | $PhC(=O)CH_2$ | H | $CH_3$ |
| $CH_3$ | $CH_3$ | $PhC(=O)CH_2$ | H | $CH_3$ |
| H | $CH_3CH_2$ | $PhC(=O)CH_2$ | $CH_3$ | $CH_3$ |
| $CH_3$ | $CH_3$ | $PhC(=O)CH_2$ | $CH_3$ | $CH_3$ |
| H | $CH_3CH_2$ | $PhC(=O)CH_2$ | $CH_3CH_2$ | $CH_3$ |
| $CH_3$ | $CH_3$ | $PhC(=O)CH_2$ | $CH_3CH_2$ | $CH_3$ |
| H | $CH_3CH_2$ | $PhC(=O)CH_2$ | $CH_3CH_2CH_2$ | $CH_3$ |
| $CH_3$ | $CH_3$ | $PhC(=O)CH_2$ | $CH_3CH_2CH_2$ | $CH_3$ |
| H | $CH_3CH_2$ | $PhC(=O)CH_2$ | H | Cl |
| $CH_3$ | $CH_3$ | $PhC(=O)CH_2$ | H | Cl |
| H | $CH_3CH_2$ | $PhC(=O)CH_2$ | $CH_3$ | Cl |
| $CH_3$ | $CH_3$ | $PhC(=O)CH_2$ | $CH_3$ | Cl |
| H | $CH_3CH_2$ | $PhC(=O)CH_2$ | $CH_3CH_2$ | Cl |
| $CH_3$ | $CH_3$ | $PhC(=O)CH_2$ | $CH_3CH_2$ | Cl |
| H | $CH_3CH_2$ | $PhC(=O)CH_2$ | $CH_3CH_2CH_2$ | Cl |
| $CH_3$ | $CH_3$ | $PhC(=O)CH_2$ | $CH_3CH_2CH_2$ | Cl |

TABLE 3

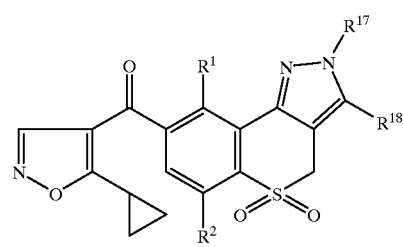

| $R^1$ | $R^2$ | $R^{17}$ | $R^{18}$ |
|---|---|---|---|
| H | H | H | H |
| $CH_3$ | H | H | H |
| $CH_3$ | $CH_3$ | H | H |
| Cl | H | H | H |
| Cl | $CH_3$ | H | H |
| Cl | Cl | H | H |
| H | H | $CH_3$ | H |
| $CH_3$ | H | $CH_3$ | H |
| $CH_3$ | $CH_3$ | $CH_3$ | H |
| Cl | H | $CH_3$ | H |
| Cl | $CH_3$ | $CH_3$ | H |
| Cl | Cl | $CH_3$ | H |
| H | H | $CH_3CH_2$ | H |
| $CH_3$ | H | $CH_3CH_2$ | H |
| $CH_3$ | $CH_3$ | $CH_3CH_2$ | H |
| Cl | H | $CH_3CH_2$ | H |
| Cl | $CH_3$ | $CH_3CH_2$ | H |
| Cl | Cl | $CH_3CH_2$ | H |
| H | H | $CH_3CH_2CH_2$ | H |
| $CH_3$ | H | $CH_3CH_2CH_2$ | H |
| $CH_3$ | $CH_3$ | $CH_3CH_2CH_2$ | H |
| Cl | H | $CH_3CH_2CH_2$ | H |
| Cl | $CH_3$ | $CH_3CH_2CH_2$ | H |
| Cl | Cl | $CH_3CH_2CH_2$ | H |
| H | H | H | $CH_3$ |
| $CH_3$ | H | H | $CH_3$ |
| $CH_3$ | $CH_3$ | H | $CH_3$ |
| Cl | H | H | $CH_3$ |
| Cl | $CH_3$ | H | $CH_3$ |
| Cl | Cl | H | $CH_3$ |
| H | H | $CH_3$ | $CH_3$ |
| $CH_3$ | H | $CH_3$ | $CH_3$ |
| $CH_3$ | $CH_3$ | $CH_3$ | $CH_3$ |
| Cl | H | $CH_3$ | $CH_3$ |
| Cl | $CH_3$ | $CH_3$ | $CH_3$ |
| Cl | Cl | $CH_3$ | $CH_3$ |
| H | H | $CH_3CH_2$ | $CH_3$ |
| $CH_3$ | H | $CH_3CH_2$ | $CH_3$ |
| $CH_3$ | $CH_3$ | $CH_3CH_2$ | $CH_3$ |
| Cl | H | $CH_3CH_2$ | $CH_3$ |
| Cl | $CH_3$ | $CH_3CH_2$ | $CH_3$ |
| Cl | Cl | $CH_3CH_2$ | $CH_3$ |
| H | H | $CH_3CH_2CH_2$ | $CH_3$ |
| $CH_3$ | H | $CH_3CH_2CH_2$ | $CH_3$ |
| $CH_3$ | $CH_3$ | $CH_3CH_2CH_2$ | $CH_3$ |
| Cl | H | $CH_3CH_2CH_2$ | $CH_3$ |
| Cl | $CH_3$ | $CH_3CH_2CH_2$ | $CH_3$ |
| Cl | Cl | $CH_3CH_2CH_2$ | $CH_3$ |
| H | H | H | Cl |
| $CH_3$ | H | H | Cl |
| $CH_3$ | $CH_3$ | H | Cl |
| Cl | H | H | Cl |
| Cl | $CH_3$ | H | Cl |
| Cl | Cl | H | Cl |
| H | H | $CH_3$ | Cl |
| $CH_3$ | H | $CH_3$ | Cl |
| $CH_3$ | $CH_3$ | $CH_3$ | Cl |
| Cl | H | $CH_3$ | Cl |
| Cl | $CH_3$ | $CH_3$ | Cl |
| Cl | Cl | $CH_3$ | Cl |
| H | H | $CH_3CH_2$ | Cl |
| $CH_3$ | H | $CH_3CH_2$ | Cl |
| $CH_3$ | $CH_3$ | $CH_3CH_2$ | Cl |
| Cl | H | $CH_3CH_2$ | Cl |

TABLE 3-continued

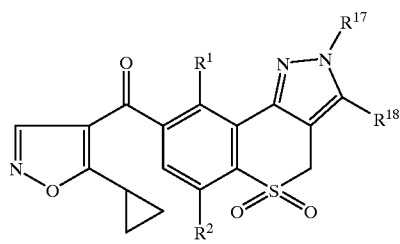

| R¹ | R² | R¹⁷ | R¹⁸ |
|---|---|---|---|
| Cl | CH₃ | CH₃CH₂ | Cl |
| Cl | Cl | CH₃CH₂CH₂ | Cl |
| H | H | CH₃CH₂CH₂ | Cl |
| CH₃ | H | CH₃CH₂CH₂ | Cl |
| CH₃ | CH₃ | CH₃CH₂CH₂ | Cl |
| Cl | H | CH₃CH₂CH₂ | Cl |
| Cl | CH₃ | CH₃CH₂CH₂ | Cl |
| Cl | Cl | CH₃CH₂CH₂ | Cl |

TABLE 4

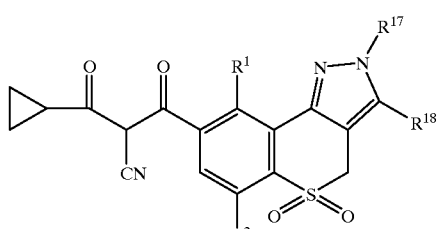

| R¹ | R² | R¹⁷ | R¹⁸ |
|---|---|---|---|
| H | H | H | H |
| CH₃ | H | H | H |
| CH₃ | CH₃ | H | H |
| Cl | H | H | H |
| Cl | CH₃ | H | H |
| Cl | Cl | H | H |
| H | H | CH₃ | H |
| CH₃ | H | CH₃ | H |
| CH₃ | CH₃ | CH₃ | H |
| Cl | H | CH₃ | H |
| Cl | CH₃ | CH₃ | H |
| Cl | Cl | CH₃ | H |
| H | H | CH₃CH₂ | H |
| CH₃ | H | CH₃CH₂ | H |
| CH₃ | CH₃ | CH₃CH₂ | H |
| Cl | H | CH₃CH₂ | H |
| Cl | CH₃ | CH₃CH₂ | H |
| Cl | Cl | CH₃CH₂ | H |
| H | H | CH₃CH₂CH₂ | H |
| CH₃ | H | CH₃CH₂CH₂ | H |
| CH₃ | CH₃ | CH₃CH₂CH₂ | H |
| Cl | H | CH₃CH₂CH₂ | H |
| Cl | CH₃ | CH₃CH₂CH₂ | H |
| Cl | Cl | CH₃CH₂CH₂ | H |
| H | H | H | CH₃ |
| CH₃ | H | H | CH₃ |
| CH₃ | CH₃ | H | CH₃ |
| Cl | H | H | CH₃ |
| Cl | CH₃ | H | CH₃ |
| Cl | Cl | H | CH₃ |
| H | H | CH₃ | CH₃ |
| CH₃ | H | CH₃ | CH₃ |
| CH₃ | CH₃ | CH₃ | CH₃ |
| Cl | H | CH₃ | CH₃ |
| Cl | CH₃ | CH₃ | CH₃ |
| Cl | Cl | CH₃ | CH₃ |

TABLE 4-continued

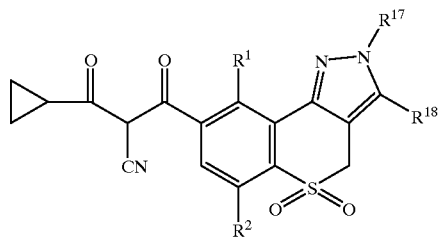

| R¹ | R² | R¹⁷ | R¹⁸ |
|---|---|---|---|
| H | H | CH₃CH₂ | CH₃ |
| CH₃ | H | CH₃CH₂ | CH₃ |
| CH₃ | CH₃ | CH₃CH₂ | CH₃ |
| Cl | H | CH₃CH₂ | CH₃ |
| Cl | CH₃ | CH₃CH₂ | CH₃ |
| Cl | Cl | CH₃CH₂CH₂ | CH₃ |
| H | H | CH₃CH₂CH₂ | CH₃ |
| CH₃ | H | CH₃CH₂CH₂ | CH₃ |
| CH₃ | CH₃ | CH₃CH₂CH₂ | CH₃ |
| Cl | H | CH₃CH₂CH₂ | CH₃ |
| Cl | CH₃ | CH₃CH₂CH₂ | CH₃ |
| Cl | Cl | CH₃CH₂CH₂ | CH₃ |
| H | H | H | Cl |
| CH₃ | H | H | Cl |
| CH₃ | CH₃ | H | Cl |
| Cl | H | H | Cl |
| Cl | CH₃ | H | Cl |
| Cl | Cl | H | Cl |
| H | H | CH₃ | Cl |
| CH₃ | H | CH₃ | Cl |
| CH₃ | CH₃ | CH₃ | Cl |
| Cl | H | CH₃ | Cl |
| Cl | CH₃ | CH₃ | Cl |
| Cl | Cl | CH₃ | Cl |
| H | H | CH₃CH₂ | Cl |
| CH₃ | H | CH₃CH₂ | Cl |
| CH₃ | CH₃ | CH₃CH₂ | Cl |
| Cl | H | CH₃CH₂ | Cl |
| Cl | CH₃ | CH₃CH₂ | Cl |
| Cl | Cl | CH₃CH₂ | Cl |
| H | H | CH₃CH₂CH₂ | Cl |
| CH₃ | H | CH₃CH₂CH₂ | Cl |
| CH₃ | CH₃ | CH₃CH₂CH₂ | Cl |
| Cl | H | CH₃CH₂CH₂ | Cl |
| Cl | CH₃ | CH₃CH₂CH₂ | Cl |
| Cl | Cl | CH₃CH₂CH₂ | Cl |

TABLE 5

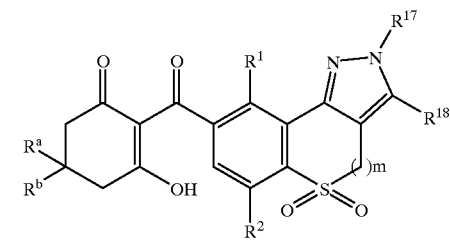

| Rᵃ | Rᵇ | R¹ | R² | m | R¹⁷ | R¹⁸ |
|---|---|---|---|---|---|---|
| H | H | H | H | 1 | H | H |
| CH₃ | H | H | H | 1 | H | H |
| CH₃ | CH₃ | H | H | 1 | H | H |
| H | H | CH₃ | H | 1 | H | H |
| CH₃ | H | CH₃ | H | 1 | H | H |
| CH₃ | CH₃ | CH₃ | H | 1 | H | H |
| H | H | Cl | H | 1 | H | H |
| CH₃ | H | Cl | H | 1 | H | H |

TABLE 5-continued

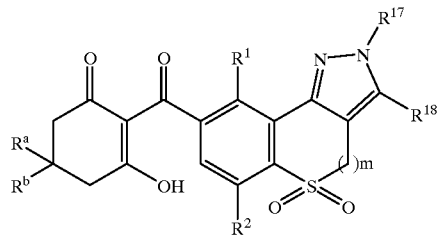

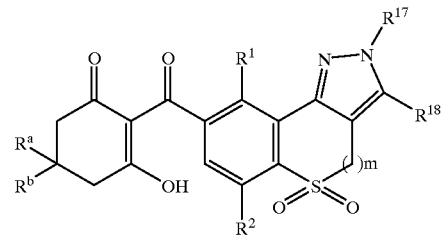

| $R^a$ | $R^b$ | $R^1$ | $R^2$ | m | $R^{17}$ | $R^{18}$ |
|---|---|---|---|---|---|---|
| $CH_3$ | $CH_3$ | Cl | H | 1 | H | H |
| H | H | H | $CH_3$ | 1 | H | H |
| $CH_3$ | H | H | $CH_3$ | 1 | H | H |
| $CH_3$ | $CH_3$ | H | $CH_3$ | 1 | H | H |
| H | H | $CH_3$ | $CH_3$ | 1 | H | H |
| $CH_3$ | H | $CH_3$ | $CH_3$ | 1 | H | H |
| $CH_3$ | $CH_3$ | $CH_3$ | $CH_3$ | 1 | H | H |
| H | H | Cl | $CH_3$ | 1 | H | H |
| $CH_3$ | H | Cl | $CH_3$ | 1 | H | H |
| $CH_3$ | $CH_3$ | Cl | $CH_3$ | 1 | H | H |
| H | H | H | Cl | 1 | H | H |
| $CH_3$ | H | H | Cl | 1 | H | H |
| $CH_3$ | $CH_3$ | H | Cl | 1 | H | H |
| H | H | $CH_3$ | Cl | 1 | H | H |
| $CH_3$ | H | $CH_3$ | Cl | 1 | H | H |
| $CH_3$ | $CH_3$ | $CH_3$ | Cl | 1 | H | H |
| H | H | Cl | Cl | 1 | H | H |
| $CH_3$ | H | Cl | Cl | 1 | H | H |
| $CH_3$ | $CH_3$ | Cl | Cl | 1 | H | H |
| H | H | H | H | 1 | $CH_3$ | H |
| $CH_3$ | H | H | H | 1 | $CH_3$ | H |
| $CH_3$ | $CH_3$ | H | H | 1 | $CH_3$ | H |
| H | H | $CH_3$ | H | 1 | $CH_3$ | H |
| $CH_3$ | H | $CH_3$ | H | 1 | $CH_3$ | H |
| $CH_3$ | $CH_3$ | $CH_3$ | H | 1 | $CH_3$ | H |
| H | H | Cl | H | 1 | $CH_3$ | H |
| $CH_3$ | H | Cl | H | 1 | $CH_3$ | H |
| $CH_3$ | $CH_3$ | Cl | H | 1 | $CH_3$ | H |
| H | H | H | $CH_3$ | 1 | $CH_3$ | H |
| $CH_3$ | H | H | $CH_3$ | 1 | $CH_3$ | H |
| $CH_3$ | $CH_3$ | H | $CH_3$ | 1 | $CH_3$ | H |
| H | H | $CH_3$ | $CH_3$ | 1 | $CH_3$ | H |
| $CH_3$ | H | $CH_3$ | $CH_3$ | 1 | $CH_3$ | H |
| $CH_3$ | $CH_3$ | $CH_3$ | $CH_3$ | 1 | $CH_3$ | H |
| H | H | Cl | $CH_3$ | 1 | $CH_3$ | H |
| $CH_3$ | H | Cl | $CH_3$ | 1 | $CH_3$ | H |
| $CH_3$ | $CH_3$ | Cl | $CH_3$ | 1 | $CH_3$ | H |
| H | H | H | Cl | 1 | $CH_3$ | H |
| $CH_3$ | H | H | Cl | 1 | $CH_3$ | H |
| $CH_3$ | $CH_3$ | H | Cl | 1 | $CH_3$ | H |
| H | H | $CH_3$ | Cl | 1 | $CH_3$ | H |
| $CH_3$ | H | $CH_3$ | Cl | 1 | $CH_3$ | H |
| $CH_3$ | $CH_3$ | $CH_3$ | Cl | 1 | $CH_3$ | H |
| H | H | Cl | Cl | 1 | $CH_3$ | H |
| $CH_3$ | H | Cl | Cl | 1 | $CH_3$ | H |
| $CH_3$ | $CH_3$ | Cl | Cl | 1 | $CH_3$ | H |
| H | H | H | H | 1 | $CH_3CH_2$ | H |
| $CH_3$ | H | H | H | 1 | $CH_3CH_2$ | H |
| $CH_3$ | $CH_3$ | H | H | 1 | $CH_3CH_2$ | H |
| H | H | $CH_3$ | H | 1 | $CH_3CH_2$ | H |
| $CH_3$ | H | $CH_3$ | H | 1 | $CH_3CH_2$ | H |
| $CH_3$ | $CH_3$ | $CH_3$ | H | 1 | $CH_3CH_2$ | H |
| H | H | Cl | H | 1 | $CH_3CH_2$ | H |
| $CH_3$ | H | Cl | H | 1 | $CH_3CH_2$ | H |
| $CH_3$ | $CH_3$ | Cl | H | 1 | $CH_3CH_2$ | H |
| H | H | H | $CH_3$ | 1 | $CH_3CH_2$ | H |
| $CH_3$ | H | H | $CH_3$ | 1 | $CH_3CH_2$ | H |
| $CH_3$ | $CH_3$ | H | $CH_3$ | 1 | $CH_3CH_2$ | H |
| H | H | $CH_3$ | $CH_3$ | 1 | $CH_3CH_2$ | H |
| $CH_3$ | H | $CH_3$ | $CH_3$ | 1 | $CH_3CH_2$ | H |
| $CH_3$ | $CH_3$ | $CH_3$ | $CH_3$ | 1 | $CH_3CH_2$ | H |
| H | H | Cl | $CH_3$ | 1 | $CH_3CH_2$ | H |
| $CH_3$ | H | Cl | $CH_3$ | 1 | $CH_3CH_2$ | H |
| $CH_3$ | $CH_3$ | Cl | $CH_3$ | 1 | $CH_3CH_2$ | H |
| H | H | H | Cl | 1 | $CH_3CH_2$ | H |
| $CH_3$ | H | H | Cl | 1 | $CH_3CH_2$ | H |
| $CH_3$ | $CH_3$ | H | Cl | 1 | $CH_3CH_2$ | H |
| H | H | $CH_3$ | Cl | 1 | $CH_3CH_2$ | H |
| $CH_3$ | H | $CH_3$ | Cl | 1 | $CH_3CH_2$ | H |
| $CH_3$ | $CH_3$ | $CH_3$ | Cl | 1 | $CH_3CH_2$ | H |
| H | H | Cl | Cl | 1 | $CH_3CH_2$ | H |
| $CH_3$ | H | Cl | Cl | 1 | $CH_3CH_2$ | H |
| $CH_3$ | $CH_3$ | Cl | Cl | 1 | $CH_3CH_2$ | H |
| H | H | H | H | 1 | $CH_3CH_2CH_2$ | H |
| $CH_3$ | H | H | H | 1 | $CH_3CH_2CH_2$ | H |
| $CH_3$ | $CH_3$ | H | H | 1 | $CH_3CH_2CH_2$ | H |
| H | H | $CH_3$ | H | 1 | $CH_3CH_2CH_2$ | H |
| $CH_3$ | H | $CH_3$ | H | 1 | $CH_3CH_2CH_2$ | H |
| $CH_3$ | $CH_3$ | $CH_3$ | H | 1 | $CH_3CH_2CH_2$ | H |
| H | H | Cl | H | 1 | $CH_3CH_2CH_2$ | H |
| $CH_3$ | H | Cl | H | 1 | $CH_3CH_2CH_2$ | H |
| $CH_3$ | $CH_3$ | Cl | H | 1 | $CH_3CH_2CH_2$ | H |
| H | H | H | $CH_3$ | 1 | $CH_3CH_2CH_2$ | H |
| $CH_3$ | H | H | $CH_3$ | 1 | $CH_3CH_2CH_2$ | H |
| $CH_3$ | $CH_3$ | H | $CH_3$ | 1 | $CH_3CH_2CH_2$ | H |
| H | H | $CH_3$ | $CH_3$ | 1 | $CH_3CH_2CH_2$ | H |
| $CH_3$ | H | $CH_3$ | $CH_3$ | 1 | $CH_3CH_2CH_2$ | H |
| $CH_3$ | $CH_3$ | $CH_3$ | $CH_3$ | 1 | $CH_3CH_2CH_2$ | H |
| H | H | Cl | $CH_3$ | 1 | $CH_3CH_2CH_2$ | H |
| $CH_3$ | H | Cl | $CH_3$ | 1 | $CH_3CH_2CH_2$ | H |
| $CH_3$ | $CH_3$ | Cl | $CH_3$ | 1 | $CH_3CH_2CH_2$ | H |
| H | H | H | Cl | 1 | $CH_3CH_2CH_2$ | H |
| $CH_3$ | H | H | Cl | 1 | $CH_3CH_2CH_2$ | H |
| $CH_3$ | $CH_3$ | H | Cl | 1 | $CH_3CH_2CH_2$ | H |
| H | H | $CH_3$ | Cl | 1 | $CH_3CH_2CH_2$ | H |
| $CH_3$ | H | $CH_3$ | Cl | 1 | $CH_3CH_2CH_2$ | H |
| $CH_3$ | $CH_3$ | $CH_3$ | Cl | 1 | $CH_3CH_2CH_2$ | H |
| H | H | Cl | Cl | 1 | $CH_3CH_2CH_2$ | H |
| $CH_3$ | H | Cl | Cl | 1 | $CH_3CH_2CH_2$ | H |
| $CH_3$ | $CH_3$ | Cl | Cl | 1 | $CH_3CH_2CH_2$ | H |
| H | H | H | H | 1 | H | $CH_3$ |
| $CH_3$ | H | H | H | 1 | H | $CH_3$ |
| $CH_3$ | $CH_3$ | H | H | 1 | H | $CH_3$ |
| H | H | $CH_3$ | H | 1 | H | $CH_3$ |
| $CH_3$ | H | $CH_3$ | H | 1 | H | $CH_3$ |
| $CH_3$ | $CH_3$ | $CH_3$ | H | 1 | H | $CH_3$ |
| H | H | Cl | H | 1 | H | $CH_3$ |
| $CH_3$ | H | Cl | H | 1 | H | $CH_3$ |
| $CH_3$ | $CH_3$ | Cl | H | 1 | H | $CH_3$ |
| H | H | H | $CH_3$ | 1 | H | $CH_3$ |
| $CH_3$ | H | H | $CH_3$ | 1 | H | $CH_3$ |
| $CH_3$ | $CH_3$ | H | $CH_3$ | 1 | H | $CH_3$ |
| H | H | $CH_3$ | $CH_3$ | 1 | H | $CH_3$ |
| $CH_3$ | H | $CH_3$ | $CH_3$ | 1 | H | $CH_3$ |
| $CH_3$ | $CH_3$ | $CH_3$ | $CH_3$ | 1 | H | $CH_3$ |
| H | H | Cl | $CH_3$ | 1 | H | $CH_3$ |
| $CH_3$ | H | Cl | $CH_3$ | 1 | H | $CH_3$ |
| $CH_3$ | $CH_3$ | Cl | $CH_3$ | 1 | H | $CH_3$ |
| H | H | H | Cl | 1 | H | $CH_3$ |
| $CH_3$ | H | H | Cl | 1 | H | $CH_3$ |
| $CH_3$ | $CH_3$ | H | Cl | 1 | H | $CH_3$ |
| H | H | $CH_3$ | Cl | 1 | H | $CH_3$ |
| $CH_3$ | H | $CH_3$ | Cl | 1 | H | $CH_3$ |
| $CH_3$ | $CH_3$ | $CH_3$ | Cl | 1 | H | $CH_3$ |
| H | H | Cl | Cl | 1 | H | $CH_3$ |
| $CH_3$ | H | Cl | Cl | 1 | H | $CH_3$ |
| $CH_3$ | $CH_3$ | Cl | Cl | 1 | H | $CH_3$ |
| H | H | H | H | 1 | $CH_3$ | $CH_3$ |

TABLE 5-continued

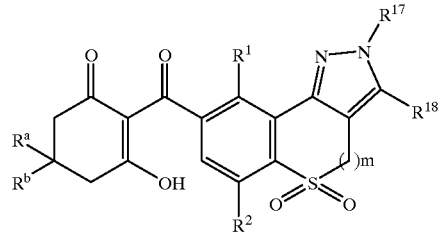

| $R^a$ | $R^b$ | $R^1$ | $R^2$ | m | $R^{17}$ | $R^{18}$ |
|---|---|---|---|---|---|---|
| CH₃ | H | H | H | 1 | CH₃ | CH₃ |
| CH₃ | CH₃ | H | H | 1 | CH₃ | CH₃ |
| H | H | CH₃ | H | 1 | CH₃ | CH₃ |
| CH₃ | H | CH₃ | H | 1 | CH₃ | CH₃ |
| CH₃ | CH₃ | CH₃ | H | 1 | CH₃ | CH₃ |
| H | H | Cl | H | 1 | CH₃ | CH₃ |
| CH₃ | H | Cl | H | 1 | CH₃ | CH₃ |
| CH₃ | CH₃ | Cl | H | 1 | CH₃ | CH₃ |
| H | H | H | CH₃ | 1 | CH₃ | CH₃ |
| CH₃ | H | H | CH₃ | 1 | CH₃ | CH₃ |
| CH₃ | CH₃ | H | CH₃ | 1 | CH₃ | CH₃ |
| H | H | CH₃ | CH₃ | 1 | CH₃ | CH₃ |
| CH₃ | H | CH₃ | CH₃ | 1 | CH₃ | CH₃ |
| CH₃ | CH₃ | CH₃ | CH₃ | 1 | CH₃ | CH₃ |
| H | H | Cl | CH₃ | 1 | CH₃ | CH₃ |
| CH₃ | H | Cl | CH₃ | 1 | CH₃ | CH₃ |
| CH₃ | CH₃ | Cl | CH₃ | 1 | CH₃ | CH₃ |
| H | H | H | Cl | 1 | CH₃ | CH₃ |
| CH₃ | H | H | Cl | 1 | CH₃ | CH₃ |
| CH₃ | CH₃ | H | Cl | 1 | CH₃ | CH₃ |
| H | H | CH₃ | Cl | 1 | CH₃ | CH₃ |
| CH₃ | H | CH₃ | Cl | 1 | CH₃ | CH₃ |
| CH₃ | CH₃ | CH₃ | Cl | 1 | CH₃ | CH₃ |
| H | H | Cl | Cl | 1 | CH₃ | CH₃ |
| CH₃ | H | Cl | Cl | 1 | CH₃ | CH₃ |
| CH₃ | CH₃ | Cl | Cl | 1 | CH₃ | CH₃ |
| H | H | H | H | 1 | CH₃CH₂ | CH₃ |
| CH₃ | H | H | H | 1 | CH₃CH₂ | CH₃ |
| CH₃ | CH₃ | H | H | 1 | CH₃CH₂ | CH₃ |
| H | H | CH₃ | H | 1 | CH₃CH₂ | CH₃ |
| CH₃ | H | CH₃ | H | 1 | CH₃CH₂ | CH₃ |
| CH₃ | CH₃ | CH₃ | H | 1 | CH₃CH₂ | CH₃ |
| H | H | Cl | H | 1 | CH₃CH₂ | CH₃ |
| CH₃ | H | Cl | H | 1 | CH₃CH₂ | CH₃ |
| CH₃ | CH₃ | Cl | H | 1 | CH₃CH₂ | CH₃ |
| H | H | H | CH₃ | 1 | CH₃CH₂ | CH₃ |
| CH₃ | H | H | CH₃ | 1 | CH₃CH₂ | CH₃ |
| CH₃ | CH₃ | H | CH₃ | 1 | CH₃CH₂ | CH₃ |
| H | H | CH₃ | CH₃ | 1 | CH₃CH₂ | CH₃ |
| CH₃ | H | CH₃ | CH₃ | 1 | CH₃CH₂ | CH₃ |
| CH₃ | CH₃ | CH₃ | CH₃ | 1 | CH₃CH₂ | CH₃ |
| H | H | Cl | CH₃ | 1 | CH₃CH₂ | CH₃ |
| CH₃ | H | Cl | CH₃ | 1 | CH₃CH₂ | CH₃ |
| CH₃ | CH₃ | Cl | CH₃ | 1 | CH₃CH₂ | CH₃ |
| H | H | H | Cl | 1 | CH₃CH₂ | CH₃ |
| CH₃ | H | H | Cl | 1 | CH₃CH₂ | CH₃ |
| CH₃ | CH₃ | H | Cl | 1 | CH₃CH₂ | CH₃ |
| H | H | CH₃ | Cl | 1 | CH₃CH₂ | CH₃ |
| CH₃ | H | CH₃ | Cl | 1 | CH₃CH₂ | CH₃ |
| CH₃ | CH₃ | CH₃ | Cl | 1 | CH₃CH₂ | CH₃ |
| H | H | Cl | Cl | 1 | CH₃CH₂ | CH₃ |
| CH₃ | H | Cl | Cl | 1 | CH₃CH₂ | CH₃ |
| CH₃ | CH₃ | Cl | Cl | 1 | CH₃CH₂ | CH₃ |
| H | H | H | H | 1 | CH₃CH₂CH₂ | CH₃ |
| CH₃ | H | H | H | 1 | CH₃CH₂CH₂ | CH₃ |
| CH₃ | CH₃ | H | H | 1 | CH₃CH₂CH₂ | CH₃ |
| H | H | CH₃ | H | 1 | CH₃CH₂CH₂ | CH₃ |
| CH₃ | H | CH₃ | H | 1 | CH₃CH₂CH₂ | CH₃ |
| CH₃ | CH₃ | CH₃ | H | 1 | CH₃CH₂CH₂ | CH₃ |
| H | H | Cl | H | 1 | CH₃CH₂CH₂ | CH₃ |
| CH₃ | H | Cl | H | 1 | CH₃CH₂CH₂ | CH₃ |
| CH₃ | CH₃ | Cl | H | 1 | CH₃CH₂CH₂ | CH₃ |
| H | H | H | CH₃ | 1 | CH₃CH₂CH₂ | CH₃ |
| CH₃ | H | H | CH₃ | 1 | CH₃CH₂CH₂ | CH₃ |
| CH₃ | CH₃ | H | CH₃ | 1 | CH₃CH₂CH₂ | CH₃ |
| H | H | CH₃ | CH₃ | 1 | CH₃CH₂CH₂ | CH₃ |
| CH₃ | H | CH₃ | CH₃ | 1 | CH₃CH₂CH₂ | CH₃ |
| CH₃ | CH₃ | CH₃ | CH₃ | 1 | CH₃CH₂CH₂ | CH₃ |
| H | H | Cl | CH₃ | 1 | CH₃CH₂CH₂ | CH₃ |
| CH₃ | H | Cl | CH₃ | 1 | CH₃CH₂CH₂ | CH₃ |
| CH₃ | CH₃ | Cl | CH₃ | 1 | CH₃CH₂CH₂ | CH₃ |
| H | H | H | Cl | 1 | CH₃CH₂CH₂ | CH₃ |
| CH₃ | H | H | Cl | 1 | CH₃CH₂CH₂ | CH₃ |
| CH₃ | CH₃ | H | Cl | 1 | CH₃CH₂CH₂ | CH₃ |
| H | H | CH₃ | Cl | 1 | CH₃CH₂CH₂ | CH₃ |
| CH₃ | H | CH₃ | Cl | 1 | CH₃CH₂CH₂ | CH₃ |
| CH₃ | CH₃ | CH₃ | Cl | 1 | CH₃CH₂CH₂ | CH₃ |
| H | H | Cl | Cl | 1 | CH₃CH₂CH₂ | CH₃ |
| CH₃ | H | Cl | Cl | 1 | CH₃CH₂CH₂ | CH₃ |
| CH₃ | CH₃ | Cl | Cl | 1 | CH₃CH₂CH₂ | CH₃ |
| H | H | H | H | 1 | H | Cl |
| CH₃ | H | H | H | 1 | H | Cl |
| CH₃ | CH₃ | H | H | 1 | H | Cl |
| H | H | CH₃ | H | 1 | H | Cl |
| CH₃ | H | CH₃ | H | 1 | H | Cl |
| CH₃ | CH₃ | CH₃ | H | 1 | H | Cl |
| H | H | Cl | H | 1 | H | Cl |
| CH₃ | H | Cl | H | 1 | H | Cl |
| CH₃ | CH₃ | Cl | H | 1 | H | Cl |
| H | H | H | CH₃ | 1 | H | Cl |
| CH₃ | H | H | CH₃ | 1 | H | Cl |
| CH₃ | CH₃ | H | CH₃ | 1 | H | Cl |
| H | H | CH₃ | CH₃ | 1 | H | Cl |
| CH₃ | H | CH₃ | CH₃ | 1 | H | Cl |
| CH₃ | CH₃ | CH₃ | CH₃ | 1 | H | Cl |
| H | H | Cl | CH₃ | 1 | H | Cl |
| CH₃ | H | Cl | CH₃ | 1 | H | Cl |
| CH₃ | CH₃ | Cl | CH₃ | 1 | H | Cl |
| H | H | H | Cl | 1 | H | Cl |
| CH₃ | H | H | Cl | 1 | H | Cl |
| CH₃ | CH₃ | H | Cl | 1 | H | Cl |
| H | H | CH₃ | Cl | 1 | H | Cl |
| CH₃ | H | CH₃ | Cl | 1 | H | Cl |
| CH₃ | CH₃ | CH₃ | Cl | 1 | H | Cl |
| H | H | Cl | Cl | 1 | H | Cl |
| CH₃ | H | Cl | Cl | 1 | H | Cl |
| CH₃ | CH₃ | Cl | Cl | 1 | H | Cl |
| H | H | H | H | 1 | CH₃ | Cl |
| CH₃ | H | H | H | 1 | CH₃ | Cl |
| CH₃ | CH₃ | H | H | 1 | CH₃ | Cl |
| H | H | CH₃ | H | 1 | CH₃ | Cl |
| CH₃ | H | CH₃ | H | 1 | CH₃ | Cl |
| CH₃ | CH₃ | CH₃ | H | 1 | CH₃ | Cl |
| H | H | Cl | H | 1 | CH₃ | Cl |
| CH₃ | H | Cl | H | 1 | CH₃ | Cl |
| CH₃ | CH₃ | Cl | H | 1 | CH₃ | Cl |
| H | H | H | CH₃ | 1 | CH₃ | Cl |
| CH₃ | H | H | CH₃ | 1 | CH₃ | Cl |
| CH₃ | CH₃ | H | CH₃ | 1 | CH₃ | Cl |
| H | H | CH₃ | CH₃ | 1 | CH₃ | Cl |
| CH₃ | H | CH₃ | CH₃ | 1 | CH₃ | Cl |
| CH₃ | CH₃ | CH₃ | CH₃ | 1 | CH₃ | Cl |
| H | H | Cl | CH₃ | 1 | CH₃ | Cl |
| CH₃ | H | Cl | CH₃ | 1 | CH₃ | Cl |
| CH₃ | CH₃ | Cl | CH₃ | 1 | CH₃ | Cl |
| H | H | H | Cl | 1 | CH₃ | Cl |
| CH₃ | H | H | Cl | 1 | CH₃ | Cl |
| CH₃ | CH₃ | H | Cl | 1 | CH₃ | Cl |

TABLE 5-continued

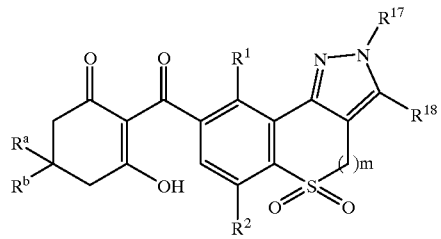

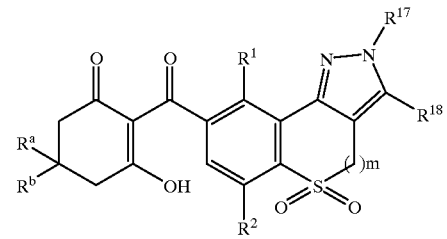

| $R^a$ | $R^b$ | $R^1$ | $R^2$ | m | $R^{17}$ | $R^{18}$ |
|---|---|---|---|---|---|---|
| H | H | CH₃ | Cl | 1 | CH₃ | Cl |
| CH₃ | H | CH₃ | Cl | 1 | CH₃ | Cl |
| CH₃ | CH₃ | CH₃ | Cl | 1 | CH₃ | Cl |
| H | H | Cl | Cl | 1 | CH₃ | Cl |
| CH₃ | H | Cl | Cl | 1 | CH₃ | Cl |
| CH₃ | CH₃ | Cl | Cl | 1 | CH₃ | Cl |
| H | H | H | H | 1 | CH₃CH₂ | Cl |
| CH₃ | H | H | H | 1 | CH₃CH₂ | Cl |
| CH₃ | CH₃ | H | H | 1 | CH₃CH₂ | Cl |
| H | H | CH₃ | H | 1 | CH₃CH₂ | Cl |
| CH₃ | H | CH₃ | H | 1 | CH₃CH₂ | Cl |
| CH₃ | CH₃ | CH₃ | H | 1 | CH₃CH₂ | Cl |
| H | H | Cl | H | 1 | CH₃CH₂ | Cl |
| CH₃ | H | Cl | H | 1 | CH₃CH₂ | Cl |
| CH₃ | CH₃ | Cl | H | 1 | CH₃CH₂ | Cl |
| H | H | H | CH₃ | 1 | CH₃CH₂ | Cl |
| CH₃ | H | H | CH₃ | 1 | CH₃CH₂ | Cl |
| CH₃ | CH₃ | H | CH₃ | 1 | CH₃CH₂ | Cl |
| H | H | CH₃ | CH₃ | 1 | CH₃CH₂ | Cl |
| CH₃ | H | CH₃ | CH₃ | 1 | CH₃CH₂ | Cl |
| CH₃ | CH₃ | CH₃ | CH₃ | 1 | CH₃CH₂ | Cl |
| H | H | Cl | CH₃ | 1 | CH₃CH₂ | Cl |
| CH₃ | H | Cl | CH₃ | 1 | CH₃CH₂ | Cl |
| CH₃ | CH₃ | Cl | CH₃ | 1 | CH₃CH₂ | Cl |
| H | H | H | Cl | 1 | CH₃CH₂ | Cl |
| CH₃ | H | H | Cl | 1 | CH₃CH₂ | Cl |
| CH₃ | CH₃ | H | Cl | 1 | CH₃CH₂ | Cl |
| H | H | CH₃ | Cl | 1 | CH₃CH₂ | Cl |
| CH₃ | H | CH₃ | Cl | 1 | CH₃CH₂ | Cl |
| CH₃ | CH₃ | CH₃ | Cl | 1 | CH₃CH₂ | Cl |
| H | H | Cl | Cl | 1 | CH₃CH₂ | Cl |
| CH₃ | H | Cl | Cl | 1 | CH₃CH₂ | Cl |
| CH₃ | CH₃ | Cl | Cl | 1 | CH₃CH₂ | Cl |
| H | H | H | H | 1 | CH₃CH₂CH₂ | Cl |
| CH₃ | H | H | H | 1 | CH₃CH₂CH₂ | Cl |
| CH₃ | CH₃ | H | H | 1 | CH₃CH₂CH₂ | Cl |
| H | H | CH₃ | H | 1 | CH₃CH₂CH₂ | Cl |
| CH₃ | H | CH₃ | H | 1 | CH₃CH₂CH₂ | Cl |
| CH₃ | CH₃ | CH₃ | H | 1 | CH₃CH₂CH₂ | Cl |
| H | H | Cl | H | 1 | CH₃CH₂CH₂ | Cl |
| CH₃ | H | Cl | H | 1 | CH₃CH₂CH₂ | Cl |
| CH₃ | CH₃ | Cl | H | 1 | CH₃CH₂CH₂ | Cl |
| H | H | H | CH₃ | 1 | CH₃CH₂CH₂ | Cl |
| CH₃ | H | H | CH₃ | 1 | CH₃CH₂CH₂ | Cl |
| CH₃ | CH₃ | H | CH₃ | 1 | CH₃CH₂CH₂ | Cl |
| H | H | CH₃ | CH₃ | 1 | CH₃CH₂CH₂ | Cl |
| CH₃ | H | CH₃ | CH₃ | 1 | CH₃CH₂CH₂ | Cl |
| CH₃ | CH₃ | CH₃ | CH₃ | 1 | CH₃CH₂CH₂ | Cl |
| H | H | Cl | CH₃ | 1 | CH₃CH₂CH₂ | Cl |
| CH₃ | H | Cl | CH₃ | 1 | CH₃CH₂CH₂ | Cl |
| CH₃ | CH₃ | Cl | CH₃ | 1 | CH₃CH₂CH₂ | Cl |
| H | H | H | Cl | 1 | CH₃CH₂CH₂ | Cl |
| CH₃ | H | H | Cl | 1 | CH₃CH₂CH₂ | Cl |
| CH₃ | CH₃ | H | Cl | 1 | CH₃CH₂CH₂ | Cl |
| H | H | CH₃ | Cl | 1 | CH₃CH₂CH₂ | Cl |
| CH₃ | H | CH₃ | Cl | 1 | CH₃CH₂CH₂ | Cl |
| CH₃ | CH₃ | CH₃ | Cl | 1 | CH₃CH₂CH₂ | Cl |
| H | H | Cl | Cl | 1 | CH₃CH₂CH₂ | Cl |
| CH₃ | H | Cl | Cl | 1 | CH₃CH₂CH₂ | Cl |
| CH₃ | CH₃ | Cl | Cl | 1 | CH₃CH₂CH₂ | Cl |
| H | H | H | H | 2 | H | H |
| H | H | CH₃ | H | 2 | H | H |
| H | H | Cl | H | 2 | H | H |
| H | H | CH₃ | CH₃ | 2 | H | H |
| H | H | Cl | CH₃ | 2 | H | H |
| H | H | Cl | Cl | 2 | H | H |
| H | H | H | H | 2 | CH₃ | H |
| H | H | CH₃ | H | 2 | CH₃ | H |
| H | H | Cl | H | 2 | CH₃ | H |
| H | H | CH₃ | CH₃ | 2 | CH₃ | H |
| H | H | Cl | CH₃ | 2 | CH₃ | H |
| H | H | Cl | Cl | 2 | CH₃ | H |
| H | H | H | H | 2 | CH₂CH₃ | H |
| H | H | CH₃ | H | 2 | CH₂CH₃ | H |
| H | H | Cl | H | 2 | CH₂CH₃ | H |
| H | H | CH₃ | CH₃ | 2 | CH₂CH₃ | H |
| H | H | Cl | CH₃ | 2 | CH₂CH₃ | H |
| H | H | Cl | Cl | 2 | CH₂CH₃ | H |
| H | H | H | H | 2 | CH₂CH₂CH₃ | H |
| H | H | CH₃ | H | 2 | CH₂CH₂CH₃ | H |
| H | H | Cl | H | 2 | CH₂CH₂CH₃ | H |
| H | H | CH₃ | CH₃ | 2 | CH₂CH₂CH₃ | H |
| H | H | Cl | CH₃ | 2 | CH₂CH₂CH₃ | H |
| H | H | Cl | Cl | 2 | CH₂CH₂CH₃ | H |
| H | H | H | H | 2 | phenyl | H |
| H | H | CH₃ | H | 2 | phenyl | H |
| H | H | Cl | H | 2 | phenyl | H |
| H | H | CH₃ | CH₃ | 2 | phenyl | H |
| H | H | Cl | CH₃ | 2 | phenyl | H |
| H | H | Cl | Cl | 2 | phenyl | H |
| H | H | H | H | 2 | H | CH₃ |
| H | H | CH₃ | H | 2 | H | CH₃ |
| H | H | Cl | H | 2 | H | CH₃ |
| H | H | CH₃ | CH₃ | 2 | H | CH₃ |
| H | H | Cl | CH₃ | 2 | H | CH₃ |
| H | H | Cl | Cl | 2 | H | CH₃ |
| H | H | H | H | 2 | CH₃ | CH₃ |
| H | H | CH₃ | H | 2 | CH₃ | CH₃ |
| H | H | Cl | H | 2 | CH₃ | CH₃ |
| H | H | CH₃ | CH₃ | 2 | CH₃ | CH₃ |
| H | H | Cl | CH₃ | 2 | CH₃ | CH₃ |
| H | H | Cl | Cl | 2 | CH₃ | CH₃ |
| H | H | H | H | 2 | CH₂CH₃ | CH₃ |
| H | H | CH₃ | H | 2 | CH₂CH₃ | CH₃ |
| H | H | Cl | H | 2 | CH₂CH₃ | CH₃ |
| H | H | CH₃ | CH₃ | 2 | CH₂CH₃ | CH₃ |
| H | H | Cl | CH₃ | 2 | CH₂CH₃ | CH₃ |
| H | H | Cl | Cl | 2 | CH₂CH₃ | CH₃ |
| H | H | H | H | 2 | CH₂CH₂CH₃ | CH₃ |
| H | H | CH₃ | H | 2 | CH₂CH₂CH₃ | CH₃ |
| H | H | Cl | H | 2 | CH₂CH₂CH₃ | CH₃ |
| H | H | CH₃ | CH₃ | 2 | CH₂CH₂CH₃ | CH₃ |
| H | H | Cl | CH₃ | 2 | CH₂CH₂CH₃ | CH₃ |
| H | H | Cl | Cl | 2 | CH₂CH₂CH₃ | CH₃ |
| H | H | H | H | 2 | phenyl | CH₃ |
| H | H | CH₃ | H | 2 | phenyl | CH₃ |
| H | H | Cl | H | 2 | phenyl | CH₃ |
| H | H | CH₃ | CH₃ | 2 | phenyl | CH₃ |
| H | H | Cl | CH₃ | 2 | phenyl | CH₃ |
| H | H | Cl | Cl | 2 | phenyl | CH₃ |
| H | H | H | H | 2 | H | Cl |
| H | H | CH₃ | H | 2 | H | Cl |
| H | H | Cl | H | 2 | H | Cl |
| H | H | CH₃ | CH₃ | 2 | H | Cl |
| H | H | Cl | CH₃ | 2 | H | Cl |
| H | H | Cl | Cl | 2 | H | Cl |
| H | H | H | H | 2 | CH₃ | Cl |
| H | H | CH₃ | H | 2 | CH₃ | Cl |

TABLE 5-continued

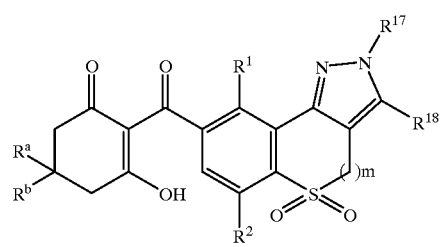

| R$^a$ | R$^b$ | R$^1$ | R$^2$ | m | R$^{17}$ | R$^{18}$ |
|---|---|---|---|---|---|---|
| H | H | Cl | H | 2 | CH$_3$ | Cl |
| H | H | CH$_3$ | CH$_3$ | 2 | CH$_3$ | Cl |
| H | H | Cl | CH$_3$ | 2 | CH$_3$ | Cl |
| H | H | Cl | Cl | 2 | CH$_3$ | Cl |
| H | H | H | H | 2 | CH$_2$CH$_3$ | Cl |
| H | H | CH$_3$ | H | 2 | CH$_2$CH$_3$ | Cl |
| H | H | Cl | H | 2 | CH$_2$CH$_3$ | Cl |
| H | H | CH$_3$ | CH$_3$ | 2 | CH$_2$CH$_3$ | Cl |
| H | H | Cl | CH$_3$ | 2 | CH$_2$CH$_3$ | Cl |
| H | H | Cl | Cl | 2 | CH$_2$CH$_3$ | Cl |
| H | H | H | H | 2 | CH$_2$CH$_2$CH$_3$ | Cl |
| H | H | CH$_3$ | H | 2 | CH$_2$CH$_2$CH$_3$ | Cl |
| H | H | Cl | H | 2 | CH$_2$CH$_2$CH$_3$ | Cl |
| H | H | CH$_3$ | CH$_3$ | 2 | CH$_2$CH$_2$CH$_3$ | Cl |
| H | H | Cl | CH$_3$ | 2 | CH$_2$CH$_2$CH$_3$ | Cl |
| H | H | Cl | Cl | 2 | CH$_2$CH$_2$CH$_3$ | Cl |
| H | H | H | H | 2 | phenyl | Cl |
| H | H | CH$_3$ | H | 2 | phenyl | Cl |
| H | H | Cl | H | 2 | phenyl | Cl |
| H | H | CH$_3$ | CH$_3$ | 2 | phenyl | Cl |
| H | H | Cl | CH$_3$ | 2 | phenyl | Cl |
| H | H | Cl | Cl | 2 | phenyl | Cl |

TABLE 6

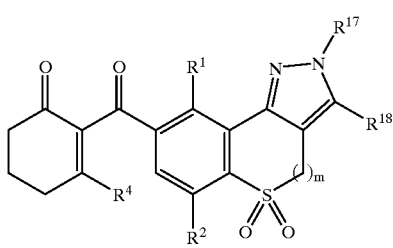

| R$^4$ | R$^1$ | R$^2$ | m | R$^{17}$ | R$^{18}$ |
|---|---|---|---|---|---|
| SH | H | H | 1 | H | H |
| Cl | H | H | 1 | H | H |
| SH | CH$_3$ | H | 1 | H | H |
| Cl | CH$_3$ | H | 1 | H | H |
| SH | Cl | H | 1 | H | H |
| Cl | Cl | H | 1 | H | H |
| SH | CH$_3$ | CH$_3$ | 1 | H | H |
| Cl | CH$_3$ | CH$_3$ | 1 | H | H |
| SH | Cl | Cl | 1 | H | H |
| Cl | Cl | Cl | 1 | H | H |
| SH | H | H | 2 | H | H |
| Cl | H | H | 2 | H | H |
| SH | CH$_3$ | H | 2 | H | H |
| Cl | CH$_3$ | H | 2 | H | H |
| SH | Cl | H | 2 | H | H |
| Cl | Cl | H | 2 | H | H |
| SH | CH$_3$ | CH$_3$ | 2 | H | H |
| Cl | CH$_3$ | CH$_3$ | 2 | H | H |
| SH | Cl | Cl | 2 | H | H |
| Cl | Cl | Cl | 2 | H | H |
| SH | H | H | 1 | CH$_3$ | H |
| Cl | H | H | 1 | CH$_3$ | H |

TABLE 6-continued

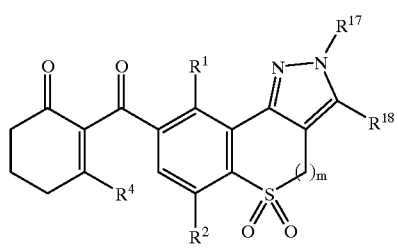

| R$^4$ | R$^1$ | R$^2$ | m | R$^{17}$ | R$^{18}$ |
|---|---|---|---|---|---|
| SH | CH$_3$ | H | 1 | CH$_3$ | H |
| Cl | CH$_3$ | H | 1 | CH$_3$ | H |
| SH | Cl | H | 1 | CH$_3$ | H |
| Cl | Cl | H | 1 | CH$_3$ | H |
| SH | CH$_3$ | CH$_3$ | 1 | CH$_3$ | H |
| Cl | CH$_3$ | CH$_3$ | 1 | CH$_3$ | H |
| SH | Cl | Cl | 1 | CH$_3$ | H |
| Cl | Cl | Cl | 1 | CH$_3$ | H |
| SH | H | H | 2 | CH$_3$ | H |
| Cl | H | H | 2 | CH$_3$ | H |
| SH | CH$_3$ | H | 2 | CH$_3$ | H |
| Cl | CH$_3$ | H | 2 | CH$_3$ | H |
| SH | Cl | H | 2 | CH$_3$ | H |
| Cl | Cl | H | 2 | CH$_3$ | H |
| SH | CH$_3$ | CH$_3$ | 2 | CH$_3$ | H |
| Cl | CH$_3$ | CH$_3$ | 2 | CH$_3$ | H |
| SH | Cl | Cl | 2 | CH$_3$ | H |
| Cl | Cl | Cl | 2 | CH$_3$ | H |
| SH | H | H | 1 | CH$_2$CH$_3$ | H |
| Cl | H | H | 1 | CH$_2$CH$_3$ | H |
| SH | CH$_3$ | H | 1 | CH$_2$CH$_3$ | H |
| Cl | CH$_3$ | H | 1 | CH$_2$CH$_3$ | H |
| SH | Cl | H | 1 | CH$_2$CH$_3$ | H |
| Cl | Cl | H | 1 | CH$_2$CH$_3$ | H |
| SH | CH$_3$ | CH$_3$ | 1 | CH$_2$CH$_3$ | H |
| Cl | CH$_3$ | CH$_3$ | 1 | CH$_2$CH$_3$ | H |
| SH | Cl | Cl | 1 | CH$_2$CH$_3$ | H |
| Cl | Cl | Cl | 1 | CH$_2$CH$_3$ | H |
| SH | H | H | 2 | CH$_2$CH$_3$ | H |
| Cl | H | H | 2 | CH$_2$CH$_3$ | H |
| SH | CH$_3$ | H | 2 | CH$_2$CH$_3$ | H |
| Cl | CH$_3$ | H | 2 | CH$_2$CH$_3$ | H |
| SH | Cl | H | 2 | CH$_2$CH$_3$ | H |
| Cl | Cl | H | 2 | CH$_2$CH$_3$ | H |
| SH | CH$_3$ | CH$_3$ | 2 | CH$_2$CH$_3$ | H |
| Cl | CH$_3$ | CH$_3$ | 2 | CH$_2$CH$_3$ | H |
| SH | Cl | Cl | 2 | CH$_2$CH$_3$ | H |
| Cl | Cl | Cl | 2 | CH$_2$CH$_3$ | H |
| SH | H | H | 1 | CH$_2$CH$_2$CH$_3$ | H |
| Cl | H | H | 1 | CH$_2$CH$_2$CH$_3$ | H |
| SH | CH$_3$ | H | 1 | CH$_2$CH$_2$CH$_3$ | H |
| Cl | CH$_3$ | H | 1 | CH$_2$CH$_2$CH$_3$ | H |
| SH | Cl | H | 1 | CH$_2$CH$_2$CH$_3$ | H |
| Cl | Cl | H | 1 | CH$_2$CH$_2$CH$_3$ | H |
| SH | CH$_3$ | CH$_3$ | 1 | CH$_2$CH$_2$CH$_3$ | H |
| Cl | CH$_3$ | CH$_3$ | 1 | CH$_2$CH$_2$CH$_3$ | H |
| SH | Cl | Cl | 1 | CH$_2$CH$_2$CH$_3$ | H |
| Cl | Cl | Cl | 1 | CH$_2$CH$_2$CH$_3$ | H |
| SH | H | H | 2 | CH$_2$CH$_2$CH$_3$ | H |
| Cl | H | H | 2 | CH$_2$CH$_2$CH$_3$ | H |
| SH | CH$_3$ | H | 2 | CH$_2$CH$_2$CH$_3$ | H |
| Cl | CH$_3$ | H | 2 | CH$_2$CH$_2$CH$_3$ | H |
| SH | Cl | H | 2 | CH$_2$CH$_2$CH$_3$ | H |
| Cl | Cl | H | 2 | CH$_2$CH$_2$CH$_3$ | H |
| SH | CH$_3$ | CH$_3$ | 2 | CH$_2$CH$_2$CH$_3$ | H |
| Cl | CH$_3$ | CH$_3$ | 2 | CH$_2$CH$_2$CH$_3$ | H |
| SH | Cl | Cl | 2 | CH$_2$CH$_2$CH$_3$ | H |
| Cl | Cl | Cl | 2 | CH$_2$CH$_2$CH$_3$ | H |
| SH | H | H | 1 | H | CH$_3$ |
| Cl | H | H | 1 | H | CH$_3$ |
| SH | CH$_3$ | H | 1 | H | CH$_3$ |
| Cl | CH$_3$ | H | 1 | H | CH$_3$ |
| SH | Cl | H | 1 | H | CH$_3$ |
| Cl | Cl | H | 1 | H | CH$_3$ |

TABLE 6-continued

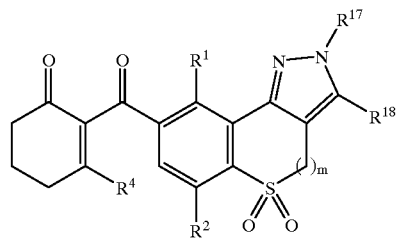
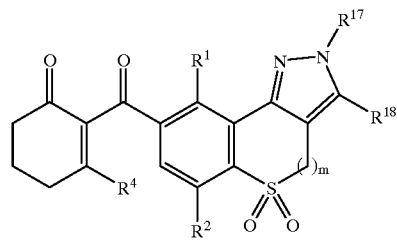

| R⁴ | R¹ | R² | m | R¹⁷ | R¹⁸ |
|---|---|---|---|---|---|
| SH | $CH_3$ | $CH_3$ | 1 | H | $CH_3$ |
| Cl | $CH_3$ | $CH_3$ | 1 | H | $CH_3$ |
| SH | Cl | Cl | 1 | H | $CH_3$ |
| Cl | Cl | Cl | 1 | H | $CH_3$ |
| SH | H | H | 2 | H | $CH_3$ |
| Cl | H | H | 2 | H | $CH_3$ |
| SH | $CH_3$ | H | 2 | H | $CH_3$ |
| Cl | $CH_3$ | H | 2 | H | $CH_3$ |
| SH | Cl | H | 2 | H | $CH_3$ |
| Cl | Cl | H | 2 | H | $CH_3$ |
| SH | $CH_3$ | $CH_3$ | 2 | H | $CH_3$ |
| Cl | $CH_3$ | $CH_3$ | 2 | H | $CH_3$ |
| SH | Cl | Cl | 2 | H | $CH_3$ |
| Cl | Cl | Cl | 2 | H | $CH_3$ |
| SH | H | H | 1 | $CH_3$ | $CH_3$ |
| Cl | H | H | 1 | $CH_3$ | $CH_3$ |
| SH | $CH_3$ | H | 1 | $CH_3$ | $CH_3$ |
| Cl | $CH_3$ | H | 1 | $CH_3$ | $CH_3$ |
| SH | Cl | H | 1 | $CH_3$ | $CH_3$ |
| Cl | Cl | H | 1 | $CH_3$ | $CH_3$ |
| SH | $CH_3$ | $CH_3$ | 1 | $CH_3$ | $CH_3$ |
| Cl | $CH_3$ | $CH_3$ | 1 | $CH_3$ | $CH_3$ |
| SH | Cl | Cl | 1 | $CH_3$ | $CH_3$ |
| Cl | Cl | Cl | 1 | $CH_3$ | $CH_3$ |
| SH | H | H | 2 | $CH_3$ | $CH_3$ |
| Cl | H | H | 2 | $CH_3$ | $CH_3$ |
| SH | $CH_3$ | H | 2 | $CH_3$ | $CH_3$ |
| Cl | $CH_3$ | H | 2 | $CH_3$ | $CH_3$ |
| SH | Cl | H | 2 | $CH_3$ | $CH_3$ |
| Cl | Cl | H | 2 | $CH_3$ | $CH_3$ |
| SH | $CH_3$ | $CH_3$ | 2 | $CH_3$ | $CH_3$ |
| Cl | $CH_3$ | $CH_3$ | 2 | $CH_3$ | $CH_3$ |
| SH | Cl | Cl | 2 | $CH_3$ | $CH_3$ |
| Cl | Cl | Cl | 2 | $CH_3$ | $CH_3$ |
| SH | H | H | 1 | $CH_2CH_3$ | $CH_3$ |
| Cl | H | H | 1 | $CH_2CH_3$ | $CH_3$ |
| SH | $CH_3$ | H | 1 | $CH_2CH_3$ | $CH_3$ |
| Cl | $CH_3$ | H | 1 | $CH_2CH_3$ | $CH_3$ |
| SH | Cl | H | 1 | $CH_2CH_3$ | $CH_3$ |
| Cl | Cl | H | 1 | $CH_2CH_3$ | $CH_3$ |
| SH | $CH_3$ | $CH_3$ | 1 | $CH_2CH_3$ | $CH_3$ |
| Cl | $CH_3$ | $CH_3$ | 1 | $CH_2CH_3$ | $CH_3$ |
| SH | Cl | Cl | 1 | $CH_2CH_3$ | $CH_3$ |
| Cl | Cl | Cl | 1 | $CH_2CH_3$ | $CH_3$ |
| SH | H | H | 2 | $CH_2CH_3$ | $CH_3$ |
| Cl | H | H | 2 | $CH_2CH_3$ | $CH_3$ |
| SH | $CH_3$ | H | 2 | $CH_2CH_3$ | $CH_3$ |
| Cl | $CH_3$ | H | 2 | $CH_2CH_3$ | $CH_3$ |
| SH | Cl | H | 2 | $CH_2CH_3$ | $CH_3$ |
| Cl | Cl | H | 2 | $CH_2CH_3$ | $CH_3$ |
| SH | $CH_3$ | $CH_3$ | 2 | $CH_2CH_3$ | $CH_3$ |
| Cl | $CH_3$ | $CH_3$ | 2 | $CH_2CH_3$ | $CH_3$ |
| SH | Cl | Cl | 2 | $CH_2CH_3$ | $CH_3$ |
| Cl | Cl | Cl | 2 | $CH_2CH_3$ | $CH_3$ |
| SH | H | H | 1 | $CH_2CH_2CH_3$ | $CH_3$ |
| Cl | H | H | 1 | $CH_2CH_2CH_3$ | $CH_3$ |
| SH | $CH_3$ | H | 1 | $CH_2CH_2CH_3$ | $CH_3$ |
| Cl | $CH_3$ | H | 1 | $CH_2CH_2CH_3$ | $CH_3$ |
| SH | Cl | H | 1 | $CH_2CH_2CH_3$ | $CH_3$ |
| Cl | Cl | H | 1 | $CH_2CH_2CH_3$ | $CH_3$ |
| SH | $CH_3$ | $CH_3$ | 1 | $CH_2CH_2CH_3$ | $CH_3$ |
| Cl | $CH_3$ | $CH_3$ | 1 | $CH_2CH_2CH_3$ | $CH_3$ |
| SH | Cl | Cl | 1 | $CH_2CH_2CH_3$ | $CH_3$ |
| Cl | Cl | Cl | 1 | $CH_2CH_2CH_3$ | $CH_3$ |
| SH | H | H | 2 | $CH_2CH_2CH_3$ | $CH_3$ |
| Cl | H | H | 2 | $CH_2CH_2CH_3$ | $CH_3$ |
| SH | $CH_3$ | H | 2 | $CH_2CH_2CH_3$ | $CH_3$ |
| Cl | $CH_3$ | H | 2 | $CH_2CH_2CH_3$ | $CH_3$ |
| SH | Cl | H | 2 | $CH_2CH_2CH_3$ | $CH_3$ |
| Cl | Cl | H | 2 | $CH_2CH_2CH_3$ | $CH_3$ |
| SH | $CH_3$ | $CH_3$ | 2 | $CH_2CH_2CH_3$ | $CH_3$ |
| Cl | $CH_3$ | $CH_3$ | 2 | $CH_2CH_2CH_3$ | $CH_3$ |
| SH | Cl | Cl | 2 | $CH_2CH_2CH_3$ | $CH_3$ |
| Cl | Cl | Cl | 2 | $CH_2CH_2CH_3$ | $CH_3$ |
| SH | H | H | 1 | H | Cl |
| Cl | H | H | 1 | H | Cl |
| SH | $CH_3$ | H | 1 | H | Cl |
| Cl | $CH_3$ | H | 1 | H | Cl |
| SH | Cl | H | 1 | H | Cl |
| Cl | Cl | H | 1 | H | Cl |
| SH | $CH_3$ | $CH_3$ | 1 | H | Cl |
| Cl | $CH_3$ | $CH_3$ | 1 | H | Cl |
| SH | Cl | Cl | 1 | H | Cl |
| Cl | Cl | Cl | 1 | H | Cl |
| SH | H | H | 2 | H | Cl |
| Cl | H | H | 2 | H | Cl |
| SH | $CH_3$ | H | 2 | H | Cl |
| Cl | $CH_3$ | H | 2 | H | Cl |
| SH | Cl | H | 2 | H | Cl |
| Cl | Cl | H | 2 | H | Cl |
| SH | $CH_3$ | $CH_3$ | 2 | H | Cl |
| Cl | $CH_3$ | $CH_3$ | 2 | H | Cl |
| SH | Cl | Cl | 2 | H | Cl |
| Cl | Cl | Cl | 2 | H | Cl |
| SH | H | H | 1 | $CH_3$ | Cl |
| Cl | H | H | 1 | $CH_3$ | Cl |
| SH | $CH_3$ | H | 1 | $CH_3$ | Cl |
| Cl | $CH_3$ | H | 1 | $CH_3$ | Cl |
| SH | Cl | H | 1 | $CH_3$ | Cl |
| Cl | Cl | H | 1 | $CH_3$ | Cl |
| SH | $CH_3$ | $CH_3$ | 1 | $CH_3$ | Cl |
| Cl | $CH_3$ | $CH_3$ | 1 | $CH_3$ | Cl |
| SH | Cl | Cl | 1 | $CH_3$ | Cl |
| Cl | Cl | Cl | 1 | $CH_3$ | Cl |
| SH | H | H | 2 | $CH_3$ | Cl |
| Cl | H | H | 2 | $CH_3$ | Cl |
| SH | $CH_3$ | H | 2 | $CH_3$ | Cl |
| Cl | $CH_3$ | H | 2 | $CH_3$ | Cl |
| SH | $CH_3$ | $CH_3$ | 2 | $CH_3$ | Cl |
| Cl | $CH_3$ | $CH_3$ | 2 | $CH_3$ | Cl |
| SH | Cl | Cl | 2 | $CH_3$ | Cl |
| Cl | Cl | Cl | 2 | $CH_3$ | Cl |
| SH | H | H | 1 | $CH_2CH_3$ | Cl |
| Cl | H | H | 1 | $CH_2CH_3$ | Cl |
| SH | $CH_3$ | H | 1 | $CH_2CH_3$ | Cl |
| Cl | $CH_3$ | H | 1 | $CH_2CH_3$ | Cl |
| SH | Cl | H | 1 | $CH_2CH_3$ | Cl |
| Cl | Cl | H | 1 | $CH_2CH_3$ | Cl |
| SH | $CH_3$ | $CH_3$ | 1 | $CH_2CH_3$ | Cl |
| Cl | $CH_3$ | $CH_3$ | 1 | $CH_2CH_3$ | Cl |
| SH | Cl | Cl | 1 | $CH_2CH_3$ | Cl |
| Cl | Cl | Cl | 1 | $CH_2CH_3$ | Cl |
| SH | H | H | 2 | $CH_2CH_3$ | Cl |
| Cl | H | H | 2 | $CH_2CH_3$ | Cl |
| SH | $CH_3$ | H | 2 | $CH_2CH_3$ | Cl |
| Cl | $CH_3$ | H | 2 | $CH_2CH_3$ | Cl |

TABLE 6-continued

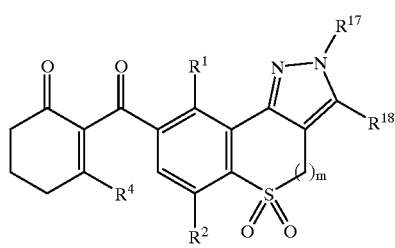

| R⁴ | R¹ | R² | m | R¹⁷ | R¹⁸ |
|---|---|---|---|---|---|
| SH | Cl | H | 2 | CH₂CH₃ | Cl |
| Cl | Cl | H | 2 | CH₂CH₃ | Cl |
| SH | CH₃ | CH₃ | 2 | CH₂CH₃ | Cl |
| Cl | CH₃ | CH₃ | 2 | CH₂CH₃ | Cl |
| SH | Cl | Cl | 2 | CH₂CH₃ | Cl |
| Cl | Cl | Cl | 2 | CH₂CH₃ | Cl |
| SH | H | H | 1 | CH₂CH₂CH₃ | Cl |
| Cl | H | H | 1 | CH₂CH₂CH₃ | Cl |
| SH | CH₃ | H | 1 | CH₂CH₂CH₃ | Cl |
| Cl | CH₃ | H | 1 | CH₂CH₂CH₃ | Cl |
| SH | Cl | H | 1 | CH₂CH₂CH₃ | Cl |
| Cl | Cl | H | 1 | CH₂CH₂CH₃ | Cl |
| SH | CH₃ | CH₃ | 1 | CH₂CH₂CH₃ | Cl |
| Cl | CH₃ | CH₃ | 1 | CH₂CH₂CH₃ | Cl |
| SH | Cl | Cl | 1 | CH₂CH₂CH₃ | Cl |
| Cl | Cl | Cl | 1 | CH₂CH₂CH₃ | Cl |
| SH | H | H | 2 | CH₂CH₂CH₃ | Cl |
| Cl | H | H | 2 | CH₂CH₂CH₃ | Cl |
| SH | CH₃ | H | 2 | CH₂CH₂CH₃ | Cl |
| Cl | CH₃ | H | 2 | CH₂CH₂CH₃ | Cl |
| SH | Cl | H | 2 | CH₂CH₂CH₃ | Cl |
| Cl | Cl | H | 2 | CH₂CH₂CH₃ | Cl |
| SH | CH₃ | CH₃ | 2 | CH₂CH₂CH₃ | Cl |
| Cl | CH₃ | CH₃ | 2 | CH₂CH₂CH₃ | Cl |
| SH | Cl | Cl | 2 | CH₂CH₂CH₃ | Cl |
| Cl | Cl | Cl | 2 | CH₂CH₂CH₃ | Cl |

TABLE 7

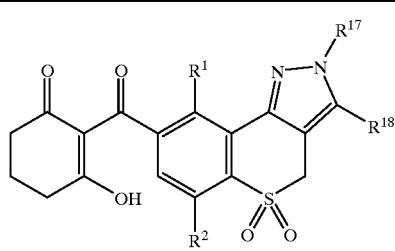

| R¹ | R² | R¹⁷ | R¹⁸ |
|---|---|---|---|
| H | H | CH(CH₃)₂ | H |
| CH₃ | H | CH(CH₃)₂ | H |
| Cl | H | CH(CH₃)₂ | H |
| CH₃ | CH₃ | CH(CH₃)₂ | H |
| Cl | Cl | CH(CH₃)₂ | H |
| H | H | phenyl | H |
| CH₃ | H | phenyl | H |
| Cl | H | phenyl | H |
| CH₃ | CH₃ | phenyl | H |
| Cl | Cl | phenyl | H |
| H | H | (4-CH₃)Ph | H |
| CH₃ | H | (4-CH₃)Ph | H |
| Cl | H | (4-CH₃)Ph | H |
| CH₃ | CH₃ | (4-CH₃)Ph | H |
| Cl | Cl | (4-CH₃)Ph | H |
| H | H | (4-Cl)Ph | H |
| CH₃ | H | (4-Cl)Ph | H |
| Cl | H | (4-Cl)Ph | H |

TABLE 7-continued

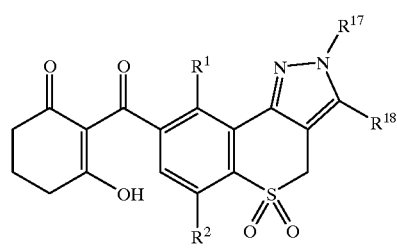

| R¹ | R² | R¹⁷ | R¹⁸ |
|---|---|---|---|
| CH₃ | CH₃ | (4-Cl)Ph | H |
| Cl | Cl | (4-Cl)Ph | H |
| H | H | (4-NO₂)Ph | H |
| CH₃ | H | (4-NO₂)Ph | H |
| Cl | H | (4-NO₂)Ph | H |
| CH₃ | CH₃ | (4-NO₂)Ph | H |
| Cl | Cl | (4-NO₂)Ph | H |
| H | H | (4-CN)Ph | H |
| CH₃ | H | (4-CN)Ph | H |
| Cl | H | (4-CN)Ph | H |
| CH₃ | CH₃ | (4-CN)Ph | H |
| Cl | Cl | (4-CN)Ph | H |
| H | H | 2-pyridyl | H |
| CH₃ | H | 2-pyridyl | H |
| Cl | H | 2-pyridyl | H |
| CH₃ | CH₃ | 2-pyridyl | H |
| Cl | Cl | 2-pyridyl | H |
| H | H | 4-pyridyl | H |
| CH₃ | H | 4-pyridyl | H |
| Cl | H | 4-pyridyl | H |
| CH₃ | CH₃ | 4-pyridyl | H |
| Cl | Cl | 4-pyridyl | H |
| H | H | CH₂CF₃ | H |
| CH₃ | H | CH₂CF₃ | H |
| Cl | H | CH₂CF₃ | H |
| CH₃ | CH₃ | CH₂CF₃ | H |
| Cl | Cl | CH₂CF₃ | H |
| H | H | CH(CH₃)₂ | Cl |
| CH₃ | H | CH(CH₃)₂ | Cl |
| Cl | H | CH(CH₃)₂ | Cl |
| CH₃ | CH₃ | CH(CH₃)₂ | Cl |
| Cl | Cl | CH(CH₃)₂ | Cl |
| H | H | phenyl | Cl |
| CH₃ | H | phenyl | Cl |
| Cl | H | phenyl | Cl |
| CH₃ | CH₃ | phenyl | Cl |
| Cl | Cl | phenyl | Cl |
| H | H | (4-CH₃)Ph | Cl |
| CH₃ | H | (4-CH₃)Ph | Cl |
| Cl | H | (4-CH₃)Ph | Cl |
| CH₃ | CH₃ | (4-CH₃)Ph | Cl |
| Cl | Cl | (4-CH₃)Ph | Cl |
| H | H | (4-Cl)Ph | Cl |
| CH₃ | H | (4-Cl)Ph | Cl |
| Cl | H | (4-Cl)Ph | Cl |
| CH₃ | CH₃ | (4-Cl)Ph | Cl |
| Cl | Cl | (4-Cl)Ph | Cl |
| H | H | (4-NO₂)Ph | Cl |
| CH₃ | H | (4-NO₂)Ph | Cl |
| Cl | H | (4-NO₂)Ph | Cl |
| CH₃ | CH₃ | (4-NO₂)Ph | Cl |
| Cl | Cl | (4-NO₂)Ph | Cl |
| H | H | (4-CN)Ph | Cl |
| CH₃ | H | (4-CN)Ph | Cl |
| Cl | H | (4-CN)Ph | Cl |
| CH₃ | CH₃ | (4-CN)Ph | Cl |
| Cl | Cl | (4-CN)Ph | Cl |
| H | H | 2-pyridyl | Cl |
| CH₃ | H | 2-pyridyl | Cl |
| Cl | H | 2-pyridyl | Cl |
| CH₃ | CH₃ | 2-pyridyl | Cl |
| Cl | Cl | 2-pyridyl | Cl |
| H | H | 4-pyridyl | Cl |
| CH₃ | H | 4-pyridyl | Cl |

TABLE 7-continued

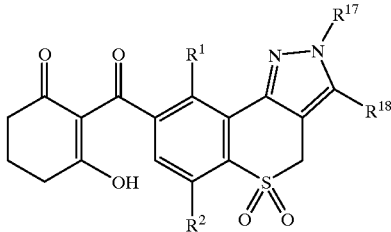

| R¹ | R² | R¹⁷ | R¹⁸ |
|---|---|---|---|
| Cl | H | 4-pyridyl | Cl |
| CH₃ | CH₃ | 4-pyridyl | Cl |
| Cl | Cl | 4-pyridyl | Cl |
| H | H | CH₂CF₃ | Cl |
| CH₃ | H | CH₂CF₃ | Cl |
| Cl | H | CH₂CF₃ | Cl |
| CH₃ | CH₃ | CH₂CF₃ | Cl |
| Cl | Cl | CH₂CF₃ | Cl |
| H | H | CH(CH₃)₂ | CH₃ |
| CH₃ | H | CH(CH₃)₂ | CH₃ |
| Cl | H | CH(CH₃)₂ | CH₃ |
| CH₃ | CH₃ | CH(CH₃)₂ | CH₃ |
| Cl | Cl | CH(CH₃)₂ | CH₃ |
| H | H | phenyl | CH₃ |
| CH₃ | H | phenyl | CH₃ |
| Cl | H | phenyl | CH₃ |
| CH₃ | CH₃ | phenyl | CH₃ |
| Cl | Cl | phenyl | CH₃ |
| H | H | (4-CH₃)Ph | CH₃ |
| CH₃ | H | (4-CH₃)Ph | CH₃ |
| Cl | H | (4-CH₃)Ph | CH₃ |
| CH₃ | CH₃ | (4-CH₃)Ph | CH₃ |
| Cl | Cl | (4-CH₃)Ph | CH₃ |
| H | H | (4-Cl)Ph | CH₃ |
| CH₃ | H | (4-Cl)Ph | CH₃ |
| Cl | H | (4-Cl)Ph | CH₃ |
| CH₃ | CH₃ | (4-Cl)Ph | CH₃ |
| Cl | Cl | (4-Cl)Ph | CH₃ |
| H | H | (4-NO₂)Ph | CH₃ |
| CH₃ | H | (4-NO₂)Ph | CH₃ |
| Cl | H | (4-NO₂)Ph | CH₃ |
| CH₃ | CH₃ | (4-NO₂)Ph | CH₃ |
| Cl | Cl | (4-NO₂)Ph | CH₃ |
| H | H | (4-CN)Ph | CH₃ |
| CH₃ | H | (4-CN)Ph | CH₃ |
| Cl | H | (4-CN)Ph | CH₃ |
| CH₃ | CH₃ | (4-CN)Ph | CH₃ |
| Cl | Cl | (4-CN)Ph | CH₃ |
| H | H | 2-pyridyl | CH₃ |
| CH₃ | H | 2-pyridyl | CH₃ |
| Cl | H | 2-pyridyl | CH₃ |
| CH₃ | CH₃ | 2-pyridyl | CH₃ |
| Cl | Cl | 2-pyridyl | CH₃ |
| H | H | 4-pyridyl | CH₃ |
| CH₃ | H | 4-pyridyl | CH₃ |
| Cl | H | 4-pyridyl | CH₃ |
| CH₃ | CH₃ | 4-pyridyl | CH₃ |
| Cl | Cl | 4-pyridyl | CH₃ |
| H | H | CH₂CF₃ | CH₃ |
| CH₃ | H | CH₂CF₃ | CH₃ |
| Cl | H | CH₂CF₃ | CH₃ |
| CH₃ | CH₃ | CH₂CF₃ | CH₃ |
| Cl | Cl | CH₂CF₃ | CH₃ |

TABLE 8

| R⁴ | R¹ | R² | R¹⁷ | R¹⁸ |
|---|---|---|---|---|
| OH | CH₂CH₃ | H | H | H |
| SH | CH₂CH₃ | H | H | H |
| Cl | CH₂CH₃ | H | H | H |
| OH | NO₂ | H | H | H |
| SH | NO₂ | H | H | H |
| Cl | NO₂ | H | H | H |
| OH | OCH₃ | H | H | H |
| SH | OCH₃ | H | H | H |
| Cl | OCH₃ | H | H | H |
| OH | CH₂CH₃ | CH₃ | H | H |
| SH | CH₂CH₃ | CH₃ | H | H |
| Cl | CH₂CH₃ | CH₃ | H | H |
| OH | NO₂ | CH₃ | H | H |
| SH | NO₂ | CH₃ | H | H |
| Cl | NO₂ | CH₃ | H | H |
| OH | OCH₃ | CH₃ | H | H |
| SH | OCH₃ | CH₃ | H | H |
| Cl | OCH₃ | CH₃ | H | H |
| OH | CH₂CH₃ | Cl | H | H |
| SH | CH₂CH₃ | Cl | H | H |
| Cl | CH₂CH₃ | Cl | H | H |
| OH | NO₂ | Cl | H | H |
| SH | NO₂ | Cl | H | H |
| Cl | NO₂ | Cl | H | H |
| OH | OCH₃ | Cl | H | H |
| SH | OCH₃ | Cl | H | H |
| Cl | OCH₃ | Cl | H | H |
| OH | CH₂CH₃ | H | CH₃ | H |
| SH | CH₂CH₃ | H | CH₃ | H |
| Cl | CH₂CH₃ | H | CH₃ | H |
| OH | NO₂ | H | CH₃ | H |
| SH | NO₂ | H | CH₃ | H |
| Cl | NO₂ | H | CH₃ | H |
| OH | OCH₃ | H | CH₃ | H |
| SH | OCH₃ | H | CH₃ | H |
| Cl | OCH₃ | H | CH₃ | H |
| OH | CH₂CH₃ | CH₃ | CH₃ | H |
| SH | CH₂CH₃ | CH₃ | CH₃ | H |
| Cl | CH₂CH₃ | CH₃ | CH₃ | H |
| OH | NO₂ | CH₃ | CH₃ | H |
| SH | NO₂ | CH₃ | CH₃ | H |
| Cl | NO₂ | CH₃ | CH₃ | H |
| OH | OCH₃ | CH₃ | CH₃ | H |
| SH | OCH₃ | CH₃ | CH₃ | H |
| Cl | OCH₃ | CH₃ | CH₃ | H |
| OH | CH₂CH₃ | Cl | CH₃ | H |
| SH | CH₂CH₃ | Cl | CH₃ | H |
| Cl | CH₂CH₃ | Cl | CH₃ | H |
| OH | NO₂ | Cl | CH₃ | H |
| SH | NO₂ | Cl | CH₃ | H |
| Cl | NO₂ | Cl | CH₃ | H |
| OH | OCH₃ | Cl | CH₃ | H |
| SH | OCH₃ | Cl | CH₃ | H |
| Cl | OCH₃ | Cl | CH₃ | H |
| OH | CH₂CH₃ | H | CH₂CH₃ | H |
| SH | CH₂CH₃ | H | CH₂CH₃ | H |
| Cl | CH₂CH₃ | H | CH₂CH₃ | H |
| OH | NO₂ | H | CH₂CH₃ | H |
| SH | NO₂ | H | CH₂CH₃ | H |
| Cl | NO₂ | H | CH₂CH₃ | H |
| OH | OCH₃ | H | CH₂CH₃ | H |
| SH | OCH₃ | H | CH₂CH₃ | H |
| Cl | OCH₃ | H | CH₂CH₃ | H |
| OH | CH₂CH₃ | CH₃ | CH₂CH₃ | H |

TABLE 8-continued

| R⁴ | R¹ | R² | R¹⁷ | R¹⁸ |
|---|---|---|---|---|
| SH | CH₂CH₃ | CH₃ | CH₂CH₃ | H |
| Cl | CH₂CH₃ | CH₃ | CH₂CH₃ | H |
| OH | NO₂ | CH₃ | CH₂CH₃ | H |
| SH | NO₂ | CH₃ | CH₂CH₃ | H |
| Cl | NO₂ | CH₃ | CH₂CH₃ | H |
| OH | OCH₃ | CH₃ | CH₂CH₃ | H |
| SH | OCH₃ | CH₃ | CH₂CH₃ | H |
| Cl | OCH₃ | CH₃ | CH₂CH₃ | H |
| OH | CH₂CH₃ | Cl | CH₂CH₃ | H |
| SH | CH₂CH₃ | Cl | CH₂CH₃ | H |
| Cl | CH₂CH₃ | Cl | CH₂CH₃ | H |
| OH | NO₂ | Cl | CH₂CH₃ | H |
| SH | NO₂ | Cl | CH₂CH₃ | H |
| Cl | NO₂ | Cl | CH₂CH₃ | H |
| OH | OCH₃ | Cl | CH₂CH₃ | H |
| SH | OCH₃ | Cl | CH₂CH₃ | H |
| Cl | OCH₃ | Cl | CH₂CH₃ | H |
| OH | CH₂CH₃ | H | CH₂CH₂CH₃ | H |
| SH | CH₂CH₃ | H | CH₂CH₂CH₃ | H |
| Cl | CH₂CH₃ | H | CH₂CH₂CH₃ | H |
| OH | NO₂ | H | CH₂CH₂CH₃ | H |
| SH | NO₂ | H | CH₂CH₂CH₃ | H |
| Cl | NO₂ | H | CH₂CH₂CH₃ | H |
| OH | OCH₃ | H | CH₂CH₂CH₃ | H |
| SH | OCH₃ | H | CH₂CH₂CH₃ | H |
| Cl | OCH₃ | H | CH₂CH₂CH₃ | H |
| OH | CH₂CH₃ | CH₃ | CH₂CH₂CH₃ | H |
| SH | CH₂CH₃ | CH₃ | CH₂CH₂CH₃ | H |
| Cl | CH₂CH₃ | CH₃ | CH₂CH₂CH₃ | H |
| OH | NO₂ | CH₃ | CH₂CH₂CH₃ | H |
| SH | NO₂ | CH₃ | CH₂CH₂CH₃ | H |
| Cl | NO₂ | CH₃ | CH₂CH₂CH₃ | H |
| OH | OCH₃ | CH₃ | CH₂CH₂CH₃ | H |
| SH | OCH₃ | CH₃ | CH₂CH₂CH₃ | H |
| Cl | OCH₃ | CH₃ | CH₂CH₂CH₃ | H |
| OH | CH₂CH₃ | Cl | CH₂CH₂CH₃ | H |
| SH | CH₂CH₃ | Cl | CH₂CH₂CH₃ | H |
| Cl | CH₂CH₃ | Cl | CH₂CH₂CH₃ | H |
| OH | NO₂ | Cl | CH₂CH₂CH₃ | H |
| SH | NO₂ | Cl | CH₂CH₂CH₃ | H |
| Cl | NO₂ | Cl | CH₂CH₂CH₃ | H |
| OH | OCH₃ | Cl | CH₂CH₂CH₃ | H |
| SH | OCH₃ | Cl | CH₂CH₂CH₃ | H |
| Cl | OCH₃ | Cl | CH₂CH₂CH₃ | H |
| OH | CH₂CH₃ | H | H | CH₃ |
| SH | CH₂CH₃ | H | H | CH₃ |
| Cl | CH₂CH₃ | H | H | CH₃ |
| OH | NO₂ | H | H | CH₃ |
| SH | NO₂ | H | H | CH₃ |
| Cl | NO₂ | H | H | CH₃ |
| OH | OCH₃ | H | H | CH₃ |
| SH | OCH₃ | H | H | CH₃ |
| Cl | OCH₃ | H | H | CH₃ |
| OH | CH₂CH₃ | CH₃ | H | CH₃ |
| SH | CH₂CH₃ | CH₃ | H | CH₃ |
| Cl | CH₂CH₃ | CH₃ | H | CH₃ |
| OH | NO₂ | CH₃ | H | CH₃ |
| SH | NO₂ | CH₃ | H | CH₃ |
| Cl | NO₂ | CH₃ | H | CH₃ |
| OH | OCH₃ | CH₃ | H | CH₃ |
| SH | OCH₃ | CH₃ | H | CH₃ |
| Cl | OCH₃ | CH₃ | H | CH₃ |
| OH | CH₂CH₃ | Cl | H | CH₃ |
| SH | CH₂CH₃ | Cl | H | CH₃ |
| Cl | CH₂CH₃ | Cl | H | CH₃ |
| OH | NO₂ | Cl | H | CH₃ |
| SH | NO₂ | Cl | H | CH₃ |
| Cl | NO₂ | Cl | H | CH₃ |
| OH | OCH₃ | Cl | H | CH₃ |
| SH | OCH₃ | Cl | H | CH₃ |
| Cl | OCH₃ | Cl | H | CH₃ |
| OH | CH₂CH₃ | H | CH₃ | CH₃ |
| SH | CH₂CH₃ | H | CH₃ | CH₃ |
| Cl | CH₂CH₃ | H | CH₃ | CH₃ |
| OH | NO₂ | H | CH₃ | CH₃ |
| SH | NO₂ | H | CH₃ | CH₃ |
| Cl | NO₂ | H | CH₃ | CH₃ |
| OH | OCH₃ | H | CH₃ | CH₃ |
| SH | OCH₃ | H | CH₃ | CH₃ |
| Cl | OCH₃ | H | CH₃ | CH₃ |
| OH | CH₂CH₃ | CH₃ | CH₃ | CH₃ |
| SH | CH₂CH₃ | CH₃ | CH₃ | CH₃ |
| Cl | CH₂CH₃ | CH₃ | CH₃ | CH₃ |
| OH | NO₂ | CH₃ | CH₃ | CH₃ |
| SH | NO₂ | CH₃ | CH₃ | CH₃ |
| Cl | NO₂ | CH₃ | CH₃ | CH₃ |
| OH | OCH₃ | CH₃ | CH₃ | CH₃ |
| SH | OCH₃ | CH₃ | CH₃ | CH₃ |
| Cl | OCH₃ | CH₃ | CH₃ | CH₃ |
| OH | CH₂CH₃ | Cl | CH₃ | CH₃ |
| SH | CH₂CH₃ | Cl | CH₃ | CH₃ |
| Cl | CH₂CH₃ | Cl | CH₃ | CH₃ |
| OH | NO₂ | Cl | CH₃ | CH₃ |
| SH | NO₂ | Cl | CH₃ | CH₃ |
| Cl | NO₂ | Cl | CH₃ | CH₃ |
| OH | OCH₃ | Cl | CH₃ | CH₃ |
| SH | OCH₃ | Cl | CH₃ | CH₃ |
| Cl | OCH₃ | Cl | CH₃ | CH₃ |
| OH | CH₂CH₃ | H | CH₂CH₃ | CH₃ |
| SH | CH₂CH₃ | H | CH₂CH₃ | CH₃ |
| Cl | CH₂CH₃ | H | CH₂CH₃ | CH₃ |
| OH | NO₂ | H | CH₂CH₃ | CH₃ |
| SH | NO₂ | H | CH₂CH₃ | CH₃ |
| Cl | NO₂ | H | CH₂CH₃ | CH₃ |
| OH | OCH₃ | H | CH₂CH₃ | CH₃ |
| SH | OCH₃ | H | CH₂CH₃ | CH₃ |
| Cl | OCH₃ | H | CH₂CH₃ | CH₃ |
| OH | CH₂CH₃ | CH₃ | CH₂CH₃ | CH₃ |
| SH | CH₂CH₃ | CH₃ | CH₂CH₃ | CH₃ |
| Cl | CH₂CH₃ | CH₃ | CH₂CH₃ | CH₃ |
| OH | NO₂ | CH₃ | CH₂CH₃ | CH₃ |
| SH | NO₂ | CH₃ | CH₂CH₃ | CH₃ |
| Cl | NO₂ | CH₃ | CH₂CH₃ | CH₃ |
| OH | OCH₃ | CH₃ | CH₂CH₃ | CH₃ |
| SH | OCH₃ | CH₃ | CH₂CH₃ | CH₃ |
| Cl | OCH₃ | CH₃ | CH₂CH₃ | CH₃ |
| OH | CH₂CH₃ | Cl | CH₂CH₃ | CH₃ |
| SH | CH₂CH₃ | Cl | CH₂CH₃ | CH₃ |
| Cl | CH₂CH₃ | Cl | CH₂CH₃ | CH₃ |
| OH | NO₂ | Cl | CH₂CH₃ | CH₃ |
| SH | NO₂ | Cl | CH₂CH₃ | CH₃ |
| Cl | NO₂ | Cl | CH₂CH₃ | CH₃ |
| OH | OCH₃ | Cl | CH₂CH₃ | CH₃ |
| SH | OCH₃ | Cl | CH₂CH₃ | CH₃ |
| Cl | OCH₃ | Cl | CH₂CH₃ | CH₃ |
| OH | CH₂CH₃ | H | CH₂CH₂CH₃ | CH₃ |
| SH | CH₂CH₃ | H | CH₂CH₂CH₃ | CH₃ |
| Cl | CH₂CH₃ | H | CH₂CH₂CH₃ | CH₃ |

TABLE 8-continued

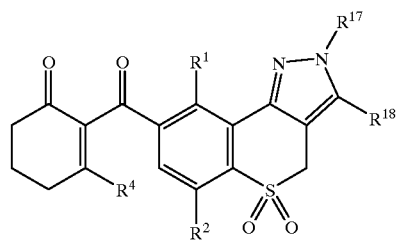

| R⁴ | R¹ | R² | R¹⁷ | R¹⁸ |
|---|---|---|---|---|
| OH | NO₂ | H | CH₂CH₂CH₃ | CH₃ |
| SH | NO₂ | H | CH₂CH₂CH₃ | CH₃ |
| Cl | NO₂ | H | CH₂CH₂CH₃ | CH₃ |
| OH | OCH₃ | H | CH₂CH₂CH₃ | CH₃ |
| SH | OCH₃ | H | CH₂CH₂CH₃ | CH₃ |
| Cl | OCH₃ | H | CH₂CH₂CH₃ | CH₃ |
| OH | CH₂CH₃ | CH₃ | CH₂CH₂CH₃ | CH₃ |
| SH | CH₂CH₃ | CH₃ | CH₂CH₂CH₃ | CH₃ |
| Cl | CH₂CH₃ | CH₃ | CH₂CH₂CH₃ | CH₃ |
| OH | NO₂ | CH₃ | CH₂CH₂CH₃ | CH₃ |
| SH | NO₂ | CH₃ | CH₂CH₂CH₃ | CH₃ |
| Cl | NO₂ | CH₃ | CH₂CH₂CH₃ | CH₃ |
| OH | OCH₃ | CH₃ | CH₂CH₂CH₃ | CH₃ |
| SH | OCH₃ | CH₃ | CH₂CH₂CH₃ | CH₃ |
| Cl | OCH₃ | CH₃ | CH₂CH₂CH₃ | CH₃ |
| OH | CH₂CH₃ | Cl | CH₂CH₂CH₃ | CH₃ |
| SH | CH₂CH₃ | Cl | CH₂CH₂CH₃ | CH₃ |
| Cl | CH₂CH₃ | Cl | CH₂CH₂CH₃ | CH₃ |
| OH | NO₂ | Cl | CH₂CH₂CH₃ | CH₃ |
| SH | NO₂ | Cl | CH₂CH₂CH₃ | CH₃ |
| Cl | NO₂ | Cl | CH₂CH₂CH₃ | CH₃ |
| OH | OCH₃ | Cl | CH₂CH₂CH₃ | CH₃ |
| SH | OCH₃ | Cl | CH₂CH₂CH₃ | CH₃ |
| Cl | OCH₃ | Cl | CH₂CH₂CH₃ | CH₃ |
| OH | CH₂CH₃ | H | H | Cl |
| SH | CH₂CH₃ | H | H | Cl |
| Cl | CH₂CH₃ | H | H | Cl |
| OH | NO₂ | H | H | Cl |
| SH | NO₂ | H | H | Cl |
| Cl | NO₂ | H | H | Cl |
| OH | OCH₃ | H | H | Cl |
| SH | OCH₃ | H | H | Cl |
| Cl | OCH₃ | H | H | Cl |
| OH | CH₂CH₃ | CH₃ | H | Cl |
| SH | CH₂CH₃ | CH₃ | H | Cl |
| Cl | CH₂CH₃ | CH₃ | H | Cl |
| OH | NO₂ | CH₃ | H | Cl |
| SH | NO₂ | CH₃ | H | Cl |
| Cl | NO₂ | CH₃ | H | Cl |
| OH | OCH₃ | CH₃ | H | Cl |
| SH | OCH₃ | CH₃ | H | Cl |
| Cl | OCH₃ | CH₃ | H | Cl |
| OH | CH₂CH₃ | Cl | H | Cl |
| SH | CH₂CH₃ | Cl | H | Cl |
| Cl | CH₂CH₃ | Cl | H | Cl |
| OH | NO₂ | Cl | H | Cl |
| SH | NO₂ | Cl | H | Cl |
| Cl | NO₂ | Cl | H | Cl |
| OH | OCH₃ | Cl | H | Cl |
| SH | OCH₃ | Cl | H | Cl |
| Cl | OCH₃ | Cl | H | Cl |
| OH | CH₂CH₃ | H | CH₃ | Cl |
| SH | CH₂CH₃ | H | CH₃ | Cl |
| Cl | CH₂CH₃ | H | CH₃ | Cl |
| OH | NO₂ | H | CH₃ | Cl |
| SH | NO₂ | H | CH₃ | Cl |
| Cl | NO₂ | H | CH₃ | Cl |
| OH | OCH₃ | H | CH₃ | Cl |
| SH | OCH₃ | H | CH₃ | Cl |
| Cl | OCH₃ | H | CH₃ | Cl |
| OH | CH₂CH₃ | CH₃ | CH₃ | Cl |
| SH | CH₂CH₃ | CH₃ | CH₃ | Cl |
| Cl | CH₂CH₃ | CH₃ | CH₃ | Cl |
| OH | NO₂ | CH₃ | CH₃ | Cl |

TABLE 8-continued

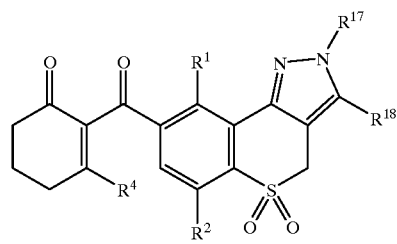

| R⁴ | R¹ | R² | R¹⁷ | R¹⁸ |
|---|---|---|---|---|
| SH | NO₂ | CH₃ | CH₃ | Cl |
| Cl | NO₂ | CH₃ | CH₃ | Cl |
| OH | OCH₃ | CH₃ | CH₃ | Cl |
| SH | OCH₃ | CH₃ | CH₃ | Cl |
| Cl | OCH₃ | CH₃ | CH₃ | Cl |
| OH | CH₂CH₃ | Cl | CH₃ | Cl |
| SH | CH₂CH₃ | Cl | CH₃ | Cl |
| Cl | CH₂CH₃ | Cl | CH₃ | Cl |
| OH | NO₂ | Cl | CH₃ | Cl |
| SH | NO₂ | Cl | CH₃ | Cl |
| Cl | NO₂ | Cl | CH₃ | Cl |
| OH | OCH₃ | Cl | CH₃ | Cl |
| SH | OCH₃ | Cl | CH₃ | Cl |
| Cl | OCH₃ | Cl | CH₃ | Cl |
| OH | CH₂CH₃ | H | CH₂CH₃ | Cl |
| SH | CH₂CH₃ | H | CH₂CH₃ | Cl |
| Cl | CH₂CH₃ | H | CH₂CH₃ | Cl |
| OH | NO₂ | H | CH₂CH₃ | Cl |
| SH | NO₂ | H | CH₂CH₃ | Cl |
| Cl | NO₂ | H | CH₂CH₃ | Cl |
| OH | OCH₃ | H | CH₂CH₃ | Cl |
| SH | OCH₃ | H | CH₂CH₃ | Cl |
| Cl | OCH₃ | H | CH₂CH₃ | Cl |
| OH | CH₂CH₃ | CH₃ | CH₂CH₃ | Cl |
| SH | CH₂CH₃ | CH₃ | CH₂CH₃ | Cl |
| Cl | CH₂CH₃ | CH₃ | CH₂CH₃ | Cl |
| OH | NO₂ | CH₃ | CH₂CH₃ | Cl |
| SH | NO₂ | CH₃ | CH₂CH₃ | Cl |
| Cl | NO₂ | CH₃ | CH₂CH₃ | Cl |
| OH | OCH₃ | CH₃ | CH₂CH₃ | Cl |
| SH | OCH₃ | CH₃ | CH₂CH₃ | Cl |
| Cl | OCH₃ | CH₃ | CH₂CH₃ | Cl |
| OH | CH₂CH₃ | Cl | CH₂CH₃ | Cl |
| SH | CH₂CH₃ | Cl | CH₂CH₃ | Cl |
| Cl | CH₂CH₃ | Cl | CH₂CH₃ | Cl |
| OH | NO₂ | Cl | CH₂CH₃ | Cl |
| SH | NO₂ | Cl | CH₂CH₃ | Cl |
| Cl | NO₂ | Cl | CH₂CH₃ | Cl |
| OH | OCH₃ | Cl | CH₂CH₃ | Cl |
| SH | OCH₃ | Cl | CH₂CH₃ | Cl |
| Cl | OCH₃ | Cl | CH₂CH₃ | Cl |
| OH | CH₂CH₃ | H | CH₂CH₂CH₃ | Cl |
| SH | CH₂CH₃ | H | CH₂CH₂CH₃ | Cl |
| Cl | CH₂CH₃ | H | CH₂CH₂CH₃ | Cl |
| OH | NO₂ | H | CH₂CH₂CH₃ | Cl |
| SH | NO₂ | H | CH₂CH₂CH₃ | Cl |
| Cl | NO₂ | H | CH₂CH₂CH₃ | Cl |
| OH | OCH₃ | H | CH₂CH₂CH₃ | Cl |
| SH | OCH₃ | H | CH₂CH₂CH₃ | Cl |
| Cl | OCH₃ | H | CH₂CH₂CH₃ | Cl |
| OH | CH₂CH₃ | CH₃ | CH₂CH₂CH₃ | Cl |
| SH | CH₂CH₃ | CH₃ | CH₂CH₂CH₃ | Cl |
| Cl | CH₂CH₃ | CH₃ | CH₂CH₂CH₃ | Cl |
| OH | NO₂ | CH₃ | CH₂CH₂CH₃ | Cl |
| SH | NO₂ | CH₃ | CH₂CH₂CH₃ | Cl |
| Cl | NO₂ | CH₃ | CH₂CH₂CH₃ | Cl |
| OH | OCH₃ | CH₃ | CH₂CH₂CH₃ | Cl |
| SH | OCH₃ | CH₃ | CH₂CH₂CH₃ | Cl |
| Cl | OCH₃ | CH₃ | CH₂CH₂CH₃ | Cl |
| OH | CH₂CH₃ | Cl | CH₂CH₂CH₃ | Cl |
| SH | CH₂CH₃ | Cl | CH₂CH₂CH₃ | Cl |
| Cl | CH₂CH₃ | Cl | CH₂CH₂CH₃ | Cl |
| OH | NO₂ | Cl | CH₂CH₂CH₃ | Cl |
| SH | NO₂ | Cl | CH₂CH₂CH₃ | Cl |

TABLE 8-continued

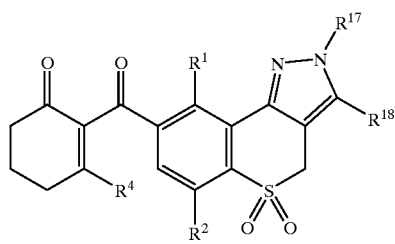

| R⁴ | R¹ | R² | R¹⁷ | R¹⁸ |
|---|---|---|---|---|
| Cl | NO₂ | Cl | CH₂CH₂CH₃ | Cl |
| OH | OCH₃ | Cl | CH₂CH₂CH₃ | Cl |
| SH | OCH₃ | Cl | CH₂CH₂CH₃ | Cl |
| Cl | OCH₃ | Cl | CH₂CH₂CH₃ | Cl |

TABLE 9

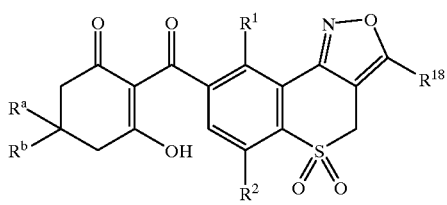

| Rᵃ | Rᵇ | R¹ | R² | R¹⁸ |
|---|---|---|---|---|
| H | H | H | H | H |
| CH₃ | H | H | H | H |
| CH₃ | CH₃ | H | H | H |
| H | H | CH₃ | H | H |
| CH₃ | H | CH₃ | H | H |
| CH₃ | CH₃ | CH₃ | H | H |
| H | H | Cl | H | H |
| CH₃ | H | Cl | H | H |
| CH₃ | CH₃ | Cl | H | H |
| H | H | H | CH₃ | H |
| CH₃ | H | H | CH₃ | H |
| CH₃ | CH₃ | H | CH₃ | H |
| H | H | CH₃ | CH₃ | H |
| CH₃ | H | CH₃ | CH₃ | H |
| CH₃ | CH₃ | CH₃ | CH₃ | H |
| H | H | Cl | CH₃ | H |
| CH₃ | H | Cl | CH₃ | H |
| CH₃ | CH₃ | Cl | CH₃ | H |
| H | H | H | Cl | H |
| CH₃ | H | H | Cl | H |
| CH₃ | CH₃ | H | Cl | H |
| H | H | CH₃ | Cl | H |
| CH₃ | H | CH₃ | Cl | H |
| CH₃ | CH₃ | CH₃ | Cl | H |
| H | H | Cl | Cl | H |
| CH₃ | H | Cl | Cl | H |
| CH₃ | CH₃ | Cl | Cl | H |
| H | H | H | H | CH₃ |
| CH₃ | H | H | H | CH₃ |
| CH₃ | CH₃ | H | H | CH₃ |
| H | H | CH₃ | H | CH₃ |
| CH₃ | H | CH₃ | H | CH₃ |
| CH₃ | CH₃ | CH₃ | H | CH₃ |
| H | H | Cl | H | CH₃ |
| CH₃ | H | Cl | H | CH₃ |
| CH₃ | CH₃ | Cl | H | CH₃ |
| H | H | H | CH₃ | CH₃ |
| CH₃ | H | H | CH₃ | CH₃ |
| CH₃ | CH₃ | H | CH₃ | CH₃ |
| H | H | CH₃ | CH₃ | CH₃ |
| CH₃ | H | CH₃ | CH₃ | CH₃ |
| CH₃ | CH₃ | CH₃ | CH₃ | CH₃ |

TABLE 9-continued

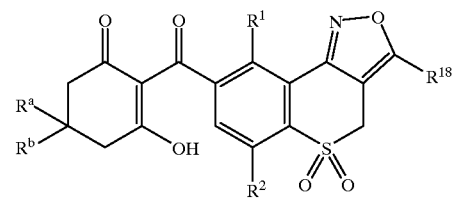

| Rᵃ | Rᵇ | R¹ | R² | R¹⁸ |
|---|---|---|---|---|
| H | H | Cl | CH₃ | CH₃ |
| CH₃ | H | Cl | CH₃ | CH₃ |
| CH₃ | CH₃ | Cl | CH₃ | CH₃ |
| H | H | H | Cl | CH₃ |
| CH₃ | H | H | Cl | CH₃ |
| CH₃ | CH₃ | H | Cl | CH₃ |
| H | H | CH₃ | Cl | CH₃ |
| CH₃ | H | CH₃ | Cl | CH₃ |
| CH₃ | CH₃ | CH₃ | Cl | CH₃ |
| H | H | Cl | Cl | CH₃ |
| CH₃ | H | Cl | Cl | CH₃ |
| CH₃ | CH₃ | Cl | Cl | CH₃ |
| H | H | H | H | Cl |
| CH₃ | H | H | H | Cl |
| CH₃ | CH₃ | H | H | Cl |
| H | H | CH₃ | H | Cl |
| CH₃ | H | CH₃ | H | Cl |
| CH₃ | CH₃ | CH₃ | H | Cl |
| H | H | Cl | H | Cl |
| CH₃ | H | Cl | H | Cl |
| CH₃ | CH₃ | Cl | H | Cl |
| H | H | H | CH₃ | Cl |
| CH₃ | H | H | CH₃ | Cl |
| CH₃ | CH₃ | H | CH₃ | Cl |
| H | H | CH₃ | CH₃ | Cl |
| CH₃ | H | CH₃ | CH₃ | Cl |
| CH₃ | CH₃ | CH₃ | CH₃ | Cl |
| H | H | Cl | CH₃ | Cl |
| CH₃ | H | Cl | CH₃ | Cl |
| CH₃ | CH₃ | Cl | CH₃ | Cl |
| H | H | H | Cl | Cl |
| CH₃ | H | H | Cl | Cl |
| CH₃ | CH₃ | H | Cl | Cl |
| H | H | CH₃ | Cl | Cl |
| CH₃ | H | CH₃ | Cl | Cl |
| CH₃ | CH₃ | CH₃ | Cl | Cl |
| H | H | Cl | Cl | Cl |
| CH₃ | H | Cl | Cl | Cl |
| CH₃ | CH₃ | Cl | Cl | Cl |

TABLE 10

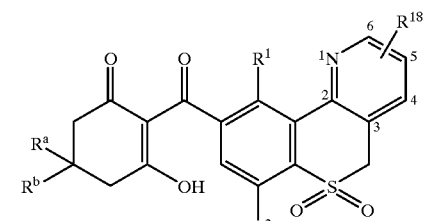

| Rᵃ | Rᵇ | R¹ | R² | R¹⁸ |
|---|---|---|---|---|
| H | H | H | H | H |
| CH₃ | H | H | H | H |
| CH₃ | CH₃ | H | H | H |
| H | H | CH₃ | H | H |
| CH₃ | H | CH₃ | H | H |
| CH₃ | CH₃ | CH₃ | H | H |
| H | H | Cl | H | H |

TABLE 10-continued

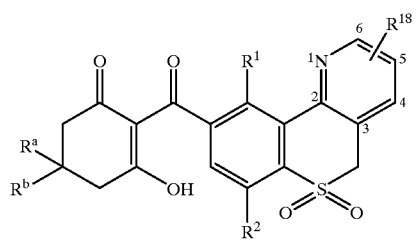

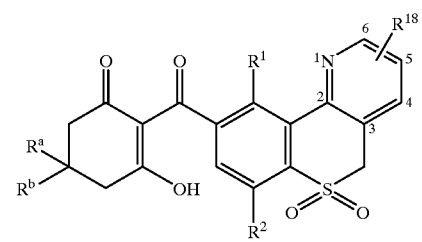

| $R^a$ | $R^b$ | $R^1$ | $R^2$ | $R^{18}$ |
|---|---|---|---|---|
| CH$_3$ | H | Cl | H | H |
| CH$_3$ | CH$_3$ | Cl | H | H |
| H | H | H | CH$_3$ | H |
| CH$_3$ | H | H | CH$_3$ | H |
| CH$_3$ | CH$_3$ | H | CH$_3$ | H |
| H | H | CH$_3$ | CH$_3$ | H |
| CH$_3$ | H | CH$_3$ | CH$_3$ | H |
| CH$_3$ | CH$_3$ | CH$_3$ | CH$_3$ | H |
| H | H | Cl | CH$_3$ | H |
| CH$_3$ | H | Cl | CH$_3$ | H |
| CH$_3$ | CH$_3$ | Cl | CH$_3$ | H |
| H | H | H | Cl | H |
| CH$_3$ | H | H | Cl | H |
| CH$_3$ | CH$_3$ | H | Cl | H |
| H | H | CH$_3$ | Cl | H |
| CH$_3$ | H | CH$_3$ | Cl | H |
| CH$_3$ | CH$_3$ | CH$_3$ | Cl | H |
| H | H | Cl | Cl | H |
| CH$_3$ | H | Cl | Cl | H |
| CH$_3$ | CH$_3$ | Cl | Cl | H |
| H | H | H | H | 6-CH$_3$ |
| CH$_3$ | H | H | H | 6-CH$_3$ |
| CH$_3$ | CH$_3$ | H | H | 6-CH$_3$ |
| H | H | CH$_3$ | H | 6-CH$_3$ |
| CH$_3$ | H | CH$_3$ | H | 6-CH$_3$ |
| CH$_3$ | CH$_3$ | CH$_3$ | H | 6-CH$_3$ |
| H | H | Cl | H | 6-CH$_3$ |
| CH$_3$ | H | Cl | H | 6-CH$_3$ |
| CH$_3$ | CH$_3$ | Cl | H | 6-CH$_3$ |
| H | H | H | CH$_3$ | 6-CH$_3$ |
| CH$_3$ | H | H | CH$_3$ | 6-CH$_3$ |
| CH$_3$ | CH$_3$ | H | CH$_3$ | 6-CH$_3$ |
| H | H | CH$_3$ | CH$_3$ | 6-CH$_3$ |
| CH$_3$ | H | CH$_3$ | CH$_3$ | 6-CH$_3$ |
| CH$_3$ | CH$_3$ | CH$_3$ | CH$_3$ | 6-CH$_3$ |
| H | H | Cl | CH$_3$ | 6-CH$_3$ |
| CH$_3$ | H | Cl | CH$_3$ | 6-CH$_3$ |
| CH$_3$ | CH$_3$ | Cl | CH$_3$ | 6-CH$_3$ |
| H | H | H | Cl | 6-CH$_3$ |
| CH$_3$ | H | H | Cl | 6-CH$_3$ |
| CH$_3$ | CH$_3$ | H | Cl | 6-CH$_3$ |
| H | H | CH$_3$ | Cl | 6-CH$_3$ |
| CH$_3$ | H | CH$_3$ | Cl | 6-CH$_3$ |
| CH$_3$ | CH$_3$ | CH$_3$ | Cl | 6-CH$_3$ |
| H | H | Cl | Cl | 6-CH$_3$ |
| CH$_3$ | H | Cl | Cl | 6-CH$_3$ |
| CH$_3$ | CH$_3$ | Cl | Cl | 6-CH$_3$ |
| H | H | H | H | 5-CH$_3$ |
| CH$_3$ | H | H | H | 5-CH$_3$ |
| CH$_3$ | CH$_3$ | H | H | 5-CH$_3$ |
| H | H | CH$_3$ | H | 5-CH$_3$ |
| CH$_3$ | H | CH$_3$ | H | 5-CH$_3$ |
| CH$_3$ | CH$_3$ | CH$_3$ | H | 5-CH$_3$ |
| H | H | Cl | H | 5-CH$_3$ |
| CH$_3$ | H | Cl | H | 5-CH$_3$ |
| CH$_3$ | CH$_3$ | Cl | H | 5-CH$_3$ |
| H | H | H | CH$_3$ | 5-CH$_3$ |
| CH$_3$ | H | H | CH$_3$ | 5-CH$_3$ |
| CH$_3$ | CH$_3$ | H | CH$_3$ | 5-CH$_3$ |
| H | H | CH$_3$ | CH$_3$ | 5-CH$_3$ |
| CH$_3$ | H | CH$_3$ | CH$_3$ | 5-CH$_3$ |
| CH$_3$ | CH$_3$ | CH$_3$ | CH$_3$ | 5-CH$_3$ |
| H | H | Cl | CH$_3$ | 5-CH$_3$ |
| CH$_3$ | H | Cl | CH$_3$ | 5-CH$_3$ |
| CH$_3$ | CH$_3$ | Cl | CH$_3$ | 5-CH$_3$ |
| H | H | H | Cl | 5-CH$_3$ |
| CH$_3$ | H | H | Cl | 5-CH$_3$ |
| CH$_3$ | CH$_3$ | H | Cl | 5-CH$_3$ |
| H | H | CH$_3$ | Cl | 5-CH$_3$ |
| CH$_3$ | H | CH$_3$ | Cl | 5-CH$_3$ |
| CH$_3$ | CH$_3$ | CH$_3$ | Cl | 5-CH$_3$ |
| H | H | Cl | Cl | 5-CH$_3$ |
| CH$_3$ | H | Cl | Cl | 5-CH$_3$ |
| CH$_3$ | CH$_3$ | Cl | Cl | 5-CH$_3$ |
| H | H | H | H | 4-CH$_3$ |
| CH$_3$ | H | H | H | 4-CH$_3$ |
| CH$_3$ | CH$_3$ | H | H | 4-CH$_3$ |
| H | H | CH$_3$ | H | 4-CH$_3$ |
| CH$_3$ | H | CH$_3$ | H | 4-CH$_3$ |
| CH$_3$ | CH$_3$ | CH$_3$ | H | 4-CH$_3$ |
| H | H | Cl | H | 4-CH$_3$ |
| CH$_3$ | H | Cl | H | 4-CH$_3$ |
| CH$_3$ | CH$_3$ | Cl | H | 4-CH$_3$ |
| H | H | H | CH$_3$ | 4-CH$_3$ |
| CH$_3$ | H | H | CH$_3$ | 4-CH$_3$ |
| CH$_3$ | CH$_3$ | H | CH$_3$ | 4-CH$_3$ |
| H | H | CH$_3$ | CH$_3$ | 4-CH$_3$ |
| CH$_3$ | H | CH$_3$ | CH$_3$ | 4-CH$_3$ |
| CH$_3$ | CH$_3$ | CH$_3$ | CH$_3$ | 4-CH$_3$ |
| H | H | Cl | CH$_3$ | 4-CH$_3$ |
| CH$_3$ | H | Cl | CH$_3$ | 4-CH$_3$ |
| CH$_3$ | CH$_3$ | Cl | CH$_3$ | 4-CH$_3$ |
| H | H | H | Cl | 4-CH$_3$ |
| CH$_3$ | H | H | Cl | 4-CH$_3$ |
| CH$_3$ | CH$_3$ | H | Cl | 4-CH$_3$ |
| H | H | CH$_3$ | Cl | 4-CH$_3$ |
| CH$_3$ | H | CH$_3$ | Cl | 4-CH$_3$ |
| CH$_3$ | CH$_3$ | CH$_3$ | Cl | 4-CH$_3$ |
| H | H | Cl | Cl | 4-CH$_3$ |
| CH$_3$ | H | Cl | Cl | 4-CH$_3$ |
| CH$_3$ | CH$_3$ | Cl | Cl | 4-CH$_3$ |
| H | H | H | H | 6-Cl |
| CH$_3$ | H | H | H | 6-Cl |
| CH$_3$ | CH$_3$ | H | H | 6-Cl |
| H | H | CH$_3$ | H | 6-Cl |
| CH$_3$ | H | CH$_3$ | H | 6-Cl |
| CH$_3$ | CH$_3$ | CH$_3$ | H | 6-Cl |
| H | H | Cl | H | 6-Cl |
| CH$_3$ | H | Cl | H | 6-Cl |
| CH$_3$ | CH$_3$ | Cl | H | 6-Cl |
| H | H | H | CH$_3$ | 6-Cl |
| CH$_3$ | H | H | CH$_3$ | 6-Cl |
| CH$_3$ | CH$_3$ | H | CH$_3$ | 6-Cl |
| H | H | CH$_3$ | CH$_3$ | 6-Cl |
| CH$_3$ | H | CH$_3$ | CH$_3$ | 6-Cl |
| CH$_3$ | CH$_3$ | CH$_3$ | CH$_3$ | 6-Cl |
| H | H | Cl | CH$_3$ | 6-Cl |
| CH$_3$ | H | Cl | CH$_3$ | 6-Cl |
| CH$_3$ | CH$_3$ | Cl | CH$_3$ | 6-Cl |
| H | H | H | Cl | 6-Cl |
| CH$_3$ | H | H | Cl | 6-Cl |
| CH$_3$ | CH$_3$ | H | Cl | 6-Cl |
| H | H | CH$_3$ | Cl | 6-Cl |
| CH$_3$ | H | CH$_3$ | Cl | 6-Cl |
| CH$_3$ | CH$_3$ | CH$_3$ | Cl | 6-Cl |
| H | H | Cl | Cl | 6-Cl |
| CH$_3$ | H | Cl | Cl | 6-Cl |
| CH$_3$ | CH$_3$ | Cl | Cl | 6-Cl |

TABLE 10-continued

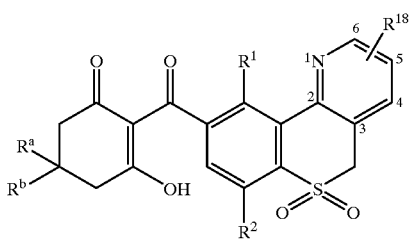

| $R^a$ | $R^b$ | $R^1$ | $R^2$ | $R^{18}$ |
|---|---|---|---|---|
| H | H | H | H | 4-Cl |
| $CH_3$ | H | H | H | 4-Cl |
| $CH_3$ | $CH_3$ | H | H | 4-Cl |
| H | H | $CH_3$ | H | 4-Cl |
| $CH_3$ | H | $CH_3$ | H | 4-Cl |
| $CH_3$ | $CH_3$ | $CH_3$ | H | 4-Cl |
| H | H | Cl | H | 4-Cl |
| $CH_3$ | H | Cl | H | 4-Cl |
| $CH_3$ | $CH_3$ | Cl | H | 4-Cl |
| H | H | H | $CH_3$ | 4-Cl |
| $CH_3$ | H | H | $CH_3$ | 4-Cl |
| $CH_3$ | $CH_3$ | H | $CH_3$ | 4-Cl |
| H | H | $CH_3$ | $CH_3$ | 4-Cl |
| $CH_3$ | H | $CH_3$ | $CH_3$ | 4-Cl |
| $CH_3$ | $CH_3$ | $CH_3$ | $CH_3$ | 4-Cl |
| H | H | Cl | $CH_3$ | 4-Cl |
| $CH_3$ | H | Cl | $CH_3$ | 4-Cl |
| $CH_3$ | $CH_3$ | Cl | $CH_3$ | 4-Cl |
| H | H | H | Cl | 4-Cl |
| $CH_3$ | H | H | Cl | 4-Cl |
| $CH_3$ | $CH_3$ | H | Cl | 4-Cl |
| H | H | $CH_3$ | Cl | 4-Cl |
| $CH_3$ | H | $CH_3$ | Cl | 4-Cl |
| $CH_3$ | $CH_3$ | $CH_3$ | Cl | 4-Cl |
| H | H | Cl | Cl | 4-Cl |
| $CH_3$ | H | Cl | Cl | 4-Cl |
| $CH_3$ | $CH_3$ | Cl | Cl | 4-Cl |

TABLE 11

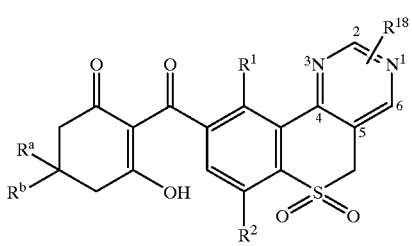

| $R^a$ | $R^b$ | $R^1$ | $R^2$ | $R^{18}$ |
|---|---|---|---|---|
| H | H | H | H | H |
| $CH_3$ | H | H | H | H |
| $CH_3$ | $CH_3$ | H | H | H |
| H | H | $CH_3$ | H | H |
| $CH_3$ | H | $CH_3$ | H | H |
| $CH_3$ | $CH_3$ | $CH_3$ | H | H |
| H | H | Cl | H | H |
| $CH_3$ | H | Cl | H | H |
| $CH_3$ | $CH_3$ | Cl | H | H |
| H | H | H | $CH_3$ | H |
| $CH_3$ | H | H | $CH_3$ | H |
| $CH_3$ | $CH_3$ | H | $CH_3$ | H |
| H | H | $CH_3$ | $CH_3$ | H |
| $CH_3$ | H | $CH_3$ | $CH_3$ | H |
| $CH_3$ | $CH_3$ | $CH_3$ | $CH_3$ | H |
| H | H | Cl | $CH_3$ | H |
| $CH_3$ | H | Cl | $CH_3$ | H |
| $CH_3$ | $CH_3$ | Cl | $CH_3$ | H |

TABLE 11-continued

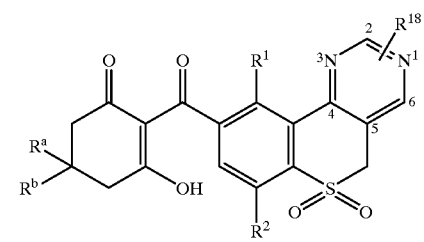

| $R^a$ | $R^b$ | $R^1$ | $R^2$ | $R^{18}$ |
|---|---|---|---|---|
| H | H | H | Cl | H |
| $CH_3$ | H | H | Cl | H |
| $CH_3$ | $CH_3$ | H | Cl | H |
| H | H | $CH_3$ | Cl | H |
| $CH_3$ | H | $CH_3$ | Cl | H |
| $CH_3$ | $CH_3$ | $CH_3$ | Cl | H |
| H | H | Cl | Cl | H |
| $CH_3$ | H | Cl | Cl | H |
| $CH_3$ | $CH_3$ | Cl | Cl | H |
| H | H | H | H | 2-$CH_3$ |
| $CH_3$ | H | H | H | 2-$CH_3$ |
| $CH_3$ | $CH_3$ | H | H | 2-$CH_3$ |
| H | H | $CH_3$ | H | 2-$CH_3$ |
| $CH_3$ | H | $CH_3$ | H | 2-$CH_3$ |
| $CH_3$ | $CH_3$ | $CH_3$ | H | 2-$CH_3$ |
| H | H | Cl | H | 2-$CH_3$ |
| $CH_3$ | H | Cl | H | 2-$CH_3$ |
| $CH_3$ | $CH_3$ | Cl | H | 2-$CH_3$ |
| H | H | H | $CH_3$ | 2-$CH_3$ |
| $CH_3$ | H | H | $CH_3$ | 2-$CH_3$ |
| $CH_3$ | $CH_3$ | H | $CH_3$ | 2-$CH_3$ |
| H | H | $CH_3$ | $CH_3$ | 2-$CH_3$ |
| $CH_3$ | H | $CH_3$ | $CH_3$ | 2-$CH_3$ |
| $CH_3$ | $CH_3$ | $CH_3$ | $CH_3$ | 2-$CH_3$ |
| H | H | Cl | $CH_3$ | 2-$CH_3$ |
| $CH_3$ | H | Cl | $CH_3$ | 2-$CH_3$ |
| $CH_3$ | $CH_3$ | Cl | $CH_3$ | 2-$CH_3$ |
| H | H | H | Cl | 2-$CH_3$ |
| $CH_3$ | H | H | Cl | 2-$CH_3$ |
| $CH_3$ | $CH_3$ | H | Cl | 2-$CH_3$ |
| H | H | $CH_3$ | Cl | 2-$CH_3$ |
| $CH_3$ | H | $CH_3$ | Cl | 2-$CH_3$ |
| $CH_3$ | $CH_3$ | $CH_3$ | Cl | 2-$CH_3$ |
| H | H | Cl | Cl | 2-$CH_3$ |
| $CH_3$ | H | Cl | Cl | 2-$CH_3$ |
| $CH_3$ | $CH_3$ | Cl | Cl | 2-$CH_3$ |
| H | H | H | H | 6-$CH_3$ |
| $CH_3$ | H | H | H | 6-$CH_3$ |
| $CH_3$ | $CH_3$ | H | H | 6-$CH_3$ |
| H | H | $CH_3$ | H | 6-$CH_3$ |
| $CH_3$ | H | $CH_3$ | H | 6-$CH_3$ |
| $CH_3$ | $CH_3$ | $CH_3$ | H | 6-$CH_3$ |
| H | H | Cl | H | 6-$CH_3$ |
| $CH_3$ | H | Cl | H | 6-$CH_3$ |
| $CH_3$ | $CH_3$ | Cl | H | 6-$CH_3$ |
| H | H | H | $CH_3$ | 6-$CH_3$ |
| $CH_3$ | H | H | $CH_3$ | 6-$CH_3$ |
| $CH_3$ | $CH_3$ | H | $CH_3$ | 6-$CH_3$ |
| H | H | $CH_3$ | $CH_3$ | 6-$CH_3$ |
| $CH_3$ | H | $CH_3$ | $CH_3$ | 6-$CH_3$ |
| $CH_3$ | $CH_3$ | $CH_3$ | $CH_3$ | 6-$CH_3$ |
| H | H | Cl | $CH_3$ | 6-$CH_3$ |
| $CH_3$ | H | Cl | $CH_3$ | 6-$CH_3$ |
| $CH_3$ | $CH_3$ | Cl | $CH_3$ | 6-$CH_3$ |
| H | H | H | Cl | 6-$CH_3$ |
| $CH_3$ | H | H | Cl | 6-$CH_3$ |
| $CH_3$ | $CH_3$ | H | Cl | 6-$CH_3$ |
| H | H | $CH_3$ | Cl | 6-$CH_3$ |
| $CH_3$ | H | $CH_3$ | Cl | 6-$CH_3$ |
| $CH_3$ | $CH_3$ | $CH_3$ | Cl | 6-$CH_3$ |
| H | H | Cl | Cl | 6-$CH_3$ |
| $CH_3$ | H | Cl | Cl | 6-$CH_3$ |
| $CH_3$ | $CH_3$ | Cl | Cl | 6-$CH_3$ |
| H | H | H | H | 2-Cl |

TABLE 11-continued

| Rᵃ | Rᵇ | R¹ | R² | R¹⁸ |
|---|---|---|---|---|
| CH₃ | H | H | H | 2-Cl |
| CH₃ | CH₃ | H | H | 2-Cl |
| H | H | CH₃ | H | 2-Cl |
| CH₃ | H | CH₃ | H | 2-Cl |
| CH₃ | CH₃ | CH₃ | H | 2-Cl |
| H | H | Cl | H | 2-Cl |
| CH₃ | H | Cl | H | 2-Cl |
| CH₃ | CH₃ | Cl | H | 2-Cl |
| H | H | H | CH₃ | 2-Cl |
| CH₃ | H | H | CH₃ | 2-Cl |
| CH₃ | CH₃ | H | CH₃ | 2-Cl |
| H | H | CH₃ | CH₃ | 2-Cl |
| CH₃ | H | CH₃ | CH₃ | 2-Cl |
| CH₃ | CH₃ | CH₃ | CH₃ | 2-Cl |
| H | H | Cl | CH₃ | 2-Cl |
| CH₃ | H | Cl | CH₃ | 2-Cl |
| CH₃ | CH₃ | Cl | CH₃ | 2-Cl |
| H | H | H | Cl | 2-Cl |
| CH₃ | H | H | Cl | 2-Cl |
| CH₃ | CH₃ | H | Cl | 2-Cl |
| H | H | CH₃ | Cl | 2-Cl |
| CH₃ | H | CH₃ | Cl | 2-Cl |
| CH₃ | CH₃ | CH₃ | Cl | 2-Cl |
| H | H | Cl | Cl | 2-Cl |
| CH₃ | H | Cl | Cl | 2-Cl |
| CH₃ | CH₃ | Cl | Cl | 2-Cl |

TABLE 12

| Rᵃ | Rᵇ | R¹ | R² | m | R¹⁷ | R¹⁸ |
|---|---|---|---|---|---|---|
| CH₃ | CH₃ | H | H | 1 | H | H |
| H | CH₃CH₂ | H | H | 1 | H | H |
| CH₃ | CH₃ | CH₃ | H | 1 | H | H |
| H | CH₃CH₂ | CH₃ | H | 1 | H | H |
| CH₃ | CH₃ | Cl | H | 1 | H | H |
| H | CH₃CH₂ | Cl | H | 1 | H | H |
| CH₃ | CH₃ | H | CH₃ | 1 | H | H |
| H | CH₃CH₂ | H | CH₃ | 1 | H | H |
| CH₃ | CH₃ | CH₃ | CH₃ | 1 | H | H |
| H | CH₃CH₂ | CH₃ | CH₃ | 1 | H | H |
| CH₃ | CH₃ | Cl | CH₃ | 1 | H | H |
| H | CH₃CH₂ | Cl | CH₃ | 1 | H | H |
| CH₃ | CH₃ | H | Cl | 1 | H | H |
| H | CH₃CH₂ | H | Cl | 1 | H | H |
| CH₃ | CH₃ | CH₃ | Cl | 1 | H | H |
| H | CH₃CH₂ | CH₃ | Cl | 1 | H | H |
| CH₃ | CH₃ | Cl | Cl | 1 | H | H |
| H | CH₃CH₂ | Cl | Cl | 1 | H | H |

TABLE 12-continued

| Rᵃ | Rᵇ | R¹ | R² | m | R¹⁷ | R¹⁸ |
|---|---|---|---|---|---|---|
| CH₃ | CH₃ | H | H | 1 | CH₃ | H |
| H | CH₃CH₂ | H | H | 1 | CH₃ | H |
| CH₃ | CH₃ | CH₃ | H | 1 | CH₃ | H |
| H | CH₃CH₂ | CH₃ | H | 1 | CH₃ | H |
| CH₃ | CH₃ | Cl | H | 1 | CH₃ | H |
| H | CH₃CH₂ | Cl | H | 1 | CH₃ | H |
| CH₃ | CH₃ | H | CH₃ | 1 | CH₃ | H |
| H | CH₃CH₂ | H | CH₃ | 1 | CH₃ | H |
| CH₃ | CH₃ | CH₃ | CH₃ | 1 | CH₃ | H |
| H | CH₃CH₂ | CH₃ | CH₃ | 1 | CH₃ | H |
| CH₃ | CH₃ | Cl | CH₃ | 1 | CH₃ | H |
| H | CH₃CH₂ | Cl | CH₃ | 1 | CH₃ | H |
| CH₃ | CH₃ | H | Cl | 1 | CH₃ | H |
| H | CH₃CH₂ | H | Cl | 1 | CH₃ | H |
| CH₃ | CH₃ | CH₃ | Cl | 1 | CH₃ | H |
| H | CH₃CH₂ | CH₃ | Cl | 1 | CH₃ | H |
| CH₃ | CH₃ | Cl | Cl | 1 | CH₃ | H |
| H | CH₃CH₂ | Cl | Cl | 1 | CH₃ | H |
| CH₃ | CH₃ | H | H | 1 | CH₃CH₂ | H |
| H | CH₃CH₂ | H | H | 1 | CH₃CH₂ | H |
| CH₃ | CH₃ | CH₃ | H | 1 | CH₃CH₂ | H |
| H | CH₃CH₂ | CH₃ | H | 1 | CH₃CH₂ | H |
| CH₃ | CH₃ | Cl | H | 1 | CH₃CH₂ | H |
| H | CH₃CH₂ | Cl | H | 1 | CH₃CH₂ | H |
| CH₃ | CH₃ | H | CH₃ | 1 | CH₃CH₂ | H |
| H | CH₃CH₂ | H | CH₃ | 1 | CH₃CH₂ | H |
| CH₃ | CH₃ | CH₃ | CH₃ | 1 | CH₃CH₂ | H |
| H | CH₃CH₂ | CH₃ | CH₃ | 1 | CH₃CH₂ | H |
| CH₃ | CH₃ | Cl | CH₃ | 1 | CH₃CH₂ | H |
| H | CH₃CH₂ | Cl | CH₃ | 1 | CH₃CH₂ | H |
| CH₃ | CH₃ | H | Cl | 1 | CH₃CH₂ | H |
| H | CH₃CH₂ | H | Cl | 1 | CH₃CH₂ | H |
| CH₃ | CH₃ | CH₃ | Cl | 1 | CH₃CH₂ | H |
| H | CH₃CH₂ | CH₃ | Cl | 1 | CH₃CH₂ | H |
| CH₃ | CH₃ | Cl | Cl | 1 | CH₃CH₂ | H |
| H | CH₃CH₂ | Cl | Cl | 1 | CH₃CH₂ | H |
| CH₃ | CH₃ | H | H | 1 | CH₃CH₂CH₂ | H |
| H | CH₃CH₂ | H | H | 1 | CH₃CH₂CH₂ | H |
| CH₃ | CH₃ | CH₃ | H | 1 | CH₃CH₂CH₂ | H |
| H | CH₃CH₂ | CH₃ | H | 1 | CH₃CH₂CH₂ | H |
| CH₃ | CH₃ | Cl | H | 1 | CH₃CH₂CH₂ | H |
| H | CH₃CH₂ | Cl | H | 1 | CH₃CH₂CH₂ | H |
| CH₃ | CH₃ | H | CH₃ | 1 | CH₃CH₂CH₂ | H |
| H | CH₃CH₂ | H | CH₃ | 1 | CH₃CH₂CH₂ | H |
| CH₃ | CH₃ | CH₃ | CH₃ | 1 | CH₃CH₂CH₂ | H |
| H | CH₃CH₂ | CH₃ | CH₃ | 1 | CH₃CH₂CH₂ | H |
| CH₃ | CH₃ | Cl | CH₃ | 1 | CH₃CH₂CH₂ | H |
| H | CH₃CH₂ | Cl | CH₃ | 1 | CH₃CH₂CH₂ | H |
| CH₃ | CH₃ | H | Cl | 1 | CH₃CH₂CH₂ | H |
| H | CH₃CH₂ | H | Cl | 1 | CH₃CH₂CH₂ | H |
| CH₃ | CH₃ | CH₃ | Cl | 1 | CH₃CH₂CH₂ | H |
| H | CH₃CH₂ | CH₃ | Cl | 1 | CH₃CH₂CH₂ | H |
| CH₃ | CH₃ | Cl | Cl | 1 | CH₃CH₂CH₂ | H |
| H | CH₃CH₂ | Cl | Cl | 1 | CH₃CH₂CH₂ | H |
| CH₃ | CH₃ | H | H | 1 | H | CH₃ |
| H | CH₃CH₂ | H | H | 1 | H | CH₃ |
| CH₃ | CH₃ | CH₃ | H | 1 | H | CH₃ |
| H | CH₃CH₂ | CH₃ | H | 1 | H | CH₃ |
| CH₃ | CH₃ | Cl | H | 1 | H | CH₃ |
| H | CH₃CH₂ | Cl | H | 1 | H | CH₃ |
| CH₃ | CH₃ | H | CH₃ | 1 | H | CH₃ |
| H | CH₃CH₂ | H | CH₃ | 1 | H | CH₃ |
| CH₃ | CH₃ | CH₃ | CH₃ | 1 | H | CH₃ |
| H | CH₃CH₂ | CH₃ | CH₃ | 1 | H | CH₃ |

TABLE 12-continued

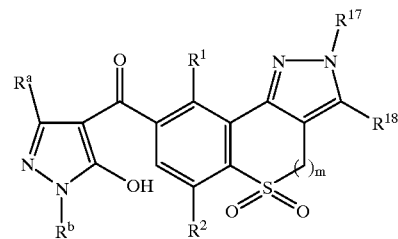

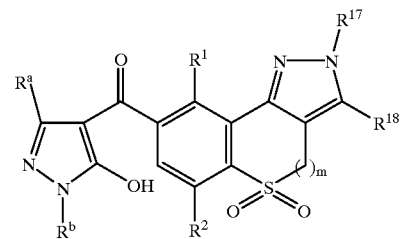

| $R^a$ | $R^b$ | $R^1$ | $R^2$ | m | $R^{17}$ | $R^{18}$ | | $R^a$ | $R^b$ | $R^1$ | $R^2$ | m | $R^{17}$ | $R^{18}$ |
|---|---|---|---|---|---|---|---|---|---|---|---|---|---|---|
| $CH_3$ | $CH_3$ | Cl | $CH_3$ | 1 | H | $CH_3$ | | $CH_3$ | $CH_3$ | $CH_3$ | H | 1 | H | Cl |
| H | $CH_3CH_2$ | Cl | $CH_3$ | 1 | H | $CH_3$ | | H | $CH_3CH_2$ | $CH_3$ | H | 1 | H | Cl |
| $CH_3$ | $CH_3$ | H | Cl | 1 | H | $CH_3$ | | $CH_3$ | $CH_3$ | Cl | H | 1 | H | Cl |
| H | $CH_3CH_2$ | H | Cl | 1 | H | $CH_3$ | | H | $CH_3CH_2$ | Cl | H | 1 | H | Cl |
| $CH_3$ | $CH_3$ | $CH_3$ | Cl | 1 | H | $CH_3$ | | $CH_3$ | $CH_3$ | H | $CH_3$ | 1 | H | Cl |
| H | $CH_3CH_2$ | $CH_3$ | Cl | 1 | H | $CH_3$ | | H | $CH_3CH_2$ | H | $CH_3$ | 1 | H | Cl |
| $CH_3$ | $CH_3$ | Cl | Cl | 1 | H | $CH_3$ | | $CH_3$ | $CH_3$ | $CH_3$ | $CH_3$ | 1 | H | Cl |
| H | $CH_3CH_2$ | Cl | Cl | 1 | H | $CH_3$ | | H | $CH_3CH_2$ | $CH_3$ | $CH_3$ | 1 | H | Cl |
| $CH_3$ | $CH_3$ | H | H | 1 | $CH_3$ | $CH_3$ | | $CH_3$ | $CH_3$ | Cl | $CH_3$ | 1 | H | Cl |
| H | $CH_3CH_2$ | H | H | 1 | $CH_3$ | $CH_3$ | | H | $CH_3CH_2$ | Cl | $CH_3$ | 1 | H | Cl |
| $CH_3$ | $CH_3$ | $CH_3$ | H | 1 | $CH_3$ | $CH_3$ | | $CH_3$ | $CH_3$ | H | Cl | 1 | H | Cl |
| H | $CH_3CH_2$ | $CH_3$ | H | 1 | $CH_3$ | $CH_3$ | | H | $CH_3CH_2$ | H | Cl | 1 | H | Cl |
| $CH_3$ | $CH_3$ | Cl | H | 1 | $CH_3$ | $CH_3$ | | $CH_3$ | $CH_3$ | $CH_3$ | Cl | 1 | H | Cl |
| H | $CH_3CH_2$ | Cl | H | 1 | $CH_3$ | $CH_3$ | | H | $CH_3CH_2$ | $CH_3$ | Cl | 1 | H | Cl |
| $CH_3$ | $CH_3$ | H | $CH_3$ | 1 | $CH_3$ | $CH_3$ | | $CH_3$ | $CH_3$ | Cl | Cl | 1 | H | Cl |
| H | $CH_3CH_2$ | H | $CH_3$ | 1 | $CH_3$ | $CH_3$ | | H | $CH_3CH_2$ | Cl | Cl | 1 | H | Cl |
| $CH_3$ | $CH_3$ | $CH_3$ | $CH_3$ | 1 | $CH_3$ | $CH_3$ | | $CH_3$ | $CH_3$ | H | H | 1 | $CH_3$ | Cl |
| H | $CH_3CH_2$ | $CH_3$ | $CH_3$ | 1 | $CH_3$ | $CH_3$ | | H | $CH_3CH_2$ | H | H | 1 | $CH_3$ | Cl |
| $CH_3$ | $CH_3$ | Cl | $CH_3$ | 1 | $CH_3$ | $CH_3$ | | $CH_3$ | $CH_3$ | $CH_3$ | H | 1 | $CH_3$ | Cl |
| H | $CH_3CH_2$ | Cl | $CH_3$ | 1 | $CH_3$ | $CH_3$ | | H | $CH_3CH_2$ | $CH_3$ | H | 1 | $CH_3$ | Cl |
| $CH_3$ | $CH_3$ | H | Cl | 1 | $CH_3$ | $CH_3$ | | $CH_3$ | $CH_3$ | Cl | H | 1 | $CH_3$ | Cl |
| H | $CH_3CH_2$ | H | Cl | 1 | $CH_3$ | $CH_3$ | | H | $CH_3CH_2$ | Cl | H | 1 | $CH_3$ | Cl |
| $CH_3$ | $CH_3$ | $CH_3$ | Cl | 1 | $CH_3$ | $CH_3$ | | $CH_3$ | $CH_3$ | H | $CH_3$ | 1 | $CH_3$ | Cl |
| H | $CH_3CH_2$ | $CH_3$ | Cl | 1 | $CH_3$ | $CH_3$ | | H | $CH_3CH_2$ | H | $CH_3$ | 1 | $CH_3$ | Cl |
| $CH_3$ | $CH_3$ | Cl | Cl | 1 | $CH_3$ | $CH_3$ | | $CH_3$ | $CH_3$ | $CH_3$ | $CH_3$ | 1 | $CH_3$ | Cl |
| H | $CH_3CH_2$ | Cl | Cl | 1 | $CH_3$ | $CH_3$ | | H | $CH_3CH_2$ | $CH_3$ | $CH_3$ | 1 | $CH_3$ | Cl |
| $CH_3$ | $CH_3$ | H | H | 1 | $CH_3CH_2$ | $CH_3$ | | $CH_3$ | $CH_3$ | Cl | $CH_3$ | 1 | $CH_3$ | Cl |
| H | $CH_3CH_2$ | H | H | 1 | $CH_3CH_2$ | $CH_3$ | | H | $CH_3CH_2$ | Cl | $CH_3$ | 1 | $CH_3$ | Cl |
| $CH_3$ | $CH_3$ | $CH_3$ | H | 1 | $CH_3CH_2$ | $CH_3$ | | $CH_3$ | $CH_3$ | H | Cl | 1 | $CH_3$ | Cl |
| H | $CH_3CH_2$ | $CH_3$ | H | 1 | $CH_3CH_2$ | $CH_3$ | | H | $CH_3CH_2$ | H | Cl | 1 | $CH_3$ | Cl |
| $CH_3$ | $CH_3$ | Cl | H | 1 | $CH_3CH_2$ | $CH_3$ | | $CH_3$ | $CH_3$ | $CH_3$ | Cl | 1 | $CH_3$ | Cl |
| H | $CH_3CH_2$ | Cl | H | 1 | $CH_3CH_2$ | $CH_3$ | | H | $CH_3CH_2$ | $CH_3$ | Cl | 1 | $CH_3$ | Cl |
| $CH_3$ | $CH_3$ | H | $CH_3$ | 1 | $CH_3CH_2$ | $CH_3$ | | $CH_3$ | $CH_3$ | Cl | Cl | 1 | $CH_3$ | Cl |
| H | $CH_3CH_2$ | H | $CH_3$ | 1 | $CH_3CH_2$ | $CH_3$ | | H | $CH_3CH_2$ | Cl | Cl | 1 | $CH_3$ | Cl |
| $CH_3$ | $CH_3$ | $CH_3$ | $CH_3$ | 1 | $CH_3CH_2$ | $CH_3$ | | $CH_3$ | $CH_3$ | H | H | 1 | $CH_3CH_2$ | Cl |
| H | $CH_3CH_2$ | $CH_3$ | $CH_3$ | 1 | $CH_3CH_2$ | $CH_3$ | | H | $CH_3CH_2$ | H | H | 1 | $CH_3CH_2$ | Cl |
| $CH_3$ | $CH_3$ | Cl | $CH_3$ | 1 | $CH_3CH_2$ | $CH_3$ | | $CH_3$ | $CH_3$ | $CH_3$ | H | 1 | $CH_3CH_2$ | Cl |
| H | $CH_3CH_2$ | Cl | $CH_3$ | 1 | $CH_3CH_2$ | $CH_3$ | | H | $CH_3CH_2$ | $CH_3$ | H | 1 | $CH_3CH_2$ | Cl |
| $CH_3$ | $CH_3$ | H | Cl | 1 | $CH_3CH_2$ | $CH_3$ | | $CH_3$ | $CH_3$ | Cl | H | 1 | $CH_3CH_2$ | Cl |
| H | $CH_3CH_2$ | H | Cl | 1 | $CH_3CH_2$ | $CH_3$ | | H | $CH_3CH_2$ | Cl | H | 1 | $CH_3CH_2$ | Cl |
| $CH_3$ | $CH_3$ | $CH_3$ | Cl | 1 | $CH_3CH_2$ | $CH_3$ | | $CH_3$ | $CH_3$ | H | $CH_3$ | 1 | $CH_3CH_2$ | Cl |
| H | $CH_3CH_2$ | $CH_3$ | Cl | 1 | $CH_3CH_2$ | $CH_3$ | | H | $CH_3CH_2$ | H | $CH_3$ | 1 | $CH_3CH_2$ | Cl |
| $CH_3$ | $CH_3$ | Cl | Cl | 1 | $CH_3CH_2$ | $CH_3$ | | $CH_3$ | $CH_3$ | $CH_3$ | $CH_3$ | 1 | $CH_3CH_2$ | Cl |
| H | $CH_3CH_2$ | Cl | Cl | 1 | $CH_3CH_2$ | $CH_3$ | | H | $CH_3CH_2$ | $CH_3$ | $CH_3$ | 1 | $CH_3CH_2$ | Cl |
| $CH_3$ | $CH_3$ | H | H | 1 | $CH_3CH_2CH_2$ | $CH_3$ | | $CH_3$ | $CH_3$ | Cl | $CH_3$ | 1 | $CH_3CH_2$ | Cl |
| H | $CH_3CH_2$ | H | H | 1 | $CH_3CH_2CH_2$ | $CH_3$ | | H | $CH_3CH_2$ | Cl | $CH_3$ | 1 | $CH_3CH_2$ | Cl |
| $CH_3$ | $CH_3$ | $CH_3$ | H | 1 | $CH_3CH_2CH_2$ | $CH_3$ | | $CH_3$ | $CH_3$ | H | Cl | 1 | $CH_3CH_2$ | Cl |
| H | $CH_3CH_2$ | $CH_3$ | H | 1 | $CH_3CH_2CH_2$ | $CH_3$ | | H | $CH_3CH_2$ | H | Cl | 1 | $CH_3CH_2$ | Cl |
| $CH_3$ | $CH_3$ | Cl | H | 1 | $CH_3CH_2CH_2$ | $CH_3$ | | $CH_3$ | $CH_3$ | $CH_3$ | Cl | 1 | $CH_3CH_2$ | Cl |
| H | $CH_3CH_2$ | Cl | H | 1 | $CH_3CH_2CH_2$ | $CH_3$ | | H | $CH_3CH_2$ | $CH_3$ | Cl | 1 | $CH_3CH_3$ | Cl |
| $CH_3$ | $CH_3$ | H | $CH_3$ | 1 | $CH_3CH_2CH_2$ | $CH_3$ | | $CH_3$ | $CH_3$ | Cl | Cl | 1 | $CH_3CH_2$ | Cl |
| H | $CH_3CH_2$ | H | $CH_3$ | 1 | $CH_3CH_2CH_2$ | $CH_3$ | | H | $CH_3CH_2$ | Cl | Cl | 1 | $CH_3CH_2$ | Cl |
| $CH_3$ | $CH_3$ | $CH_3$ | $CH_3$ | 1 | $CH_3CH_2CH_2$ | $CH_3$ | | $CH_3$ | $CH_3$ | H | H | 1 | $CH_3CH_2CH_2$ | Cl |
| H | $CH_3CH_2$ | $CH_3$ | $CH_3$ | 1 | $CH_3CH_2CH_2$ | $CH_3$ | | H | $CH_3CH_2$ | H | H | 1 | $CH_3CH_2CH_2$ | Cl |
| $CH_3$ | $CH_3$ | Cl | $CH_3$ | 1 | $CH_3CH_2CH_2$ | $CH_3$ | | $CH_3$ | $CH_3$ | $CH_3$ | H | 1 | $CH_3CH_2CH_2$ | Cl |
| H | $CH_3CH_2$ | Cl | $CH_3$ | 1 | $CH_3CH_2CH_2$ | $CH_3$ | | H | $CH_3CH_2$ | $CH_3$ | H | 1 | $CH_3CH_2CH_2$ | Cl |
| $CH_3$ | $CH_3$ | H | Cl | 1 | $CH_3CH_2CH_2$ | $CH_3$ | | $CH_3$ | $CH_3$ | Cl | H | 1 | $CH_3CH_2CH_2$ | Cl |
| H | $CH_3CH_2$ | H | Cl | 1 | $CH_3CH_2CH_2$ | $CH_3$ | | H | $CH_3CH_2$ | Cl | H | 1 | $CH_3CH_2CH_2$ | Cl |
| $CH_3$ | $CH_3$ | $CH_3$ | Cl | 1 | $CH_3CH_2CH_2$ | $CH_3$ | | $CH_3$ | $CH_3$ | H | $CH_3$ | 1 | $CH_3CH_2CH_2$ | Cl |
| H | $CH_3CH_2$ | $CH_3$ | Cl | 1 | $CH_3CH_2CH_2$ | $CH_3$ | | H | $CH_3CH_2$ | H | $CH_3$ | 1 | $CH_3CH_2CH_2$ | Cl |
| $CH_3$ | $CH_3$ | Cl | Cl | 1 | $CH_3CH_2CH_2$ | $CH_3$ | | $CH_3$ | $CH_3$ | $CH_3$ | $CH_3$ | 1 | $CH_3CH_2CH_2$ | Cl |
| H | $CH_3CH_2$ | Cl | Cl | 1 | $CH_3CH_2CH_2$ | $CH_3$ | | H | $CH_3CH_2$ | $CH_3$ | $CH_3$ | 1 | $CH_3CH_2CH_2$ | Cl |
| $CH_3$ | $CH_3$ | H | H | 1 | H | Cl | | $CH_3$ | $CH_3$ | Cl | $CH_3$ | 1 | $CH_3CH_2CH_2$ | Cl |
| H | $CH_3CH_2$ | H | H | 1 | H | Cl | | H | $CH_3CH_2$ | Cl | $CH_3$ | 1 | $CH_3CH_2CH_2$ | Cl |

TABLE 12-continued

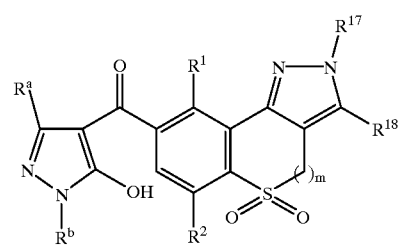

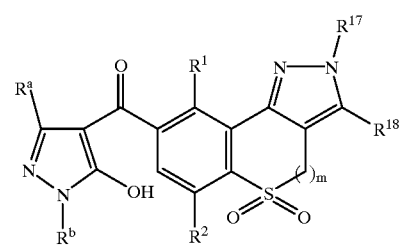

| $R^a$ | $R^b$ | $R^1$ | $R^2$ | m | $R^{17}$ | $R^{18}$ |
|---|---|---|---|---|---|---|
| CH₃ | CH₃ | H | Cl | 1 | CH₃CH₂CH₂ | Cl |
| H | CH₃CH₂ | H | Cl | 1 | CH₃CH₂CH₂ | Cl |
| CH₃ | CH₃ | CH₃ | Cl | 1 | CH₃CH₂CH₂ | Cl |
| H | CH₃CH₂ | CH₃ | Cl | 1 | CH₃CH₂CH₂ | Cl |
| CH₃ | CH₃ | Cl | Cl | 1 | CH₃CH₂CH₂ | Cl |
| H | CH₃CH₂ | Cl | Cl | 1 | CH₃CH₂CH₂ | Cl |
| H | CH₃ | H | H | 1 | H | H |
| H | CH₃ | CH₃ | H | 1 | H | H |
| H | CH₃ | Cl | H | 1 | H | H |
| H | CH₃ | H | CH₃ | 1 | H | H |
| H | CH₃ | CH₃ | CH₃ | 1 | H | H |
| H | CH₃ | Cl | CH₃ | 1 | H | H |
| H | CH₃ | H | Cl | 1 | H | H |
| H | CH₃ | CH₃ | Cl | 1 | H | H |
| H | CH₃ | Cl | Cl | 1 | H | H |
| H | CH₃ | H | H | 1 | CH₃ | H |
| H | CH₃ | CH₃ | H | 1 | CH₃ | H |
| H | CH₃ | Cl | H | 1 | CH₃ | H |
| H | CH₃ | H | CH₃ | 1 | CH₃ | H |
| H | CH₃ | CH₃ | CH₃ | 1 | CH₃ | H |
| H | CH₃ | Cl | CH₃ | 1 | CH₃ | H |
| H | CH₃ | H | Cl | 1 | CH₃ | H |
| H | CH₃ | CH₃ | Cl | 1 | CH₃ | H |
| H | CH₃ | Cl | Cl | 1 | CH₃ | H |
| H | CH₃ | H | H | 1 | CH₃CH₂ | H |
| H | CH₃ | CH₃ | H | 1 | CH₃CH₂ | H |
| H | CH₃ | Cl | H | 1 | CH₃CH₂ | H |
| H | CH₃ | H | CH₃ | 1 | CH₃CH₂ | H |
| H | CH₃ | CH₃ | CH₃ | 1 | CH₃CH₂ | H |
| H | CH₃ | Cl | CH₃ | 1 | CH₃CH₂ | H |
| H | CH₃ | H | Cl | 1 | CH₃CH₂ | H |
| H | CH₃ | CH₃ | Cl | 1 | CH₃CH₂ | H |
| H | CH₃ | Cl | Cl | 1 | CH₃CH₂ | H |
| H | CH₃ | H | H | 1 | CH₃CH₂CH₂ | H |
| H | CH₃ | CH₃ | H | 1 | CH₃CH₂CH₂ | H |
| H | CH₃ | Cl | H | 1 | CH₃CH₂CH₂ | H |
| H | CH₃ | H | CH₃ | 1 | CH₃CH₂CH₂ | H |
| H | CH₃ | CH₃ | CH₃ | 1 | CH₃CH₂CH₂ | H |
| H | CH₃ | Cl | CH₃ | 1 | CH₃CH₂CH₂ | H |
| H | CH₃ | H | Cl | 1 | CH₃CH₂CH₂ | H |
| H | CH₃ | CH₃ | Cl | 1 | CH₃CH₂CH₂ | H |
| H | CH₃ | Cl | Cl | 1 | CH₃CH₂CH₂ | H |
| H | CH₃ | H | H | 1 | H | CH₃ |
| H | CH₃ | CH₃ | H | 1 | H | CH₃ |
| H | CH₃ | Cl | H | 1 | H | CH₃ |
| H | CH₃ | H | CH₃ | 1 | H | CH₃ |
| H | CH₃ | CH₃ | CH₃ | 1 | H | CH₃ |
| H | CH₃ | Cl | CH₃ | 1 | H | CH₃ |
| H | CH₃ | H | Cl | 1 | H | CH₃ |
| H | CH₃ | CH₃ | Cl | 1 | H | CH₃ |
| H | CH₃ | Cl | Cl | 1 | H | CH₃ |
| H | CH₃ | H | H | 1 | CH₃ | CH₃ |
| H | CH₃ | CH₃ | H | 1 | CH₃ | CH₃ |
| H | CH₃ | Cl | H | 1 | CH₃ | CH₃ |
| H | CH₃ | H | CH₃ | 1 | CH₃ | CH₃ |
| H | CH₃ | CH₃ | CH₃ | 1 | CH₃ | CH₃ |
| H | CH₃ | Cl | CH₃ | 1 | CH₃ | CH₃ |
| H | CH₃ | H | Cl | 1 | CH₃ | CH₃ |
| H | CH₃ | CH₃ | Cl | 1 | CH₃ | CH₃ |
| H | CH₃ | Cl | Cl | 1 | CH₃ | CH₃ |
| H | CH₃ | H | H | 1 | CH₃CH₂ | CH₃ |
| H | CH₃ | CH₃ | H | 1 | CH₃CH₂ | CH₃ |
| H | CH₃ | Cl | H | 1 | CH₃CH₂ | CH₃ |
| H | CH₃ | H | CH₃ | 1 | CH₃CH₂ | CH₃ |
| H | CH₃ | CH₃ | CH₃ | 1 | CH₃CH₂ | CH₃ |
| H | CH₃ | Cl | CH₃ | 1 | CH₃CH₂ | CH₃ |
| H | CH₃ | H | Cl | 1 | CH₃CH₂ | CH₃ |
| H | CH₃ | CH₃ | Cl | 1 | CH₃CH₂ | CH₃ |
| H | CH₃ | Cl | Cl | 1 | CH₃CH₂ | CH₃ |
| H | CH₃ | H | H | 1 | CH₃CH₂CH₂ | CH₃ |
| H | CH₃ | CH₃ | H | 1 | CH₃CH₂CH₂ | CH₃ |
| H | CH₃ | Cl | H | 1 | CH₃CH₂CH₂ | CH₃ |
| H | CH₃ | H | CH₃ | 1 | CH₃CH₂CH₂ | CH₃ |
| H | CH₃ | CH₃ | CH₃ | 1 | CH₃CH₂CH₂ | CH₃ |
| H | CH₃ | Cl | CH₃ | 1 | CH₃CH₂CH₂ | CH₃ |
| H | CH₃ | H | Cl | 1 | CH₃CH₂CH₂ | CH₃ |
| H | CH₃ | CH₃ | Cl | 1 | CH₃CH₂CH₂ | CH₃ |
| H | CH₃ | Cl | Cl | 1 | CH₃CH₂CH₂ | CH₃ |
| H | CH₃ | H | H | 1 | H | Cl |
| H | CH₃ | CH₃ | H | 1 | H | Cl |
| H | CH₃ | Cl | H | 1 | H | Cl |
| H | CH₃ | H | CH₃ | 1 | H | Cl |
| H | CH₃ | CH₃ | CH₃ | 1 | H | Cl |
| H | CH₃ | Cl | CH₃ | 1 | H | Cl |
| H | CH₃ | H | Cl | 1 | H | Cl |
| H | CH₃ | CH₃ | Cl | 1 | H | Cl |
| H | CH₃ | Cl | Cl | 1 | H | Cl |
| H | CH₃ | H | H | 1 | CH₃ | Cl |
| H | CH₃ | CH₃ | H | 1 | CH₃ | Cl |
| H | CH₃ | Cl | H | 1 | CH₃ | Cl |
| H | CH₃ | H | CH₃ | 1 | CH₃ | Cl |
| H | CH₃ | CH₃ | CH₃ | 1 | CH₃ | Cl |
| H | CH₃ | Cl | CH₃ | 1 | CH₃ | Cl |
| H | CH₃ | H | Cl | 1 | CH₃ | Cl |
| H | CH₃ | CH₃ | Cl | 1 | CH₃ | Cl |
| H | CH₃ | Cl | Cl | 1 | CH₃ | Cl |
| H | CH₃ | H | H | 1 | CH₃CH₂ | Cl |
| H | CH₃ | CH₃ | H | 1 | CH₃CH₂ | Cl |
| H | CH₃ | Cl | H | 1 | CH₃CH₂ | Cl |
| H | CH₃ | H | CH₃ | 1 | CH₃CH₂ | Cl |
| H | CH₃ | CH₃ | CH₃ | 1 | CH₃CH₂ | Cl |
| H | CH₃ | Cl | CH₃ | 1 | CH₃CH₂ | Cl |
| H | CH₃ | H | Cl | 1 | CH₃CH₂ | Cl |
| H | CH₃ | CH₃ | Cl | 1 | CH₃CH₂ | Cl |
| H | CH₃ | Cl | Cl | 1 | CH₃CH₂ | Cl |
| H | CH₃ | H | H | 1 | CH₃CH₂CH₂ | Cl |
| H | CH₃ | CH₃ | H | 1 | CH₃CH₂CH₂ | Cl |
| H | CH₃ | Cl | H | 1 | CH₃CH₂CH₂ | Cl |
| H | CH₃ | H | CH₃ | 1 | CH₃CH₂CH₂ | Cl |
| H | CH₃ | CH₃ | CH₃ | 1 | CH₃CH₂CH₂ | Cl |
| H | CH₃ | Cl | CH₃ | 1 | CH₃CH₂CH₂ | Cl |
| H | CH₃ | H | Cl | 1 | CH₃CH₂CH₂ | Cl |
| H | CH₃ | CH₃ | Cl | 1 | CH₃CH₂CH₂ | Cl |
| H | CH₃ | Cl | Cl | 1 | CH₃CH₂CH₂ | Cl |
| H | CH₃CH₂ | H | H | 2 | H | H |
| H | CH₃CH₂ | CH₃ | H | 2 | H | H |
| H | CH₃CH₂ | Cl | H | 2 | H | H |
| H | CH₃CH₂ | H | CH₃ | 2 | H | H |
| H | CH₃CH₂ | CH₃ | CH₃ | 2 | H | H |
| H | CH₃CH₂ | Cl | CH₃ | 2 | H | H |
| H | CH₃CH₂ | H | Cl | 2 | H | H |
| H | CH₃CH₂ | CH₃ | Cl | 2 | H | H |
| H | CH₃CH₂ | Cl | Cl | 2 | H | H |
| H | CH₃CH₂ | H | H | 2 | CH₃ | H |
| H | CH₃CH₂ | CH₃ | H | 2 | CH₃ | H |
| H | CH₃CH₂ | Cl | H | 2 | CH₃ | H |
| H | CH₃CH₂ | H | CH₃ | 2 | CH₃ | H |
| H | CH₃CH₂ | CH₃ | CH₃ | 2 | CH₃ | H |

TABLE 12-continued

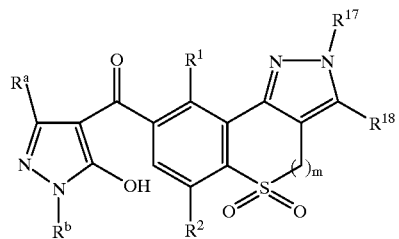

| Rᵃ | Rᵇ | R¹ | R² | m | R¹⁷ | R¹⁸ |
|---|---|---|---|---|---|---|
| H | CH₃CH₂ | Cl | CH₃ | 2 | CH₃ | H |
| H | CH₃CH₂ | H | Cl | 2 | CH₃ | H |
| H | CH₃CH₂ | CH₃ | Cl | 2 | CH₃ | H |
| H | CH₃CH₂ | Cl | Cl | 2 | CH₃ | H |
| H | CH₃CH₂ | H | H | 2 | CH₃CH₂ | H |
| H | CH₃CH₂ | CH₃ | H | 2 | CH₃CH₂ | H |
| H | CH₃CH₂ | Cl | H | 2 | CH₃CH₂ | H |
| H | CH₃CH₂ | H | CH₃ | 2 | CH₃CH₂ | H |
| H | CH₃CH₂ | CH₃ | CH₃ | 2 | CH₃CH₂ | H |
| H | CH₃CH₂ | Cl | CH₃ | 2 | CH₃CH₂ | H |
| H | CH₃CH₂ | H | Cl | 2 | CH₃CH₂ | H |
| H | CH₃CH₂ | CH₃ | Cl | 2 | CH₃CH₂ | H |
| H | CH₃CH₂ | Cl | Cl | 2 | CH₃CH₂ | H |
| H | CH₃CH₂ | H | H | 2 | CH₃CH₂CH₂ | H |
| H | CH₃CH₂ | CH₃ | H | 2 | CH₃CH₂CH₂ | H |
| H | CH₃CH₂ | Cl | H | 2 | CH₃CH₂CH₂ | H |
| H | CH₃CH₂ | H | CH₃ | 2 | CH₃CH₂CH₂ | H |
| H | CH₃CH₂ | CH₃ | CH₃ | 2 | CH₃CH₂CH₂ | H |
| H | CH₃CH₂ | Cl | CH₃ | 2 | CH₃CH₂CH₂ | H |
| H | CH₃CH₂ | H | Cl | 2 | CH₃CH₂CH₂ | H |
| H | CH₃CH₂ | CH₃ | Cl | 2 | CH₃CH₂CH₂ | H |
| H | CH₃CH₂ | Cl | Cl | 2 | CH₃CH₂CH₂ | H |
| H | CH₃CH₂ | H | H | 2 | H | CH₃ |
| H | CH₃CH₂ | CH₃ | H | 2 | H | CH₃ |
| H | CH₃CH₂ | Cl | H | 2 | H | CH₃ |
| H | CH₃CH₂ | H | CH₃ | 2 | H | CH₃ |
| H | CH₃CH₂ | CH₃ | CH₃ | 2 | H | CH₃ |
| H | CH₃CH₂ | Cl | CH₃ | 2 | H | CH₃ |
| H | CH₃CH₂ | H | Cl | 2 | H | CH₃ |
| H | CH₃CH₂ | CH₃ | Cl | 2 | H | CH₃ |
| H | CH₃CH₂ | Cl | Cl | 2 | H | CH₃ |
| H | CH₃CH₂ | H | H | 2 | CH₃ | CH₃ |
| H | CH₃CH₂ | CH₃ | H | 2 | CH₃ | CH₃ |
| H | CH₃CH₂ | Cl | H | 2 | CH₃ | CH₃ |
| H | CH₃CH₂ | H | CH₃ | 2 | CH₃ | CH₃ |
| H | CH₃CH₂ | CH₃ | CH₃ | 2 | CH₃ | CH₃ |
| H | CH₃CH₂ | Cl | CH₃ | 2 | CH₃ | CH₃ |
| H | CH₃CH₂ | H | Cl | 2 | CH₃ | CH₃ |
| H | CH₃CH₂ | CH₃ | Cl | 2 | CH₃ | CH₃ |
| H | CH₃CH₂ | Cl | Cl | 2 | CH₃ | CH₃ |
| H | CH₃CH₂ | H | H | 2 | CH₃CH₂ | CH₃ |
| H | CH₃CH₂ | CH₃ | H | 2 | CH₃CH₂ | CH₃ |
| H | CH₃CH₂ | Cl | H | 2 | CH₃CH₂ | CH₃ |
| H | CH₃CH₂ | H | CH₃ | 2 | CH₃CH₂ | CH₃ |
| H | CH₃CH₂ | CH₃ | CH₃ | 2 | CH₃CH₂ | CH₃ |
| H | CH₃CH₂ | Cl | CH₃ | 2 | CH₃CH₂ | CH₃ |
| H | CH₃CH₂ | H | Cl | 2 | CH₃CH₂ | CH₃ |
| H | CH₃CH₂ | CH₃ | Cl | 2 | CH₃CH₂ | CH₃ |
| H | CH₃CH₂ | Cl | Cl | 2 | CH₃CH₂ | CH₃ |
| H | CH₃CH₂ | H | H | 2 | CH₃CH₂CH₂ | CH₃ |
| H | CH₃CH₂ | CH₃ | H | 2 | CH₃CH₂CH₂ | CH₃ |
| H | CH₃CH₂ | Cl | H | 2 | CH₃CH₂CH₂ | CH₃ |
| H | CH₃CH₂ | H | CH₃ | 2 | CH₃CH₂CH₂ | CH₃ |
| H | CH₃CH₂ | CH₃ | CH₃ | 2 | CH₃CH₂CH₂ | CH₃ |
| H | CH₃CH₂ | Cl | CH₃ | 2 | CH₃CH₂CH₂ | CH₃ |
| H | CH₃CH₂ | H | Cl | 2 | CH₃CH₂CH₂ | CH₃ |
| H | CH₃CH₂ | CH₃ | Cl | 2 | CH₃CH₂CH₂ | CH₃ |
| H | CH₃CH₂ | Cl | Cl | 2 | CH₃CH₂CH₂ | CH₃ |
| H | CH₃CH₂ | H | H | 2 | H | Cl |
| H | CH₃CH₂ | CH₃ | H | 2 | H | Cl |
| H | CH₃CH₂ | Cl | H | 2 | H | Cl |
| H | CH₃CH₂ | H | CH₃ | 2 | H | Cl |
| H | CH₃CH₂ | CH₃ | CH₃ | 2 | H | Cl |
| H | CH₃CH₂ | Cl | CH₃ | 2 | H | Cl |

TABLE 12-continued

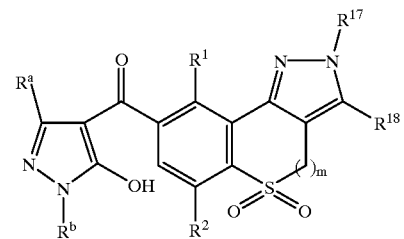

| Rᵃ | Rᵇ | R¹ | R² | m | R¹⁷ | R¹⁸ |
|---|---|---|---|---|---|---|
| H | CH₃CH₂ | H | Cl | 2 | H | Cl |
| H | CH₃CH₂ | CH₃ | Cl | 2 | H | Cl |
| H | CH₃CH₂ | Cl | Cl | 2 | H | Cl |
| H | CH₃CH₂ | H | H | 2 | CH₃ | Cl |
| H | CH₃CH₂ | CH₃ | H | 2 | CH₃ | Cl |
| H | CH₃CH₂ | Cl | H | 2 | CH₃ | Cl |
| H | CH₃CH₂ | H | CH₃ | 2 | CH₃ | Cl |
| H | CH₃CH₂ | CH₃ | CH₃ | 2 | CH₃ | Cl |
| H | CH₃CH₂ | Cl | CH₃ | 2 | CH₃ | Cl |
| H | CH₃CH₂ | H | Cl | 2 | CH₃ | Cl |
| H | CH₃CH₂ | CH₃ | Cl | 2 | CH₃ | Cl |
| H | CH₃CH₂ | Cl | Cl | 2 | CH₃ | Cl |
| H | CH₃CH₂ | H | H | 2 | CH₃CH₂ | Cl |
| H | CH₃CH₂ | CH₃ | H | 2 | CH₃CH₂ | Cl |
| H | CH₃CH₂ | Cl | H | 2 | CH₃CH₂ | Cl |
| H | CH₃CH₂ | H | CH₃ | 2 | CH₃CH₂ | Cl |
| H | CH₃CH₂ | CH₃ | CH₃ | 2 | CH₃CH₂ | Cl |
| H | CH₃CH₂ | Cl | CH₃ | 2 | CH₃CH₂ | Cl |
| H | CH₃CH₂ | H | Cl | 2 | CH₃CH₂ | Cl |
| H | CH₃CH₂ | CH₃ | Cl | 2 | CH₃CH₂ | Cl |
| H | CH₃CH₂ | Cl | Cl | 2 | CH₃CH₂ | Cl |
| H | CH₃CH₂ | H | H | 2 | CH₃CH₂CH₂ | Cl |
| H | CH₃CH₂ | CH₃ | H | 2 | CH₃CH₂CH₂ | Cl |
| H | CH₃CH₂ | Cl | H | 2 | CH₃CH₂CH₂ | Cl |
| H | CH₃CH₂ | H | CH₃ | 2 | CH₃CH₂CH₂ | Cl |
| H | CH₃CH₂ | CH₃ | CH₃ | 2 | CH₃CH₂CH₂ | Cl |
| H | CH₃CH₂ | Cl | CH₃ | 2 | CH₃CH₂CH₂ | Cl |
| H | CH₃CH₂ | H | Cl | 2 | CH₃CH₂CH₂ | Cl |
| H | CH₃CH₂ | CH₃ | Cl | 2 | CH₃CH₂CH₂ | Cl |
| H | CH₃CH₂ | Cl | Cl | 2 | CH₃CH₂CH₂ | Cl |

TABLE 13

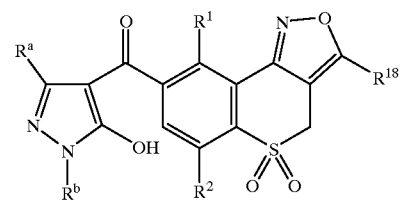

| Rᵃ | Rᵇ | R¹ | R² | R¹⁸ |
|---|---|---|---|---|
| CH₃ | CH₃ | H | H | H |
| H | CH₃CH₂ | H | H | H |
| CH₃ | CH₃ | CH₃ | H | H |
| H | CH₃CH₂ | CH₃ | H | H |
| CH₃ | CH₃ | Cl | H | H |
| H | CH₃CH₂ | Cl | H | H |
| CH₃ | CH₃ | H | CH₃ | H |
| H | CH₃CH₂ | H | CH₃ | H |
| CH₃ | CH₃ | CH₃ | CH₃ | H |
| H | CH₃CH₂ | CH₃ | CH₃ | H |
| CH₃ | CH₃ | Cl | CH₃ | H |
| H | CH₃CH₂ | Cl | CH₃ | H |
| CH₃ | CH₃ | H | Cl | H |
| H | CH₃CH₂ | H | Cl | H |
| CH₃ | CH₃ | CH₃ | Cl | H |
| H | CH₃CH₂ | CH₃ | Cl | H |

TABLE 13-continued

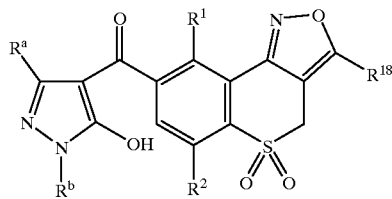

| Rᵃ | Rᵇ | R¹ | R² | R¹⁸ |
|---|---|---|---|---|
| CH₃ | CH₃ | Cl | Cl | H |
| H | CH₃CH₂ | Cl | Cl | H |
| CH₃ | CH₃ | H | H | CH₃ |
| H | CH₃CH₂ | H | H | CH₃ |
| CH₃ | CH₃ | CH₃ | H | CH₃ |
| H | CH₃CH₂ | CH₃ | H | CH₃ |
| CH₃ | CH₃ | Cl | H | CH₃ |
| H | CH₃CH₂ | Cl | H | CH₃ |
| CH₃ | CH₃ | H | CH₃ | CH₃ |
| H | CH₃CH₂ | H | CH₃ | CH₃ |
| CH₃ | CH₃ | CH₃ | CH₃ | CH₃ |
| H | CH₃CH₂ | CH₃ | CH₃ | CH₃ |
| CH₃ | CH₃ | Cl | CH₃ | CH₃ |
| H | CH₃CH₂ | Cl | CH₃ | CH₃ |
| CH₃ | CH₃ | H | Cl | CH₃ |
| H | CH₃CH₂ | H | Cl | CH₃ |
| CH₃ | CH₃ | CH₃ | Cl | CH₃ |
| H | CH₃CH₂ | CH₃ | Cl | CH₃ |
| CH₃ | CH₃ | Cl | Cl | CH₃ |
| H | CH₃CH₂ | Cl | Cl | CH₃ |
| CH₃ | CH₃ | H | H | Cl |
| H | CH₃CH₂ | H | H | Cl |
| CH₃ | CH₃ | CH₃ | H | Cl |
| H | CH₃CH₂ | CH₃ | H | Cl |
| CH₃ | CH₃ | Cl | H | Cl |
| H | CH₃CH₂ | Cl | H | Cl |
| CH₃ | CH₃ | H | CH₃ | Cl |
| H | CH₃CH₂ | H | CH₃ | Cl |
| CH₃ | CH₃ | CH₃ | CH₃ | Cl |
| H | CH₃CH₂ | CH₃ | CH₃ | Cl |
| CH₃ | CH₃ | Cl | CH₃ | Cl |
| H | CH₃CH₂ | Cl | CH₃ | Cl |
| CH₃ | CH₃ | H | Cl | Cl |
| H | CH₃CH₂ | H | Cl | Cl |
| CH₃ | CH₃ | CH₃ | Cl | Cl |
| H | CH₃CH₂ | CH₃ | Cl | Cl |
| CH₃ | CH₃ | Cl | Cl | Cl |
| H | CH₃CH₂ | Cl | Cl | Cl |
| H | CH₃ | H | H | H |
| H | CH₃ | CH₃ | H | H |
| H | CH₃ | Cl | H | H |
| H | CH₃ | H | CH₃ | H |
| H | CH₃ | CH₃ | CH₃ | H |
| H | CH₃ | Cl | CH₃ | H |
| H | CH₃ | H | Cl | H |
| H | CH₃ | CH₃ | Cl | H |
| H | CH₃ | Cl | Cl | H |
| H | CH₃ | H | H | CH₃ |
| H | CH₃ | CH₃ | H | CH₃ |
| H | CH₃ | Cl | H | CH₃ |
| H | CH₃ | H | CH₃ | CH₃ |
| H | CH₃ | CH₃ | CH₃ | CH₃ |
| H | CH₃ | Cl | CH₃ | CH₃ |
| H | CH₃ | H | Cl | CH₃ |
| H | CH₃ | CH₃ | Cl | CH₃ |
| H | CH₃ | Cl | Cl | CH₃ |
| H | CH₃ | H | H | Cl |
| H | CH₃ | CH₃ | H | Cl |
| H | CH₃ | Cl | H | Cl |
| H | CH₃ | H | CH₃ | Cl |
| H | CH₃ | CH₃ | CH₃ | Cl |
| H | CH₃ | Cl | CH₃ | Cl |
| H | CH₃ | H | Cl | Cl |
| H | CH₃ | CH₃ | Cl | Cl |
| H | CH₃ | Cl | Cl | Cl |

TABLE 14

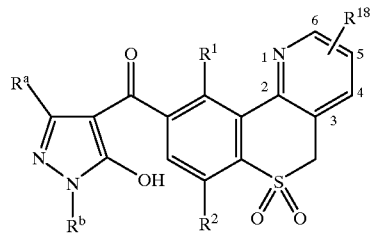

| Rᵃ | Rᵇ | R¹ | R² | R¹⁸ |
|---|---|---|---|---|
| CH₃ | CH₃ | H | H | H |
| H | CH₃CH₂ | H | H | H |
| CH₃ | CH₃ | CH₃ | H | H |
| H | CH₃CH₂ | CH₃ | H | H |
| CH₃ | CH₃ | Cl | H | H |
| H | CH₃CH₂ | Cl | H | H |
| CH₃ | CH₃ | H | CH₃ | H |
| H | CH₃CH₂ | H | CH₃ | H |
| CH₃ | CH₃ | CH₃ | CH₃ | H |
| H | CH₃CH₂ | CH₃ | CH₃ | H |
| CH₃ | CH₃ | Cl | CH₃ | H |
| H | CH₃CH₂ | Cl | CH₃ | H |
| CH₃ | CH₃ | H | Cl | H |
| H | CH₃CH₂ | H | Cl | H |
| CH₃ | CH₃ | CH₃ | Cl | H |
| H | CH₃CH₂ | CH₃ | Cl | H |
| CH₃ | CH₃ | Cl | Cl | H |
| H | CH₃CH₂ | Cl | Cl | H |
| CH₃ | CH₃ | H | H | 6-CH₃ |
| H | CH₃CH₂ | H | H | 6-CH₃ |
| CH₃ | CH₃ | CH₃ | H | 6-CH₃ |
| H | CH₃CH₂ | CH₃ | H | 6-CH₃ |
| CH₃ | CH₃ | Cl | H | 6-CH₃ |
| H | CH₃CH₂ | Cl | H | 6-CH₃ |
| CH₃ | CH₃ | H | CH₃ | 6-CH₃ |
| H | CH₃CH₂ | H | CH₃ | 6-CH₃ |
| CH₃ | CH₃ | CH₃ | CH₃ | 6-CH₃ |
| H | CH₃CH₂ | CH₃ | CH₃ | 6-CH₃ |
| CH₃ | CH₃ | Cl | CH₃ | 6-CH₃ |
| H | CH₃CH₂ | Cl | CH₃ | 6-CH₃ |
| CH₃ | CH₃ | H | Cl | 6-CH₃ |
| H | CH₃CH₂ | H | Cl | 6-CH₃ |
| CH₃ | CH₃ | CH₃ | Cl | 6-CH₃ |
| H | CH₃CH₂ | CH₃ | Cl | 6-CH₃ |
| CH₃ | CH₃ | Cl | Cl | 6-CH₃ |
| H | CH₃CH₂ | Cl | Cl | 6-CH₃ |
| CH₃ | CH₃ | H | H | 5-CH₃ |
| H | CH₃CH₂ | H | H | 5-CH₃ |
| CH₃ | CH₃ | CH₃ | H | 5-CH₃ |
| H | CH₃CH₂ | CH₃ | H | 5-CH₃ |
| CH₃ | CH₃ | Cl | H | 5-CH₃ |
| H | CH₃CH₂ | Cl | H | 5-CH₃ |
| CH₃ | CH₃ | H | CH₃ | 5-CH₃ |
| H | CH₃CH₂ | H | CH₃ | 5-CH₃ |
| CH₃ | CH₃ | CH₃ | CH₃ | 5-CH₃ |
| H | CH₃CH₂ | CH₃ | CH₃ | 5-CH₃ |
| CH₃ | CH₃ | Cl | CH₃ | 5-CH₃ |
| H | CH₃CH₂ | C | CH₃ | 5-CH₃ |
| CH₃ | CH₃ | H | Cl | 5-CH₃ |
| H | CH₃CH₂ | H | Cl | 5-CH₃ |
| CH₃ | CH₃ | CH₃ | Cl | 5-CH₃ |
| H | CH₃CH₂ | CH₃ | Cl | 5-CH₃ |
| CH₃ | CH₃ | Cl | Cl | 5-CH₃ |
| H | CH₃CH₂ | Cl | Cl | 5-CH₃ |
| CH₃ | CH₃ | H | H | 4-CH₃ |
| H | CH₃CH₂ | H | H | 4-CH₃ |
| CH₃ | CH₃ | CH₃ | H | 4-CH₃ |
| H | CH₃CH₂ | CH₃ | H | 4-CH₃ |
| CH₃ | CH₃ | Cl | H | 4-CH₃ |
| H | CH₃CH₂ | Cl | H | 4-CH₃ |
| CH₃ | CH₃ | H | CH₃ | 4-CH₃ |
| H | CH₃CH₂ | H | CH₃ | 4-CH₃ |
| CH₃ | CH₃ | CH₃ | CH₃ | 4-CH₃ |
| H | CH₃CH₂ | CH₃ | CH₃ | 4-CH₃ |

TABLE 14-continued

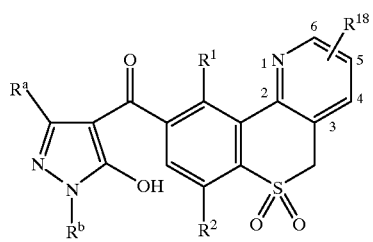

| R$^a$ | R$^b$ | R$^1$ | R$^2$ | R$^{18}$ |
|---|---|---|---|---|
| CH$_3$ | CH$_3$ | Cl | CH$_3$ | 4-CH$_3$ |
| H | CH$_3$CH$_2$ | Cl | CH$_3$ | 4-CH$_3$ |
| CH$_3$ | CH$_3$ | H | Cl | 4-CH$_3$ |
| H | CH$_3$CH$_2$ | H | Cl | 4-CH$_3$ |
| CH$_3$ | CH$_3$ | CH$_3$ | Cl | 4-CH$_3$ |
| H | CH$_3$CH$_2$ | CH$_3$ | Cl | 4-CH$_3$ |
| CH$_3$ | CH$_3$ | Cl | Cl | 4-CH$_3$ |
| H | CH$_3$CH$_2$ | Cl | Cl | 4-CH$_3$ |
| CH$_3$ | CH$_3$ | H | H | 6-Cl |
| H | CH$_3$CH$_2$ | H | H | 6-Cl |
| CH$_3$ | CH$_3$ | CH$_3$ | H | 6-Cl |
| H | CH$_3$CH$_2$ | CH$_3$ | H | 6-Cl |
| CH$_3$ | CH$_3$ | Cl | H | 6-Cl |
| H | CH$_3$CH$_2$ | Cl | H | 6-Cl |
| CH$_3$ | CH$_3$ | H | CH$_3$ | 6-Cl |
| H | CH$_3$CH$_2$ | H | CH$_3$ | 6-Cl |
| CH$_3$ | CH$_3$ | CH$_3$ | CH$_3$ | 6-Cl |
| H | CH$_3$CH$_2$ | CH$_3$ | CH$_3$ | 6-Cl |
| CH$_3$ | CH$_3$ | Cl | CH$_3$ | 6-Cl |
| H | CH$_3$CH$_2$ | Cl | CH$_3$ | 6-Cl |
| CH$_3$ | CH$_3$ | H | Cl | 6-Cl |
| H | CH$_3$CH$_2$ | H | Cl | 6-Cl |
| CH$_3$ | CH$_3$ | CH$_3$ | Cl | 6-Cl |
| H | CH$_3$CH$_2$ | CH$_3$ | Cl | 6-Cl |
| CH$_3$ | CH$_3$ | Cl | Cl | 6-Cl |
| H | CH$_3$CH$_2$ | Cl | Cl | 6-Cl |
| CH$_3$ | CH$_3$ | H | H | 4-Cl |
| H | CH$_3$CH$_2$ | H | H | 4-Cl |
| CH$_3$ | CH$_3$ | CH$_3$ | H | 4-Cl |
| H | CH$_3$CH$_2$ | CH$_3$ | H | 4-Cl |
| CH$_3$ | CH$_3$ | Cl | H | 4-Cl |
| H | CH$_3$CH$_2$ | Cl | H | 4-Cl |
| CH$_3$ | CH$_3$ | H | CH$_3$ | 4-Cl |
| H | CH$_3$CH$_2$ | H | CH$_3$ | 4-Cl |
| CH$_3$ | CH$_3$ | CH$_3$ | CH$_3$ | 4-Cl |
| H | CH$_3$CH$_2$ | CH$_3$ | CH$_3$ | 4-Cl |
| CH$_3$ | CH$_3$ | Cl | CH$_3$ | 4-Cl |
| H | CH$_3$CH$_2$ | Cl | CH$_3$ | 4-Cl |
| CH$_3$ | CH$_3$ | H | Cl | 4-Cl |
| H | CH$_3$CH$_2$ | H | Cl | 4-Cl |
| CH$_3$ | CH$_3$ | CH$_3$ | Cl | 4-Cl |
| H | CH$_3$CH$_2$ | CH$_3$ | Cl | 4-Cl |
| CH$_3$ | CH$_3$ | Cl | Cl | 4-Cl |
| H | CH$_3$CH$_2$ | Cl | Cl | 4-Cl |
| H | CH$_3$ | H | H | H |
| H | CH$_3$ | CH$_3$ | H | H |
| H | CH$_3$ | Cl | H | H |
| H | CH$_3$ | H | CH$_3$ | H |
| H | CH$_3$ | CH$_3$ | CH$_3$ | H |
| H | CH$_3$ | Cl | CH$_3$ | H |
| H | CH$_3$ | H | Cl | H |
| H | CH$_3$ | CH$_3$ | Cl | H |
| H | CH$_3$ | Cl | Cl | H |
| H | CH$_3$ | H | H | 6-CH$_3$ |
| H | CH$_3$ | CH$_3$ | H | 6-CH$_3$ |
| H | CH$_3$ | Cl | H | 6-CH$_3$ |
| H | CH$_3$ | H | CH$_3$ | 6-CH$_3$ |
| H | CH$_3$ | CH$_3$ | CH$_3$ | 6-CH$_3$ |
| H | CH$_3$ | Cl | CH$_3$ | 6-CH$_3$ |
| H | CH$_3$ | H | Cl | 6-CH$_3$ |
| H | CH$_3$ | CH$_3$ | Cl | 6-CH$_3$ |
| H | CH$_3$ | Cl | Cl | 6-CH$_3$ |
| H | CH$_3$ | H | H | 5-CH$_3$ |
| H | CH$_3$ | CH$_3$ | H | 5-CH$_3$ |

TABLE 14-continued

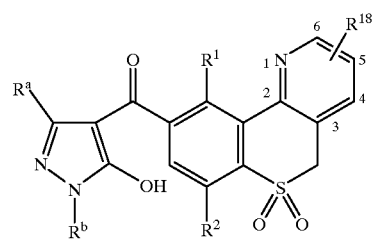

| R$^a$ | R$^b$ | R$^1$ | R$^2$ | R$^{18}$ |
|---|---|---|---|---|
| H | CH$_3$ | Cl | H | 5-CH$_3$ |
| H | CH$_3$ | H | CH$_3$ | 5-CH$_3$ |
| H | CH$_3$ | CH$_3$ | CH$_3$ | 5-CH$_3$ |
| H | CH$_3$ | Cl | CH$_3$ | 5-CH$_3$ |
| H | CH$_3$ | H | Cl | 5-CH$_3$ |
| H | CH$_3$ | CH$_3$ | Cl | 5-CH$_3$ |
| H | CH$_3$ | Cl | Cl | 5-CH$_3$ |
| H | CH$_3$ | H | H | 4-CH$_3$ |
| H | CH$_3$ | CH$_3$ | H | 4-CH$_3$ |
| H | CH$_3$ | Cl | H | 4-CH$_3$ |
| H | CH$_3$ | H | CH$_3$ | 4-CH$_3$ |
| H | CH$_3$ | CH$_3$ | CH$_3$ | 4-CH$_3$ |
| H | CH$_3$ | Cl | CH$_3$ | 4-CH$_3$ |
| H | CH$_3$ | H | Cl | 4-CH$_3$ |
| H | CH$_3$ | CH$_3$ | Cl | 4-CH$_3$ |
| H | CH$_3$ | Cl | Cl | 4-CH$_3$ |
| H | CH$_3$ | H | H | 6-Cl |
| H | CH$_3$ | CH$_3$ | H | 6-Cl |
| H | CH$_3$ | Cl | H | 6-Cl |
| H | CH$_3$ | H | CH$_3$ | 6-Cl |
| H | CH$_3$ | CH$_3$ | CH$_3$ | 6-Cl |
| H | CH$_3$ | Cl | CH$_3$ | 6-Cl |
| H | CH$_3$ | H | Cl | 6-Cl |
| H | CH$_3$ | CH$_3$ | Cl | 6-Cl |
| H | CH$_3$ | Cl | Cl | 6-Cl |
| H | CH$_3$ | H | H | 4-Cl |
| H | CH$_3$ | CH$_3$ | H | 4-Cl |
| H | CH$_3$ | Cl | H | 4-Cl |
| H | CH$_3$ | H | CH$_3$ | 4-Cl |
| H | CH$_3$ | CH$_3$ | CH$_3$ | 4-Cl |
| H | CH$_3$ | Cl | CH$_3$ | 4-Cl |
| H | CH$_3$ | H | Cl | 4-Cl |
| H | CH$_3$ | CH$_3$ | Cl | 4-Cl |
| H | CH$_3$ | Cl | Cl | 4-Cl |

TABLE 15

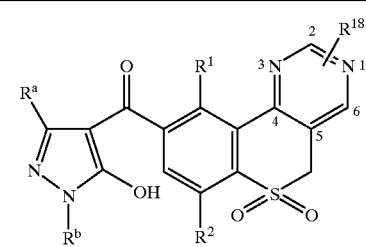

| R$^a$ | R$^b$ | R$^1$ | R$^2$ | R$^{18}$ |
|---|---|---|---|---|
| CH$_3$ | CH$_3$ | H | H | H |
| H | CH$_3$CH$_2$ | H | H | H |
| CH$_3$ | CH$_3$ | CH$_3$ | H | H |
| H | CH$_3$CH$_2$ | CH$_3$ | H | H |
| CH$_3$ | CH$_3$ | Cl | H | H |
| H | CH$_3$CH$_2$ | Cl | H | H |
| CH$_3$ | CH$_3$ | H | CH$_3$ | H |
| H | CH$_3$CH$_2$ | H | CH$_3$ | H |
| CH$_3$ | CH$_3$ | CH$_3$ | CH$_3$ | H |
| H | CH$_3$CH$_2$ | CH$_3$ | CH$_3$ | H |
| CH$_3$ | CH$_3$ | Cl | CH$_3$ | H |

TABLE 15-continued

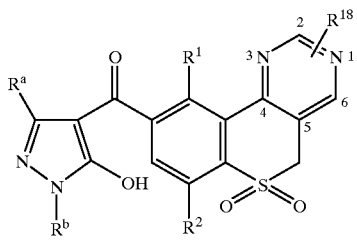

| Rª | Rᵇ | R¹ | R² | R¹⁸ |
|---|---|---|---|---|
| H | CH₃CH₂ | Cl | CH₃ | H |
| CH₃ | CH₃ | H | Cl | H |
| H | CH₃CH₂ | H | Cl | H |
| CH₃ | CH₃ | CH₃ | Cl | H |
| H | CH₃CH₂ | CH₃ | Cl | H |
| CH₃ | CH₃ | Cl | Cl | H |
| H | CH₃CH₂ | Cl | Cl | H |
| CH₃ | CH₃ | H | H | 2-CH₃ |
| H | CH₃CH₂ | H | H | 2-CH₃ |
| CH₃ | CH₃ | CH₃ | H | 2-CH₃ |
| H | CH₃CH₂ | CH₃ | H | 2-CH₃ |
| CH₃ | CH₃ | Cl | H | 2-CH₃ |
| H | CH₃CH₂ | Cl | H | 2-CH₃ |
| CH₃ | CH₃ | H | CH₃ | 2-CH₃ |
| H | CH₃CH₂ | H | CH₃ | 2-CH₃ |
| CH₃ | CH₃ | CH₃ | CH₃ | 2-CH₃ |
| H | CH₃CH₂ | CH₃ | CH₃ | 2-CH₃ |
| CH₃ | CH₃ | Cl | CH₃ | 2-CH₃ |
| H | CH₃CH₂ | Cl | CH₃ | 2-CH₃ |
| CH₃ | CH₃ | H | Cl | 2-CH₃ |
| H | CH₃CH₂ | H | Cl | 2-CH₃ |
| CH₃ | CH₃ | CH₃ | Cl | 2-CH₃ |
| H | CH₃CH₂ | CH₃ | Cl | 2-CH₃ |
| CH₃ | CH₃ | Cl | Cl | 2-CH₃ |
| H | CH₃CH₂ | Cl | Cl | 2-CH₃ |
| CH₃ | CH₃ | H | H | 6-CH₃ |
| H | CH₃CH₂ | H | H | 6-CH₃ |
| CH₃ | CH₃ | CH₃ | H | 6-CH₃ |
| H | CH₃CH₂ | CH₃ | H | 6-CH₃ |
| CH₃ | CH₃ | Cl | H | 6-CH₃ |
| H | CH₃CH₂ | Cl | H | 6-CH₃ |
| CH₃ | CH₃ | H | CH₃ | 6-CH₃ |
| H | CH₃CH₂ | H | CH₃ | 6-CH₃ |
| CH₃ | CH₃ | CH₃ | CH₃ | 6-CH₃ |
| H | CH₃CH₂ | CH₃ | CH₃ | 6-CH₃ |
| CH₃ | CH₃ | Cl | CH₃ | 6-CH₃ |
| H | CH₃CH₂ | Cl | CH₃ | 6-CH₃ |
| CH₃ | CH₃ | H | Cl | 6-CH₃ |
| H | CH₃CH₂ | H | Cl | 6-CH₃ |
| CH₃ | CH₃ | CH₃ | Cl | 6-CH₃ |
| H | CH₃CH₂ | CH₃ | Cl | 6-CH₃ |
| CH₃ | CH₃ | Cl | Cl | 6-CH₃ |
| H | CH₃CH₂ | Cl | Cl | 6-CH₃ |
| CH₃ | CH₃ | H | H | 2-Cl |
| H | CH₃CH₂ | H | H | 2-Cl |
| CH₃ | CH₃ | CH₃ | H | 2-Cl |
| H | CH₃CH₂ | CH₃ | H | 2-Cl |
| CH₃ | CH₃ | Cl | H | 2-Cl |
| H | CH₃CH₂ | Cl | H | 2-Cl |
| CH₃ | CH₃ | H | CH₃ | 2-Cl |
| H | CH₃CH₂ | H | CH₃ | 2-Cl |
| CH₃ | CH₃ | CH₃ | CH₃ | 2-Cl |
| H | CH₃CH₂ | CH₃ | CH₃ | 2-Cl |
| CH₃ | CH₃ | Cl | CH₃ | 2-Cl |
| H | CH₃CH₂ | Cl | CH₃ | 2-Cl |
| CH₃ | CH₃ | H | Cl | 2-Cl |
| H | CH₃CH₂ | H | Cl | 2-Cl |
| CH₃ | CH₃ | CH₃ | Cl | 2-Cl |
| H | CH₃CH₂ | CH₃ | Cl | 2-Cl |
| CH₃ | CH₃ | Cl | Cl | 2-Cl |
| H | CH₃CH₂ | Cl | Cl | 2-Cl |
| H | CH₃ | H | H | H |
| H | CH₃ | CH₃ | H | H |
| H | CH₃ | Cl | H | H |

TABLE 15-continued

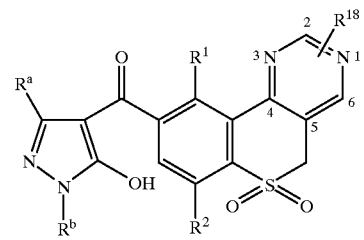

| Rª | Rᵇ | R¹ | R² | R¹⁸ |
|---|---|---|---|---|
| H | CH₃ | H | CH₃ | H |
| H | CH₃ | CH₃ | CH₃ | H |
| H | CH₃ | Cl | CH₃ | H |
| H | CH₃ | H | Cl | H |
| H | CH₃ | CH₃ | Cl | H |
| H | CH₃ | Cl | Cl | H |
| H | CH₃ | H | H | 2-CH₃ |
| H | CH₃ | CH₃ | H | 2-CH₃ |
| H | CH₃ | Cl | H | 2-CH₃ |
| H | CH₃ | H | CH₃ | 2-CH₃ |
| H | CH₃ | CH₃ | CH₃ | 2-CH₃ |
| H | CH₃ | Cl | CH₃ | 2-CH₃ |
| H | CH₃ | H | Cl | 2-CH₃ |
| H | CH₃ | CH₃ | Cl | 2-CH₃ |
| H | CH₃ | Cl | Cl | 2-CH₃ |
| H | CH₃ | H | H | 6-CH₃ |
| H | CH₃ | CH₃ | H | 6-CH₃ |
| H | CH₃ | Cl | H | 6-CH₃ |
| H | CH₃ | H | CH₃ | 6-CH₃ |
| H | CH₃ | CH₃ | CH₃ | 6-CH₃ |
| H | CH₃ | Cl | CH₃ | 6-CH₃ |
| H | CH₃ | H | Cl | 6-CH₃ |
| H | CH₃ | CH₃ | Cl | 6-CH₃ |
| H | CH₃ | Cl | Cl | 6-CH₃ |
| H | CH₃ | H | H | 2-Cl |
| H | CH₃ | CH₃ | H | 2-Cl |
| H | CH₃ | Cl | H | 2-Cl |
| H | CH₃ | H | CH₃ | 2-Cl |
| H | CH₃ | CH₃ | CH₃ | 2-Cl |
| H | CH₃ | Cl | CH₃ | 2Cl |
| H | CH₃ | H | Cl | 2-Cl |
| H | CH₃ | CH₃ | Cl | 2-Cl |
| H | CH₃ | Cl | Cl | 2-Cl |

TABLE 16

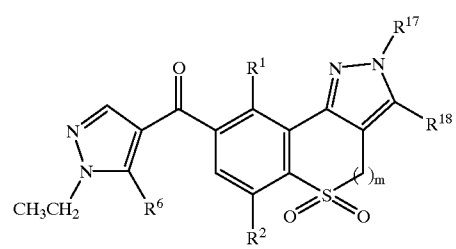

| R⁶ | R¹ | R² | m | R¹⁷ | R¹⁸ |
|---|---|---|---|---|---|
| SH | H | H | 1 | H | H |
| Cl | H | H | 1 | H | H |
| SH | CH₃ | H | 1 | H | H |
| Cl | CH₃ | H | 1 | H | H |
| SH | Cl | H | 1 | H | H |
| Cl | Cl | H | 1 | H | H |
| SH | CH₃ | CH₃ | 1 | H | H |
| Cl | CH₃ | CH₃ | 1 | H | H |
| SH | Cl | Cl | 1 | H | H |
| Cl | Cl | Cl | 1 | H | H |
| SH | H | H | 2 | H | H |

TABLE 16-continued

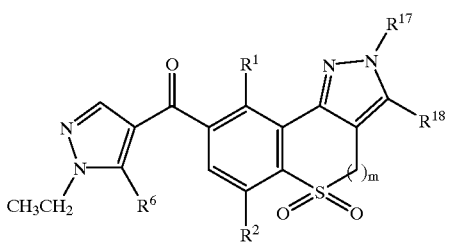

| R⁶ | R¹ | R² | m | R¹⁷ | R¹⁸ |
|---|---|---|---|---|---|
| Cl | H | H | 2 | H | H |
| SH | CH₃ | H | 2 | H | H |
| Cl | CH₃ | H | 2 | H | H |
| SH | Cl | H | 2 | H | H |
| Cl | Cl | H | 2 | H | H |
| SH | CH₃ | CH₃ | 2 | H | H |
| Cl | CH₃ | CH₃ | 2 | H | H |
| SH | Cl | Cl | 2 | H | H |
| Cl | Cl | Cl | 2 | H | H |
| SH | H | H | 1 | CH₃ | H |
| Cl | H | H | 1 | CH₃ | H |
| SH | CH₃ | H | 1 | CH₃ | H |
| Cl | CH₃ | H | 1 | CH₃ | H |
| SH | Cl | H | 1 | CH₃ | H |
| Cl | Cl | H | 1 | CH₃ | H |
| SH | CH₃ | CH₃ | 1 | CH₃ | H |
| Cl | CH₃ | CH₃ | 1 | CH₃ | H |
| SH | Cl | Cl | 1 | CH₃ | H |
| Cl | Cl | Cl | 1 | CH₃ | H |
| SH | H | H | 2 | CH₃ | H |
| Cl | H | H | 2 | CH₃ | H |
| SH | CH₃ | H | 2 | CH₃ | H |
| Cl | CH₃ | H | 2 | CH₃ | H |
| SH | Cl | H | 2 | CH₃ | H |
| Cl | Cl | H | 2 | CH₃ | H |
| SH | CH₃ | CH₃ | 2 | CH₃ | H |
| Cl | CH₃ | CH₃ | 2 | CH₃ | H |
| SH | Cl | Cl | 2 | CH₃ | H |
| Cl | Cl | Cl | 2 | CH₃ | H |
| SH | H | H | 1 | CH₂CH₃ | H |
| Cl | H | H | 1 | CH₂CH₃ | H |
| SH | CH₃ | H | 1 | CH₂CH₃ | H |
| Cl | CH₃ | H | 1 | CH₂CH₃ | H |
| SH | Cl | H | 1 | CH₂CH₃ | H |
| Cl | Cl | H | 1 | CH₂CH₃ | H |
| SH | CH₃ | CH₃ | 1 | CH₂CH₃ | H |
| Cl | CH₃ | CH₃ | 1 | CH₂CH₃ | H |
| SH | Cl | Cl | 1 | CH₂CH₃ | H |
| Cl | Cl | Cl | 1 | CH₂CH₃ | H |
| SH | H | H | 2 | CH₂CH₃ | H |
| Cl | H | H | 2 | CH₂CH₃ | H |
| SH | CH₃ | H | 2 | CH₂CH₃ | H |
| Cl | CH₃ | H | 2 | CH₂CH₃ | H |
| SH | Cl | H | 2 | CH₂CH₃ | H |
| Cl | Cl | H | 2 | CH₂CH₃ | H |
| SH | CH₃ | CH₃ | 2 | CH₂CH₃ | H |
| Cl | CH₃ | CH₃ | 2 | CH₂CH₃ | H |
| SH | Cl | Cl | 2 | CH₂CH₃ | H |
| Cl | Cl | Cl | 2 | CH₂CH₃ | H |
| SH | H | H | 1 | CH₂CH₂CH₃ | H |
| Cl | H | H | 1 | CH₂CH₂CH₃ | H |
| SH | CH₃ | H | 1 | CH₂CH₂CH₃ | H |
| Cl | CH₃ | H | 1 | CH₂CH₂CH₃ | H |
| SH | Cl | H | 1 | CH₂CH₂CH₃ | H |
| Cl | Cl | H | 1 | CH₂CH₂CH₃ | H |
| SH | CH₃ | CH₃ | 1 | CH₂CH₂CH₃ | H |
| Cl | CH₃ | CH₃ | 1 | CH₂CH₂CH₃ | H |
| SH | Cl | Cl | 1 | CH₂CH₂CH₃ | H |
| Cl | Cl | Cl | 1 | CH₂CH₂CH₃ | H |
| SH | H | H | 2 | CH₂CH₂CH₃ | H |
| Cl | H | H | 2 | CH₂CH₂CH₃ | H |
| SH | CH₃ | H | 2 | CH₂CH₂CH₃ | H |
| Cl | CH₃ | H | 2 | CH₂CH₂CH₃ | H |
| SH | Cl | H | 2 | CH₂CH₂CH₃ | H |

TABLE 16-continued

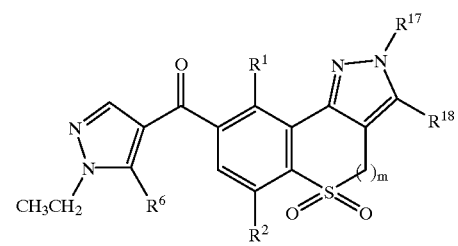

| R⁶ | R¹ | R² | m | R¹⁷ | R¹⁸ |
|---|---|---|---|---|---|
| Cl | Cl | H | 2 | CH₂CH₂CH₃ | H |
| SH | CH₃ | CH₃ | 2 | CH₂CH₂CH₃ | H |
| Cl | CH₃ | CH₃ | 2 | CH₂CH₂CH₃ | H |
| SH | Cl | Cl | 2 | CH₂CH₂CH₃ | H |
| Cl | Cl | Cl | 2 | CH₂CH₂CH₃ | H |
| SH | H | H | 1 | H | CH₃ |
| Cl | H | H | 1 | H | CH₃ |
| SH | CH₃ | H | 1 | H | CH₃ |
| Cl | CH₃ | H | 1 | H | CH₃ |
| SH | Cl | H | 1 | H | CH₃ |
| Cl | Cl | H | 1 | H | CH₃ |
| SH | CH₃ | CH₃ | 1 | H | CH₃ |
| Cl | CH₃ | CH₃ | 1 | H | CH₃ |
| SH | Cl | Cl | 1 | H | CH₃ |
| Cl | Cl | Cl | 1 | H | CH₃ |
| SH | H | H | 2 | H | CH₃ |
| Cl | H | H | 2 | H | CH₃ |
| SH | CH₃ | H | 2 | H | CH₃ |
| Cl | CH₃ | H | 2 | H | CH₃ |
| SH | Cl | H | 2 | H | CH₃ |
| Cl | Cl | H | 2 | H | CH₃ |
| SH | CH₃ | CH₃ | 2 | H | CH₃ |
| Cl | CH₃ | CH₃ | 2 | H | CH₃ |
| SH | Cl | Cl | 2 | H | CH₃ |
| Cl | Cl | Cl | 2 | H | CH₃ |
| SH | H | H | 1 | CH₃ | CH₃ |
| Cl | H | H | 1 | CH₃ | CH₃ |
| SH | CH₃ | H | 1 | CH₃ | CH₃ |
| Cl | CH₃ | H | 1 | CH₃ | CH₃ |
| SH | Cl | H | 1 | CH₃ | CH₃ |
| Cl | Cl | H | 1 | CH₃ | CH₃ |
| SH | CH₃ | CH₃ | 1 | CH₃ | CH₃ |
| Cl | CH₃ | CH₃ | 1 | CH₃ | CH₃ |
| SH | Cl | Cl | 1 | CH₃ | CH₃ |
| Cl | Cl | Cl | 1 | CH₃ | CH₃ |
| SH | H | H | 2 | CH₃ | CH₃ |
| Cl | H | H | 2 | CH₃ | CH₃ |
| SH | CH₃ | H | 2 | CH₃ | CH₃ |
| Cl | CH₃ | H | 2 | CH₃ | CH₃ |
| SH | Cl | H | 2 | CH₃ | CH₃ |
| Cl | Cl | H | 2 | CH₃ | CH₃ |
| SH | CH₃ | CH₃ | 2 | CH₃ | CH₃ |
| Cl | CH₃ | CH₃ | 2 | CH₃ | CH₃ |
| SH | Cl | Cl | 2 | CH₃ | CH₃ |
| Cl | Cl | Cl | 2 | CH₃ | CH₃ |
| SH | H | H | 1 | CH₂CH₃ | CH₃ |
| Cl | H | H | 1 | CH₂CH₃ | CH₃ |
| SH | CH₃ | H | 1 | CH₂CH₃ | CH₃ |
| Cl | CH₃ | H | 1 | CH₂CH₃ | CH₃ |
| SH | Cl | H | 1 | CH₂CH₃ | CH₃ |
| Cl | Cl | H | 1 | CH₂CH₃ | CH₃ |
| SH | CH₃ | CH₃ | 1 | CH₂CH₃ | CH₃ |
| Cl | CH₃ | CH₃ | 1 | CH₂CH₃ | CH₃ |
| SH | Cl | Cl | 1 | CH₂CH₃ | CH₃ |
| Cl | Cl | Cl | 1 | CH₂CH₃ | CH₃ |
| SH | H | H | 2 | CH₂CH₃ | CH₃ |
| Cl | H | H | 2 | CH₂CH₃ | CH₃ |
| SH | CH₃ | H | 2 | CH₂CH₃ | CH₃ |
| Cl | CH₃ | H | 2 | CH₂CH₃ | CH₃ |
| SH | Cl | H | 2 | CH₂CH₃ | CH₃ |
| Cl | Cl | H | 2 | CH₂CH₃ | CH₃ |
| SH | CH₃ | CH₃ | 2 | CH₂CH₃ | CH₃ |
| Cl | CH₃ | CH₃ | 2 | CH₂CH₃ | CH₃ |
| SH | Cl | Cl | 2 | CH₂CH₃ | CH₃ |

TABLE 16-continued

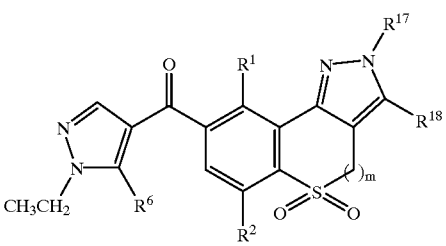

| R⁶ | R¹ | R² | m | R¹⁷ | R¹⁸ |
|---|---|---|---|---|---|
| Cl | Cl | Cl | 2 | $CH_2CH_3$ | $CH_3$ |
| SH | H | H | 1 | $CH_2CH_2CH_3$ | $CH_3$ |
| Cl | H | H | 1 | $CH_2CH_2CH_3$ | $CH_3$ |
| SH | $CH_3$ | H | 1 | $CH_2CH_2CH_3$ | $CH_3$ |
| Cl | $CH_3$ | H | 1 | $CH_2CH_2CH_3$ | $CH_3$ |
| SH | Cl | H | 1 | $CH_2CH_2CH_3$ | $CH_3$ |
| Cl | Cl | H | 1 | $CH_2CH_2CH_3$ | $CH_3$ |
| SH | $CH_3$ | $CH_3$ | 1 | $CH_2CH_2CH_3$ | $CH_3$ |
| Cl | $CH_3$ | $CH_3$ | 1 | $CH_2CH_2CH_3$ | $CH_3$ |
| SH | Cl | Cl | 1 | $CH_2CH_2CH_3$ | $CH_3$ |
| Cl | Cl | Cl | 1 | $CH_2CH_2CH_3$ | $CH_3$ |
| SH | H | H | 2 | $CH_2CH_2CH_3$ | $CH_3$ |
| Cl | H | H | 2 | $CH_2CH_2CH_3$ | $CH_3$ |
| SH | $CH_3$ | H | 2 | $CH_2CH_2CH_3$ | $CH_3$ |
| Cl | $CH_3$ | H | 2 | $CH_2CH_2CH_3$ | $CH_3$ |
| SH | Cl | H | 2 | $CH_2CH_2CH_3$ | $CH_3$ |
| Cl | Cl | H | 2 | $CH_2CH_2CH_3$ | $CH_3$ |
| SH | $CH_3$ | $CH_3$ | 2 | $CH_2CH_2CH_3$ | $CH_3$ |
| Cl | $CH_3$ | $CH_3$ | 2 | $CH_2CH_2CH_3$ | $CH_3$ |
| SH | Cl | Cl | 2 | $CH_2CH_2CH_3$ | $CH_3$ |
| Cl | Cl | Cl | 2 | $CH_2CH_2CH_3$ | $CH_3$ |
| SH | H | H | 1 | H | Cl |
| Cl | H | H | 1 | H | Cl |
| SH | $CH_3$ | H | 1 | H | Cl |
| Cl | $CH_3$ | H | 1 | H | Cl |
| SH | Cl | H | 1 | H | Cl |
| Cl | Cl | H | 1 | H | Cl |
| SH | $CH_3$ | $CH_3$ | 1 | H | Cl |
| Cl | $CH_3$ | $CH_3$ | 1 | H | Cl |
| SH | Cl | Cl | 1 | H | Cl |
| Cl | Cl | Cl | 1 | H | Cl |
| SH | H | H | 2 | H | Cl |
| Cl | H | H | 2 | H | Cl |
| SH | $CH_3$ | H | 2 | H | Cl |
| Cl | $CH_3$ | H | 2 | H | Cl |
| SH | Cl | H | 1 | H | Cl |
| Cl | Cl | H | 2 | H | Cl |
| SH | $CH_3$ | $CH_3$ | 2 | H | Cl |
| Cl | $CH_3$ | $CH_3$ | 2 | H | Cl |
| SH | Cl | Cl | 2 | H | Cl |
| Cl | Cl | Cl | 2 | H | Cl |
| SH | H | H | 1 | $CH_3$ | Cl |
| Cl | H | H | 1 | $CH_3$ | Cl |
| SH | $CH_3$ | H | 1 | $CH_3$ | Cl |
| Cl | $CH_3$ | H | 1 | $CH_3$ | Cl |
| SH | Cl | H | 1 | $CH_3$ | Cl |
| Cl | Cl | H | 1 | $CH_3$ | Cl |
| SH | $CH_3$ | $CH_3$ | 1 | $CH_3$ | Cl |
| Cl | $CH_3$ | $CH_3$ | 1 | $CH_3$ | Cl |
| SH | Cl | Cl | 1 | $CH_3$ | Cl |
| Cl | Cl | Cl | 1 | $CH_3$ | Cl |
| SH | H | H | 2 | $CH_3$ | Cl |
| Cl | H | H | 2 | $CH_3$ | Cl |
| SH | $CH_3$ | H | 2 | $CH_3$ | Cl |
| Cl | $CH_3$ | H | 2 | $CH_3$ | Cl |
| SH | Cl | H | 2 | $CH_3$ | Cl |
| Cl | Cl | H | 2 | $CH_3$ | Cl |
| SH | $CH_3$ | $CH_3$ | 2 | $CH_3$ | Cl |
| Cl | $CH_3$ | $CH_3$ | 2 | $CH_3$ | Cl |
| SH | Cl | Cl | 2 | $CH_3$ | Cl |
| Cl | Cl | Cl | 2 | $CH_3$ | Cl |
| SH | H | H | 1 | $CH_2CH_3$ | Cl |
| Cl | H | H | 1 | $CH_2CH_3$ | Cl |
| SH | $CH_3$ | H | 1 | $CH_2CH_3$ | Cl |

TABLE 16-continued

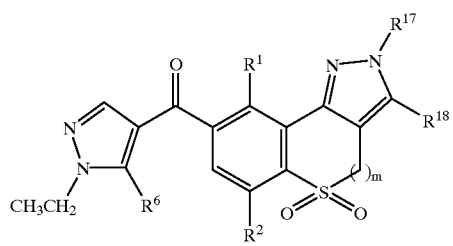

| R⁶ | R¹ | R² | m | R¹⁷ | R¹⁸ |
|---|---|---|---|---|---|
| Cl | $CH_3$ | H | 1 | $CH_2CH_3$ | Cl |
| SH | Cl | H | 1 | $CH_2CH_3$ | Cl |
| Cl | Cl | H | 1 | $CH_2CH_3$ | Cl |
| SH | $CH_3$ | $CH_3$ | 1 | $CH_2CH_3$ | Cl |
| Cl | $CH_3$ | $CH_3$ | 1 | $CH_2CH_3$ | Cl |
| SH | Cl | Cl | 1 | $CH_2CH_3$ | Cl |
| Cl | Cl | Cl | 1 | $CH_2CH_3$ | Cl |
| SH | H | H | 2 | $CH_2CH_3$ | Cl |
| Cl | H | H | 2 | $CH_2CH_3$ | Cl |
| SH | $CH_3$ | H | 2 | $CH_2CH_3$ | Cl |
| Cl | $CH_3$ | H | 2 | $CH_2CH_3$ | Cl |
| SH | Cl | H | 2 | $CH_2CH_3$ | Cl |
| Cl | Cl | H | 2 | $CH_2CH_3$ | Cl |
| SH | $CH_3$ | $CH_3$ | 2 | $CH_2CH_3$ | Cl |
| Cl | $CH_3$ | $CH_3$ | 2 | $CH_2CH_3$ | CJ |
| SH | Cl | Cl | 2 | $CH_2CH_3$ | Cl |
| Cl | Cl | Cl | 2 | $CH_2CH_3$ | Cl |
| SH | H | H | 1 | $CH_2CH_2CH_3$ | Cl |
| Cl | H | H | 1 | $CH_2CH_2CH_3$ | Cl |
| SH | $CH_3$ | H | 1 | $CH_2CH_2CH_3$ | Cl |
| Cl | $CH_3$ | H | 1 | $CH_2CH_2CH_3$ | Cl |
| SH | Cl | H | 1 | $CH_2CH_2CH_3$ | Cl |
| Cl | Cl | H | 1 | $CH_2CH_2CH_3$ | Cl |
| SH | $CH_3$ | $CH_3$ | 1 | $CH_2CH_2CH_3$ | Cl |
| Cl | $CH_3$ | $CH_3$ | 1 | $CH_2CH_2CH_3$ | Cl |
| SH | Cl | Cl | 1 | $CH_2CH_2CH_3$ | Cl |
| Cl | Cl | Cl | 1 | $CH_2CH_2CH_3$ | Cl |
| SH | H | H | 2 | $CH_2CH_2CH_3$ | Cl |
| Cl | H | H | 2 | $CH_2CH_2CH_3$ | Cl |
| SH | $CH_3$ | H | 2 | $CH_2CH_2CH_3$ | Cl |
| Cl | $CH_3$ | H | 2 | $CH_2CH_2CH_3$ | Cl |
| SH | Cl | H | 2 | $CH_2CH_2CH_3$ | Cl |
| Cl | Cl | H | 2 | $CH_2CH_2CH_3$ | Cl |
| SH | $CH_3$ | $CH_3$ | 2 | $CH_2CH_2CH_3$ | Cl |
| Cl | $CH_3$ | $CH_3$ | 2 | $CH_2CH_2CH_3$ | Cl |
| SH | Cl | Cl | 2 | $CH_2CH_2CH_3$ | Cl |
| Cl | Cl | Cl | 2 | $CH_2CH_2CH_3$ | Cl |

TABLE 17

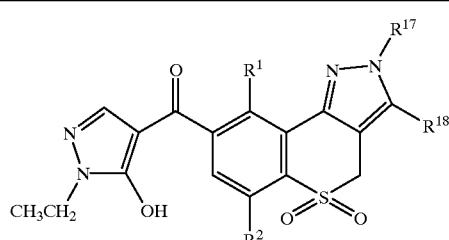

| R¹ | R² | R¹⁷ | R¹⁸ |
|---|---|---|---|
| H | H | $CH(CH_3)_2$ | H |
| $CH_3$ | H | $CH(CH_3)_2$ | H |
| Cl | H | $CH(CH_3)_2$ | H |
| $CH_3$ | $CH_3$ | $CH(CH_3)_2$ | H |
| Cl | Cl | $CH(CH_3)_2$ | H |
| H | H | phenyl | H |
| $CH_3$ | H | phenyl | H |

TABLE 17-continued

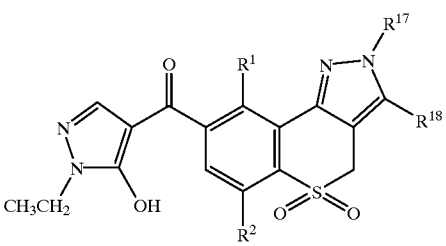

| R¹ | R² | R¹⁷ | R¹⁸ |
|---|---|---|---|
| Cl | H | phenyl | H |
| CH₃ | CH₃ | phenyl | H |
| Cl | Cl | phenyl | H |
| H | H | (4-CH₃)Ph | H |
| CH₃ | H | (4-CH₃)Ph | H |
| Cl | H | (4-CH₃)Ph | H |
| CH₃ | CH₃ | (4-CH₃)Ph | H |
| Cl | Cl | (4-CH₃)Ph | H |
| H | H | (4-Cl)Ph | H |
| CH₃ | H | (4-Cl)Ph | H |
| Cl | H | (4-Cl)Ph | H |
| CH₃ | CH₃ | (4-Cl)Ph | H |
| Cl | Cl | (4-Cl)Ph | H |
| H | H | (4-NO₂)Ph | H |
| CH₃ | H | (4-NO₂)Ph | H |
| Cl | H | (4-NO₂)Ph | H |
| CH₃ | CH₃ | (4-NO₂)Ph | H |
| Cl | Cl | (4-NO₂)Ph | H |
| H | H | (4-CN)Ph | H |
| CH₃ | H | (4-CN)Ph | H |
| Cl | H | (4-CN)Ph | H |
| CH₃ | CH₃ | (4-CN)Ph | H |
| Cl | Cl | (4-CN)Ph | H |
| H | H | 2-pyridyl | H |
| CH₃ | H | 2-pyridyl | H |
| Cl | H | 2-pyridyl | H |
| CH₃ | CH₃ | 2-pyridyl | H |
| Cl | Cl | 2-pyridyl | H |
| H | H | 4-pyridyl | H |
| CH₃ | H | 4-pyridyl | H |
| Cl | H | 4-pyridyl | H |
| CH₃ | CH₃ | 4-pyridyl | H |
| Cl | Cl | 4-pyridyl | H |
| H | H | CH₂CF₃ | H |
| CH₃ | H | CH₂CF₃ | H |
| Cl | H | CH₂CF₃ | H |
| CH₃ | CH₃ | CH₂CF₃ | H |
| Cl | Cl | CH₂CF₃ | H |
| H | H | CH(CH₃)₂ | Cl |
| CH₃ | H | CH(CH₃)₂ | Cl |
| Cl | H | CH(CH₃)₂ | Cl |
| CH₃ | CH₃ | CH(CH₃)₂ | Cl |
| Cl | Cl | CH(CH₃)₂ | CJ |
| H | H | phenyl | Cl |
| CH₃ | H | phenyl | Cl |
| Cl | H | phenyl | Cl |
| CH₃ | CH₃ | phenyl | Cl |
| Cl | Cl | phenyl | Cl |
| H | H | (4-CH₃)Ph | Cl |
| CH₃ | H | (4-CH₃)Ph | Cl |
| Cl | H | (4-CH₃)Ph | Cl |
| CH₃ | CH₃ | (4-CH₃)Ph | Cl |
| Cl | Cl | (4-CH₃)Ph | Cl |
| H | H | (4-Cl)Ph | Cl |
| CH₃ | H | (4-Cl)Ph | Cl |
| Cl | H | (4-Cl)Ph | Cl |
| CH₃ | CH₃ | (4-Cl)Ph | Cl |
| Cl | Cl | (4-Cl)Ph | Cl |
| H | H | (4-NO₂)Ph | Cl |
| CH₃ | H | (4-NO₂)Ph | Cl |
| Cl | H | (4-NO₂)Ph | Cl |
| CH₃ | CH₃ | (4-NO₂)Ph | Cl |
| Cl | Cl | (4-NO₂)Ph | Cl |
| H | H | (4-CN)Ph | Cl |
| CH₃ | H | (4-CN)Ph | Cl |
| Cl | H | (4-CN)Ph | Cl |
| CH₃ | CH₃ | (4-CN)Ph | Cl |
| Cl | Cl | (4-CN)Ph | Cl |
| H | H | 2-pyridyl | Cl |
| CH₃ | H | 2-pyridyl | Cl |
| Cl | H | 2-pyridyl | Cl |
| CH₃ | CH₃ | 2-pyridyl | Cl |
| Cl | Cl | 2-pyridyl | Cl |
| H | H | 4-pyridyl | Cl |
| CH₃ | H | 4-pyridyl | Cl |
| Cl | H | 4-pyridyl | Cl |
| CH₃ | CH₃ | 4-pyridyl | Cl |
| Cl | Cl | 4-pyridyl | Cl |
| H | H | CH₂CF₃ | Cl |
| CH₃ | H | CH₂CF₃ | Cl |
| Cl | H | CH₂CF₃ | Cl |
| CH₃ | CH₃ | CH₂CF₃ | Cl |
| Cl | Cl | CH₂CF₃ | Cl |
| H | H | CH(CH₃)₂ | CH₃ |
| CH₃ | H | CH(CH₃)₂ | CH₃ |
| Cl | H | CH(CH₃)₂ | CH₃ |
| CH₃ | CH₃ | CH(CH₃)₂ | CH₃ |
| Cl | Cl | CH(CH₃)₂ | CH₃ |
| H | H | phenyl | CH₃ |
| CH₃ | H | phenyl | CH₃ |
| Cl | H | phenyl | CH₃ |
| CH₃ | CH₃ | phenyl | CH₃ |
| Cl | Cl | phenyl | CH₃ |
| H | H | (4-CH₃)Ph | CH₃ |
| CH₃ | H | (4-CH₃)Ph | CH₃ |
| Cl | H | (4-CH₃)Ph | CH₃ |
| CH₃ | CH₃ | (4-CH₃)Ph | CH₃ |
| Cl | Cl | (4-CH₃)Ph | CH₃ |
| H | H | (4-Cl)Ph | CH₃ |
| CH₃ | H | (4-Cl)Ph | CH₃ |
| Cl | H | (4-Cl)Ph | CH₃ |
| CH₃ | CH₃ | (4-Cl)Ph | CH₃ |
| Cl | Cl | (4-Cl)Ph | CH₃ |
| H | H | (4-NO₂)Ph | CH₃ |
| CH₃ | H | (4-NO₂)Ph | CH₃ |
| Cl | H | (4-NO₂)Ph | CH₃ |
| CH₃ | CH₃ | (4-NO₂)Ph | CH₃ |
| Cl | Cl | (4-NO₂)Ph | CH₃ |
| H | H | (4-CN)Ph | CH₃ |
| CH₃ | H | (4-CN)Ph | CH₃ |
| Cl | H | (4-CN)Ph | CH₃ |
| CH₃ | CH₃ | (4-CN)Ph | CH₃ |
| Cl | Cl | (4-CN)Ph | CH₃ |
| H | H | 2-pyridyl | CH₃ |
| CH₃ | H | 2-pyridyl | CH₃ |
| Cl | H | 2-pyridyl | CH₃ |
| CH₃ | CH₃ | 2-pyridyl | CH₃ |
| Cl | Cl | 2-pyridyl | CH₃ |
| H | H | 4-pyridyl | CH₃ |
| CH₃ | H | 4-pyridyl | CH₃ |
| Cl | H | 4-pyridyl | CH₃ |
| CH₃ | CH₃ | 4-pyridyl | CH₃ |
| Cl | Cl | 4-pyridyl | CH₃ |
| H | H | CH₂CF₃ | CH₃ |
| CH₃ | H | CH₂CF₃ | CH₃ |

TABLE 17-continued

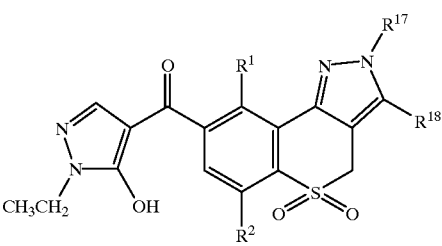

| R¹ | R² | R¹⁷ | R¹⁸ |
|---|---|---|---|
| Cl | H | CH₂CF₃ | CH₃ |
| CH₃ | CH₃ | CH₂CF₃ | CH₃ |
| Cl | Cl | CH₂CF₃ | CH₃ |

TABLE 18

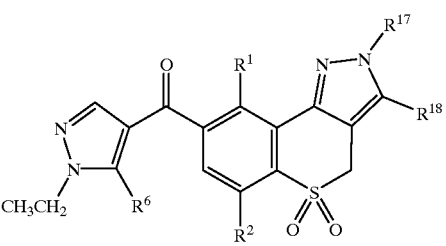

| R⁶ | R¹ | R² | R¹⁷ | R¹⁸ |
|---|---|---|---|---|
| OH | CH₂CH₃ | H | H | H |
| SH | CH₂CH₃ | H | H | H |
| Cl | CH₂CH₃ | H | H | H |
| OH | NO₂ | H | H | H |
| SH | NO₂ | H | H | H |
| Cl | NO₂ | H | H | H |
| OH | OCH₃ | H | H | H |
| SH | OCH₃ | H | H | H |
| Cl | OCH₃ | H | H | H |
| OH | CH₂CH₃ | CH₃ | H | H |
| SH | CH₂CH₃ | CH₃ | H | H |
| Cl | CH₂CH₃ | CH₃ | H | H |
| OH | NO₂ | CH₃ | H | H |
| SH | NO₂ | CH₃ | H | H |
| Cl | NO₂ | CH₃ | H | H |
| OH | OCH₃ | CH₃ | H | H |
| SH | OCH₃ | CH₃ | H | H |
| Cl | OCH₃ | CH₃ | H | H |
| OH | CH₂CH₃ | Cl | H | R |
| SH | CH₂CH₃ | Cl | H | H |
| Cl | CH₂CH₃ | Cl | H | H |
| OH | NO₂ | Cl | H | H |
| SH | NO₂ | Cl | H | H |
| Cl | NO₂ | Cl | H | H |
| OH | OCH₃ | Cl | H | H |
| SH | OCH₃ | Cl | H | H |
| Cl | OCH₃ | Cl | H | H |
| OH | CH₂CH₃ | H | CH₃ | H |
| SH | CH₂CH₃ | H | CH₃ | H |
| Cl | CH₂CH₃ | H | CH₃ | H |
| OH | NO₂ | H | CH₃ | H |
| SH | NO₂ | H | CH₃ | H |
| Cl | NO₂ | H | CH₃ | H |
| OH | OCH₃ | H | CH₃ | H |
| SH | OCH₃ | H | CH₃ | H |
| Cl | OCH₃ | H | CH₃ | H |
| OH | CH₂CH₃ | CH₃ | CH₃ | H |
| SH | CH₂CH₃ | CH₃ | CH₃ | H |
| Cl | CH₂CH₃ | CH₃ | CH₃ | H |
| OH | NO₂ | CH₃ | CH₃ | H |
| SH | NO₂ | CH₃ | CH₃ | H |

TABLE 18-continued

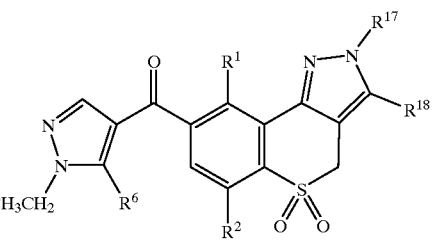

| R⁶ | R¹ | R² | R¹⁷ | R¹⁸ |
|---|---|---|---|---|
| Cl | NO₂ | CH₃ | CH₃ | H |
| OH | OCH₃ | CH₃ | CH₃ | H |
| SH | OCH₃ | CH₃ | CH₃ | H |
| Cl | OCH₃ | CH₃ | CH₃ | H |
| OH | CH₂CH₃ | Cl | CH₃ | H |
| SH | CH₂CH₃ | Cl | CH₃ | H |
| Cl | CH₂CH₃ | Cl | CH₃ | H |
| OH | NO₂ | Cl | CH₃ | H |
| SH | NO₂ | Cl | CH₃ | H |
| Cl | NO₂ | Cl | CH₃ | H |
| OH | OCH₃ | Cl | CH₃ | H |
| SH | OCH₃ | Cl | CH₃ | H |
| Cl | OCH₃ | Cl | CH₃ | H |
| OH | CH₂CH₃ | H | CH₂CH₃ | H |
| SH | CH₂CH₃ | H | CH₂CH₃ | H |
| Cl | CH₂CH₃ | H | CH₂CH₃ | H |
| OH | NO₂ | H | CH₂CH₃ | H |
| SH | NO₂ | H | CH₂CH₃ | H |
| Cl | NO₂ | H | CH₂CH₃ | H |
| OH | OCH₃ | H | CH₂CH₃ | H |
| SH | OCH₃ | H | CH₂CH₃ | H |
| Cl | OCH₃ | H | CH₂CH₃ | H |
| OH | CH₂CH₃ | CH₃ | CH₂CH₃ | H |
| SH | CH₂CH₃ | CH₃ | CH₂CH₃ | H |
| Cl | CH₂CH₃ | CH₃ | CH₂CH₃ | H |
| OH | NO₂ | CH₃ | CH₂CH₃ | H |
| SH | NO₂ | CH₃ | CH₂CH₃ | H |
| Cl | NO₂ | CH₃ | CH₂CH₃ | H |
| OH | OCH₃ | CH₃ | CH₂CH₃ | H |
| SH | OCH₃ | CH₃ | CH₂CH₃ | H |
| Cl | OCH₃ | CH₃ | CH₂CH₃ | H |
| OH | CH₂CH₃ | Cl | CH₂CH₃ | H |
| SH | CH₂CH₃ | Cl | CH₂CH₃ | H |
| Cl | CH₂CH₃ | Cl | CH₂CH₃ | H |
| OH | NO₂ | Cl | CH₂CH₃ | H |
| SH | NO₂ | Cl | CH₂CH₃ | H |
| Cl | NO₂ | Cl | CH₂CH₃ | H |
| OH | OCH₃ | Cl | CH₂CH₃ | H |
| SH | OCH₃ | Cl | CH₂CH₃ | H |
| Cl | OCH₃ | Cl | CH₂CH₃ | H |
| OH | CH₂CH₃ | H | CH₂CH₂CH₃ | H |
| SH | CH₂CH₃ | H | CH₂CH₂CH₃ | H |
| Cl | CH₂CH₃ | H | CH₂CH₂CH₃ | H |
| OH | NO₂ | H | CH₂CH₂CH₃ | H |
| SH | NO₂ | H | CH₂CH₂CH₃ | H |
| Cl | NO₂ | H | CH₂CH₂CH₃ | H |
| OH | OCH₃ | H | CH₂CH₂CH₃ | H |
| SH | OCH₃ | H | CH₂CH₂CH₃ | H |
| Cl | OCH₃ | H | CH₂CH₂CH₃ | H |
| OH | CH₂CH₃ | CH₃ | CH₂CH₂CH₃ | H |
| SH | CH₂CH₃ | CH₃ | CH₂CH₂CH₃ | H |
| Cl | CH₂CH₃ | CH₃ | CH₂CH₂CH₃ | H |
| OH | NO₂ | CH₃ | CH₂CH₂CH₃ | H |
| SH | NO₂ | CH₃ | CH₂CH₂CH₃ | H |
| Cl | NO₂ | CH₃ | CH₂CH₂CH₃ | H |
| OH | OCH₃ | CH₃ | CH₂CH₂CH₃ | H |
| SH | OCH₃ | CH₃ | CH₂CH₂CH₃ | H |
| Cl | OCH₃ | CH₃ | CH₂CH₂CH₃ | H |
| OH | CH₂CH₃ | Cl | CH₂CH₂CH₃ | H |
| SH | CH₂CH₃ | Cl | CH₂CH₂CH₃ | H |
| Cl | CH₂CH₃ | Cl | CH₂CH₂CH₃ | H |
| OH | NO₂ | Cl | CH₂CH₂CH₃ | H |
| SH | NO₂ | Cl | CH₂CH₂CH₃ | H |
| Cl | NO₂ | Cl | CH₂CH₂CH₃ | H |

TABLE 18-continued

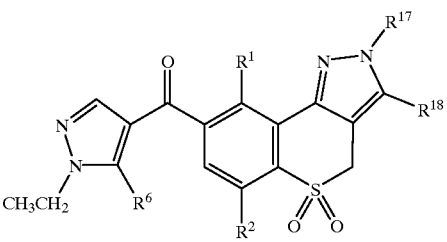

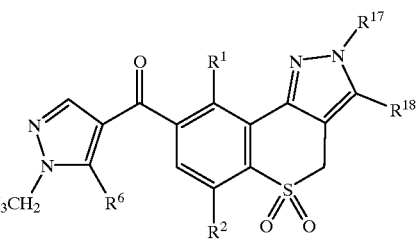

| R⁶ | R¹ | R² | R¹⁷ | R¹⁸ |
|---|---|---|---|---|
| OH | OCH₃ | Cl | CH₂CH₂CH₃ | H |
| SH | OCH₃ | Cl | CH₂CH₂CH₃ | H |
| Cl | OCH₃ | Cl | CH₂CH₂CH₃ | H |
| OH | CH₂CH₃ | H | H | CH₃ |
| SH | CH₂CH₃ | H | H | CH₃ |
| Cl | CH₂CH₃ | H | H | CH₃ |
| OH | NO₂ | H | H | CH₃ |
| SH | NO₂ | H | H | CH₃ |
| Cl | NO₂ | H | H | CH₃ |
| OH | OCH₃ | H | H | CH₃ |
| SH | OCH₃ | H | H | CH₃ |
| Cl | OCH₃ | H | H | CH₃ |
| OH | CH₂CH₃ | CH₃ | H | CH₃ |
| SH | CH₂CH₃ | CH₃ | H | CH₃ |
| Cl | CH₂CH₃ | CH₃ | H | CH₃ |
| OH | NO₂ | CH₃ | H | CH₃ |
| SH | NO₂ | CH₃ | H | CH₃ |
| Cl | NO₂ | CH₃ | H | CH₃ |
| OH | OCH₃ | CH₃ | H | CH₃ |
| SH | OCH₃ | CH₃ | H | CH₃ |
| Cl | OCH₃ | CH₃ | H | CH₃ |
| OH | CH₂CH₃ | Cl | H | CH₃ |
| SH | CH₂CH₃ | Cl | H | CH₃ |
| Cl | CH₂CH₃ | Cl | H | CH₃ |
| OH | NO₂ | Cl | H | CH₃ |
| SH | NO₂ | Cl | H | CH₃ |
| Cl | NO₂ | Cl | H | CH₃ |
| OH | OCH₃ | Cl | H | CH₃ |
| SH | OCH₃ | Cl | H | CH₃ |
| Cl | OCH₃ | Cl | H | CH₃ |
| OH | CH₂CH₃ | H | CH₃ | CH₃ |
| SH | CH₂CH₃ | H | CH₃ | CH₃ |
| Cl | CH₂CH₃ | H | CH₃ | CH₃ |
| OH | NO₂ | H | CH₃ | CH₃ |
| SH | NO₂ | H | CH₃ | CH₃ |
| Cl | NO₂ | H | CH₃ | CH₃ |
| OH | OCH₃ | H | CH₃ | CH₃ |
| SH | OCH₃ | H | CH₃ | CH₃ |
| Cl | OCH₃ | H | CH₃ | CH₃ |
| OH | CH₂CH₃ | CH₃ | CH₃ | CH₃ |
| SH | CH₂CH₃ | CH₃ | CH₃ | CH₃ |
| Cl | CH₂CH₃ | CH₃ | CH₃ | CH₃ |
| OH | NO₂ | CH₃ | CH₃ | CH₃ |
| SH | NO₂ | CH₃ | CH₃ | CH₃ |
| Cl | NO₂ | CH₃ | CH₃ | CH₃ |
| OH | OCH₃ | CH₃ | CH₃ | CH₃ |
| SH | OCH₃ | CH₃ | CH₃ | CH₃ |
| Cl | OCH₃ | CH₃ | CH₃ | CH₃ |
| OH | CH₂CH₃ | Cl | CH₃ | CH₃ |
| SH | CH₂CH₃ | Cl | CH₃ | CH₃ |
| Cl | CH₂CH₃ | Cl | CH₃ | CH₃ |
| OH | NO₂ | Cl | CH₃ | CH₃ |
| SH | NO₂ | Cl | CH₃ | CH₃ |
| Cl | NO₂ | Cl | CH₃ | CH₃ |
| OH | OCH₃ | Cl | CH₃ | CH₃ |
| SH | OCH₃ | Cl | CH₃ | CH₃ |
| Cl | OCH₃ | Cl | CH₃ | CH₃ |
| OH | CH₂CH₃ | H | CH₂CH₃ | CH₃ |
| SH | CH₂CH₃ | H | CH₂CH₃ | CH₃ |
| Cl | CH₂CH₃ | H | CH₂CH₃ | CH₃ |
| OH | NO₂ | H | CH₂CH₃ | CH₃ |
| SH | NO₂ | H | CH₂CH₃ | CH₃ |
| Cl | NO₂ | H | CH₂CH₃ | CH₃ |
| OH | OCH₃ | H | CH₂CH₃ | CH₃ |
| SH | OCH₃ | H | CH₂CH₃ | CH₃ |
| Cl | OCH₃ | H | CH₂CH₃ | CH₃ |
| OH | CH₂CH₃ | CH₃ | CH₂CH₃ | CH₃ |
| SH | CH₂CH₃ | CH₃ | CH₂CH₃ | CH₃ |
| Cl | CH₂CH₃ | CH₃ | CH₂CH₃ | CH₃ |
| OH | NO₂ | CH₃ | CH₂CH₃ | CH₃ |
| SH | NO₂ | CH₃ | CH₂CH₃ | CH₃ |
| Cl | NO₂ | CH₃ | CH₂CH₃ | CH₃ |
| OH | OCH₃ | CH₃ | CH₂CH₃ | CH₃ |
| SH | OCH₃ | CH₃ | CH₂CH₃ | CH₃ |
| Cl | OCH₃ | CH₃ | CH₂CH₃ | CH₃ |
| OH | CH₂CH₃ | Cl | CH₂CH₃ | CH₃ |
| SH | CH₂CH₃ | Cl | CH₂CH₃ | CH₃ |
| Cl | CH₂CH₃ | Cl | CH₂CH₃ | CH₃ |
| OH | NO₂ | Cl | CH₂CH₃ | CH₃ |
| SH | NO₂ | Cl | CH₂CH₃ | CH₃ |
| Cl | NO₂ | Cl | CH₂CH₃ | CH₃ |
| OH | OCH₃ | Cl | CH₂CH₃ | CH₃ |
| SH | OCH₃ | Cl | CH₂CH₃ | CH₃ |
| Cl | OCH₃ | Cl | CH₂CH₃ | CH₃ |
| OH | CH₂CH₃ | H | CH₂CH₂CH₃ | CH₃ |
| SH | CH₂CH₃ | H | CH₂CH₂CH₃ | CH₃ |
| Cl | CH₂CH₃ | H | CH₂CH₂CH₃ | CH₃ |
| OH | NO₂ | H | CH₂CH₂CH₃ | CH₃ |
| SH | NO₂ | H | CH₂CH₂CH₃ | CH₃ |
| Cl | NO₂ | H | CH₂CH₂CH₃ | CH₃ |
| OH | OCH₃ | H | CH₂CH₂CH₃ | CH₃ |
| SH | OCH₃ | H | CH₂CH₂CH₃ | CH₃ |
| Cl | OCH₃ | H | CH₂CH₂CH₃ | CH₃ |
| OH | CH₂CH₃ | CH₃ | CH₂CH₂CH₃ | CH₃ |
| SH | CH₂CH₃ | CH₃ | CH₂CH₂CH₃ | CH₃ |
| Cl | CH₂CH₃ | CH₃ | CH₂CH₂CH₃ | CH₃ |
| OH | NO₂ | CH₃ | CH₂CH₂CH₃ | CH₃ |
| SH | NO₂ | CH₃ | CH₂CH₂CH₃ | CH₃ |
| Cl | NO₂ | CH₃ | CH₂CH₂CH₃ | CH₃ |
| OH | OCH₃ | CH₃ | CH₂CH₂CH₃ | CH₃ |
| SH | OCH₃ | CH₃ | CH₂CH₂CH₃ | CH₃ |
| Cl | OCH₃ | CH₃ | CH₂CH₂CH₃ | CH₃ |
| OH | CH₂CH₃ | Cl | CH₂CH₂CH₃ | CH₃ |
| SH | CH₂CH₃ | Cl | CH₂CH₂CH₃ | CH₃ |
| Cl | CH₂CH₃ | Cl | CH₂CH₂CH₃ | CH₃ |
| OH | NO₂ | Cl | CH₂CH₂CH₃ | CH₃ |
| SH | NO₂ | Cl | CH₂CH₂CH₃ | CH₃ |
| Cl | NO₂ | Cl | CH₂CH₂CH₃ | CH₃ |
| OH | OCH₃ | Cl | CH₂CH₂CH₃ | CH₃ |
| SH | OCH₃ | Cl | CH₂CH₂CH₃ | CH₃ |
| Cl | OCH₃ | Cl | CH₂CH₂CH₃ | CH₃ |
| OH | CH₂CH₃ | H | H | Cl |
| SH | CH₂CH₃ | H | H | Cl |
| Cl | CH₂CH₃ | H | H | Cl |
| OH | NO₂ | H | H | Cl |
| SH | NO₂ | H | H | Cl |
| Cl | NO₂ | H | H | Cl |
| OH | OCH₃ | H | H | Cl |
| SH | OCH₃ | H | H | Cl |
| Cl | OCH₃ | H | H | Cl |
| OH | CH₂CH₃ | CH₃ | H | Cl |
| SH | CH₂CH₃ | CH₃ | H | Cl |
| Cl | CH₂CH₃ | CH₃ | H | Cl |
| OH | NO₂ | CH₃ | H | Cl |
| SH | NO₂ | CH₃ | H | Cl |
| Cl | NO₂ | CH₃ | H | Cl |
| OH | OCH₃ | CH₃ | H | Cl |
| SH | OCH₃ | CH₃ | H | Cl |

TABLE 18-continued

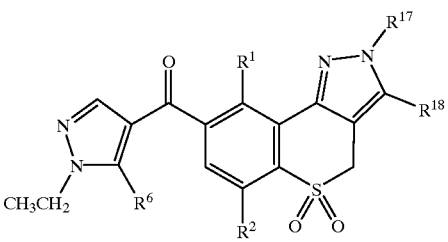

| R⁶ | R¹ | R² | R¹⁷ | R¹⁸ |
|---|---|---|---|---|
| Cl | OCH₃ | CH₃ | H | Cl |
| OH | CH₂CH₃ | Cl | H | Cl |
| SH | CH₂CH₃ | Cl | H | Cl |
| Cl | CH₂CH₃ | Cl | H | Cl |
| OH | NO₂ | Cl | H | Cl |
| SH | NO₂ | Cl | H | Cl |
| Cl | NO₂ | Cl | H | Cl |
| OH | OCH₃ | Cl | H | Cl |
| SH | OCH₃ | Cl | H | Cl |
| Cl | OCH₃ | Cl | H | Cl |
| OH | CH₂CH₃ | H | CH₃ | Cl |
| SH | CH₂CH₃ | H | CH₃ | Cl |
| Cl | CH₂CH₃ | H | CH₃ | Cl |
| OH | NO₂ | H | CH₃ | Cl |
| SH | NO₂ | H | CH₃ | Cl |
| Cl | NO₂ | H | CH₃ | Cl |
| OH | OCH₃ | H | CH₃ | Cl |
| SH | OCH₃ | H | CH₃ | Cl |
| Cl | OCH₃ | H | CH₃ | Cl |
| OH | CH₂CH₃ | CH₃ | CH₃ | Cl |
| SH | CH₂CH₃ | CH₃ | CH₃ | Cl |
| Cl | CH₂CH₃ | CH₃ | CH₃ | Cl |
| OH | NO₂ | CH₃ | CH₃ | Cl |
| SH | NO₂ | CH₃ | CH₃ | Cl |
| Cl | NO₂ | CH₃ | CH₃ | Cl |
| OH | OCH₃ | CH₃ | CH₃ | Cl |
| SH | OCH₃ | CH₃ | CH₃ | Cl |
| Cl | OCH₃ | CH₃ | CH₃ | Cl |
| OH | CH₂CH₃ | Cl | CH₃ | Cl |
| SH | CH₂CH₃ | Cl | CH₃ | Cl |
| Cl | CH₂CH₃ | Cl | CH₃ | Cl |
| OH | NO₂ | Cl | CH₃ | Cl |
| SH | NO₂ | Cl | CH₃ | Cl |
| Cl | NO₂ | Cl | CH₃ | Cl |
| OH | OCH₃ | Cl | CH₃ | Cl |
| SH | OCH₃ | Cl | CH₃ | Cl |
| Cl | OCH₃ | Cl | CH₃ | Cl |
| OH | CH₂CH₃ | H | CH₂CH₃ | Cl |
| SH | CH₂CH₃ | H | CH₂CH₃ | Cl |
| Cl | CH₂CH₃ | H | CH₂CH₃ | Cl |
| OH | NO₂ | H | CH₂CH₃ | Cl |
| SH | NO₂ | H | CH₂CH₃ | Cl |
| Cl | NO₂ | H | CH₂CH₃ | Cl |
| OH | OCH₃ | H | CH₂CH₃ | Cl |
| SH | OCH₃ | H | CH₂CH₃ | Cl |
| Cl | OCH₃ | H | CH₂CH₃ | Cl |
| OH | CH₂CH₃ | CH₃ | CH₂CH₃ | Cl |
| SH | CH₂CH₃ | CH₃ | CH₂CH₃ | Cl |
| Cl | CH₂CH₃ | CH₃ | CH₂CH₃ | Cl |
| OH | NO₂ | CH₃ | CH₂CH₃ | Cl |
| SH | NO₂ | CH₃ | CH₂CH₃ | Cl |
| Cl | NO₂ | CH₃ | CH₂CH₃ | Cl |
| OH | OCH₃ | CH₃ | CH₂CH₃ | Cl |
| SH | OCH₃ | CH₃ | CH₂CH₃ | Cl |
| Cl | OCH₃ | CH₃ | CH₂CH₃ | Cl |
| OH | CH₂CH₃ | Cl | CH₂CH₃ | Cl |
| SH | CH₂CH₃ | Cl | CH₂CH₃ | Cl |
| Cl | CH₂CH₃ | Cl | CH₂CH₃ | Cl |
| OH | NO₂ | Cl | CH₂CH₃ | Cl |
| SH | NO₂ | Cl | CH₂CH₃ | Cl |
| Cl | NO₂ | Cl | CH₂CH₃ | Cl |
| OH | OCH₃ | Cl | CH₂CH₃ | Cl |
| SH | OCH₃ | Cl | CH₂CH₃ | Cl |
| Cl | OCH₃ | Cl | CH₂CH₃ | Cl |

TABLE 18-continued

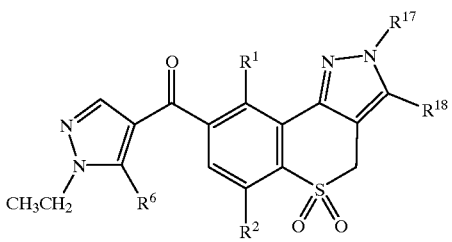

| R⁶ | R¹ | R² | R¹⁷ | R¹⁸ |
|---|---|---|---|---|
| OH | CH₂CH₃ | H | CH₂CH₂CH₃ | Cl |
| SH | CH₂CH₃ | H | CH₂CH₂CH₃ | Cl |
| Cl | CH₂CH₃ | H | CH₂CH₂CH₃ | Cl |
| OH | NO₂ | H | CH₂CH₂CH₃ | Cl |
| SH | NO₂ | H | CH₂CH₂CH₃ | Cl |
| Cl | NO₂ | H | CH₂CH₂CH₃ | Cl |
| OH | OCH₃ | H | CH₂CH₂CH₃ | Cl |
| SH | OCH₃ | H | CH₂CH₂CH₃ | Cl |
| Cl | OCH₃ | H | CH₂CH₂CH₃ | Cl |
| OH | CH₂CH₃ | CH₃ | CH₂CH₂CH₃ | Cl |
| SH | CH₂CH₃ | CH₃ | CH₂CH₂CH₃ | Cl |
| Cl | CH₂CH₃ | CH₃ | CH₂CH₂CH₃ | Cl |
| OH | NO₂ | CH₃ | CH₂CH₂CH₃ | Cl |
| SH | NO₂ | CH₃ | CH₂CH₂CH₃ | Cl |
| Cl | NO₂ | CH₃ | CH₂CH₂CH₃ | Cl |
| OH | OCH₃ | CH₃ | CH₂CH₂CH₃ | Cl |
| SH | OCH₃ | CH₃ | CH₂CH₂CH₃ | Cl |
| Cl | OCH₃ | CH₃ | CH₂CH₂CH₃ | Cl |
| OH | CH₂CH₃ | Cl | CH₂CH₂CH₃ | Cl |
| SH | CH₂CH₃ | Cl | CH₂CH₂CH₃ | Cl |
| Cl | CH₂CH₃ | Cl | CH₂CH₂CH₃ | Cl |
| OH | NO₂ | Cl | CH₂CH₂CH₃ | Cl |
| SH | NO₂ | Cl | CH₂CH₂CH₃ | Cl |
| Cl | NO₂ | Cl | CH₂CH₂CH₃ | Cl |
| OH | OCH₃ | Cl | CH₂CH₂CH₃ | Cl |
| SH | OCH₃ | Cl | CH₂CH₂CH₃ | Cl |
| Cl | OCH₃ | Cl | CH₂CH₂CH₃ | Cl |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, N.Y., 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A–C.

Example A
High Strength Concentrate

| | |
| --- | --- |
| Compound 2 | 98.5% |
| silica aerogel | 0.5% |
| synthetic amorphous fine silica | 1.0%. |

Example B
Wettable Powder

| | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C
Granule

| | |
| --- | --- |
| Compound 15 | 10.0% |
| attapulgite granules (low volatile matter, 0.71/0.30 mm; U.S.S. No. 25–50 sieves) | 90.0%. |

Example D
Extruded Pellet

| | |
| --- | --- |
| Compound 6 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them will have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds will be useful for the control of selected grass and broadleaf weeds with tolerance to important agronomic crops which include but are not limited to barley, cotton, wheat, rape, sugar beets, corn (maize), soybeans, rice, tomato, potato, and plantation crops including coffee, cocoa, oil palm, rubber, sugarcane, citrus, grapes, fruit trees, nut trees, banana, plantain, pineapple, hops, tea, forests such as eucalyptus and conifers, e.g., loblolly pine, and turf species, e.g., Kentucky bluegrass, St. Augustine grass, Kentucky fescue and Bermuda grass. Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clodinafop, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4(1-methylethyl)-5-oxo-1 H-imidazol-2-yl]-5-methyl-3pyridinecarboxylic acid (AC 263,222), difenzoquat metilsulfate, diflufenican, dimepiperate, dimethenamid, dimethylarsinic acid and its sodium salt, dinitramine, dimethenamid, diquat dibromide, dithiopyr, diuron, DNOC, endothal, EPTC, esprocarb, ethalfluralin, ethametsulfuron-methyl, ethofumesate, ethyl α,2-dichloro-5-[4(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, fluridone, flurochloridone, fluroxypyr, fluthiacet-methyl, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox (AC 299 263), imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole (RPA 201772), lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo-1H,3H-[1,3,4] thiadiazolo[3,4-α]pyridazin-1-ylidene)amino]phenyl] thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl) amino]carbonyl]amino]sulfonyl]-1-(2-pyridinyl)-1H-pyrazole-4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, 3-oxetanyl 2-[[[[(4,6-dimethyl-2-pyrimidinyl) amino]carbonyl]amino]sulfonyl]benzoate (CGA 277476), oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, sulfosulfuron, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

Certain combinations of compounds of this invention with other herbicides may provide synergistic herbicidal effects on weeds or may provide enhanced crop safety.

Preferred for better control of undesired vegetation in winter wheat, winter barley, spring wheat, spring barley, and peas (e.g., lower use rate, broader spectrum of weeds controlled, or enhanced crop safety) or for preventing the development of resistant weeds in winter wheat, winter barley, spring wheat, spring barley, and peas are mixtures of a compound of this invention with one or more of the herbicides selected from the group tribenuron-methyl, thifensulfuron-methyl, metsulfuron-methyl, chlorsulfuron, triasulfuron, 2,4-D, dicamba, bromoxynil, MCPA, fluroxypyr, clopyralid, fenoxaprop, diclofop, tralkoxydim, clodinafop, imazamethabenz, sulfosulfuron, difenzoquat, propanil, prosulfuron, metribuzin, glyphosate, triallate, trifluralin, paraquat, diallate, linuron, diflufenican, pendimethalin, cyanazine, neburon, terbutryn, prosulfocarb, isoproturon, chlortoluron, methabenzthiazuron, metoxuron, simazine, ioxynil, mecoprop, metosulam, fluroglycophen-ethyl, flamprop-M-isopropyl, benzoylpropethyl, ethametsulfuron-methyl, quinclorac, and bentazone Specifically preferred mixtures for use in winter wheat, winter barley, spring wheat, spring barley, and peas are selected from the group:

a) 2-[(2,4-dihydro-2,6,9-trimethyl[1]benzothiopyrano[4, 3-c]pyrazol-8-yl)carbonyl]-1,3-cyclohexanedione S,S-dioxide (mixture partner A, generally applied at a rateof 4 to 280 g/ha, preferably applied at a rate of 8 to 70 g /ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | tribenuron-methyl | 1:10–300:1 | 1:1–14:1 | 1–50 | 5–20 |
| 2 | thifensulfuron-methyl | 1:25–300:1 | 1:2–7:1 | 1–100 | 10–40 |
| 3 | thifensulfuron-methyl in combination with | 1:10–300:1 | 1:1–7:1 | 1–50 | 10–20 |
|   | tribenuron-methyl | 1:5–300:1 | 2:1–14:1 | 1–20 | 5–10 |
| 4 | metsulfuron-methyl | 1:5–300:1 | 3:1–35:1 | 1–20 | 2–6 |
| 5 | thifensulfuron-methyl in combination with | 1:25–300:1 | 1:2–7:1 | 1–100 | 10–40 |
|   | metsulfuron-methyl | 1:5–300:1 | 3:1–35:1 | 1–20 | 2–6 |
| 6 | thifensulfuron-methyl in combination with | 1:10–300:1 | 1:1–7:1 | 1–50 | 10–20 |
|   | tribenuron-methyl in combination with | 1:10–300:1 | 1:1–7:1 | 1–20 | 5–10 |
|   | metsulfuron-methyl | 1:5–300:1 | 3:1–35:1 | 1–20 | 2–6 |
| 7 | chlorsulfuron | 1:10–300:1 | 2:3–7:1 | 1–50 | 10–30 |
| 8 | chlorsulfuron in combination with | 1:10–300:1 | 1:1–7:1 | 1–50 | 10–20 |
|   | metsulfuron-methyl | 1:2–300:1 | 5:1–35:1 | 1–10 | 2–4 |
| 9 | triasulfuron | 1:10–300:1 | 2:3–7:1 | 1–50 | 10–30 |
| 10 | 2,4-D | 1:1000–3:1 | 1:100–1:3 | 100–4000 | 200–2000 |
| 11 | dicamba | 1:150–10:1 | 1:15–1:1 | 30–600 | 70–300 |
| 12 | bromoxynil | 1:500–3:1 | 1:50–1:4 | 100–2000 | 250–1000 |
| 13 | MCPA | 1:500–6:1 | 1:50–1:1 | 50–2000 | 100–1000 |
| 14 | bromoxynil in combination with | 1:500–3:1 | 1:50–1:4 | 100–2000 | 250–1000 |
|   | MCPA | 1:500–6:1 | 1:50–1:1 | 50–2000 | 100–1000 |
| 15 | fluroxypyr | 1:150–10:1 | 1:15–1:1 | 30–600 | 70–300 |
| 16 | clopyralid | 1:125–30:1 | 1:12–1:1 | 10–500 | 50–250 |
| 17 | fenoxaprop in combination with | 1:50–30:1 | 1:5–2:1 | 10–200 | 40–100 |
|   | fenchlorazole | 1:12–300:1 | 1:1–7:1 | 1–50 | 10–25 |
| 18 | diclofop | 1:500–3:1 | 1:50–1:7 | 100–2000 | 500–1000 |
| 19 | tralkoxydim | 1:125–3:1 | 1:15–1:2 | 100–500 | 150–300 |
| 20 | clodinafop in combination with | 1:50–30:1 | 1:5–2:1 | 10–200 | 40–100 |
|   | cloquintocet-mexyl | 1:12–300:1 | 1:1–7:1 | 1–50 | 10–25 |
| 21 | sulfosulfuron | 1:12–300:1 | 1:2–20:1 | 1–50 | 4–40 |
| 22 | prosulfuron | 1:125–125:1 | 1:3–3:1 | 4–300 | 20–70 |
| 23 | metribuzin | 1:250–30:1 | 1:25–1:1 | 10–1000 | 50–500 |
| 24 | glyphosate | 1:500–3:1 | 1:50–1:4 | 100–2000 | 250–1000 |
| 25 | ethametsulfuron-methyl | 1:10–300:1 | 2:3–7:1 | 1–50 | 10–30 | b) 2-[(2-ethyl-2,4-dihydro-6,9-dimethyl[1]benzothiopyrano[4,3-c]pyrazol-8-yl)carbonyl]-1,3-cyclohexanedione S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | tribenuron-methyl | 1:10–300:1 | 1:1–14:1 | 1–50 | 5–20 |
| 2 | thifensulfuron-methyl | 1:25–300:1 | 1:2–7:1 | 1–100 | 10–40 |
| 3 | thifensulfuron-methyl in combination with | 1:10–300:1 | 1:1–7:1 | 1–50 | 10–20 |
|   | tribenuron-methyl | 1:5–300:1 | 2:1–14:1 | 1–20 | 5–10 |
| 4 | metsulfuron-methyl | 1:5–300:1 | 3:1–35:1 | 1–20 | 2–6 |
| 5 | thifensulfuron-methyl in combination with | 1:25–300:1 | 1:2–7:1 | 1–100 | 10–40 |
|   | metsulfuron-methyl | 1:5–300:1 | 3:1–35:1 | 1–20 | 2–6 |
| 6 | thifensulfuron-methyl in combination with | 1:10–300:1 | 1:1–7:1 | 1–50 | 10–20 |
|   | tribenuron-methyl in combination with | 1:10–300:1 | 1:1–7:1 | 1–20 | 5–10 |
|   | metsulfuron-methyl | 1:5–300:1 | 3:1–35:1 | 1–20 | 2–6 |
| 7 | chlorsulfuron | 1:10–300:1 | 2:3–7:1 | 1–50 | 10–30 |
| 8 | chlorsulfuron in combination with | 1:10–300:1 | 1:1–7:1 | 1–50 | 10–20 |
|   | metsulfuron-methyl | 1:2–300:1 | 5:1–35:1 | 1–10 | 2–4 |
| 9 | triasulfuron | 1:10–300:1 | 2:3–7:1 | 1–50 | 10–30 |

-continued

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 10 | 2,4-D | 1:1000–3:1 | 1:100–1:3 | 100–4000 | 200–2000 |
| 11 | dicamba | 1:150–10:1 | 1:15–1:1 | 30–600 | 70–300 |
| 12 | bromoxynil | 1:500–3:1 | 1:50–1:4 | 100–2000 | 250–1000 |
| 13 | MCPA | 1:500–6:1 | 1:50–1:1 | 50–2000 | 100–1000 |
| 14 | bromoxynil in combination with MCPA | 1:500–3:1<br>1:500–6:1 | 1:50–1:4<br>1:50–1:1 | 100–2000<br>50–2000 | 250–1000<br>100–1000 |
| 15 | fluroxypyr | 1:150–10:1 | 1:15–1:1 | 30–600 | 70–300 |
| 16 | clopyralid | 1:125–30:1 | 1:12–1:1 | 10–500 | 50–250 |
| 17 | fenoxaprop in combination with fenchlorazole | 1:50–30:1<br>1:12–300:1 | 1:5–2:1<br>1:1–7:1 | 10–200<br>1–50 | 40–100<br>10–25 |
| 18 | diclofop | 1:500–3:1 | 1:50–1:7 | 100–2000 | 500–1000 |
| 19 | tralkoxydim | 1:125–3:1 | 1:15–1:2 | 100–500 | 150–300 |
| 20 | clodinafop in combination with cloquintocet-mexyl | 1:50–30:1<br>1:12–300:1 | 1:5–2:1<br>1:1–7:1 | 10–200<br>1–50 | 40–100<br>10–25 |
| 21 | sulfosulfuron | 1:12–300:1 | 1:2–20:1 | 1–50 | 4–40 |
| 22 | prosulfuron | 1:125–125:1 | 1:3–3:1 | 4–300 | 20–70 |
| 23 | metribuzin | 1:250–30:1 | 1:25–1:1 | 10–1000 | 50–500 |
| 24 | glyphosate | 1:500–3:1 | 1:50–1:4 | 100–2000 | 250–1000 |
| 25 | ethametsulfuron-methyl | 1:10–300:1 | 2:3–7:1 | 1–50 | 10–30 | c) 2-[(2,4-dihydro-2,6,9-trimethyl[1]benzothiopyrano[4,3-c]pyrazol-8-yl)carbonyl]-5-methyl-1,3-cyclohexanedione S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | tribenuron-methyl | 1:10–300:1 | 1:1–14:1 | 1–50 | 5–20 |
| 2 | thifensulfuron-methyl | 1:25–300:1 | 1:2–7:1 | 1–100 | 10–40 |
| 3 | thifensulfuron-methyl in combination with tribenuron-methyl | 1:10–300:1<br>1:5–300:1 | 1:1–7:1<br>2:1–14:1 | 1–50<br>1–20 | 10–20<br>5–10 |
| 4 | metsulfuron-methyl | 1:5–300:1 | 3:1–35:1 | 1–20 | 2–6 |
| 5 | thifensulfuron-methyl in combination with metsulfuron-methyl | 1:25–300:1<br>1:5–300:1 | 1:2–7:1<br>3:1–35:1 | 1–100<br>1–20 | 10–40<br>2–6 |
| 6 | thifensulfuron-methyl in combination with tribenuron-methyl in combination with metsulfuron-methyl | 1:10–300:1<br>1:10–300:1<br>1:5–300:1 | 1:1–7:1<br>1:1–7:1<br>3:1–35:1 | 1–50<br>1–20<br>1–20 | 10–20<br>5–10<br>2–6 |
| 7 | chlorsulfuron | 1:10–300:1 | 2:3–7:1 | 1–50 | 10–30 |
| 8 | chlorsulfuron in combination with metsulfuron-methyl | 1:10–300:1<br>1:2–300:1 | 1:1–7:1<br>5:1–35:1 | 1–50<br>1–10 | 10–20<br>2–4 |
| 9 | triasulfuron | 1:10–300:1 | 2:3–7:1 | 1–50 | 10–30 |
| 10 | 2,4-D | 1:1000–3:1 | 1:100–1:3 | 100–4000 | 200–2000 |
| 11 | dicamba | 1:150–10:1 | 1:15–1:1 | 30–600 | 70–300 |
| 12 | bromoxynil | 1:500–3:1 | 1:50–1:4 | 100–2000 | 250–1000 |
| 13 | MCPA | 1:500–6:1 | 1:50–1:1 | 50–2000 | 100–1000 |
| 14 | bromoxynil in combination with MCPA | 1:500–3:1<br>1:500–6:1 | 1:50–1:4<br>1:50–1:1 | 100–2000<br>50–2000 | 250–1000<br>100–1000 |
| 15 | fluroxypyr | 1:150–10:1 | 1:15–1:1 | 30–600 | 70–300 |
| 16 | clopyralid | 1:125–30:1 | 1:12–1:1 | 10–500 | 50–250 |
| 17 | fenoxaprop in combination with fenchlorazole | 1:50–30:1<br>1:12–300:1 | 1:5–2:1<br>1:1–7:1 | 10–200<br>1–50 | 40–100<br>10–25 |
| 18 | diclofop | 1:500–3:1 | 1:50–1:7 | 100–2000 | 500–1000 |
| 19 | tralkoxydim | 1:125–3:1 | 1:15–1:2 | 100–500 | 150–300 |
| 20 | clodinafop in combination with cloquintocet-mexyl | 1:50–30:1<br>1:12–300:1 | 1:5–2:1<br>1:1–7:1 | 10–200<br>1–50 | 40–100<br>10–25 |
| 21 | sulfosulfuron | 1:12–300:1 | 1:2–20:1 | 1–50 | 4–40 |
| 22 | prosulfuron | 1:125–125:1 | 1:3–3:1 | 4–300 | 20–70 |

-continued

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 23 | metribuzin | 1:250–30:1 | 1:25–1:1 | 10–1000 | 50–500 |
| 24 | glyphosate | 1:500–3:1 | 1:50–1:4 | 100–2000 | 250–1000 |
| 25 | ethametsulfuron-methyl | 1:10–300:1 | 2:3–7:1 | 1–50 | 10–30 | d) (2,4-dihydro-2,6,9-trimethyl[1]benzothiopyrano[4,3-c]pyrazol-8-yl)(1-ethyl-5-hydroxy-1H-pyrazol-4-yl)methanone S,S-dioxide (mixture partner A, generally applied at a rate of 4 to 280 g/ha, preferably applied at a rate of 8 to 70 g/ha) in combination with:

e) 2-[(3-chloro-2-ethyl-2,4-dihydro-6,9-dimethyl[1]benzothiopyrano[4,3-c]pyrazol-8-yl)carbonyl]-1,3-cyclohexanedione S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | tribenuron-methyl | 1:10–300:1 | 1:1–14:1 | 1–50 | 5–20 |
| 2 | thifensulfuron-methyl | 1:25–300:1 | 1:2–7:1 | 1–100 | 10–40 |
| 3 | thifensulfuron-methyl in combination with tribenuron-methyl | 1:10–300:1<br>1:5–300:1 | 1:1–7:1<br>2:1–14:1 | 1–50<br>1–20 | 10–20<br>5–10 |
| 4 | metsulfuron-methyl | 1:5–300:1 | 3:1–35:1 | 1–20 | 2–6 |
| 5 | thifensulfuron-methyl in combination with metsulfuron-methyl | 1:25–300:1<br>1:5–300:1 | 1:2–7:1<br>3:1–35:1 | 1–100<br>1–20 | 10–40<br>2–6 |
| 6 | thifensulfuron-methyl in combination with tribenuron-methyl in combination with metsulfuron-methyl | 1:10–300:1<br>1:10–300:1<br>1:5–300:1 | 1:1–7:1<br>1:1–7:1<br>3:1–35:1 | 1–50<br>1–20<br>1–20 | 10–20<br>5–10<br>2–6 |
| 7 | chlorsulfuron | 1:10–300:1 | 2:3–7:1 | 1–50 | 10–30 |
| 8 | chlorsulfuron in combination with metsulfuron-methyl | 1:10–300:1<br>1:2–300:1 | 1:1–7:1<br>5:1–35:1 | 1–50<br>1–10 | 10–20<br>2–4 |
| 9 | triasulfuron | 1:10–300:1 | 2:3–7:1 | 1–50 | 10–30 |
| 10 | 2,4-D | 1:1000–3:1 | 1:100–1:3 | 100–4000 | 200–2000 |
| 11 | dicamba | 1:150–10:1 | 1:15–1:1 | 30–600 | 70–300 |
| 12 | bromoxynil | 1:500–3:1 | 1:50–1:4 | 100–2000 | 250–1000 |
| 13 | MCPA | 1:500–6:1 | 1:50–1:1 | 50–2000 | 100–1000 |
| 14 | bromoxynil in combination with MCPA | 1:500–3:1<br>1:500–6:1 | 1:50–1:4<br>1:50–1:1 | 100–2000<br>50–2000 | 250–1000<br>100–1000 |
| 15 | fluroxypyr | 1:150–10:1 | 1:15–1:1 | 30–600 | 70–300 |
| 16 | clopyralid | 1:125–30:1 | 1:12–1:1 | 10–500 | 50–250 |
| 17 | fenoxaprop in combination with fenchlorazole | 1:50–30:1<br>1:12–300:1 | 1:5–2:1<br>1:1–7:1 | 10–200<br>1–50 | 40–100<br>10–25 |
| 18 | diclofop | 1:500–3:1 | 1:50–1:7 | 100–2000 | 500–1000 |
| 19 | tralkoxydim | 1:125–3:1 | 1:15–1:2 | 100–500 | 150–300 |
| 20 | clodinafop in combination with cloquintocet-mexyl | 1:50–30:1<br>1:12–300:1 | 1:5–2:1<br>1:1–7:1 | 10–200<br>1–50 | 40–100<br>10–25 |
| 21 | sulfosulfuron | 1:12–300:1 | 1:2–20:1 | 1–50 | 4–40 |
| 22 | prosulfuron | 1:125–125:1 | 1:3–3:1 | 4–300 | 20–70 |
| 23 | metribuzin | 1:250–30:1 | 1:25–1:1 | 10–1000 | 50–500 |
| 24 | glyphosate | 1:500–3:1 | 1:50–1:4 | 100–2000 | 250–1000 |
| 25 | ethametsulfuron-methyl | 1:10–300:1 | 2:3–7:1 | 1–50 | 10–30 |

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | tribenuron-methyl | 1:10–300:1 | 1:1–14:1 | 1–50 | 5–20 |
| 2 | thifensulfuron-methyl | 1:25–300:1 | 1:2–7:1 | 1–100 | 10–40 |
| 3 | thifensulfuron-methyl in combination with | 1:10–300:1 | 1:1–7:1 | 1–50 | 10–20 |
|  | tribenuron-methyl | 1:5–300:1 | 2:1–14:1 | 1–20 | 5–10 |
| 4 | metsulfuron-methyl | 1:5–300:1 | 3:1–35:1 | 1–20 | 2–6 |
| 5 | thifensulfuron-methyl in combination with | 1:25–300:1 | 1:2–7:1 | 1–100 | 10–40 |
|  | metsulfuron-methyl | 1:5–300:1 | 3:1–35:1 | 1–20 | 2–6 |
| 6 | thifensulfuron-methyl in combination with | 1:10–300:1 | 1:1–7:1 | 1–50 | 10–20 |
|  | tribenuron-methyl in combination with | 1:10–300:1 | 1:1–7:1 | 1–20 | 5–10 |
|  | metsulfuron-methyl | 1:5–300:1 | 3:1–35:1 | 1–20 | 2–6 |
| 7 | chlorsulfuron | 1:10–300:1 | 2:3–7:1 | 1–50 | 10–30 |
| 8 | chlorsulfuron in combination with | 1:10–300:1 | 1:1–7:1 | 1–50 | 10–20 |
|  | metsulfuron-methyl | 1:2–300:1 | 5:1–35:1 | 1–10 | 2–4 |
| 9 | triasulfuron | 1:10–300:1 | 2:3–7:1 | 1–50 | 10–30 |
| 10 | 2,4-D | 1:1000–3:1 | 1:100–1:3 | 100–4000 | 200–2000 |
| 11 | dicamba | 1:150–10:1 | 1:15–1:1 | 30–600 | 70–300 |
| 12 | bromoxynil | 1:500–3:1 | 1:50–1:4 | 100–2000 | 250–1000 |
| 13 | MCPA | 1:500–6:1 | 1:50–1:1 | 50–2000 | 100–1000 |
| 14 | bromoxynil in combination with | 1:500–3:1 | 1:50–1:4 | 100–2000 | 250–1000 |
|  | MCPA | 1:500–6:1 | 1:50–1:1 | 50–2000 | 100–1000 |
| 15 | fluroxypyr | 1:150–10:1 | 1:15–1:1 | 30–600 | 70–300 |
| 16 | clopyralid | 1:125–30:1 | 1:12–1:1 | 10–500 | 50–250 |
| 17 | fenoxaprop in combination with | 1:50–30:1 | 1:5–2:1 | 10–200 | 40–100 |
|  | fenchlorazole | 1:12–300:1 | 1:1–7:1 | 1–50 | 10–25 |
| 18 | diclofop | 1:500–3:1 | 1:50–1:7 | 100–2000 | 500–1000 |
| 19 | tralkoxydim | 1:125–3:1 | 1:15–1:2 | 100–500 | 150–300 |
| 20 | clodinafop in combination with | 1:50–30:1 | 1:5–2:1 | 10–200 | 40–100 |
|  | cloquintocet-mexyl | 1:12–300:1 | 1:1–7:1 | 1–50 | 10–25 |
| 21 | sulfosulfuron | 1:12–300:1 | 1:2–20:1 | 1–50 | 4–40 |
| 22 | prosulfuron | 1:125–125:1 | 1:3–3:1 | 4–300 | 20–70 |
| 23 | metribuzin | 1:250–30:1 | 1:25–1:1 | 10–1000 | 50–500 |
| 24 | glyphosate | 1:500–3:1 | 1:50–1:4 | 100–2000 | 250–1000 |
| 25 | ethametsulfuron-methyl | 1:10–300:1 | 2:3–7:1 | 1–50 | 10–30 | f) 2-[(4,5-dihydro-2,7,10-trimethyl-2H[1]benzothiepino[5,4-c]pyrazol-9-yl)carbonyl]-5-methyl-1,3-cyclohexanedione S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | tribenuron-methyl | 1:10–300:1 | 1:1–14:1 | 1–50 | 5–20 |
| 2 | thifensulfuron-methyl | 1:25–300:1 | 1:2–7:1 | 1–100 | 10–40 |
| 3 | thifensulfuron-methyl in combination with | 1:10–300:1 | 1:1–7:1 | 1–50 | 10–20 |
|  | tribenuron-methyl | 1:5–300:1 | 2:1–14:1 | 1–20 | 5–10 |
| 4 | metsulfuron-methyl | 1:5–300:1 | 3:1–35:1 | 1–20 | 2–6 |
| 5 | thifensulfuron-methyl in combination with | 1:25–300:1 | 1:2–7:1 | 1–100 | 10–40 |
|  | metsulfuron-methyl | 1:5–300:1 | 3:1–35:1 | 1–20 | 2–6 |
| 6 | thifensulfuron-methyl in combination with | 1:10–300:1 | 1:1–7:1 | 1–50 | 10–20 |
|  | tribenuron-methyl in combination with | 1:10–300:1 | 1:1–7:1 | 1–20 | 5–10 |
|  | metsulfuron-methyl | 1:5–300:1 | 3:1–35:1 | 1–20 | 2–6 |
| 7 | chlorsulfuron | 1:10–300:1 | 2:3–7:1 | 1–50 | 10–30 |
| 8 | chlorsulfuron in combination with | 1:10–300:1 | 1:1–7:1 | 1–50 | 10–20 |
|  | metsulfuron-methyl | 1:2–300:1 | 5:1–35:1 | 1–10 | 2–4 |
| 9 | triasulfuron | 1:10–300:1 | 2:3–7:1 | 1–50 | 10–30 |

-continued

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 10 | 2,4-D | 1:1000–3:1 | 1:100–1:3 | 100–4000 | 200–2000 |
| 11 | dicamba | 1:150–10:1 | 1:15–1:1 | 30–600 | 70–300 |
| 12 | bromoxynil | 1:500–3:1 | 1:50–1:4 | 100–2000 | 250–1000 |
| 13 | MCPA | 1:500–6:1 | 1:50–1:1 | 50–2000 | 100–1000 |
| 14 | bromoxynil in combination with | 1:500–3:1 | 1:50–1:4 | 100–2000 | 250–1000 |
|    | MCPA | 1:500–6:1 | 1:50–1:1 | 50–2000 | 100–1000 |
| 15 | fluroxypyr | 1:150–10:1 | 1:15–1:1 | 30–600 | 70–300 |
| 16 | clopyralid | 1:125–30:1 | 1:12–1:1 | 10–500 | 50–250 |
| 17 | fenoxaprop in combination with | 1:50–30:1 | 1:5–2:1 | 10–200 | 40–100 |
|    | fenchlorazole | 1:12–300:1 | 1:1–7:1 | 1–50 | 10–25 |
| 18 | diclofop | 1:500–3:1 | 1:50–1:7 | 100–2000 | 500–1000 |
| 19 | tralkoxydim | 1:125–3:1 | 1:15–1:2 | 100–500 | 150–300 |
| 20 | clodinafop in combination with | 1:50–30:1 | 1:5–2:1 | 10–200 | 40–100 |
|    | cloquintocet-mexyl | 1:12–300:1 | 1:1–7:1 | 1–50 | 10–25 |
| 21 | sulfosulfuron | 1:12–300:1 | 1:2–20:1 | 1–50 | 4–40 |
| 22 | prosulfuron | 1:125–125:1 | 1:3–3:1 | 4–300 | 20–70 |
| 23 | metribuzin | 1:250–30:1 | 1:25–1:1 | 10–1000 | 50–500 |
| 24 | glyphosate | 1:500–3:1 | 1:50–1:4 | 100–2000 | 250–1000 |
| 25 | ethametsulfuron-methyl | 1:10–300:1 | 2:3–7:1 | 1–50 | 10–30 |

Preferred for better control of undesired vegetation in corn (e.g., lower use rate, broader spectrum of weeds controlled, or enhanced crop safety) or for preventing the development of resistant weeds in corn are mixtures of a compound of this invention with one or more of the herbicides selected from the group thifensulfuron-methyl, rimsulfuron, nicosulfuron, primisulfuron, atrazine, terbuthylazine, 2,4-D, dicamba, bromoxynil, imazethapyr, clopyralid, prosulfuron, glyphosate, glyphosate-trimesium, glufosinate, fluthiacet-methyl, quizalofop-P-ethyl, bentazone, flumetsulam, halosulfuron, sethoxydim, and flumiclorac-pentyl.

Specifically preferred mixtures for use in corn are selected from the group:

a) 2-[(2,4-dihydro-2,6,9-trimethyl[1]benzothiopyrano[4,3-c]pyrazol-8-yl)carbonyl]-1,3-cyclohexanedione S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | rimsulfuron | 1:5–300:1 | 1:1–70:1 | 1–20 | 1–10 |
| 2 | thifensulfuron-methyl | 1:2–300:1 | 1:1–70:1 | 1–10 | 1–5 |
| 3 | nicosulfuron | 1:10–300:1 | 1:1–70:1 | 1–50 | 1–10 |
| 4 | rimsulfuron in combination with | 1:5–300:1 | 1:1–70:1 | 1–20 | 1–10 |
|   | nicosulfuron | 1:10–300:1 | 1:1–70:1 | 1–50 | 1–10 |
| 5 | rimfensulfuron in combination with | 1:5–300:1 | 1:1–70:1 | 1–50 | 1–10 |
|   | thifensulfuron-methyl | 1:2–300:1 | 1:1–70:1 | 1–10 | 1–5 |
| 6 | prosulfuron | 1:10–300:1 | 2:1–70:1 | 1–50 | 1–10 |
| 7 | prosulfuron in combination with | 1:10–300:1 | 2:1–70:1 | 1–50 | 1–10 |
|   | primisulfuron | 1:10–300:1 | 2:1–70:1 | 1–50 | 1–10 |
| 8 | atrazine | 1:500–3:1 | 1:25–1:1 | 100–2000 | 100–500 |
| 9 | terbuthylazine | 1:500–3:1 | 1:25–1:1 | 100–2000 | 100–500 |
| 10 | dicamba | 1:125–30:1 | 1:5–7:1 | 10–500 | 10–100 |
| 11 | 2,4-D | 1:250–6:1 | 1:25–1:1 | 50–1000 | 50–500 |
| 12 | bromoxynil | 1:250–6:1 | 1:25–1:1 | 50–1000 | 50–500 |
| 13 | imazethapyr | 1:25–300:1 | 1:2–14:1 | 1–100 | 5–50 |
| 14 | glyphosate | 1:250–6:1 | 1:25–1:1 | 50–1000 | 50–500 |
| 15 | glufosinate | 1:250–6:1 | 1:25–1:1 | 50–1000 | 50–500 |
| 16 | glyphosate-trimesium | 1:250–6:1 | 1:25–1:1 | 50–1000 | 50–500 | b) 2-[(2-ethyl-2,4-dihydro-6,9-dimethyl[1]benzothiopyrano[4,3-c]pyrazol-8-yl)carbonyl]-1,3-cyclohexanedione S,S-dioxide (mixture partner A, generally applied at a rate of 4 to 280 g/ha, preferably applied at a rate of 8 to 70 g /ha) in combination with:

| Combination Number | Mixture Partner B | Ratio Range of A:B | Preferred Ratio Range of A:B | Use Rate Range of B (g/ha) | Preferred Use Rate Range of B (g/ha) |
| --- | --- | --- | --- | --- | --- |
| 1 | rimsulfuron | 1:5–300:1 | 1:1–70:1 | 1–20 | 1–10 |
| 2 | thifensulfuron-methyl | 1:2–300:1 | 1:1–70:1 | 1–10 | 1–5 |
| 3 | nicosulfuron | 1:10–300:1 | 1:1–70:1 | 1–50 | 1–10 |
| 4 | rimsulfuron in combination with nicosulfuron | 1:5–300:1 1:10–300:1 | 1:1–70:1 1:1–70:1 | 1–20 1–50 | 1–10 1–10 |
| 5 | rimfensulfuron in combination with thifensulfuron-methyl | 1:5–300:1 1:2–300:1 | 1:1–70:1 1:1–70:1 | 1–50 1–10 | 1–10 1–5 |
| 6 | prosulfuron | 1:10–300:1 | 2:1–70:1 | 1–50 | 1–10 |
| 7 | prosulfuron in combination with primisulfuron | 1:10–300:1 1:10–300:1 | 2:1–70:1 2:1–70:1 | 1–50 1–50 | 1–10 1–10 |
| 8 | atrazine | 1:500–3:1 | 1:25–1:1 | 100–2000 | 100–500 |
| 9 | terbuthylazine | 1:500–3:1 | 1:25–1:1 | 100–2000 | 100–500 |
| 10 | dicamba | 1:125–30:1 | 1:5–7:1 | 10–500 | 10–100 |
| 11 | 2,4-D | 1:250–6:1 | 1:25–1:1 | 50–1000 | 50–500 |
| 12 | bromoxynil | 1:250–6:1 | 1:25–1:1 | 50–1000 | 50–500 |
| 13 | imazethapyr | 1:25–300:1 | 1:2–14:1 | 1–100 | 5–50 |
| 14 | glyphosate | 1:250–6:1 | 1:25–1:1 | 50–1000 | 50–500 |
| 15 | glufosinate | 1:250–6:1 | 1:25–1:1 | 50–1000 | 50–500 |
| 16 | glyphosate-trimesium | 1:250–6:1 | 1:25–1:1 | 50–1000 | 50–500 | c) 2-[(2,4-dihydro-2,6,9-trimethyl[1]benzothiopyrano[4,3-c]pyrazol-8-yl)carbonyl]-5-methyl-1,3-cyclohexanedione S,S-dioxide (mixture partner A, generally applied at a rate of 4 to 280 g/ha, preferably applied at a rate of 8 to 70 g/ha) in combination with:

d) (2,4-dihydro-2,6,9-trimethyl[1]benzothiopyrano[4,3-c]pyrazol-8-yl)(1-ethyl-5-hydroxy-1H-pyrazol-4-yl)methanone S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
| --- | --- | --- | --- | --- | --- |
| 1 | rimsulfuron | 1:5–300:1 | 1:1–70:1 | 1–20 | 1–10 |
| 2 | thifensulfuron-methyl | 1:2–300:1 | 1:1–70:1 | 1–10 | 1–5 |
| 3 | nicosulfuron | 1:10–300:1 | 1:1–70:1 | 1–50 | 1–10 |
| 4 | rimsulfuron in combination with nicosulfuron | 1:5–300:1 1:10–300:1 | 1:1–70:1 1:1–70:1 | 1–20 1–50 | 1–10 1–10 |
| 5 | rimfensulfuron in combination with thifensulfuron-methyl | 1:5–300:1 1:2–300:1 | 1:1–70:1 1:1–70:1 | 1–50 1–10 | 1–10 1–5 |
| 6 | prosulfuron | 1:10–300:1 | 2:1–70:1 | 1–50 | 1–10 |
| 7 | prosulfuron in combination with primisulfuron | 1:10–300:1 1:10–300:1 | 2:1–70:1 2:1–70:1 | 1–50 1–50 | 1–10 1–10 |
| 8 | atrazine | 1:500–3:1 | 1:25–1:1 | 100–2000 | 100–500 |
| 9 | terbuthylazine | 1:500–3:1 | 1:25–1:1 | 100–2000 | 100–500 |
| 10 | dicamba | 1:125–30:1 | 1:5–7:1 | 10–500 | 10–100 |
| 11 | 2,4-D | 1:250–6:1 | 1:25–1:1 | 50–1000 | 50–500 |
| 12 | bromoxynil | 1:250–6:1 | 1:25–1:1 | 50–1000 | 50–500 |
| 13 | imazethapyr | 1:25–300:1 | 1:2–14:1 | 1–100 | 5–50 |
| 14 | glyphosate | 1:250–6:1 | 1:25–1:1 | 50–1000 | 50–500 |
| 15 | glufosinate | 1:250–6:1 | 1:25–1:1 | 50–1000 | 50–500 |
| 16 | glyphosate-trimesium | 1:250–6:1 | 1:25–1:1 | 50–1000 | 50–500 |

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | rimsulfuron | 1:5–300:1 | 1:1–70:1 | 1–20 | 1–10 |
| 2 | thifensulfuron-methyl | 1:2–300:1 | 1:1–70:1 | 1–10 | 1–5 |
| 3 | nicosulfuron | 1:10–300:1 | 1:1–70:1 | 1–50 | 1–10 |
| 4 | rimsulfuron in combination with nicosulfuron | 1:5–300:1 1:10–300:1 | 1:1–70:1 1:1–70:1 | 1–20 1–50 | 1–10 1–10 |
| 5 | rimsulfuron in combination with thifensulfuron-methyl | 1:5–300:1 1:2–300:1 | 1:1–70:1 1:1–70:1 | 1–20 1–10 | 1–10 1–5 |
| 6 | prosulfuron | 1:10–300:1 | 2:1–70:1 | 1–50 | 1–10 |
| 7 | prosulfuron in combination with primisulfuron | 1:10–300:1 1:10–300:1 | 2:1–70:1 2:1–70:1 | 1–50 1–50 | 1–10 1–10 |
| 8 | atrazine | 1:500–3:1 | 1:25–1:1 | 100–2000 | 100–500 |
| 9 | terbuthylazine | 1:500–3:1 | 1:25–1:1 | 100–2000 | 100–500 |
| 10 | dicamba | 1:125–30:1 | 1:5–7:1 | 10–500 | 10–100 |
| 11 | 2,4-D | 1:250–6:1 | 1:25–1:1 | 50–1000 | 50–500 |
| 12 | bromoxynil | 1:250–6:1 | 1:25–1:1 | 50–1000 | 50–500 |
| 13 | imazethapyr | 1:25–300:1 | 1:25–14:1 | 1–100 | 5–50 |
| 14 | glyphosate | 1:250–6:1 | 1:25–1:1 | 50–1000 | 50–500 |
| 15 | glufosinate | 1:250–6:1 | 1:25–1:1 | 50–1000 | 50–500 |
| 16 | glyphosate-trimesium | 1:250–6:1 | 1:25–1:1 | 50–1000 | 50–500 | e) 2-[(3-chloro-2-ethyl-2,4-dihydro-6,9-dimethyl[1]benzothiopyrano[4,3-c]pyrazol-8-yl)carbonyl]-1,3-cyclohexanedione S,S-dioxide (mixture partner A, generally applied at a rate of 4 to 280 g/ha, preferably applied at a rate of 8 to 70 g/ha) in combination with:

| Combination Number | Mixture Partner B | Ratio Range of A:B | Preferred Ratio Range of A:B | Use Rate Range of B (g/ha) | Preferred Use Rate Range of B (g/ha) |
|---|---|---|---|---|---|
| 1 | rimsulfuron | 1:5–300:1 | 1:1–70:1 | 1–20 | 1–10 |
| 2 | thifensulfuron-methyl | 1:2–300:1 | 1:1–70:1 | 1–10 | 1–5 |
| 3 | nicosulfuron | 1:10–300:1 | 1:1–70:1 | 1–50 | 1–10 |
| 4 | rimsulfuron in combination with nicosulfuron | 1:5–300:1 1:10–300:1 | 1:1–70:1 1:1–70:1 | 1–20 1–50 | 1–10 1–10 |
| 5 | rimsulfuron in combination with thifensulfuron-methyl | 1:5–300:1 1:2–300:1 | 1:1–70:1 1:1–70:1 | 1–20 1–10 | 1–10 1–5 |
| 6 | prosulfuron | 1:10–300:1 | 2:1–70:1 | 1–50 | 1–10 |
| 7 | prosulfuron in combination with primisulfuron | 1:10–300:1 1:10–300:1 | 2:1–70:1 2:1–70:1 | 1–50 1–50 | 1–10 1–10 |
| 8 | atrazine | 1:500–3:1 | 1:25–1:1 | 100–2000 | 100–500 |
| 9 | terbuthylazine | 1:500–3:1 | 1:25–1:1 | 100–2000 | 100–500 |
| 10 | dicamba | 1:125–30:1 | 1:5–7:1 | 10–500 | 10–100 |
| 11 | 2,4-D | 1:250–6:1 | 1:25–1:1 | 50–1000 | 50–500 |
| 12 | bromoxynil | 1:250–6:1 | 1:25–1:1 | 50–1000 | 50–500 |
| 13 | imazethapyr | 1:25–300:1 | 1:2–14:1 | 1–100 | 5–50 |
| 14 | glyphosate | 1:250–6:1 | 1:25–1:1 | 50–1000 | 50–500 |
| 15 | glufosinate | 1:250–6:1 | 1:25–1:1 | 50–1000 | 50–500 |
| 16 | glyphosate-trimesium | 1:250–6:1 | 1:25–1:1 | 50–1000 | 50–500 | f) 2-[(4,5-dihydro-2,7,10-trimethyl-2H[1]benzothiepino[5,4-c]pyrazol-9-yl)carbonyl]-5-methyl-1,3-cyclohexanedione S,S-dioxide (mixture partner A, generally applied at a rate of 4 to 280 g/ha, preferably applied at a rate of 8 to 70 g l/ha) in combination with:

| Combination Number | Mixture Partner B | Ratio Range of A:B | Preferred Ratio Range of A:B | Use Rate Range of B (g/ha) | Use Rate Range of B (g/ha) |
|---|---|---|---|---|---|
| 1 | rimsulfuron | 1:5–300:1 | 1:1–70:1 | 1–20 | 1–10 |
| 2 | thifensulfuron-methyl | 1:2–300:1 | 1:1–70:1 | 1–10 | 1–5 |
| 3 | nicosulfuron | 1:10–300:1 | 1:1–70:1 | 1–50 | 1–10 |
| 4 | rimsulfuron in combination with nicosulfuron | 1:5–300:1 1:10–300:1 | 1:1–70:1 1:1–70:1 | 1–20 1–50 | 1–10 1–10 |
| 5 | rimsulfuron in combination with thifensulfuron-methyl | 1:5–300:1 1:2–300:1 | 1:1–70:1 1:1–70:1 | 1–20 1–10 | 1–10 1–5 |
| 6 | prosulfuron | 1:10–300:1 | 2:1–70:1 | 1–50 | 1–10 |
| 7 | prosulfuron in combination with primisulfuron | 1:10–300:1 1:10–300:1 | 2:1–70:1 2:1–70:1 | 1–50 1–50 | 1–10 1–10 |
| 8 | atrazine | 1:500–3:1 | 1:25–1:1 | 100–2000 | 100–500 |
| 9 | terbuthylazine | 1:500–3:1 | 1:25–1:1 | 100–2000 | 100–500 |
| 10 | dicamba | 1:125–30:1 | 1:5–7:1 | 10–500 | 10–100 |
| 11 | 2,4-D | 1:250–6:1 | 1:25–1:1 | 50–1000 | 50–500 |
| 12 | bromoxynil | 1:250–6:1 | 1:25–1:1 | 50–1000 | 50–500 |
| 13 | imazethapyr | 1:25–300:1 | 1:2–14:1 | 1–100 | 5–50 |
| 14 | glyphosate | 1:250–6:1 | 1:25–1:1 | 50–1000 | 50–500 |
| 15 | glufosinate | 1:250–6:1 | 1:25–1:1 | 50–1000 | 50–500 |
| 16 | glyphosate-trimesium | 1:250–6:1 | 1:25–1:1 | 50–1000 | 50–500 |

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control. The following Tests demonstrate the control efficacy of the compounds of this invention against specific weeds. The weed control afforded by the compounds is not limited, however, to these species. See Index Tables A–D for compound descriptions. The following abbreviation is used in the Index Tables which follow: Ph=phenyl. The abbreviation "dec." indicates that the compound appeared to decompose on melting.

The abbreviation "Ex." stands for "Example" and is followed by a number indicating in which example the compound is prepared.

INDEX TABLE A

| Cmpd | $R^a$ | $R^b$ | R | $R^1$ | n | m.p.(° C.) |
|---|---|---|---|---|---|---|
| 1 | H | H | OH | $CH_3$ | 2 | 228 (dec.) |
| 2 | H | H | OH | $CH_2CH_3$ | 2 | 205 (dec.) |
| 3 | H | H | OH | $CH(CH_3)_2$ | 2 | 92 (dec.) |
| 4 | H | H | OH | $CH_2CH_2CH_3$ | 2 | 104 (dec.) |
| 5 | $CH_3$ | $CH_3$ | OH | $CH_3$ | 2 | 106 (dec.) |
| 6 | $CH_3$ | H | OH | $CH_3$ | 2 | >210 |
| 7 | H | H | OH | $CH_3$ | 0 | 98 (dec.) |
| 8 | H | H | OH | $CH_3$ | 1 | 95 (dec.) |
| 9 | H | H | Cl | $CH_2CH_3$ | 2 | 157–159 (dec.) |
| 10 | H | H | $OCH_3$ | $CH_2CH_3$ | 2 | semi-solid * |
| 11 | H | H | $OSO_2Ph$ | $CH_2CH_3$ | 2 | semi-solid * |
| 12 | H | H | $O^-Et_3NH^+$ | $CH_2CH_3$ | 2 | 171–182 |
| 13 | H | H | $O^-K^+$ | $CH_2CH_3$ | 2 | 208–210 (dec.) |
| 14 | H | H | $O^-Na^+$ | $CH_2CH_3$ | 2 | 210–212 (dec.) |
| 32 | H | H | OH | phenyl | 2 | 237–240 |
| 33 | H | H | (2-$CH_3$)phenylthio | phenyl | 2 | >245 |
| 34 | H | H | (2-Cl)phenylthio | $CH_2CH_3$ | 2 | 204–208 |
| 35 | H | H | (3-methoxy)phenylthio | $CH_2CH_2CH_3$ | 2 | 198–200 |
| 36 | H | H | (4-$CH_3$)phenylthio | $CH_2CH_2CH_3$ | 2 | 218–224 |

INDEX TABLE A-continued

| Cmpd | R$^a$ | R$^b$ | R | R$^1$ | n | m.p.(° C.) |
|---|---|---|---|---|---|---|
| 37 | H | H | (2-CH$_3$)phenylthio | CH$_2$CH$_2$CH$_3$ | 2 | 226–228 |
| 38 | H | H | (2,6-diCl)phenylthio | CH$_2$CH$_2$CH$_3$ | 2 | 190–197 |
| 39 | H | H | phenylthio | CH$_2$CH$_2$CH$_3$ | 2 | 230–233 |
| 40 | H | H | benzylthio | CH$_2$CH$_2$CH$_3$ | 2 | 197-199 |
| 41 | H | H | phenylthio | CH$_2$CH$_3$ | 2 | 261–262 |
| 42 | H | H | Cl | CH$_3$ | 2 | 140–141 (dec.) |
| 43 | H | H | O$^-$Na$^+$ | CH$_3$ | 2 | >230 |

INDEX TABLE B

| Cmpd | R$^1$ | R$^2$ | R$^3$ | n | m.p. (° C.) |
|---|---|---|---|---|---|
| 15 | CH$_2$CH$_3$ | H | CH$_2$CH$_3$ | 2 | 97 (dec.) |
| 16 | CH$_2$CH$_3$ | H | CH$_3$ | 2 | 133 (dec.) |
| 17 | CH$_3$ | H | CH$_3$ | 2 | 134 (dec.) |
| 18 | CH$_2$CH$_3$ | SO$_2$CH$_2$Cl | CH$_3$ | 2 | oil * |
| 19 | CH$_3$ | H | CH$_3$ | 0 | 90–91 (dec.) |
| 20 | CH$_2$CH$_3$ | H | CH$_3$ | 0 | 58 (dec.) |
| 21 | CH$_3$ | H | CH$_3$ | 1 | semi-solid * |
| 22 | CH$_2$CH$_3$ | H | CH$_3$ | 1 | 124 (dec.) |
| 23 | CH$_3$ | SO$_2$Ph | CH$_3$ | 2 | 78 (dec.) |
| 44 | CH$_2$CH$_3$ | (4-CH$_3$)phenylsulfonyl | CH$_3$ | 2 | 74–75 |
| 45 | CH$_2$CH$_3$ | C(=O)Ph | CH$_3$ | 2 | 208–210 |
| 46 | CH$_2$CH$_3$ | SO$_2$CH$_3$ | CH$_3$ | 2 | 194–196 |
| 47 | CH$_2$CH$_3$ | SO$_2$Ph | CH$_3$ | 2 | oil * |
| 48 | CH$_2$CH$_3$ | Na | CH$_3$ | 2 | >230 |

INDEX TABLE C

| Cmpd No. | Structure | m.p. (° C.) |
|---|---|---|
| 24 | 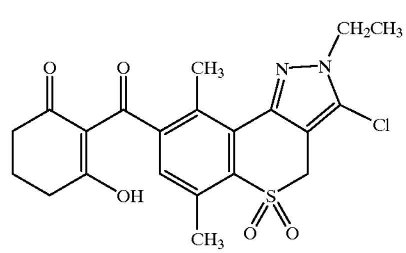 | 196 (dec.) |

INDEX TABLE C-continued

| Cmpd No. | Structure | m.p. (° C.) |
|---|---|---|
| 25 | 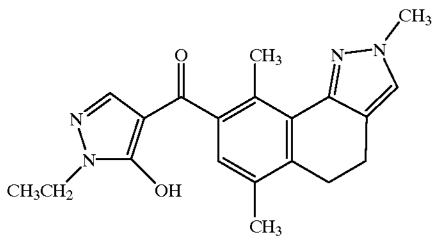 | 150–152 |
| 26 | 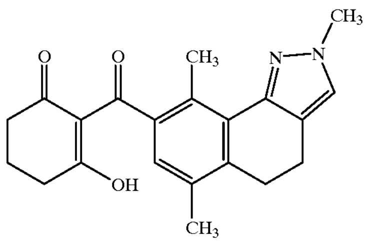 | 75 (dec.) |
| 27 | 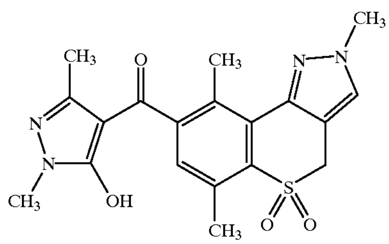 | 120 (dec.) |
| 28 | 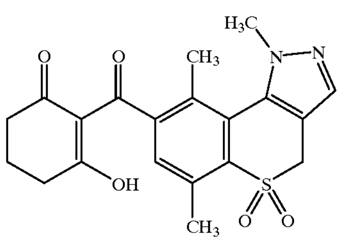 | >220 |
| 29 | 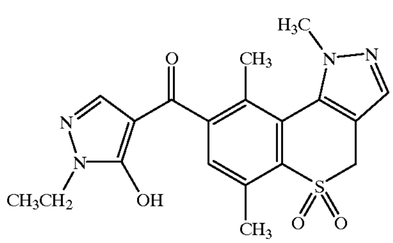 | 96 (dec.) |
| 30 | 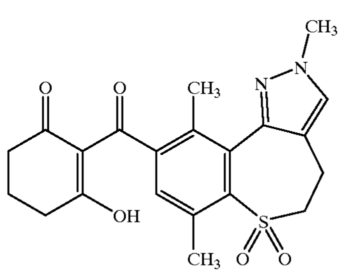 | * |

INDEX TABLE C-continued

| Cmpd No. | Structure | m.p. (° C.) |
|---|---|---|
| 31 | 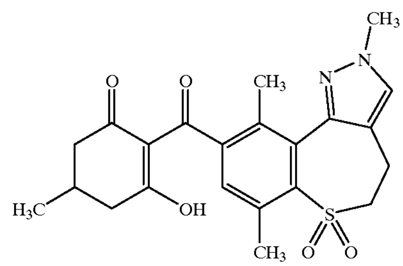 | 115 (dec.) |
| 49 | 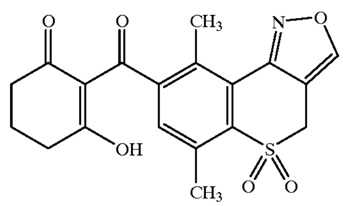 | 230–234 (dec.) |
| 50 | 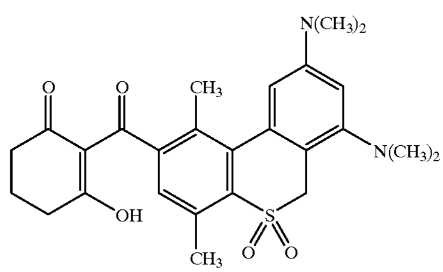 | 122 (dec.) |
| 51 | 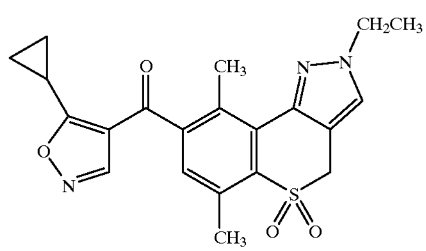 | 69–71 |
| 52 | 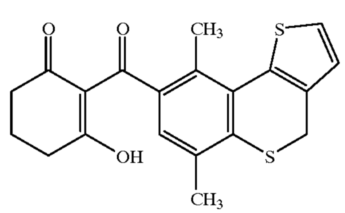 | 171–173 |
| 53 | 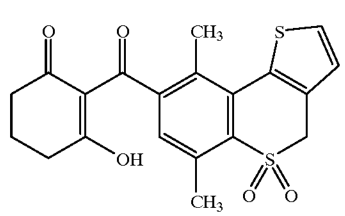 | 212–216 |

INDEX TABLE C-continued

| Cmpd No. | Structure | m.p. (° C.) |
|---|---|---|
| 54 | [structure] | 202–206 |
| 55 | [structure] | 229–250 |

*See Index Table D for ¹H NMR data.

INDEX TABLE D

| Cmpd No. | ¹H NMR Data (CDCl₃ solution unless indicated otherwise)[a] |
|---|---|
| 10 | δ7.44(s, 1H), 6.78(s, 1H), 4.38(s, 2H), 4.2(q, 2H), 3.1(m, 2H), 2.8(m, 2H), 2.71(s, 3H), 2.54(s, 3H), 2.2(m, 1H), 1.8(m, 1H), 1.52(t, 3H), 1.48(s, 3H). |
| 11 | δ7.7–7.3(m, 6H), 7.1(s, 1H), 4.36(s, 2H), 4.21(q, 2H), 3.1(t, 2H), 2.7–2.5(m, 8H), 2.2(m, 2H), 1.54(t, 3H). |
| 18 | δ7.48(s, 1H), 7.43(s, 1H), 7.12(s, 1H), 5.46(s, 2H), 4.41(s, 2H), 4.22(q, 2H), 3.97(s, 3H), 2.76(s, 3H), 2.64(s, 3H), 1.54(t, 3H). |
| 21 | δ7.50(s, 1H), 7.36(s, 1H), 7.2(s, 1H), 4.4(d, 1H), 4.0(s, 3H), 3.8 (d, 1H), 3.72(s, 3H), 2.75(s, 3H), 2.74(s, 3H). |
| 30 | δ7.29(s, 1H), 6.92(s, 1H), 3.95(s, 3H), 3.64(t, 2H), 2.9–2.74(m, 4H), 2.73(s, 3H), 2.44(m, 2H), 2.26(s, 3H), 2.05(m, 2H). |
| 47 | δ7.97(d, 2H), 7.7–7.5(m, 3H), 7.45(s, 1H), 7.34(s, 1H), 6.91(s, 1H), 4.3(s, 2H), 4.12 (q, 2H), 3.86(s, 3H), 2.63(s, 3H), 2.51(s, 3H), 1.43(t, 3H). |

[a]¹H NMR data are in ppm downfield from tetramethylsilane. Couplings are designated by (s)-singlet, (d)-doublet, (t)-triplet, (q)-quartet, (m)-multiplet.

Test A

The compounds evaluated in this test were formulated in a non-phytotoxic solvent mixture which included a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and Late watergrass (*Echinochloa oryzicola*) grown to the 2 leaf stage for testing.

All plant species were grown using normal greenhouse practices. Visual evaluations of injury expressed on treated plants, when compared to untreated controls, were recorded approximately fourteen to twenty one days after application of the test compound. Plant response this ratings, summarized in Table A, were recorded on a 0 to 100 scale where 0 is no effect and 100 is complete control. A dash (-) response means no test result.

TABLE A

| Rate 250 g/ha | COMPOUND | | | Rate 250 g/ha | COMPOUND | |
|---|---|---|---|---|---|---|
| | 1 | 19 | 28 | | 1 | 28 |
| POSTEMERGENCE | | | | PREEMERGENCE | | |
| Barley Igri | 90 | — | 15 | Barley Igri | 65 | 0 |
| Barnyard 2 | 100 | 0 | 95 | Barnyardgrass | 100 | 20 |

TABLE A-continued

| | | | | | | |
|---|---|---|---|---|---|---|
| Barnyardgrass | 90 | — | 90 | Bedstraw | 40 | 0 |
| Bedstraw | 100 | — | 45 | Blackgrass | 65 | 0 |
| Blackgrass | 95 | — | 40 | Chickweed | 100 | 30 |
| Chickweed | 100 | — | 50 | Cocklebur | 100 | 0 |
| Cocklebur | 90 | — | 85 | Corn | 10 | 20 |
| Corn | 80 | — | 0 | Cotton | 100 | 45 |
| Cotton | 100 | — | 90 | Crabgrass | 100 | 100 |
| Crabgrass | 90 | — | 90 | Downy Brome | 90 | 0 |
| Downy Brome | 85 | — | 25 | Giant foxtail | 100 | 0 |
| Duck salad | 70 | 15 | 60 | Italn. Rygrass | 80 | 0 |
| Giant foxtail | 90 | — | 85 | Johnsongrass | 100 | 0 |
| Italn. Rygrass | 85 | — | 0 | Lambsquarter | 100 | 95 |
| Johnsongrass | 100 | — | 90 | Morningglory | 80 | 50 |
| Lambsquarter | 100 | — | 100 | Rape | 30 | 20 |
| Morningglory | 100 | — | 95 | Redroot Pigweed | 100 | 90 |
| Rape | 100 | — | 85 | Soybean | 70 | 60 |
| Redroot Pigweed | 95 | — | 90 | Speedwell | 100 | 95 |
| Rice Japonica | 95 | 0 | 95 | Sugar beet | 100 | 100 |
| Soybean | 90 | — | 90 | Velvetleaf | 100 | 100 |
| Speedwell | 100 | — | 95 | Wheat | 0 | 0 |
| Sugar beet | 100 | — | 100 | Wild buckwheat | 80 | 55 |
| Umbrella sedge | 95 | 10 | 95 | Wild oat | 85 | 0 |
| Velvetleaf | 100 | — | 90 | | | |
| Watergrass 2 | 100 | — | 30 | | | |
| Wheat | 80 | — | 45 | | | |
| Wild buckwheat | 100 | — | 65 | | | |
| Wild oat | 100 | — | 15 | | | |

| | COMPOUND | | | | | | | | |
|---|---|---|---|---|---|---|---|---|---|
| Rate 125 g/ha | 1 | 2 | 3 | 12 | 14 | 16 | 19 | 25 | 26 | 28 |

POSTEMERGENCE

| | | | | | | | | | | |
|---|---|---|---|---|---|---|---|---|---|---|
| Barley Igri | 80 | 70 | 30 | 55 | 65 | 0 | — | 0 | 10 | 10 |
| Barnyard 2 | 100 | — | 80 | 90 | — | — | 10 | 15 | 25 | 80 |
| Barnyardgrass | 90 | 95 | 95 | 100 | 95 | 100 | — | 90 | 90 | 90 |
| Bedstraw | 95 | 80 | 90 | 80 | 90 | 100 | — | 70 | 70 | 45 |
| Blackgrass | 95 | 95 | 60 | 85 | 90 | 80 | — | 0 | 30 | 35 |
| Chickweed | 100 | 100 | 100 | 100 | 100 | 100 | — | — | — | 50 |
| Cocklebur | 90 | 90 | 90 | 95 | 95 | 100 | — | 90 | 90 | 85 |
| Corn | 80 | 10 | 0 | 0 | 10 | 55 | — | 10 | 20 | 0 |
| Cotton | 100 | 100 | 90 | 100 | 100 | 100 | — | 70 | 90 | 90 |
| Crabgrass | 90 | 95 | 90 | 95 | 95 | 100 | — | 85 | 50 | 90 |
| Downy Brome | 85 | 90 | 60 | 80 | 90 | 65 | — | 0 | 0 | 25 |
| Duck salad | 70 | — | 50 | 90 | — | — | 0 | 10 | 70 | 35 |
| Giant foxtail | 90 | 95 | 70 | 95 | 95 | 100 | — | 60 | 70 | 70 |
| Italn. Rygrass | 85 | 75 | 50 | 95 | 70 | 0 | — | 0 | 0 | 0 |
| Johnsongrass | 95 | 100 | 90 | 80 | 95 | 90 | — | 20 | 40 | 80 |
| Lambsguarter | 100 | 100 | 95 | 100 | 100 | 95 | — | 90 | 90 | 100 |
| Morningglory | 100 | 90 | 90 | 90 | 90 | 90 | — | 40 | 90 | 90 |
| Rape | 100 | 90 | 80 | — | 95 | 10 | — | 50 | 90 | 85 |
| Redroot Pigweed | 95 | 90 | 90 | 100 | 95 | 95 | — | 90 | 80 | — |
| Rice Japonica | 95 | — | 55 | 90 | — | — | 0 | 0 | 60 | 95 |
| Soybean | 90 | 90 | 90 | 95 | 90 | 50 | — | 55 | 60 | 90 |
| Speedwell | 100 | 100 | 100 | 100 | 100 | 100 | — | 80 | 70 | 85 |
| Sugar beet | 100 | 100 | 100 | 100 | 100 | 100 | — | — | — | 100 |
| Umbrella sedge | 95 | — | 50 | 90 | — | — | 25 | 50 | 85 | 90 |
| Velvetleaf | 100 | 100 | 100 | 100 | 100 | 100 | — | 90 | 90 | 90 |
| Watergrass 2 | 95 | — | 80 | — | — | — | — | — | — | — |
| Wheat | 70 | 90 | 50 | 70 | 85 | 0 | — | 0 | 0 | 30 |
| Wild buckwheat | 100 | 95 | — | 80 | 90 | 70 | — | 0 | 60 | 65 |
| Wild oat | 100 | 100 | 65 | 95 | 100 | 95 | — | 0 | 20 | 0 |

| | COMPOUND | | | | | | | | |
|---|---|---|---|---|---|---|---|---|---|
| Rate 125 g/ha | 1 | 2 | 3 | 12 | 14 | 16 | 25 | 26 | 28 |

PREEMERGENCE

| | | | | | | | | | |
|---|---|---|---|---|---|---|---|---|---|
| Barley Igri | 0 | 0 | 0 | 0 | 0 | 0 | 0 | 0 | 0 |
| Barnyardgrass | 100 | 95 | 70 | 95 | 100 | 100 | 0 | 50 | 10 |
| Bedstraw | 30 | 50 | 10 | 70 | 55 | 90 | 0 | 30 | 0 |
| Blackgrass | 10 | 20 | 10 | 0 | 10 | 10 | 0 | 30 | 0 |
| Chickweed | 95 | 100 | 90 | 100 | 100 | 90 | 0 | 100 | 30 |
| Cocklebur | 100 | 20 | 75 | 35 | 40 | 20 | 0 | 0 | 0 |
| Corn | 0 | 0 | 0 | 0 | 0 | 0 | 0 | 0 | 0 |
| Cotton | 100 | 50 | 20 | 30 | 30 | 10 | 20 | 40 | 35 |
| Crabgrass | 100 | 100 | 100 | 100 | 100 | 100 | 0 | 70 | 65 |

TABLE A-continued

| | | | | | | | | | |
|---|---|---|---|---|---|---|---|---|---|
| Downy Brome | 40 | 0 | 0 | 95 | 55 | 0 | 0 | 0 | 0 |
| Giant foxtail | 100 | 90 | 40 | 80 | 90 | 90 | 0 | 30 | 0 |
| Italn. Rygrass | 80 | 0 | 30 | 0 | 30 | 0 | 10 | 0 | 0 |
| Johnsongrass | 95 | 75 | 80 | 70 | 60 | 30 | 0 | 20 | 0 |
| Lambsquarter | 100 | 100 | 100 | 100 | 100 | 100 | 30 | 95 | 95 |
| Morningglory | 40 | 40 | 60 | 100 | 60 | 40 | 0 | 40 | 50 |
| Rape | 0 | 85 | 20 | — | 75 | 0 | 0 | 0 | 0 |
| Redroot Pigweed | 100 | — | 90 | — | — | 80 | 0 | 70 | 60 |
| Soybean | 70 | 30 | 30 | 40 | 40 | 0 | 10 | 30 | 50 |
| Speedwell | 100 | 100 | 95 | 100 | 100 | 100 | — | 30 | 80 |
| Sugar beet | 100 | 100 | 100 | 100 | 100 | 90 | — | — | 100 |
| Velvetleaf | 100 | 100 | 100 | 100 | 100 | 100 | 0 | 75 | 100 |
| Wheat | 0 | 30 | 0 | 0 | 35 | 0 | 0 | 0 | 0 |
| Wild buckwheat | 10 | 0 | 10 | 20 | 20 | 0 | 0 | 0 | 10 |
| Wild oat | 80 | 30 | 40 | 0 | 25 | 0 | 0 | 0 | 0 |

| | COMPOUND | | | | | | | | | | | |
|---|---|---|---|---|---|---|---|---|---|---|---|---|
| Rate 62 g/ha | 1 | 2 | 3 | 4 | 12 | 14 | 16 | 18 | 19 | 24 | 25 | 26 | 28 |

POSTEMERGENCE

| | | | | | | | | | | | | | |
|---|---|---|---|---|---|---|---|---|---|---|---|---|---|
| Barley Igri | 70 | 25 | 20 | 10 | 45 | 45 | 0 | 0 | — | 20 | 0 | 0 | 10 |
| Barnyard 2 | 95 | — | 75 | 30 | 90 | — | — | 100 | 0 | 0 | 10 | 10 | 45 |
| Barnyardgrass | 90 | 95 | 95 | 90 | 100 | 95 | 100 | 90 | — | 90 | 90 | 90 | 90 |
| Bedstraw | 95 | 90 | 80 | 70 | 80 | 90 | 95 | 90 | — | 80 | 60 | 70 | 40 |
| Blackgrass | 90 | 60 | 50 | 60 | 75 | 90 | 70 | 60 | — | 60 | 0 | 30 | 20 |
| Chickweed | 100 | 100 | 100 | 90 | 100 | 100 | 100 | 95 | — | 95 | — | 70 | 50 |
| Cocklebur | 90 | 90 | 90 | 90 | 95 | 90 | 100 | 90 | — | 90 | 90 | 80 | 80 |
| Corn | 80 | 20 | 0 | 0 | 0 | 5 | 45 | 45 | — | 0 | 10 | 10 | 0 |
| Cotton | 100 | 100 | 90 | 95 | 100 | 100 | 100 | 100 | — | 80 | 60 | 80 | 90 |
| Crabgrass | 90 | 90 | 90 | 95 | 90 | 90 | 90 | 90 | — | 90 | 80 | 50 | 90 |
| Downy Brome | 80 | 65 | 30 | 30 | 80 | 80 | 20 | 60 | — | 75 | 0 | 0 | 10 |
| Duck salad | 50 | — | 30 | 40 | 70 | — | — | 70 | 0 | 0 | 0 | 0 | 35 |
| Giant foxtail | 90 | 90 | 50 | 70 | 90 | 90 | 90 | 90 | — | 80 | 50 | 60 | 50 |
| Italn. Rygrass | 60 | 70 | 20 | 30 | 60 | 50 | 0 | 30 | — | 10 | 0 | 0 | 0 |
| Johnsongrass | 95 | 50 | 90 | 70 | 80 | 90 | 70 | 100 | — | 70 | 20 | 35 | 60 |
| Lambsquarter | 100 | 100 | 95 | 100 | 100 | 100 | 95 | 100 | — | 90 | 70 | 90 | 100 |
| Morningglory | 95 | 95 | 90 | 90 | 90 | 90 | 90 | 90 | — | 90 | 30 | 85 | 90 |
| Rape | 95 | 95 | 80 | 70 | — | 90 | 10 | 0 | — | — | 30 | 80 | 40 |
| Redroot Pigweed | 95 | 95 | 90 | 90 | 95 | 90 | 90 | 90 | — | 75 | 90 | 70 | 90 |
| Rice Japonica | 90 | — | 35 | 50 | 80 | — | — | 25 | 20 | 0 | 0 | 50 | 55 |
| Soybean | 90 | 90 | 80 | 90 | 95 | 90 | 40 | 60 | — | 90 | 55 | 50 | 90 |
| Speedwell | 100 | 100 | 100 | 100 | 100 | 95 | 100 | 100 | — | 100 | 40 | — | 80 |
| Sugar beet | 100 | 100 | 100 | 100 | 100 | 100 | 100 | 80 | — | — | — | — | 100 |
| Umbrella sedge | 95 | — | 40 | 80 | 80 | — | — | 70 | 0 | 0 | 30 | 60 | 25 |
| Velvetleaf | 100 | 100 | 100 | 90 | 100 | 100 | 100 | 90 | — | 90 | 85 | 80 | 90 |
| Watergrass 2 | 95 | — | 70 | 25 | — | — | — | — | — | — | — | — | 30 |
| Wheat | 45 | 50 | 40 | 30 | 65 | 75 | 0 | 10 | — | 20 | 0 | 0 | 20 |
| Wild buckwheat | 80 | 80 | 85 | 80 | 70 | 90 | — | 30 | — | 0 | 0 | 20 | 65 |
| Wild oat | 100 | 95 | 50 | 60 | 95 | 95 | 95 | 60 | — | 70 | 0 | 0 | 0 |

| | COMPOUND | | | | | | | | | | | |
|---|---|---|---|---|---|---|---|---|---|---|---|---|
| Rate 62 g/ha | 1 | 2 | 3 | 4 | 12 | 14 | 16 | 18 | 24 | 25 | 26 | 28 |

PREEMERGENCE

| | | | | | | | | | | | | |
|---|---|---|---|---|---|---|---|---|---|---|---|---|
| Barley Igri | 0 | 0 | 0 | — | 0 | 0 | 0 | 0 | 0 | 0 | 0 | 0 |
| Barnyardgrass | 95 | 85 | 50 | 60 | 45 | 90 | 30 | 10 | 0 | 0 | 10 | 0 |
| Bedstraw | 0 | 0 | 10 | — | 70 | 30 | 40 | 20 | 0 | 0 | 0 | 0 |
| Blackgrass | 0 | 20 | 0 | — | — | 10 | 0 | 20 | 10 | 0 | 20 | 0 |
| Chickweed | 95 | 100 | 45 | — | 100 | 100 | 80 | 60 | 50 | 0 | 90 | 10 |
| Cocklebur | 70 | 10 | 40 | 65 | 20 | 30 | 0 | 0 | 0 | 0 | 0 | 0 |
| Corn | 0 | 0 | 0 | 0 | 0 | 0 | 0 | 0 | 0 | 0 | 0 | 0 |
| Cotton | 90 | 50 | 10 | 0 | 30 | 20 | 10 | 20 | 0 | 10 | 20 | 25 |
| Crabgrass | 100 | 95 | 100 | 80 | 100 | 100 | 70 | 100 | 70 | 0 | 40 | 30 |
| Downy Brome | 25 | 0 | 0 | — | 95 | 30 | 0 | 0 | — | 0 | 0 | 0 |
| Giant foxtail | 95 | 60 | 10 | 0 | 40 | 70 | 50 | 70 | 0 | 0 | 10 | 0 |
| Italn. Rygrass | 60 | 0 | 20 | — | 0 | 0 | 0 | 0 | 0 | 0 | 0 | 0 |
| Johnsongrass | 30 | 45 | 50 | 80 | 40 | 30 | 20 | 0 | 0 | 0 | 0 | 0 |
| Lambsquarter | 100 | 100 | 100 | — | 100 | 100 | 100 | 100 | 95 | 20 | 95 | 95 |
| Morningglory | 30 | 0 | 30 | 0 | 30 | 20 | 40 | 0 | 0 | 0 | 0 | 0 |
| Rape | 0 | — | 0 | — | 0 | 25 | 0 | 0 | 0 | 0 | 0 | 0 |
| Redroot Pigweed | 95 | — | 80 | 60 | — | — | 70 | 60 | 0 | — | 30 | 10 |
| Soybean | 50 | 30 | 10 | 10 | 30 | 30 | 0 | 0 | 0 | 0 | 0 | 40 |
| Speedwell | 95 | 100 | 95 | — | 100 | 100 | 100 | 100 | 100 | 0 | 30 | 80 |
| Sugar beet | 90 | 100 | 100 | — | 100 | 100 | 80 | — | — | — | — | 95 |
| Velvetleaf | 100 | 100 | 100 | 60 | 100 | 100 | 100 | 100 | 100 | 0 | 0 | 60 |

TABLE A-continued

| | | | | | | | | | | | | | | | |
|---|---|---|---|---|---|---|---|---|---|---|---|---|---|---|---|
| Wheat | 0 | 30 | 0 | — | 0 | 35 | 0 | 0 | 0 | 0 | 0 | 0 | 0 | | |
| Wild buckwheat | 0 | 0 | 0 | 0 | — | 20 | 0 | 0 | 10 | 0 | 0 | 0 | 0 | | |
| Wild oat | 70 | 30 | 30 | — | 0 | 25 | 0 | 0 | 10 | 0 | 0 | 0 | 0 | | |

| | COMPOUND | | | | | | | | | | | | | | |
|---|---|---|---|---|---|---|---|---|---|---|---|---|---|---|---|
| Rate 31 g/ha | 1 | 2 | 3 | 4 | 5 | 6 | 12 | 14 | 16 | 18 | 19 | 24 | 25 | 26 | 27 | 2 |

POSTEMERGENCE

| | | | | | | | | | | | | | | | | |
|---|---|---|---|---|---|---|---|---|---|---|---|---|---|---|---|---|
| Barley Igri | 30 | 25 | 10 | 5 | 40 | 85 | 40 | 30 | 0 | 0 | — | 20 | 0 | 0 | 0 | |
| Barnyard 2 | 95 | 80 | 70 | 20 | 20 | 20 | 90 | — | 20 | 10 | 20 | 0 | 0 | 0 | 15 | 1 |
| Barnyardgrass | 90 | 95 | 90 | 90 | 90 | 95 | 100 | 95 | 100 | 90 | — | 90 | 80 | 90 | 95 | 9 |
| Bedstraw | 90 | 70 | 80 | 70 | 100 | 80 | 65 | 70 | 80 | 90 | — | 80 | 30 | 60 | 75 | 3 |
| Blackgrass | 80 | 45 | 40 | 10 | 90 | 95 | 60 | 70 | 60 | 50 | — | 50 | 0 | 15 | 55 | 1 |
| Chickweed | 100 | 100 | 100 | 90 | — | 95 | 100 | 100 | 100 | — | — | — | — | 40 | — | 5 |
| Cocklebur | 90 | 90 | 90 | 90 | 90 | 90 | 90 | 90 | 95 | 90 | — | 90 | 90 | 80 | 90 | 7 |
| Corn | 70 | 0 | 0 | 0 | 0 | 0 | 0 | 0 | 40 | 30 | — | 0 | 0 | 5 | 30 | |
| Cotton | 100 | 95 | 90 | 95 | 90 | 100 | 100 | 100 | 100 | 100 | — | 80 | 40 | 60 | 80 | 8 |
| Crabgrass | 90 | 90 | 90 | 90 | 90 | 95 | 85 | 90 | 90 | 90 | — | 80 | 70 | 40 | 90 | 9 |
| Downy Brome | 70 | 50 | 10 | 10 | 70 | 75 | 0 | 70 | 0 | 60 | — | 40 | 0 | 0 | 30 | 1 |
| Duck salad | 40 | 0 | 10 | 30 | 80 | 75 | 70 | — | 80 | 50 | 0 | 0 | 0 | 0 | 70 | |
| Giant foxtail | 90 | 90 | 50 | 50 | 90 | 90 | 70 | 85 | 90 | 80 | — | 80 | 40 | 60 | 60 | 5 |
| Italn. Rygrass | 30 | 25 | 20 | 10 | 30 | 55 | 20 | 50 | 0 | 10 | — | 0 | 0 | 0 | 0 | |
| Johnsongrass | 95 | 75 | 70 | 40 | 90 | 90 | 70 | 85 | 60 | 80 | — | 60 | 10 | 30 | 80 | 5 |
| Lambsquarter | 100 | 100 | 95 | 90 | 100 | 100 | 90 | 100 | 95 | 90 | — | 70 | 60 | 90 | 100 | 10 |
| Morningglory | 90 | 95 | 90 | 90 | 90 | 90 | 90 | 90 | 90 | 90 | — | 90 | 20 | 80 | 70 | 9 |
| Rape | 90 | 80 | 70 | 50 | 80 | 50 | — | 40 | 0 | 0 | — | 90 | 0 | 50 | 70 | 4 |
| Redroot Pigweed | 90 | 90 | 90 | 75 | 90 | 80 | 90 | 90 | 85 | 90 | — | — | 75 | 50 | 90 | 9 |
| Rice Japonica | 75 | 30 | 35 | 40 | 45 | 35 | 30 | — | 20 | 10 | 0 | 0 | 0 | 0 | 60 | 2 |
| Soybean | 90 | 90 | 70 | 80 | 90 | 90 | 85 | 90 | 35 | 50 | — | 90 | 45 | 40 | 85 | 8 |
| Speedwell | 100 | 100 | 100 | 100 | 90 | 95 | 85 | 95 | 85 | 100 | — | — | 25 | 30 | 100 | 8 |
| Sugar beet | 100 | 100 | 100 | 100 | — | 100 | 100 | 100 | 100 | — | — | — | — | — | — | 10 |
| Umbrella sedge | 85 | 20 | 30 | 60 | 75 | 80 | 80 | — | 70 | 25 | 0 | 0 | 10 | 30 | 85 | 2 |
| Velvetleaf | 100 | 100 | 100 | 90 | 90 | 95 | 100 | 100 | 100 | 90 | — | 90 | 85 | 80 | 90 | 9 |
| Watergrass 2 | 70 | 85 | 50 | 20 | — | — | — | — | — | — | — | — | — | — | — | |
| Wheat | 35 | 35 | 30 | 15 | 70 | 95 | 45 | 70 | 0 | 10 | — | 10 | 0 | 0 | 30 | 1 |
| Wild buckwheat | 70 | 75 | 80 | 50 | 75 | 95 | 65 | 90 | 70 | 20 | — | 0 | 0 | 0 | 40 | 6 |
| Wild oat | 100 | 80 | 35 | 40 | 90 | 100 | 75 | 90 | 95 | 40 | — | 70 | 0 | 0 | 70 | |

| | COMPOUND | | | | | | | | | | | | | | |
|---|---|---|---|---|---|---|---|---|---|---|---|---|---|---|---|
| Rate 31 g/ha | 1 | 2 | 3 | 4 | 5 | 6 | 12 | 14 | 16 | 18 | 24 | 25 | 26 | 27 | 28 | 3 |

PREEMERGENCE

| | | | | | | | | | | | | | | | | |
|---|---|---|---|---|---|---|---|---|---|---|---|---|---|---|---|---|
| Barley Igri | 0 | 0 | 0 | — | 0 | 0 | 0 | 0 | 0 | 0 | 0 | 0 | 0 | 0 | | |
| Barnyardgrass | 80 | 15 | 10 | 20 | 70 | 35 | 10 | 70 | 0 | 0 | 0 | 0 | 0 | 0 | 0 | 1 |
| Bedstraw | 0 | 0 | 10 | — | 40 | 0 | 25 | 30 | 0 | 10 | 0 | 0 | 0 | 70 | 0 | |
| Blackgrass | 0 | 0 | 0 | — | 10 | 15 | 0 | 10 | 0 | 20 | 0 | 0 | 10 | 0 | 0 | |
| Chickweed | 95 | 10 | 30 | — | 0 | 85 | 95 | 100 | 50 | 60 | 0 | 0 | 70 | 0 | 0 | 9 |
| Cocklebur | 30 | 20 | 30 | 30 | 20 | 0 | — | 20 | 0 | 0 | 0 | 0 | 0 | 0 | 0 | |
| Corn | 0 | 0 | 0 | 0 | 0 | 0 | 0 | 0 | 0 | 0 | 0 | 0 | 0 | 0 | 0 | |
| Cotton | 30 | 30 | 10 | 0 | 0 | 30 | — | 10 | 0 | 20 | 0 | 0 | 10 | 0 | 20 | 3 |
| Crabgrass | 95 | 95 | 100 | 35 | 100 | 90 | 90 | 100 | 70 | 80 | 30 | 0 | 0 | 80 | 10 | 4 |
| Downy Brome | 0 | 0 | 0 | — | 0 | 0 | 95 | 30 | 0 | 0 | 0 | 0 | 0 | 0 | 0 | |
| Giant foxtail | 75 | 20 | 0 | 0 | 50 | 40 | 20 | 30 | 30 | 50 | 0 | 0 | 0 | 10 | 0 | 1 |
| Italn. Rygrass | 40 | 0 | 10 | — | 0 | 0 | 0 | 0 | 0 | 0 | 0 | 0 | 0 | 0 | 0 | |
| Johnsongrass | 20 | 10 | — | 0 | 10 | 20 | 20 | 20 | 0 | 0 | 0 | 0 | 0 | 0 | 0 | |
| Lambsquarter | 100 | 95 | 100 | — | 95 | 100 | 100 | 100 | 90 | 100 | 60 | 0 | 60 | 90 | 95 | 10 |
| Morningglory | 10 | 20 | 0 | 0 | 0 | 10 | — | — | 20 | 0 | 0 | 0 | 0 | 0 | 0 | 10 |
| Rape | 0 | 0 | 0 | — | 0 | 0 | — | 0 | 0 | 0 | 0 | 0 | 0 | 10 | 0 | |
| Redroot Pigweed | 30 | 80 | 70 | 30 | 70 | — | — | — | 50 | — | 0 | 0 | 0 | 70 | — | 7 |
| Soybean | 40 | 0 | 0 | 10 | 0 | 10 | 30 | 10 | 0 | 0 | 0 | 0 | 0 | 0 | 40 | |
| Speedwell | 70 | 100 | 95 | — | 0 | 100 | 100 | 100 | 100 | 100 | 0 | — | — | 50 | 80 | 10 |
| Sugar beet | 30 | 100 | 95 | — | — | 80 | 100 | 100 | 50 | — | — | — | — | — | 95 | 9 |
| Velvetleaf | 100 | 100 | 100 | 30 | 100 | 100 | 100 | 100 | 60 | 100 | 80 | 0 | 0 | 90 | 60 | 3 |
| Wheat | 0 | 0 | 0 | — | 0 | 30 | 0 | 30 | 0 | 0 | 0 | 0 | 0 | 0 | 0 | |
| Wild buckwheat | 0 | 0 | 0 | — | 0 | 0 | 0 | 0 | 0 | 0 | 0 | 0 | 0 | 0 | 0 | |
| Wild oat | 40 | 0 | 10 | — | 0 | 25 | 0 | 25 | 0 | 0 | 10 | 0 | 0 | 0 | 0 | |

| | COMPOUND | | | | | | | | | | | | | | |
|---|---|---|---|---|---|---|---|---|---|---|---|---|---|---|---|
| Rate 16 g/ha | 1 | 2 | 3 | 4 | 5 | 6 | 12 | 14 | 16 | 18 | 24 | 25 | 26 | 27 | 30 | 31 |

POSTEMERGENCE

| | | | | | | | | | | | | | | | | |
|---|---|---|---|---|---|---|---|---|---|---|---|---|---|---|---|---|
| Barley Igri | 55 | 10 | 0 | 0 | 40 | 60 | 40 | 10 | 0 | 0 | 20 | 0 | 0 | 0 | 20 | 50 |
| Barnyard 2 | 55 | 70 | 30 | 15 | 10 | 15 | 90 | — | 20 | 10 | 0 | 0 | 0 | 15 | 10 | 0 |

TABLE A-continued

| | | | | | | | | | | | | | | | | |
|---|---|---|---|---|---|---|---|---|---|---|---|---|---|---|---|---|
| Barnyardgrass | 95 | 90 | 90 | 90 | 90 | 95 | 95 | 95 | 100 | 90 | 90 | 40 | 85 | 95 | 100 | 95 |
| Bedstraw | 70 | 0 | — | 60 | 90 | 70 | 60 | 55 | 80 | 80 | 80 | 30 | 50 | 50 | 70 | 60 |
| Blackgrass | 85 | 35 | 35 | 0 | 75 | 90 | 40 | 60 | 30 | 30 | 50 | 0 | 10 | 35 | 50 | 80 |
| Chickweed | 100 | 100 | 95 | 70 | 90 | 90 | 95 | 95 | 90 | — | — | — | — | — | 90 | — |
| Cocklebur | 100 | 90 | 90 | 90 | 90 | 90 | 90 | 90 | 90 | 90 | 90 | 80 | 70 | 90 | — | 70 |
| Corn | 75 | 0 | 0 | 0 | 0 | 0 | 0 | 0 | 40 | 10 | 0 | 0 | 0 | 20 | 0 | 0 |
| Cotton | 100 | 95 | 85 | 85 | 70 | 100 | 100 | 90 | 90 | 90 | 70 | 40 | 45 | 80 | 90 | 80 |
| Crabgrass | 95 | 90 | 85 | 90 | 90 | 90 | 75 | 85 | 85 | 85 | 80 | 60 | 40 | 80 | 95 | 90 |
| Downy Brome | 55 | 10 | 0 | 0 | 70 | 40 | 0 | 45 | 0 | 30 | 40 | 0 | 0 | 10 | 50 | 20 |
| Duck salad | 30 | 0 | 0 | 20 | 75 | 25 | 70 | — | 40 | 35 | 0 | 0 | 0 | 35 | 0 | 0 |
| Giant foxtail | 95 | 90 | 45 | 30 | 70 | 85 | 60 | 80 | 85 | 70 | 60 | 25 | 50 | 50 | 80 | 90 |
| Italn. Rygrass | 40 | 25 | 10 | 0 | 30 | 0 | 0 | 35 | 0 | 0 | 0 | 0 | 0 | 0 | 30 | 40 |
| Johnsongrass | 100 | 75 | 70 | 40 | 90 | 90 | 50 | 75 | 60 | 70 | 40 | 0 | 30 | 70 | 80 | 90 |
| Lambsquarter | 95 | 100 | 95 | 90 | 90 | 95 | 90 | 90 | 90 | 80 | 55 | 55 | 70 | 80 | 90 | 60 |
| Morningglory | 90 | 90 | 85 | 90 | 90 | 80 | 90 | 90 | 90 | 85 | 90 | 10 | 80 | 50 | 60 | 60 |
| Rape | 25 | 80 | 70 | 30 | 80 | 10 | — | 30 | 0 | 0 | 80 | 0 | 20 | 50 | 90 | 20 |
| Redroot Pigweed | 90 | 90 | 80 | 75 | 90 | 70 | 85 | 80 | 80 | 75 | 60 | 65 | 50 | 80 | 80 | 80 |
| Rice Japonica | 40 | 25 | 25 | 10 | 0 | 25 | 20 | — | 20 | 10 | 0 | 0 | 0 | 20 | 0 | 0 |
| Soybean | 90 | 70 | 70 | 80 | 80 | 80 | 85 | 90 | 25 | 40 | 80 | 35 | 30 | 80 | 70 | 80 |
| Speedwell | 95 | 95 | 100 | 80 | — | 80 | 80 | 90 | 95 | 80 | 80 | — | — | 80 | — | — |
| Sugar beet | 100 | 100 | 100 | 100 | — | 95 | 100 | 100 | 95 | — | — | — | — | — | 100 | — |
| Umbrella sedge | 20 | 0 | 0 | 30 | 50 | 80 | 80 | — | 40 | 0 | 0 | 0 | 15 | 15 | 15 | 0 |
| Velvetleaf | 100 | 100 | 100 | 90 | 90 | 90 | 95 | 100 | 95 | 90 | 90 | 80 | 80 | 80 | 100 | 90 |
| Watergrass 2 | 30 | 25 | 30 | — | — | — | — | — | — | — | — | — | — | — | — | — |
| Wheat | 30 | 25 | 20 | 10 | 50 | 85 | 20 | 50 | 0 | 0 | 10 | 0 | 0 | 20 | 60 | 65 |
| Wild buckwheat | 85 | 65 | 60 | 30 | 40 | 75 | 30 | 75 | 70 | 0 | 0 | 0 | 0 | 30 | 30 | 20 |
| Wild oat | 90 | 65 | 25 | 25 | 70 | 95 | 65 | 80 | 70 | 30 | 50 | 0 | 0 | 50 | 90 | 90 |
| PREEMERGENCE | | | | | | | | | | | | | | | | |
| Barley Igri | 0 | 0 | 0 | — | 0 | 0 | 0 | 0 | 0 | 0 | 0 | 0 | 0 | 0 | 0 | 0 |
| Barnyardgrass | 60 | 0 | 0 | 0 | 30 | 10 | 0 | 10 | 0 | 0 | 0 | 0 | 0 | 0 | 0 | 0 |
| Bedstraw | 0 | 0 | 0 | — | 10 | 0 | — | 0 | 0 | 0 | 0 | 0 | 0 | 50 | 0 | 0 |
| Blackgrass | 0 | 0 | 0 | — | 0 | 10 | 0 | 10 | 0 | 0 | 0 | 0 | 0 | 0 | 0 | 30 |
| Chickweed | 20 | 0 | 30 | — | 0 | 10 | 95 | 100 | 30 | 40 | 0 | 0 | 30 | 0 | — | 100 |
| Cocklebur | 20 | 0 | 20 | 10 | 0 | 0 | 20 | 20 | 0 | 0 | 0 | 0 | 0 | 0 | 0 | 0 |
| Corn | 20 | 0 | 0 | 0 | 0 | 0 | 0 | 0 | 0 | 0 | 0 | 0 | 0 | 0 | 0 | 0 |
| Cotton | 0 | 30 | 0 | 0 | 0 | 30 | — | 0 | 0 | 10 | 0 | 0 | 0 | 0 | 0 | 0 |
| Crabgrass | 60 | 80 | 100 | 20 | 75 | 80 | 40 | 75 | 30 | 80 | 0 | 0 | 0 | 20 | 20 | — |
| Downy Brome | 0 | 0 | 0 | — | 0 | 0 | 95 | 30 | 0 | 0 | 0 | 0 | 0 | 0 | 0 | 0 |
| Giant foxtail | 20 | 10 | 0 | 0 | 10 | 20 | 10 | 15 | 0 | 0 | 0 | 0 | 0 | 10 | 0 | 25 |
| Italn. Rygrass | 0 | 0 | 10 | — | 0 | 0 | 0 | 0 | 0 | 0 | 0 | 0 | 0 | 0 | 0 | 0 |
| Johnsongrass | 20 | 0 | 40 | 0 | 0 | 10 | 0 | — | 0 | 0 | 0 | 0 | 0 | 0 | 0 | 10 |
| Lambsquarter | 70 | 95 | 100 | — | 95 | 100 | 100 | 100 | 90 | 60 | 10 | 0 | 40 | — | 0 | 10 |
| Morningglory | 20 | 0 | 0 | 0 | 0 | 0 | 0 | 0 | 20 | 0 | 0 | 0 | 0 | 0 | 20 | 10 |
| Rape | 0 | 0 | 0 | — | 0 | 0 | — | 0 | 0 | 0 | 0 | 0 | 0 | 0 | 0 | 0 |
| Redroot Pigweed | 40 | 30 | 70 | 0 | 40 | — | — | — | 0 | 20 | 0 | 0 | 0 | 40 | 50 | 30 |
| Soybean | 30 | 0 | 0 | 0 | 0 | 10 | 20 | 0 | 0 | 0 | 0 | 0 | 0 | 0 | 0 | 0 |
| Speedwell | 100 | 100 | 90 | — | — | 100 | 100 | 100 | 80 | 70 | 0 | 0 | 0 | 0 | 95 | 70 |
| Sugar beet | 25 | 0 | 10 | — | — | — | 90 | 55 | 0 | — | — | — | — | — | 0 | — |
| Velvetleaf | 85 | 90 | 85 | 20 | 100 | 100 | 90 | 100 | 40 | 70 | 30 | 0 | 0 | 70 | 0 | 80 |
| Wheat | 0 | 0 | 0 | — | 0 | 30 | 0 | 30 | 0 | 0 | 0 | 0 | 0 | 0 | 0 | 0 |
| Wild buckwheat | 0 | 0 | 0 | — | 0 | 0 | 0 | 0 | 0 | 0 | 0 | 0 | 0 | 0 | 0 | 0 |
| Wild oat | 0 | 0 | 10 | — | 0 | 25 | 0 | 25 | 0 | 0 | 0 | 0 | 0 | 0 | 0 | 0 |

| | COMPOUND | | | | | | | | | | | |
|---|---|---|---|---|---|---|---|---|---|---|---|---|
| Rate 8 g/ha | 1 | 2 | 4 | 5 | 6 | 12 | 14 | 16 | 18 | 24 | 27 | 30 | 31 |
| POSTEMERGENCE | | | | | | | | | | | | | |
| Barley Igri | 35 | 0 | 0 | 30 | 50 | 40 | 10 | 0 | 0 | 0 | 0 | 0 | 10 |
| Barnyard 2 | 35 | 40 | 10 | 10 | 0 | 10 | — | 15 | 0 | 0 | 10 | 0 | 0 |
| Barnyardgrass | 95 | 90 | 90 | 90 | 95 | 95 | 90 | 90 | 90 | 90 | 95 | 95 | 95 |
| Bedstraw | 60 | 0 | 50 | 90 | 40 | 10 | 30 | 80 | 80 | 60 | 50 | 40 | 50 |
| Blackgrass | 60 | 10 | 0 | 60 | 80 | 0 | 40 | 10 | 20 | 30 | 20 | 30 | 40 |
| Chickweed | 95 | 90 | 70 | 90 | 80 | 75 | 90 | 75 | — | 90 | — | 80 | — |
| Cocklebur | 100 | 90 | 70 | 90 | 90 | 85 | 85 | 90 | 90 | 85 | 90 | 90 | 60 |
| Corn | 55 | 0 | 0 | 0 | 0 | 0 | 0 | 15 | 5 | 0 | 15 | 0 | 0 |
| Cotton | 100 | 90 | 85 | 60 | 90 | 95 | 90 | 70 | 40 | 70 | 70 | 80 | 50 |
| Crabgrass | 90 | 85 | 70 | 90 | 85 | 60 | 75 | 80 | 85 | 80 | 80 | 85 | 80 |
| Downy Brome | 40 | 0 | 0 | 70 | 30 | 0 | 35 | 0 | 20 | 10 | 0 | 30 | 20 |
| Duck salad | 30 | 0 | 10 | 0 | 10 | 0 | — | 10 | 0 | 0 | 0 | 0 | 0 |
| Giant foxtail | 90 | 85 | 20 | 70 | 75 | 40 | 55 | 75 | 40 | 35 | 40 | 75 | 80 |
| Italn. Rygrass | 30 | 10 | 0 | 20 | 0 | 0 | 20 | 0 | 0 | 0 | 0 | 20 | 0 |
| Johnsongrass | 95 | 65 | 30 | 70 | 85 | 35 | 70 | 40 | 35 | 20 | 70 | 80 | 85 |
| Lambsquarter | 85 | 95 | 90 | 90 | 95 | 85 | 85 | 80 | 80 | 20 | 70 | 80 | 50 |
| Morningglory | 90 | 90 | 30 | 90 | 80 | 85 | 90 | 40 | 15 | 90 | 40 | 40 | 50 |
| Rape | 10 | 75 | 10 | 80 | 0 | — | 30 | 0 | 0 | 30 | 30 | 70 | 10 |
| Redroot Pigweed | 90 | 90 | 65 | 85 | 60 | 80 | 80 | 70 | — | 50 | 80 | 55 | 70 |

TABLE A-continued

| | | | | | | | | | | | | | |
|---|---|---|---|---|---|---|---|---|---|---|---|---|---|
| Rice Japonica | 35 | 10 | 10 | 0 | 10 | 0 | — | 15 | 0 | 0 | 10 | 0 | 0 |
| Soybean | 90 | 70 | 70 | 75 | 80 | 70 | 85 | 40 | 15 | 70 | 75 | 70 | 70 |
| Speedwell | 90 | 70 | 80 | 60 | 80 | 70 | 85 | 60 | 70 | 70 | 70 | 0 | 80 |
| Sugar beet | 100 | 100 | 90 | — | 90 | 95 | 100 | — | — | — | — | 100 | — |
| Umbrella sedge | 20 | 0 | 20 | 0 | 20 | 60 | — | 20 | 0 | 0 | 0 | 0 | 0 |
| Velvetleaf | 100 | 100 | 70 | 90 | 90 | 95 | 95 | 90 | 80 | 85 | 80 | 90 | 90 |
| Watergrass 2 | 25 | 10 | 0 | — | — | — | — | — | — | — | — | — | — |
| Wheat | 10 | 0 | 0 | 35 | 80 | 0 | 35 | 0 | 0 | 0 | 10 | 10 | 15 |
| Wild buckwheat | 60 | 65 | 30 | 30 | 50 | 30 | 35 | 40 | 0 | 0 | 20 | 20 | 0 |
| Wild oat | 90 | 25 | 10 | 55 | 90 | 20 | 70 | 0 | 10 | 35 | 30 | 70 | 50 |
| PREEMERGENCE | | | | | | | | | | | | | |
| Barley Igri | 0 | 0 | — | 0 | 0 | 0 | 0 | 0 | 0 | 0 | 0 | 0 | 0 |
| Barnyardgrass | 20 | 0 | 0 | 0 | 0 | 0 | 0 | 0 | 0 | 0 | 0 | 0 | 0 |
| Bedstraw | 0 | 0 | — | 0 | 0 | 0 | 0 | 10 | 0 | 0 | 0 | 0 | 0 |
| Blackgrass | 0 | 0 | — | 0 | 10 | 0 | 10 | 0 | 0 | 0 | 0 | 0 | 20 |
| Chickweed | 0 | 0 | — | 0 | — | — | 95 | 0 | — | 0 | — | 25 | 70 |
| Cocklebur | 10 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 |
| Cotton | 0 | 0 | 0 | 0 | 10 | 20 | — | 0 | 10 | 0 | 0 | 0 | 0 |
| Crabgrass | 20 | 20 | 0 | 30 | 50 | 10 | 30 | 60 | 40 | 0 | 10 | 0 | 40 |
| Downy Brome | 0 | 0 | — | 0 | 0 | 95 | 30 | 0 | 0 | 0 | 0 | 0 | 0 |
| Giant foxtail | 10 | 0 | 0 | 10 | 10 | 0 | 0 | 0 | 0 | 0 | 0 | 0 | 15 |
| Italn. Rygrass | 0 | 0 | — | 0 | 0 | 0 | 0 | 0 | 0 | 0 | 0 | 0 | 0 |
| Johnsongrass | 10 | 0 | 0 | 0 | 0 | 0 | 0 | 0 | 0 | 0 | 0 | 0 | 0 |
| Lambsquarter | 50 | 90 | — | 70 | 100 | 0 | 100 | 80 | 60 | 0 | 0 | 0 | 0 |
| Morningglory | 0 | 0 | 0 | 0 | 0 | 0 | 0 | 0 | 0 | 0 | 0 | 0 | 0 |
| Rape | 0 | 0 | — | 0 | — | 0 | 0 | 0 | 0 | 0 | 0 | 0 | 0 |
| Redroot Pigweed | 20 | 0 | 0 | 20 | — | — | — | 50 | 0 | 0 | 20 | 0 | 0 |
| Soybean | 10 | 0 | 0 | 0 | — | 20 | 0 | 0 | 0 | 0 | 0 | 0 | 0 |
| Speedwell | 90 | 0 | — | — | 100 | 100 | 100 | 0 | 50 | — | 0 | — | 0 |
| Sugar beet | 0 | 0 | — | — | 20 | 90 | 35 | — | — | — | — | 0 | — |
| Velvetleaf | 40 | 20 | 0 | 80 | 80 | 50 | 60 | 65 | 40 | 0 | 60 | 0 | 60 |
| Wheat | 0 | 0 | — | 0 | 30 | 0 | 30 | 0 | 0 | 0 | 0 | 0 | 0 |
| Wild buckwheat | 0 | 0 | — | 0 | 0 | — | 0 | 0 | 0 | 0 | 0 | 0 | 0 |
| Wild oat | 0 | 0 | — | 0 | 25 | 0 | 25 | 0 | 0 | 0 | 0 | 0 | 0 |

| | COMPOUND | | | | | | | |
|---|---|---|---|---|---|---|---|---|
| Rate 4 g/ha | 1 | 2 | 5 | 6 | 16 | 27 | 30 | 31 |
| POSTEMERGENCE | | | | | | | | |
| Barley Igri | 0 | 0 | 0 | 30 | 0 | 0 | 0 | 0 |
| Barnyard 2 | 30 | 25 | 0 | 0 | 10 | 0 | 0 | 0 |
| Barnyardgrass | 90 | 90 | 90 | 95 | 90 | 90 | 95 | 90 |
| Bedstraw | 45 | 0 | 50 | 35 | 60 | — | 40 | 50 |
| Blackgrass | 35 | 0 | 20 | 65 | 0 | 0 | 10 | 30 |
| Chickweed | 85 | 75 | 80 | 45 | — | — | 60 | — |
| Cocklebur | 90 | 90 | 80 | 80 | 80 | 80 | 80 | 60 |
| Corn | 20 | 0 | 0 | 0 | 10 | 10 | 0 | 0 |
| Cotton | 90 | 90 | 60 | 80 | 70 | 70 | 40 | 50 |
| Crabgrass | 80 | 80 | 75 | 85 | 80 | 60 | 60 | 70 |
| Downy Brome | 30 | 0 | 20 | 0 | 0 | 0 | 10 | 10 |
| Duck salad | 20 | 0 | 0 | 0 | 0 | 0 | 0 | 0 |
| Giant foxtail | 90 | 65 | 40 | 50 | 50 | 10 | 50 | 70 |
| Italn. Rygrass | 10 | 0 | 15 | 0 | 0 | 0 | 0 | 0 |
| Johnsongrass | 95 | 60 | 50 | 65 | 30 | 40 | 60 | 70 |
| Lambsquarter | 80 | 75 | 80 | 90 | 70 | 50 | 55 | 15 |
| Morningglory | 90 | 90 | 90 | 30 | 40 | 40 | 10 | 25 |
| Rape | 0 | 30 | 50 | 0 | 0 | 20 | 40 | 0 |
| Redroot Pigweed | 60 | 90 | 80 | 45 | 40 | 70 | 50 | 70 |
| Rice Japonica | 20 | 0 | 0 | 0 | 15 | 10 | 0 | 0 |
| Soybean | 85 | 45 | 70 | 70 | 40 | 75 | 40 | 50 |
| Speedwell | 85 | 70 | — | 60 | 30 | 70 | 0 | 60 |
| Sugar beet | 100 | 100 | — | 60 | — | — | 90 | — |
| Umbrella sedge | 10 | 0 | 0 | 0 | 10 | 0 | 0 | 0 |
| Velvetleaf | 100 | 100 | 90 | 90 | 90 | 80 | 90 | 90 |
| Watergrass 2 | 20 | 10 | — | — | — | — | — | — |
| Wheat | 0 | 0 | 10 | 35 | 0 | 0 | 0 | 0 |
| Wild buckwheat | 25 | 20 | 10 | 30 | 0 | 0 | 10 | — |
| Wild oat | 65 | 0 | 30 | 70 | 0 | 10 | 20 | 35 |
| PREEMERGENCE | | | | | | | | |
| Barley Igri | 0 | 0 | 0 | 0 | 0 | 0 | 0 | 0 |
| Barnyardgrass | 0 | 0 | 0 | 0 | 0 | 0 | 0 | 0 |
| Bedstraw | 0 | 0 | 0 | 0 | 0 | 0 | 0 | 0 |
| Blackgrass | 0 | 0 | 0 | 0 | 0 | 0 | 0 | 0 |
| Chickweed | 0 | 0 | 0 | — | 0 | 0 | 25 | 0 |

TABLE A-continued

| | | | | | | | | |
|---|---|---|---|---|---|---|---|---|
| Cocklebur | 0 | 0 | 0 | 0 | 0 | 0 | 0 | 0 |
| Corn | 0 | 0 | 0 | 0 | 0 | 0 | 0 | 0 |
| Cotton | 0 | 0 | 0 | 0 | 0 | 0 | 0 | 0 |
| Crabgrass | 0 | 10 | 10 | 20 | 30 | 0 | 0 | 0 |
| Downy Brome | 0 | 0 | 0 | 0 | 0 | 0 | 0 | 0 |
| Giant foxtail | 0 | 0 | 0 | 0 | 0 | 0 | 0 | 10 |
| Italn. Rygrass | 0 | 0 | 0 | 0 | 0 | 0 | 0 | 0 |
| Johnsongrass | 0 | 0 | 0 | 0 | 0 | 0 | 0 | 0 |
| Lambsquarter | 20 | 70 | 0 | 100 | 50 | 0 | 0 | 0 |
| Morningglory | 0 | 0 | 0 | 0 | 0 | 0 | 0 | 0 |
| Rape | 0 | 0 | 0 | 0 | 0 | 0 | 0 | 0 |
| Redroot Pigweed | 0 | 0 | 10 | — | 30 | 0 | 0 | 0 |
| Soybean | 0 | 0 | 0 | 0 | 0 | 0 | 0 | 0 |
| Speedwell | 20 | 0 | — | 30 | 0 | 0 | 95 | — |
| Sugar beet | 0 | 0 | — | 20 | — | — | 0 | — |
| Velvetleaf | 20 | 0 | 40 | 0 | 50 | 40 | 0 | 20 |
| Wheat | 0 | 0 | 0 | 30 | 0 | 0 | 0 | 0 |
| Wild buckwheat | 0 | 0 | 0 | 0 | 0 | 0 | 0 | 0 |
| Wild oat | 0 | 0 | 0 | 25 | 0 | 0 | 0 | 0 |

| Rate 2 g/ha | COMPOUND 1 | Rate 2 g/ha | COMPOUND 1 |
|---|---|---|---|
| POSTEMERGENCE | | PREEMERGENCE | |
| Barley Igri | 0 | Barley Igri | 0 |
| Barnyard 2 | 30 | Barnyardgrass | 0 |
| Barnyardgrass | 90 | Bedstraw | 0 |
| Bedstraw | 10 | Blackgrass | 0 |
| Blackgrass | 30 | Chickweed | 0 |
| Chickweed | 70 | Cocklebur | 0 |
| Cocklebur | 80 | Corn | 0 |
| Corn | 0 | Cotton | 0 |
| Cotton | 80 | Crabgrass | 0 |
| Crabgrass | 80 | Downy Brome | 0 |
| Downy Brome | 10 | Giant foxtail | 0 |
| Duck said | 20 | Italn. Rygrass | 0 |
| Giant foxtail | 80 | Johnsongrass | 0 |
| Italn. Rygrass | 0 | Lambsquarter | 20 |
| Johnsongrass | 70 | Morningglory | 0 |
| Lambsquarter | 40 | Rape | 0 |
| Morningglory | 70 | Redroot Pigweed | 0 |
| Rape | 0 | Soybean | 0 |
| Redroot Pigweed | 60 | Speedwell | 20 |
| Rice Japonica | 10 | Sugar beet | 0 |
| Soybean | 85 | Velvetleaf | 0 |
| Speedwell | 35 | Wheat | 0 |
| Sugar beet | 95 | Wild buckwheat | 0 |
| Umbrella sedge | 0 | Wild oat | 0 |
| Velvetleaf | 100 | | |
| Watergrass 2 | 20 | | |
| Wheat | 0 | | |
| Wild buckwheat | 0 | | |
| Wild oat | 40 | | |

| Rate 1 g/ha | COMPOUND 1 | Rate 1 g/ha | COMPOUND 1 |
|---|---|---|---|
| POSTEMERGENCE | | PREEMERGENCE | |
| Barley Igri | 0 | Barley Igri | 0 |
| Barnyard 2 | 30 | Barnyardgrass | 0 |
| Barnyardgrass | 90 | Bedstraw | 0 |
| Bedstraw | 0 | Blackgrass | 0 |
| Blackgrass | 10 | Chickweed | 0 |
| Chickweed | 60 | Cocklebur | 0 |
| Cocklebur | 80 | Corn | 0 |
| Corn | 0 | Cotton | 0 |
| Cotton | 50 | Crabgrass | 0 |
| Crabgrass | 70 | Downy Brome | 0 |
| Downy Brome | 0 | Giant foxtail | 0 |
| Duck salad | 0 | Italn. Rygrass | 0 |
| Giant foxtail | 60 | Johnsongrass | 0 |
| Italn. Rygrass | 0 | Lambsquarter | 10 |
| Johnsongrass | 50 | Morningglory | 0 |
| Lambsquarter | 20 | Rape | 0 |
| Morningglory | 40 | Redroot Pigweed | 0 |
| Rape | 0 | Soybean | 0 |
| Redroot Pigweed | 30 | Speedwell | 10 |

TABLE A-continued

| | | | |
|---|---|---|---|
| Rice Japonica | 10 | Sugar beet | 0 |
| Soybean | 70 | Velvetleaf | 0 |
| Speedwell | 30 | Wheat | 0 |
| Sugar beet | 95 | Wild buckwheat | 0 |
| Umbrella sedge | 0 | Wild oat | 0 |
| Velvetleaf | 90 | | |
| Watergrass 2 | 20 | | |
| Wheat | 0 | | |
| Wild buckwheat | 0 | | |
| Wild oat | 35 | | |

Test B

Compounds evaluated in this test were formulated in a non-phytotoxic solvent mixture which included a surfactant and applied to the soil surface before plant seedlings emerged (preemergence application) and to plants that were grown for various periods of time before treatment (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test, and 13 days after the last postemergence planting Plantings of these crops and weed species were adjusted to produce plants of appropriate size for the postemergence test. All plant species were grown using normal greenhouse practices. Crop and weed species include alexandergrass (*Brachiaria plantaginea*), american black nightshade (*Solanum americanum*), apple-of-Peru (*Nicandra physaloides*), arrowleaf sida (*Sida rhombifolia*), brazilian sicklepod (*Cassia tora* Brazilian), brazilian signalgrass (*Brachiaria decumbens*), capim-colchao (*Digitaria horizontalis*), cristalina soybean (*Glycine max* Cristalina), florida beggarweed (*Desmodium purpureum*), hairy beggarticks (*Bidens pilosa*), slender amaranth (*Amaranthus viridis*), southern sandur (*Cenchrus echinatus*), tall morningglory (*Ipomoea purpurea*), tropical spiderwort (*Commelina benghalensis*), W20 Soybean (*Glycine max* W20), W4-4 Soybean (*Glycine max* W4-4) and wild pointsettia (*Eupohorbia heterophylla*).

Treated plants and untreated controls were maintained in a greenhouse for approximately 13 days, after which all treated plants were compared to untreated controls and visually evaluated. Plant response ratings, summarized in Table B, are based upon a 0 to 100 scale where 0 is no effect and 100 is complete control. A dash response (-) means no test result.

TABLE B

| | COMPOUND | | | | COMPOUND | | |
|---|---|---|---|---|---|---|---|
| POSTEMERGENCE | 1 | 2 | 4 | POSTEMERGENCE | 1 | 2 | 4 |
| Rate 280 g/ha | | | | Rate 140 g/ha | | | |
| Acanthospermum | 100 | 100 | 100 | Acanthospermum | 100 | 90 | 100 |
| Alexandergrass | 100 | 100 | 100 | Alexandergrass | 100 | 100 | 100 |
| Apple-of-Peru | 100 | 100 | 100 | Apple-of-Peru | 100 | 100 | 100 |
| Arrowleaf Sida | 80 | 85 | 100 | Arrowleaf Sida | 70 | 80 | 100 |
| B. Signalgrass | 100 | 90 | 100 | B. Signalgrass | 100 | 95 | 100 |
| Bl. Nightshade | 100 | 100 | 100 | Bl. Nightshade | 100 | 100 | 100 |
| Braz Sicklepod | 60 | 65 | 100 | Braz Sicklepod | 55 | 40 | 50 |
| Capim-Colch | 100 | 100 | 100 | Capim-Colch | 100 | 85 | 100 |
| Crist. Soybean | 95 | 85 | 90 | Crist. Soybean | 100 | 95 | 90 |
| Fl. Beggarweed | 100 | 100 | 100 | Fl. Beggarweed | 100 | 100 | — |
| H. Beggarticks | 95 | 100 | 100 | H. Beggarticks | 80 | 80 | 100 |
| Morningglory | 100 | 90 | 75 | Morningglory | 100 | 100 | 100 |
| Sl. Amaranth | 100 | 100 | 80 | Sl. Amaranth | 100 | 85 | 80 |
| Tr. Spiderwort | 100 | 100 | 100 | Tr. Spiderwort | 85 | 70 | 90 |
| Wld Pointsettia | 100 | 100 | 100 | Wld Pointsettia | 100 | 100 | 100 |
| W20 Soybean | 85 | 80 | 90 | W20 Soybean | 90 | 85 | 90 |
| W4-4 Soybean | 95 | 80 | 100 | W4-4 Soybean | 95 | 85 | 100 |
| Rate 70 g/ha | | | | Rate 35 g/ha | | | |
| Acanthospermum | 100 | 90 | 100 | Acanthospermum | 100 | 80 | 100 |
| Alexandergrass | 100 | 100 | 85 | Alexandergrass | 100 | 95 | 75 |
| Apple-of-Peru | 100 | 100 | 80 | Apple-of-Peru | 70 | 100 | 70 |
| Arrowleaf Sida | 65 | 75 | 100 | Arrowleaf Sida | 60 | 65 | 100 |
| B. Signalgrass | 90 | 90 | 70 | B. Signalgrass | 90 | 80 | 70 |
| Bl. Nightshade | 100 | 100 | 100 | Bl. Nightshade | 100 | 100 | 100 |
| Braz Sicklepod | 50 | 30 | 40 | Braz Sicklepod | 15 | 15 | 20 |
| Capim-Colch | 90 | 75 | 100 | Capim-Colch | 80 | 65 | 80 |
| Crist. Soybean | 100 | 90 | 80 | Crist. Soybean | 100 | 80 | 80 |
| Fl. Beggarweed | 100 | 80 | — | Fl. Beggarweed | 80 | 80 | — |
| H. Beggarticks | 75 | 70 | 80 | H. Beggarticks | 70 | 60 | 80 |
| Morningglory | 100 | 85 | 100 | Morningglory | 100 | 70 | 85 |
| Sl. Amaranth | 75 | 80 | 70 | Sl. Amaranth | 75 | 65 | 65 |
| Tr. Spiderwort | 80 | 65 | 85 | Tr. Spiderwort | 75 | 65 | 60 |

TABLE B-continued

| POSTEMERGENCE | COMPOUND 1 | 2 | 4 | POSTEMERGENCE | COMPOUND 1 | 2 | 4 |
|---|---|---|---|---|---|---|---|
| Wld Pointsettia | 100 | 100 | 100 | Wld Pointsettia | 100 | 100 | 85 |
| W20 Soybean | 90 | 85 | 85 | W20 Soybean | 90 | 85 | 85 |
| W4-4 Soybean | 90 | 85 | 90 | W4-4 Soybean | 90 | 85 | 90 |
| Rate 17 g/ha | | | | Rate 8 g/ha | | | |
| Acanthospermum | 100 | 70 | 85 | Acanthospermum | 90 | 70 | 80 |
| Alexandergrass | 100 | 90 | 70 | Alexandergrass | 85 | 80 | 60 |
| Apple-of-Peru | 70 | 100 | 60 | Apple-of-Peru | 65 | 100 | 40 |
| Arrowleaf Sida | 60 | 65 | 70 | Arrowleaf Sida | 50 | 65 | 50 |
| B. Signalgrass | 85 | 70 | 70 | B. Signalgrass | 80 | 60 | 65 |
| Bl. Nightshade | 70 | 85 | 100 | Bl. Nightshade | 70 | 85 | 80 |
| Braz Sicklepod | 10 | 15 | 15 | Braz Sicklepod | 0 | 10 | 10 |
| Capim-Colch | 70 | 40 | 55 | Capim-Colch | 55 | 25 | 25 |
| Crist. Soybean | 100 | 75 | 80 | Crist. Soybean | 80 | 75 | 55 |
| Fl. Beggarweed | 80 | 80 | 100 | Fl. Beggarweed | 80 | 70 | 100 |
| H. Beggarticks | 65 | 55 | 65 | H. Beggarticks | 55 | 50 | 60 |
| Morningglory | 80 | 65 | 75 | Morningglory | 70 | 65 | 55 |
| Sl. Amaranth | 65 | 65 | 55 | Sl. Amaranth | 60 | 60 | 50 |
| Tr. Spiderwort | 60 | 60 | 50 | Tr. Spiderwort | 40 | 40 | 35 |
| Wld Pointsettia | 70 | 85 | 75 | Wld Pointsettia | 70 | 65 | 50 |
| W20 Soybean | 85 | 75 | 85 | W20 Soybean | 75 | 70 | 65 |
| W4-4 Soybean | 85 | 75 | 85 | W4-4 Soybean | 85 | 65 | 65 |

Test C

Compounds evaluated in this test were formulated in a non-phytotoxic solvent mixture which included a surfactant and applied to the soil surface before plant seedlings emerged (preemergence application) and to plants that were grown for various periods of time before treatment (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include American black nightshade (*Solanum americanum*), arrowleaf sida (*Sida rhombifolia*), barnyardgrass (*Echinochloa crus-galli*), cocklebur (*Xanthium strumarium*), common lambsquarters (*Chenopodium album*), common ragweed (*Ambrosia artemisiifolia*), corn (*Zea mays*), cotton (*Gossypium hirsutum*), eastern black nightshade (*Solanum ptycanthum*), fall panicum (*Panicum dichotomiflorum*), field bindweed (*Convolvulus arvensis*), Florida beggarweed (*Desmodium purpureum*), giant foxtail (*Setaria faberii*), hairy beggarticks (*Bidens pilosa*), ivyleaf morningglory (*Ipomoea hederacea*), johnsongrass (*Sorghum halepense*), ladysthumb (*Polygonum persicaria*), large crabgrass (*Digitaria sanguinalis*), purple nutsedge (*Cyperus rotundus*), redroot pigweed (*Amaranthus retroflexus*), soybean (*Glycine max*), surinam grass (*Brachiaria decumbens*), velvetleaf (*Abutiloii theophrasti*) and wild poinsettia (*Euphorbia heterophylla*).

Treated plants and untreated controls were maintained in a greenhouse for approximately 14 to 21 days, after which all treated plants were compared to untreated controls and visually evaluated. Plant response ratings, summarized in Table C, were based upon a 0 to 100 scale where 0 was no effect and 100 was complete control. A dash response (-) means no test result.

TABLE C

| Rate 280 g/ha | COMPOUND 2 | 4 | Rate 280 g/ha | COMPOUND 2 | 4 |
|---|---|---|---|---|---|
| POSTEMERGENCE | | | PREEMERGENCE | | |
| Arrowleaw Sida | 70 | 75 | Arrowleaw Sida | 95 | 100 |
| Barnyardgrass | 100 | 100 | Barnyardgrass | 100 | 90 |
| Cocklebur | 100 | 100 | Cocklebur | 95 | 55 |
| Common Ragweed | 100 | 100 | Common Ragweed 100 | 100 | |
| Corn | 10 | 10 | Corn | 0 | 0 |
| Cotton | 100 | 100 | Cotton | 100 | 25 |
| Estrn Blknight | 100 | 100 | Estrn Blknight | — | — |
| Fall Panicum | 100 | 100 | Fall Panicum | 100 | 100 |
| Field Bindweed | 100 | 90 | Field Bindweed | 90 | 90 |
| Fl Beggarweed | 100 | 100 | Fl Beggarweed | 100 | 100 |
| Giant Foxtail | 100 | 100 | Giant Foxtail | 100 | 100 |
| Hairy Beggartic | 75 | 70 | Hairy Beggartic | 100 | 60 |
| Ivyleaw Mrnglry | 100 | 100 | Ivyleaw Mrnglry | 55 | 65 |
| Johnsongrass | 95 | 80 | Johnsongrass | 75 | 55 |
| Ladysthumb | 100 | 100 | Ladysthumb | 100 | 100 |

TABLE C-continued

| | | | | | | | |
|---|---|---|---|---|---|---|---|
| Lambsquarters | 100 | 100 | | Lambsquarters | — | — | |
| Large Crabgrass | 100 | 100 | | Large Crabgrass | 100 | 100 | |
| Purple Nutsedge | 90 | 75 | | Purple Nutsedge | 80 | 60 | |
| Redroot Pigweed | 100 | — | | Redroot Pigweed | 100 | 100 | |
| Soybean | 100 | 100 | | Soybean | 70 | 20 | |
| Surinam Grass | 100 | 100 | | Surinam Grass | 100 | 90 | |
| Velvetleaf | 100 | 100 | | Velvetleaf | 100 | 100 | |
| Wild Poinsettia | 100 | 100 | | Wild Poinsettia | 95 | 90 | |

| | COMPOUND | | | | | | COMPOUND | | |
|---|---|---|---|---|---|---|---|---|---|
| Rate 140 g/ha | 1 | 2 | 4 | 5 | 6 | Rate 140 g/ha | 1 | 2 | 4 |

POSTEMERGENCE

| | | | | | | | | | |
|---|---|---|---|---|---|---|---|---|---|
| Arrowleaw Sida | 100 | 50 | 55 | 60 | 90 | Arrowleaw Sida | 100 | 40 | 45 |
| Barnyardgrass | 100 | 100 | 95 | 100 | 100 | Barnyardgrass | 100 | 100 | 25 |
| Cocklebur | 100 | 100 | 100 | 95 | 100 | Cocklebur | 90 | 75 | 40 |
| Common Ragweed | 100 | 100 | 100 | 100 | 100 | Common Ragweed | 100 | 100 | 95 |
| Corn | 0 | 0 | 0 | 45 | 5 | Corn | 0 | 0 | 0 |
| Cotton | 100 | 100 | 90 | 95 | 100 | Cotton | 45 | 65 | 10 |
| Estrn Blknight | 100 | 100 | 100 | 100 | 100 | Estrn Blknight | 100 | 100 | — |
| Fall Panicum | 100 | 95 | 95 | 100 | 100 | Fall Panicum | 100 | 100 | 100 |
| Field Bindweed | 100 | 95 | 85 | 100 | 90 | Field Bindweed | 60 | 50 | 55 |
| Fl Beggarweed | 100 | 100 | 100 | 100 | 100 | Fl Beggarweed | 100 | 100 | 100 |
| Giant Foxtail | 100 | 100 | 95 | 100 | 100 | Giant Foxtail | 100 | 95 | 70 |
| Hairy Beggartic | 85 | 65 | 65 | 95 | 100 | Hairy Beggartic | 10 | 90 | 35 |
| Ivyleaw Mrnglry | 80 | 100 | 95 | 100 | 100 | Ivyleaw Mrnglry | 70 | 30 | 25 |
| Johnsongrass | 100 | 85 | 70 | 100 | 100 | Johnsongrass | 90 | 45 | 15 |
| Ladysthumb | 100 | 100 | 100 | 100 | 100 | Ladysthumb | 100 | 100 | 100 |
| Lambsquarters | 100 | 100 | 100 | 95 | 95 | Lambsquarters | 95 | 100 | — |
| Large Crabgrass | 90 | 95 | 95 | 100 | 100 | Large Crabgrass | 100 | 100 | 90 |
| Purple Nutsedge | 85 | 80 | 45 | 20 | 100 | Purple Nutsedge | 10 | 70 | 25 |
| Redroot Pigweed | 100 | 100 | — | 100 | 90 | Redroot Pigweed | 100 | 100 | 85 |
| Soybean | 100 | 100 | 100 | 95 | 90 | Soybean | 60 | 20 | 0 |
| Surinam Grass | 100 | 90 | 90 | 90 | 100 | Surinam Grass | 100 | 80 | 65 |
| Velvetleaf | 100 | 100 | 100 | 100 | 100 | Velvetleaf | 100 | 100 | 100 |
| Wild Poinsettia | 100 | 100 | 100 | 100 | 100 | Wild Poinsettia | 100 | 45 | 30 |

| | COMPOUND | | | | | | |
|---|---|---|---|---|---|---|---|
| Rate 70 g/ha | 1 | 2 | 3 | 4 | 5 | 6 | 16 | 31 |

POSTEMERGENCE

| | | | | | | | | |
|---|---|---|---|---|---|---|---|---|
| Arrowleaw Sida | 100 | 50 | 85 | 70 | 60 | 85 | 65 | — |
| Barnyardgrass | 100 | 95 | 95 | 95 | 95 | 100 | 100 | 95 |
| Cocklebur | 95 | 100 | 85 | 95 | 95 | 95 | 95 | 60 |
| Common Ragweed | 100 | 100 | 100 | 100 | 100 | 100 | 100 | 95 |
| Corn | 0 | 10 | 10 | 0 | 30 | 5 | 60 | 0 |
| Cotton | 100 | 95 | 85 | 90 | 95 | 100 | 95 | 95 |
| Estrn Blknight | 100 | 100 | 100 | 95 | 100 | 100 | 100 | 100 |
| Fall Panicum | 100 | 95 | 80 | 100 | 100 | 100 | 95 | 95 |
| Field Bindweed | 90 | 100 | 85 | 65 | 80 | 60 | 60 | 50 |
| Fl Beggarweed | 100 | 100 | 100 | 100 | 100 | 100 | 100 | 95 |
| Giant Foxtail | 95 | 95 | 50 | 80 | 100 | 100 | 95 | 90 |
| Hairy Beggartic | 70 | 65 | 75 | 60 | 85 | 85 | 80 | 90 |
| Ivyleaw Mrnglry | 80 | 100 | 90 | 95 | 95 | 100 | 15 | 80 |
| Johnsongrass | 95 | 100 | 25 | 60 | 95 | 100 | 65 | 95 |
| Ladysthumb | 100 | 100 | 95 | 100 | 100 | 100 | 100 | 100 |
| Lambsguarters | 100 | 100 | 100 | 100 | 95 | 95 | 100 | 100 |
| Large Crabgrass | 90 | 95 | 80 | 80 | 100 | 100 | 95 | 90 |
| Purple Nutsedge | 80 | 80 | 0 | 25 | 20 | 95 | 95 | 75 |
| Redroot Pigweed | 100 | 100 | 100 | 95 | 100 | 90 | 100 | 100 |
| Soybean | 100 | 100 | 95 | 95 | 90 | 85 | 60 | 80 |
| Surinam Grass | 95 | 95 | 80 | 65 | 90 | 100 | 90 | 90 |
| Velvetleaf | 100 | 100 | 100 | 90 | 100 | 100 | 100 | 100 |
| Wild Poinsettia | 100 | 95 | 100 | 100 | 85 | 90 | 65 | 80 |

| | COMPOUND | | | |
|---|---|---|---|---|
| Rate 70 g/ha | 1 | 2 | 3 | 4 |

POSTEMERGENCE

| | | | | |
|---|---|---|---|---|
| Arrowleaw Sida | 80 | 50 | 0 | 15 |
| Barnyardgrass | 100 | 95 | 35 | 15 |
| Cocklebur | 90 | 10 | 0 | 0 |
| Common Ragweed | 95 | 100 | 95 | 55 |

TABLE C-continued

| | | | | |
|---|---|---|---|---|
| Corn | 0 | 0 | 0 | 0 |
| Cotton | 20 | 0 | 10 | 10 |
| Estrn Blknight | 100 | 100 | — | 100 |
| Fall Panicum | 100 | 100 | 75 | 85 |
| Field Bindweed | 50 | 20 | 10 | 0 |
| Fl Beggarweed | 95 | 85 | — | 100 |
| Giant Foxtail | 100 | 35 | 10 | 20 |
| Hairy Beggartic | 0 | 25 | 10 | 20 |
| Ivyleaw Mrnglry | 20 | 0 | 0 | 0 |
| Johnsongrass | 40 | 25 | 25 | 10 |
| Ladysthumb | 90 | 65 | — | 50 |
| Lambsquarters | 95 | 95 | — | 95 |
| Large Crabgrass | 100 | 100 | 100 | 100 |
| Purple Nutsedge | 5 | 60 | 0 | 0 |
| Redroot Pigweed | 90 | 80 | 55 | 35 |
| Soybean | 55 | 15 | 0 | 0 |
| Surinam Grass | 100 | 70 | 60 | 10 |
| Velvetleaf | 100 | 100 | 100 | 95 |
| Wild Poinsettia | 80 | 35 | 20 | 15 |

| | COMPOUND | | | | | | | | | |
|---|---|---|---|---|---|---|---|---|---|---|
| Rate 35 g/ha | 1 | 2 | 3 | 4 | 5 | 6 | 16 | 18 | 30 | 31 |
| POSTEMERGENCE | | | | | | | | | | |
| Arrowleaw Sida | 80 | 90 | 70 | 45 | 60 | 50 | 29 | 70 | 70 | 65 |
| Barnyardgrass | 100 | 100 | 95 | 90 | 85 | 100 | 95 | 90 | 100 | 95 |
| Cocklebur | 90 | 100 | 80 | 95 | 90 | 95 | 95 | 80 | 95 | 60 |
| Common Ragweed | 100 | 100 | 100 | 90 | 100 | 100 | 100 | 100 | 95 | 95 |
| Corn | 0 | 20 | 15 | 0 | 20 | 0 | 20 | 35 | 5 | 0 |
| Cotton | 100 | 100 | 75 | 80 | 85 | 100 | 95 | 90 | 95 | 90 |
| Estrn Blknight | 100 | 100 | 95 | 85 | 100 | 95 | 100 | 85 | 100 | 100 |
| Fall Panicum | 90 | 100 | 75 | 95 | 100 | 100 | 100 | 90 | 100 | 95 |
| Field Bindweed | 90 | 80 | 80 | 50 | 80 | 60 | 50 | 65 | 5 | 50 |
| Fl Beggarweed | 90 | 100 | 95 | 100 | 90 | 50 | 95 | 100 | 100 | 100 |
| Giant Foxtail | 80 | 95 | 40 | 65 | 85 | 100 | 100 | 85 | 100 | 90 |
| Hairy Beggartic | 70 | 70 | 60 | 40 | 60 | 80 | 70 | 70 | 70 | 80 |
| Ivyleaw Mrnglry | 70 | 95 | 80 | 95 | 90 | 80 | 40 | 60 | 60 | 65 |
| Johnsongrass | 80 | 90 | 20 | 60 | 70 | 100 | 20 | 70 | 100 | 85 |
| Ladysthumb | 100 | 100 | 95 | 90 | 100 | 100 | 100 | 100 | 100 | 100 |
| Lambsquarters | 95 | 100 | 95 | 100 | 95 | 95 | 90 | 80 | 100 | 95 |
| Large Crabgrass | 85 | 95 | 75 | 70 | 85 | 100 | 100 | 100 | 100 | 90 |
| Purple Nutsedge | 30 | 85 | 0 | 25 | 20 | 30 | 90 | 75 | 75 | — |
| Redroot Pigweed | 95 | 100 | 95 | 90 | 80 | 90 | 95 | 80 | 100 | 100 |
| Soybean | 85 | 100 | 95 | 95 | 95 | 80 | 40 | 65 | 95 | 75 |
| Surinam Grass | 90 | 95 | 70 | 65 | 80 | 95 | 90 | 75 | 20 | 85 |
| Velvetleaf | 100 | 100 | 95 | 90 | 100 | 100 | 100 | 100 | 100 | 100 |
| Wild Poinsettia | 90 | 100 | 95 | 90 | 85 | 85 | 20 | 65 | 80 | 75 |

| | COMPOUND | | | |
|---|---|---|---|---|
| Rate 35 g/ha | 1 | 2 | 3 | 4 |
| PREEMERGENCE | | | | |
| Arrowleaw Sida | 80 | 25 | 0 | 0 |
| Barnyardgrass | 20 | 15 | 10 | 0 |
| Cocklebur | 20 | 55 | 0 | 0 |
| Common Ragweed | 90 | 75 | 35 | 20 |
| Corn | 0 | 0 | 0 | 0 |
| Cotton | 5 | 100 | 0 | 0 |
| Estrn Blknight | 100 | 95 | — | 95 |
| Fall Panicum | 100 | 100 | 15 | 75 |
| Field Bindweed | 50 | 30 | 0 | 0 |
| Fl Beggarweed | — | 50 | 25 | 15 |
| Giant Foxtail | 100 | 15 | 0 | 0 |
| Hairy Beggartic | 0 | 35 | 0 | 0 |
| Ivyleaw Mrnglry | 0 | 0 | 0 | 0 |
| Johnsongrass | 10 | 0 | 0 | 0 |
| Ladysthumb | — | 30 | — | 30 |
| Lambsquarters | 0 | 95 | — | 75 |
| Large Crabgrass | — | 95 | 70 | 35 |
| Purple Nutsedge | 0 | 25 | 0 | 0 |
| Redroot Pigweed | 50 | 70 | — | 15 |
| Soybean | 40 | 0 | 0 | 0 |
| Surinam Grass | 95 | 45 | 10 | 0 |

TABLE C-continued

| | | | | |
|---|---|---|---|---|
| Velvetleaf | 100 | 100 | 100 | 70 |
| Wild Poinsettia | 50 | 25 | 0 | 0 |

| | COMPOUND | | | | | | | | | |
|---|---|---|---|---|---|---|---|---|---|---|
| Rate 17 g/ha | 1 | 2 | 3 | 4 | 5 | 6 | 16 | 18 | 30 | 31 |
| POSTEMERGENCE | | | | | | | | | | |
| Arrowleaw Sida | 50 | 60 | 65 | 35 | 10 | 50 | 20 | 70 | 20 | 80 |
| Barnyardgrass | 100 | 95 | 90 | 90 | 70 | 100 | 95 | 90 | 100 | 90 |
| Cocklebur | 90 | 100 | 70 | 90 | 90 | 90 | 85 | 85 | 85 | 50 |
| Common Ragweed | 100 | 100 | 100 | 95 | 85 | 90 | 100 | 80 | 95 | 90 |
| Corn | 0 | 0 | 0 | 0 | 5 | 0 | 20 | 25 | 5 | 0 |
| Cotton | 100 | 100 | 70 | 70 | 60 | 90 | 90 | 80 | 90 | 75 |
| Estrn Blknight | 95 | 100 | 95 | 80 | 95 | 90 | 100 | 80 | 100 | 100 |
| Fall Panicum | 70 | 85 | 45 | 40 | 85 | 100 | 100 | 85 | 95 | 85 |
| Field Bindweed | 80 | 65 | 65 | 45 | 80 | 60 | 20 | 55 | 5 | 25 |
| Fl Beggarweed | 85 | 100 | 75 | 60 | 85 | 50 | 80 | 90 | 100 | 100 |
| Giant Foxtail | 65 | 80 | 25 | 45 | 80 | 90 | 100 | 80 | 95 | 80 |
| Hairy Beggartia | 50 | 65 | 40 | 30 | 60 | 10 | 30 | 60 | 60 | 65 |
| Ivyleaw Mrnglry | 70 | 95 | 60 | 80 | 80 | 80 | 40 | 45 | 60 | 55 |
| Johnsongrass | 50 | 80 | 15 | 15 | 70 | 80 | 5 | 60 | 95 | 80 |
| Ladysthumb | 90 | 55 | 85 | 75 | 100 | 95 | 100 | 90 | 100 | 100 |
| Lambsquarters | 80 | 100 | 80 | 85 | 95 | 80 | 90 | 80 | 100 | 100 |
| Large Crabgrass | 85 | 85 | 45 | 55 | 60 | 100 | 90 | 90 | 100 | 85 |
| Purple Nutsedge | 5 | 60 | 0 | 15 | 5 | 30 | 50 | 45 | 20 | — |
| Redroot Pigweed | 80 | 95 | 80 | 90 | 75 | 80 | 90 | 80 | 100 | 95 |
| Soybean | 85 | 100 | 85 | 85 | 90 | 70 | 35 | 35 | 85 | 70 |
| Surinam Grass | 90 | 80 | 45 | 60 | 60 | 80 | 80 | 70 | 5 | 70 |
| Velvetleaf | 100 | 100 | 95 | 95 | 100 | 100 | 100 | 100 | 100 | 95 |
| Wild Poinsettia | 70 | 95 | 85 | 90 | 80 | 80 | 5 | 50 | 60 | 65 |

| | COMPOUND | | | |
|---|---|---|---|---|
| Rate 17 g/ha | 1 | 2 | 3 | 4 |
| PREEMERGENCE | | | | |
| Arrowleaw Sida | 50 | 15 | 0 | 0 |
| Barnyardgrass | 10 | 10 | 0 | 0 |
| Cocklebur | 20 | 20 | 0 | 0 |
| Common Ragweed | 20 | 55 | 0 | 0 |
| Corn | 0 | 0 | 0 | 0 |
| Cotton | 0 | 15 | 0 | 0 |
| Estrn Blknight | 0 | 60 | — | 20 |
| Fall Panicum | 50 | 65 | 0 | 15 |
| Field Bindweed | 20 | 0 | 0 | 0 |
| Fl Beggarweed | 0 | 15 | 0 | 0 |
| Giant Foxtail | 0 | 0 | 0 | 0 |
| Hairy Beggartic | 0 | 15 | 0 | 0 |
| Ivyleaw Mrnglry | 0 | 0 | 0 | 0 |
| Johnsongrass | 5 | 0 | 0 | 0 |
| Ladysthumb | — | 30 | — | 0 |
| Lambsquarters | 0 | 45 | — | 35 |
| Large Crabgrass | 100 | 15 | 35 | 0 |
| Purple Nutsedge | 0 | 0 | 0 | 0 |
| Redroot Pigweed | 0 | 20 | — | 10 |
| Soybean | 0 | 0 | 0 | 0 |
| Surinam Grass | 10 | 0 | 0 | 0 |
| Velvetleaf | 100 | 35 | 35 | 35 |
| Wild Poinsettia | 45 | 10 | 0 | 0 |

| | COMPOUND | | | | | | | | | |
|---|---|---|---|---|---|---|---|---|---|---|
| Rate 8 g/ha | 1 | 2 | 3 | 4 | 5 | 6 | 16 | 18 | 30 | 31 |
| POSTEMERGENCE | | | | | | | | | | |
| Arrowleaw Sida | 50 | 45 | 55 | 15 | 5 | 10 | 10 | 65 | — | 35 |
| Barnyardgrass | 100 | 90 | 85 | 85 | 65 | 100 | 90 | 90 | 95 | 90 |
| Cocklebur | 80 | 100 | 65 | 50 | 80 | 85 | 85 | 75 | 80 | 20 |
| Common Ragweed | 95 | 95 | 95 | 75 | 50 | 90 | 100 | 80 | 80 | 90 |
| Corn | 0 | 10 | 0 | 0 | 0 | 0 | 5 | 15 | 0 | 0 |
| Cotton | 100 | 95 | 30 | 35 | 50 | 80 | 80 | 70 | 70 | 70 |
| Estrn Blknight | 95 | 100 | 90 | 75 | 85 | 90 | 100 | 75 | 100 | 100 |
| Fall Panicum | 50 | 80 | 25 | 25 | 60 | 70 | 95 | 80 | 90 | 85 |
| Field Bindweed | 70 | 35 | 30 | 35 | 10 | 60 | 10 | 50 | 5 | 10 |
| Fl Beggarweed | 70 | 100 | 65 | 60 | 80 | 50 | 80 | 85 | 80 | 85 |

TABLE C-continued

| | | | | | | | | | | |
|---|---|---|---|---|---|---|---|---|---|---|
| Giant Foxtail | 60 | 70 | 10 | 20 | 70 | 80 | 70 | 75 | 90 | 80 |
| Hairy Beggartic | 50 | 50 | 30 | 20 | 55 | 0 | 30 | 55 | 40 | 50 |
| Ivyleaw Mrnglry | 70 | 70 | 45 | 80 | 70 | 65 | 25 | 35 | 5 | 10 |
| Johnsongrass | 30 | 50 | 10 | 20 | 60 | 55 | 5 | 55 | 65 | 40 |
| Ladysthumb | 90 | 40 | 75 | 65 | 10 | 90 | 100 | 75 | 70 | 10 |
| Lambsquarters | 70 | 95 | 75 | 75 | 90 | 40 | 90 | 75 | 80 | 65 |
| Large Crabgrass | 80 | 80 | 35 | 50 | 60 | 85 | 95 | 85 | 90 | 75 |
| Purple Nutsedge | 0 | 0 | 0 | 5 | 0 | 10 | 5 | 25 | 15 | 20 |
| Redroot Pigweed | 85 | 95 | 75 | 65 | 70 | 70 | 80 | 80 | 80 | 85 |
| Soybean | 80 | 100 | 75 | 60 | 70 | 60 | 20 | 20 | 80 | 45 |
| Surinam Grass | 80 | 65 | 25 | 40 | 40 | 45 | 70 | 65 | 0 | 20 |
| Velvetleaf | 100 | 100 | 85 | 75 | 100 | 100 | 85 | 85 | 95 | 95 |
| Wild Poinsettia | 50 | 85 | 70 | 60 | 70 | 70 | 0 | 30 | 15 | 50 |

| | COMPOUND | | | |
|---|---|---|---|---|
| Rate 8 g/ha | 1 | 2 | 3 | 4 |
| PREEMERGENCE | | | | |
| Arrowleaw Sida | 50 | 0 | 0 | 0 |
| Barnyardgrass | 0 | 0 | 0 | 0 |
| Cocklebur | 0 | 10 | 0 | 0 |
| Common Ragweed | 0 | 50 | 0 | 0 |
| Corn | 0 | 0 | 0 | 0 |
| Cotton | 0 | 0 | 0 | 0 |
| Estrn Blknight | 0 | 45 | — | — |
| Fall Panicum | 0 | 20 | 0 | 0 |
| Field Bindweed | 0 | 0 | 0 | 0 |
| Fl Beggarweed | 0 | 0 | 0 | 0 |
| Giant Foxtail | 0 | 0 | 0 | 0 |
| Hairy Beggartic | 0 | 0 | 0 | 0 |
| Ivyleaw Mrnglry | 0 | 0 | 0 | 0 |
| Johnsongrass | 0 | 0 | 0 | 0 |
| Ladysthumb | 0 | 0 | — | 0 |
| Lambsquarters | 0 | 30 | — | 10 |
| Large Crabgrass | 80 | 0 | 0 | 0 |
| Purple Nutsedge | 0 | 0 | 0 | 0 |
| Redroot Pigweed | 0 | 0 | — | 0 |
| Soybean | 0 | 0 | 0 | 0 |
| Surinam Grass | 0 | 0 | 0 | 0 |
| Velvetleaf | 70 | 15 | 10 | 20 |
| Wild Poinsettia | 0 | 10 | 0 | 0 |

| | COMPOUND | | | | | | |
|---|---|---|---|---|---|---|---|
| Rate 4 g/ha | 2 | 3 | 4 | 16 | 18 | 30 | 31 |
| POSTEMERGENCE | | | | | | | |
| Arrowleaw Sida | 35 | 45 | 15 | 5 | 55 | 5 | 35 |
| Barnyardgrass | 90 | 30 | 55 | 90 | 85 | 95 | 85 |
| Cocklebur | 95 | 30 | 45 | 70 | 65 | 70 | 10 |
| Common Ragweed | 90 | 85 | 65 | 95 | 55 | 0 | 60 |
| Corn | 0 | 0 | 0 | 0 | 10 | 0 | 0 |
| Cotton | 60 | 15 | 25 | 70 | 60 | 65 | 35 |
| Estrn Blknight | 80 | 75 | 65 | 100 | 70 | 95 | 100 |
| Fall Panicum | 60 | 10 | 20 | 90 | 70 | 80 | 40 |
| Field Bindweed | 25 | 20 | 10 | 5 | 30 | 0 | 10 |
| Fl Beggarweed | 100 | 50 | 25 | 75 | 70 | 75 | 100 |
| Giant Foxtail | 55 | 0 | 15 | 65 | 65 | 70 | 50 |
| Hairy Beggartic | 25 | 20 | 10 | 10 | 50 | 30 | 25 |
| Ivyleaw Mrnglry | 60 | 25 | 70 | 0 | 20 | 5 | 0 |
| Johnsongrass | 35 | 0 | 0 | 0 | 50 | 10 | 10 |
| Ladysthumb | 25 | 60 | 25 | 100 | 45 | 70 | 10 |
| Lambsquarters | 85 | 70 | 60 | 75 | 70 | 40 | 50 |
| Large Crabgrass | 55 | 25 | 20 | 90 | 75 | 85 | 65 |
| Purple Nutsedge | 0 | 0 | 0 | 5 | 20 | 10 | 50 |
| Redroot Pigweed | 75 | 70 | 60 | 80 | 75 | 60 | 65 |
| Soybean | 90 | 60 | 60 | 15 | 15 | 70 | 15 |
| Surinam Grass | 55 | 15 | 20 | 40 | 55 | 0 | 20 |
| Velvetleaf | 100 | 60 | 60 | 70 | 75 | 90 | 75 |
| Wild Poinsettia | 75 | 45 | 30 | 0 | 20 | 15 | 40 |

TABLE C-continued

| Rate 4 g/ha | COMPOUND | | | Rate 2 g/ha | COMPOUND | |
|---|---|---|---|---|---|---|
| | 2 | 3 | 4 | | 2 | 4 |
| PREEMERGENCE | | | | POSTEMERGENCE | | |
| Arrowleaw Sida | 0 | 0 | 0 | Arrowleaw Sida | 25 | 10 |
| Barnyardgrass | 0 | 0 | 0 | Barnyardgrass | 75 | 25 |
| Cocklebur | 0 | 0 | 0 | Cocklebur | 80 | 0 |
| Common Ragweed | 25 | 0 | 0 | Common Ragweed | 85 | 60 |
| Corn | 0 | 0 | 0 | Corn | 0 | 0 |
| Cotton | 0 | 0 | 0 | Cotton | 25 | 15 |
| Estrn Blknight | 0 | — | 0 | Estrn Blknight | 75 | 60 |
| Fall Panicun | 0 | 0 | 0 | Fall panicum | 15 | 15 |
| Field Bindweed | — | 0 | 0 | Field Bindweed | 20 | 5 |
| Fl Beggarweed | 0 | 0 | 0 | Fl Beggarweed | 100 | 50 |
| Giant Foxtail | 0 | 0 | 0 | Giant Foxtail | 15 | 0 |
| Hairy Beggartic | 0 | 0 | 0 | Hairy Beggartic | 15 | 10 |
| Ivyleaw Mrnglry | 0 | 0 | 0 | Ivyleaw Mrnglry | 40 | 10 |
| Johnsongrass | 0 | 0 | 0 | Johnsongrass | 0 | 0 |
| Ladysthumb | 0 | — | 0 | Ladysthumb | 10 | 10 |
| Lambsquarters | 0 | — | 0 | Lasbsquarters | 85 | 60 |
| Large Crabgrass | 0 | 0 | 0 | Large Crabgrass | 45 | 10 |
| Purple Nutsedge | 0 | 0 | 0 | Purple Nutsedge | 0 | 0 |
| Redroot Pigweed | 0 | 25 | 0 | Redroot Pigweed | 70 | 45 |
| Soybean | 0 | 0 | 0 | Soybean | 70 | 20 |
| Surinam Grass | 0 | 0 | 0 | Surinarn Grass | 30 | 0 |
| Velvetleaf | 10 | 0 | 0 | Velvetleaf | 95 | 15 |
| Wild Poinsettia | 0 | 0 | 0 | Wild Poinsettia | 50 | 20 |

| Rate 2 g/ha | COMPOUND | |
|---|---|---|
| | 2 | 4 |
| PREEMERGENCE | | |
| Arrowleaw Sida | 0 | 0 |
| Barnyardgrass | 0 | 0 |
| Cocklebur | 0 | 0 |
| Common Ragweed | 0 | 0 |
| Corn | 0 | 0 |
| Cotton | 0 | 0 |
| Estrn Blknight | 0 | 0 |
| Fall Panicum | 0 | 0 |
| Field Bindweed | 0 | 0 |
| Fl Beggarweed | 0 | 0 |
| Giant Foxtail | 0 | 0 |
| Hairy Beggartic | 0 | 0 |
| Ivyleaw Mrnglry | 0 | 0 |
| Johnsongrass | 0 | 0 |
| Ladysthumb | 0 | — |
| Lambsquarters | 0 | 0 |
| Large Crabgrass | 0 | 0 |
| Purple Nutsedge | 0 | 0 |
| Redroot Pigweed | 0 | 0 |
| Soybean | 0 | 0 |
| Surinam Grass | 0 | 0 |
| Velvetleaf | 0 | 0 |
| Wild Poinsettia | 0 | 0 |

Test D

Seeds of barnyardgrass (*Echinochloa crus-galli*), bindweed (*Concolculus arvensis*), black nightshade (*Solanum ptycanthum* dunal), cassia (*Cassia obtusifolia*), cocklebur (*Xanthium strumarium*), common ragweed (*Ambrosia artemisiifolia*), corn (*Zea mays*), cotton (*Gossypium hirsutam*), crabgrass (Digitaria spp.), fall panicum (*Panicum dichotomi-florum*), giant foxtail (*Setaria faberii*), green foxtail (*Setaria viridis*), jimsonweed (*Datura stramonium*), johnsongrass (*Sorghum halepense*), lambsquarter (*Chenopodium album*), morningglory (Ipomoea spp.), pigweed (*Amaranthus retroflexus*), prickly sida (*Sida spinosa*), shattercane (*Sorghum vulgare*), signalgrass (*Brachiaria platyphylla*), smartweed (*Polygonum pensylvanicum*), soybean (*Glycine max*), sunflower (*Helianthus annuus*), velvetleaf (*Abutilon theophrasti*), wild proso (*Pancium miliaceum*), woolly cupgrass (*Eriochloa villosa*), yellow foxtail (*Setaria lutescens*) and purple nutsedge (*Cyperus rotundus*) tubers were planted into a sandy loam or clay loam soil. These crops and weeds were grown in the greenhouse until the plants ranged in height from two to eighteen cm (one to four leaf stage), then treated postemergence with the test chemicals formulated in a non-phytotoxic solvent mixture which included a surfactant. Pots receiving preemergence treatments were planted immediately prior to test chemical application. Pots treated in this fashion were placed in the greenhouse and maintained according to routine greenhouse procedures.

Treated plants and untreated controls were maintained in the greenhouse approximately 14–21 days after application of the test compound. Visual evaluations of plant injury responses were then recorded. Plant response ratings, summarized in Table D, are reported on a 0 to 100 scale where 0 is no effect and 100 is complete control.

TABLE D

| POSTEMERGENCE | Rate 280 g/ha COMPOUND | | | Rate 140 g/ha COMPOUND | | |
|---|---|---|---|---|---|---|
| | 1 | 2 | 4 | 1 | 2 | 4 |
| Barnyardgrass | 100 | 100 | 100 | 100 | 100 | 100 |
| Bindweed | 95 | 95 | 100 | 95 | 100 | 100 |
| Blk Nightshade | 100 | 100 | 100 | 100 | 100 | 100 |
| Cassia | 60 | 20 | 10 | 50 | 5 | 10 |
| Cocklebur | 100 | 100 | 100 | 100 | 100 | 100 |
| Corn | 10 | 35 | 20 | 5 | 30 | 20 |
| Cotton | 90 | 90 | 100 | 90 | 100 | 100 |
| Crabgrass | 95 | 95 | 100 | 95 | 100 | 100 |
| Fall Panicum | 100 | 95 | 100 | 95 | 100 | 100 |
| Giant Foxtail | 95 | 95 | 100 | 95 | 100 | 100 |
| Green Foxtail | 95 | 95 | 100 | 95 | 100 | 100 |
| Jimsonweed | 100 | 100 | 100 | 100 | 100 | 100 |
| Johnson Grass | 95 | 95 | 100 | 95 | 100 | 100 |
| Lambsquarter | 95 | 95 | 100 | 95 | 100 | 100 |
| Morningglory | 100 | 100 | 100 | 100 | 90 | 100 |
| Nutsedge | 95 | 95 | 80 | 95 | 100 | 60 |
| Pigweed | 100 | 95 | 100 | 100 | 100 | 90 |
| Prickly Sida | 80 | 50 | 80 | 80 | 50 | 50 |
| Ragweed | 100 | 100 | 100 | 100 | 100 | 100 |
| Shattercane | 100 | 100 | 100 | 100 | 100 | 100 |
| Signalgrass | 95 | 100 | 100 | 95 | 100 | 100 |
| Smartweed | 100 | 100 | 100 | 100 | 100 | 100 |
| Soybean | 90 | 90 | 100 | 90 | 100 | 100 |
| Sunflower | 100 | 100 | 100 | 100 | 100 | 100 |
| Velvetleaf | 100 | 100 | 100 | 100 | 100 | 100 |
| Wild Proso | 95 | 95 | 100 | 95 | 100 | 100 |
| Woolly cupgrass | 95 | 95 | 80 | 95 | 100 | 80 |
| Yellow Foxtail | 95 | 95 | 100 | 95 | 100 | 100 |

| POST-EMERGENCE | Rate 70 g/ha COMPOUND | | | | Rate 35 g/ha COMPOUND | | | |
|---|---|---|---|---|---|---|---|---|
| | 1 | 2 | 4 | 28 | 1 | 2 | 4 | 28 |
| Barnyardgrass | 100 | 100 | 100 | 90 | 95 | 100 | 100 | 60 |
| Bindweed | 90 | 100 | 100 | 60 | 90 | 95 | 90 | 50 |
| Blk Nightshade | 100 | 100 | 100 | 100 | 100 | 100 | 100 | 90 |
| Cassia | 5 | 5 | 5 | 0 | 5 | 0 | 5 | 0 |
| Cocklebur | 100 | 100 | 100 | 50 | 100 | 100 | 95 | 40 |
| Corn | 5 | 50 | 15 | 0 | 0 | 30 | 15 | 0 |
| Cotton | 90 | 100 | 100 | 50 | 90 | 100 | 100 | 50 |
| Crabgrass | 95 | 100 | 100 | 70 | 90 | 90 | 100 | 50 |
| Fall Panicum | 95 | 100 | 100 | 20 | 95 | 100 | 80 | 5 |
| Giant Foxtail | 95 | 100 | 95 | 0 | 90 | 100 | 85 | 0 |
| Green Foxtail | 95 | 100 | 100 | 0 | 95 | 100 | 90 | 0 |
| Jimsonweed | 100 | 100 | 100 | 100 | 100 | 100 | 100 | 95 |
| Johnson Grass | 90 | 100 | 80 | 10 | 90 | 100 | 80 | 0 |
| Lambsquarter | 90 | 100 | 100 | 100 | 90 | 100 | 90 | 100 |
| Morningglory | 100 | 100 | 100 | 90 | 100 | 100 | 90 | 60 |
| Nutsedge | 95 | 100 | 30 | 10 | 90 | 90 | 10 | 5 |
| Pigweed | 100 | 100 | 80 | 60 | 95 | 100 | 70 | 60 |
| Prickly Sida | 50 | 60 | 20 | 0 | 10 | 50 | 5 | 0 |
| Ragweed | 100 | 100 | 100 | 40 | 100 | 100 | 100 | 40 |
| Shattercane | 100 | 100 | 100 | 0 | 100 | 100 | 100 | 0 |
| Signalgrass | 95 | 100 | 100 | — | 95 | 100 | 60 | — |
| Smartweed | 100 | 100 | 100 | 90 | 100 | 100 | 100 | 60 |
| Soybean | 90 | 100 | 95 | 70 | 90 | 100 | 95 | 70 |
| Sunflower | 100 | 100 | 100 | 30 | 100 | 100 | 100 | 30 |
| Velvetleaf | 100 | 100 | 100 | 90 | 100 | 100 | 100 | 85 |
| Wild Proso | 95 | 100 | 90 | 20 | 95 | 100 | 80 | 5 |
| Woolly cupgrass | 90 | 90 | 70 | 5 | 90 | 80 | 70 | 0 |
| Yellow Foxtail | 95 | 100 | 100 | 0 | 95 | 100 | 50 | 0 |

TABLE D-continued

| POST-EMERGENCE | Rate 17 g/ha COMPOUND | | | | Rate 8 g/ha COMPOUND | | | |
|---|---|---|---|---|---|---|---|---|
| | 1 | 2 | 4 | 28 | 1 | 2 | 4 | 28 |
| Barnyardgrass | 95 | 100 | 100 | 60 | 90 | 100 | 100 | 5 |
| Bindweed | 90 | 90 | 80 | 50 | 85 | 90 | 20 | 40 |
| Blk Nightshade | 100 | 100 | 80 | 70 | 100 | 100 | 70 | 70 |
| Cassia | 0 | 0 | 0 | 0 | 0 | 0 | 0 | 0 |
| Cocklebur | 100 | 100 | 80 | 30 | 100 | 100 | 60 | 0 |
| Corn | 0 | 5 | 0 | 0 | 0 | 5 | 0 | 0 |
| Cotton | 90 | 100 | 80 | 50 | 90 | 100 | 50 | 35 |
| Crabgrass | 90 | 90 | 80 | 5 | 80 | 80 | 60 | 0 |
| Fall Panicum | 95 | 90 | 70 | 0 | 80 | 80 | 30 | 0 |
| Giant Foxtail | 90 | 70 | 60 | 0 | 70 | 60 | 30 | 0 |
| Green Foxtail | 90 | 90 | 80 | 0 | 90 | 70 | 5 | 0 |
| Jimsonweed | 100 | 100 | 100 | 60 | 95 | 100 | 100 | 60 |
| Johnson Grass | 90 | 80 | 60 | 0 | 70 | 70 | 5 | 0 |
| Lambsquarter | 85 | 100 | 75 | 100 | 30 | 90 | 50 | 90 |
| Morningglory | 100 | 100 | 80 | 20 | 90 | 85 | 80 | 0 |
| Nutsedge | 90 | 90 | 0 | 0 | 60 | 70 | 0 | 0 |
| Pigweed | 95 | 100 | 70 | 40 | 85 | 80 | 40 | 40 |
| Prickly Sida | 0 | 50 | 0 | 0 | 0 | 30 | 0 | 0 |
| Ragweed | 100 | 100 | 100 | 40 | 90 | 95 | 60 | 30 |
| Shattercane | 100 | 100 | 70 | 0 | 90 | 80 | 40 | 0 |
| Signalgrass | 95 | 100 | 60 | — | 90 | 90 | 55 | — |
| Smartweed | 100 | 100 | 80 | 50 | 90 | 90 | 70 | 50 |
| Soybean | 90 | 100 | 90 | 60 | 80 | 90 | 70 | 55 |
| Sunflower | 100 | 100 | 85 | 0 | 90 | 100 | 80 | 0 |
| Velvetleaf | 100 | 100 | 100 | 85 | 100 | 100 | 80 | 70 |
| Wild Proso | 95 | 100 | 70 | 0 | 90 | 100 | 60 | 0 |
| Woolly cupgrass | 85 | 50 | 50 | 0 | 60 | 10 | 10 | 0 |
| Yellow Foxtail | 95 | 90 | 50 | 0 | 95 | 90 | 40 | 0 |

| POSTEMERGENCE | Rate 4 g/ha COMPOUND | |
|---|---|---|
| | 1 | 2 |
| Barnyardgrass | 100 | 100 |
| Bindweed | 70 | 90 |
| Blk Nightshade | 70 | 95 |
| Cassia | 0 | 0 |
| Cocklebur | 70 | 100 |
| Corn | 0 | 0 |
| Cotton | 70 | 95 |
| Crabgrass | 60 | 60 |
| Fall Panicum | 70 | 50 |
| Giant Foxtail | 50 | 30 |
| Green Foxtail | 60 | 30 |
| Jimsonweed | 100 | 100 |
| Johnson Grass | 30 | 40 |
| Lambsquarter | 0 | 60 |
| Morningglory | 60 | 90 |
| Nutsedge | 0 | 5 |
| Pigweed | 60 | 80 |
| Prickly Sida | 0 | 0 |
| Ragweed | 90 | 90 |
| Shattercane | 70 | 60 |
| Signalgrass | 80 | 80 |
| Smartweed | 40 | 80 |
| Soybean | 50 | 90 |
| Sunflower | 80 | 90 |
| Velvetleaf | 100 | 100 |
| Wild Proso | 80 | 80 |
| Woolly cupgrass | 70 | 10 |
| Yellow Foxtail | 80 | 85 |

Test E

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which included a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table E, are based on a scale of 0 to 10 where 0 is no effect and 10 is complete control. A dash (-) response means no test result.

TABLE E

| Rate 2000 g/ha | COMPOUND 1 | 28 | Rate 2000 g/ha | COMPOUND 1 | 28 |
|---|---|---|---|---|---|
| POSTEMERGENCE | | | Pre Soil | | |
| Barley | 9 | 6 | Barley | 6 | 0 |
| Barnyardgrass | 9 | 9 | Barnyardgrass | 10 | 8 |
| Bedstraw | 10 | 9 | Bedstraw | 9 | 8 |
| Blackgrass | 10 | 3 | Blackgrass | 9 | 4 |
| Chickweed | 10 | 9 | Chickweed | 9 | 8 |
| Cocklebur | 9 | 9 | Cocklebur | 9 | 5 |
| Corn | 10 | 4 | Corn | 6 | 0 |
| Cotton | 10 | 9 | Cotton | 9 | 7 |
| Crabgrass | 9 | 9 | Crabgrass | 10 | 10 |
| Downy brome | 9 | 7 | Downy brome | 10 | 9 |
| Giant foxtail | 9 | 8 | Giant foxtail | 10 | 9 |
| Lambsquarter | 9 | 9 | Lambsquarter | 10 | 10 |
| Morningglory | 9 | 10 | Morningglory | 10 | 9 |
| Nutsedge | 8 | 7 | Nutsedge | 10 | 4 |
| Rape | 10 | 10 | Rape | 10 | 7 |
| Rice | 8 | 9 | Rice | 10 | 10 |
| Sorghum | 10 | 8 | Sorghum | 10 | 3 |
| Soybean | 9 | 10 | Soybean | 9 | 9 |
| Sugar beet | 9 | 10 | Sugar beet | 10 | 10 |
| Velvetleaf | 10 | 10 | Velvetleaf | 10 | 10 |
| Wheat | 10 | 10 | Wheat | 8 | 4 |
| Wild buckwheat | 9 | 8 | Wild buckwheat | 10 | 7 |
| Wild oat | 10 | 5 | Wild oat | 10 | 5 |

| Rate 400 g/ha | COMPOUND 1 | 2 | 12 | 15 | 16 | 18 | 28 | 29 | Rate 400 g/ha | COMPOUND 1 | 2 | 12 | 15 | 16 | 18 | 28 | 29 |
|---|---|---|---|---|---|---|---|---|---|---|---|---|---|---|---|---|---|
| POSTEMERGENCE | | | | | | | | | PREEMERGENCE | | | | | | | | |
| Barley | 9 | 9 | 8 | 2 | 3 | 4 | 5 | 2 | Barley | 1 | 0 | 0 | 0 | 0 | 0 | 0 | 0 |
| Barnyardgrass | 9 | 9 | 10 | 9 | 10 | 9 | 9 | 9 | Barnyardgrass | 8 | 10 | 9 | 9 | 10 | 5 | 2 | 1 |
| Bedstraw | 10 | 9 | 9 | 7 | 10 | 9 | 8 | 9 | Bedstraw | 7 | 3 | 8 | 9 | 10 | 8 | 5 | 0 |
| Blackgrass | 9 | 9 | 9 | 7 | 9 | 9 | 3 | 0 | Blackgrass | 8 | 5 | 5 | 3 | 4 | 3 | 0 | 0 |
| Chickweed | 9 | 9 | 10 | 9 | 10 | 9 | 9 | 9 | Chickweed | 9 | 8 | 10 | 8 | 9 | 8 | 8 | 8 |
| Cocklebur | 9 | 9 | 10 | 9 | 10 | 10 | 9 | 9 | Cocklebur | 7 | 8 | 8 | 3 | 6 | 6 | 2 | 0 |
| Corn | 10 | 10 | 6 | 5 | 9 | 8 | 3 | 6 | Corn | 1 | 1 | 1 | 0 | 1 | 1 | 0 | 0 |
| Cotton | 10 | 10 | 10 | 9 | 10 | 10 | 9 | 9 | Cotton | 9 | 4 | 3 | 3 | 3 | 3 | 2 | 0 |
| Crabgrass | 9 | 9 | 10 | 9 | 10 | 9 | 9 | 9 | Crabgrass | 10 | 9 | 10 | 9 | 10 | 10 | 9 | 9 |
| Downy brome | 9 | 9 | 9 | 2 | 7 | 7 | 7 | 6 | Downy brome | 9 | 9 | 9 | 2 | 10 | 0 | 0 | 0 |
| Giant foxtail | 9 | 9 | 10 | 9 | 9 | 9 | 8 | 6 | Giant foxtail | 10 | 8 | 7 | 5 | 9 | 9 | 2 | 3 |
| Lambsquarter | 9 | 9 | 9 | 8 | 10 | 9 | 9 | 9 | Lambsquarter | 10 | 10 | 10 | 9 | 10 | 9 | 10 | 9 |
| Morningglory | 10 | 9 | 10 | 3 | 7 | 9 | 9 | 0 | Morningglory | 7 | 3 | 9 | 0 | 1 | 1 | 3 | 0 |
| Nutsedge | 9 | 8 | 9 | 9 | 9 | 7 | 5 | 0 | Nutsedge | 6 | 2 | 5 | 0 | 8 | 3 | 0 | 0 |
| Rape | 10 | 10 | 10 | 3 | 10 | 6 | 8 | 9 | Rape | 4 | 2 | 5 | 2 | 0 | 1 | 4 | 5 |
| Rice | 8 | 9 | 10 | 9 | 9 | 9 | 8 | 8 | Rice | 9 | 9 | 10 | 8 | 9 | 6 | 8 | 4 |
| Sorghum | 9 | 10 | 10 | 6 | 9 | 10 | 6 | 7 | Sorghum | 8 | 9 | 9 | 0 | 9 | 4 | 1 | 0 |
| Soybean | 9 | 9 | 9 | 7 | 9 | 7 | 9 | 8 | Soybean | 9 | 8 | 9 | 0 | 0 | 1 | 6 | 2 |
| Sugar beet | 10 | 10 | 10 | 8 | 10 | 10 | 10 | 10 | Sugar beet | 10 | 10 | 10 | 8 | 10 | 10 | 10 | 8 |
| Velvetleaf | 10 | 10 | 10 | 8 | 10 | 9 | 10 | 9 | Velvetleaf | 10 | 10 | 10 | 7 | 10 | 10 | 10 | 5 |
| Wheat | 9 | 9 | 9 | 6 | 9 | 8 | 9 | 2 | Wheat | 3 | 1 | 4 | 0 | 2 | 1 | 0 | 0 |
| Wild buckwheat | 9 | 9 | 9 | 2 | 10 | 9 | 8 | 8 | Wild buckwheat | 7 | 5 | 6 | 2 | 0 | 1 | 0 | 0 |
| Wild oat | 10 | 9 | 10 | 9 | 10 | 10 | 4 | 9 | Wild oat | 7 | 7 | 7 | 3 | 10 | 9 | 1 | 0 |

TABLE E-continued

| Rate 200 g/ha | COMPOUND | | | | | | | | | | | | | | | | | |
|---|---|---|---|---|---|---|---|---|---|---|---|---|---|---|---|---|---|---|
| | 1 | 2 | 3 | 4 | 5 | 6 | 9 | 10 | 16 | 19 | 20 | 21 | 23 | 24 | 25 | 26 | 27 | 30 | 31 |

POSTEMERGENCE

| | 1 | 2 | 3 | 4 | 5 | 6 | 9 | 10 | 16 | 19 | 20 | 21 | 23 | 24 | 25 | 26 | 27 | 30 | 31 |
|---|---|---|---|---|---|---|---|---|---|---|---|---|---|---|---|---|---|---|---|
| Barley | 8 | 8 | 6 | 7 | 9 | 9 | 7 | 0 | 7 | 0 | 1 | 2 | 3 | 7 | 0 | 3 | 4 | 10 | 9 |
| Barnyardgrass | 10 | 9 | 9 | 9 | 10 | 10 | 10 | 1 | 10 | 8 | 10 | 9 | 9 | 9 | 9 | 9 | 10 | 9 | 10 |
| Bedstraw | 9 | 9 | 9 | 9 | 10 | 9 | 6 | — | 9 | 5 | 8 | 7 | 9 | 9 | 6 | 9 | 10 | 9 | 8 |
| Blackgrass | 9 | 9 | 7 | 5 | 9 | 9 | 3 | 0 | 8 | 1 | 5 | 6 | 3 | 8 | 4 | 5 | 6 | 9 | 9 |
| Chickweed | 9 | 10 | 10 | 9 | 9 | 9 | 9 | 1 | 10 | 3 | 8 | 5 | 9 | 9 | 9 | — | 10 | 9 | 9 |
| Cocklebur | 10 | 9 | 9 | 9 | 10 | 10 | 10 | 0 | 10 | 9 | 10 | 10 | 10 | 9 | 10 | 10 | 10 | 10 | 10 |
| Corn | 3 | 9 | 3 | 1 | 7 | 2 | 2 | 1 | 9 | 1 | 1 | 0 | 6 | 5 | 2 | 3 | 8 | 3 | 7 |
| Cotton | 10 | 10 | 9 | 10 | 10 | 10 | 10 | 3 | 10 | 4 | 9 | 9 | 10 | 10 | 10 | 10 | 10 | 10 | 10 |
| Crabgrass | 9 | 9 | 9 | 9 | 10 | 10 | 9 | 0 | 9 | 4 | 4 | 5 | 10 | 9 | 3 | 3 | 10 | 9 | 9 |
| Downy brome | 8 | 9 | 9 | 8 | 9 | 9 | 4 | 0 | 9 | 0 | 3 | 1 | 5 | 8 | 0 | 2 | 5 | 9 | 9 |
| Giant foxtail | 9 | 9 | 5 | 8 | 9 | 10 | 9 | 1 | 9 | 2 | 2 | 5 | 10 | 9 | 3 | 5 | 9 | 9 | 9 |
| Lambsquarter | 9 | 9 | 10 | 9 | 9 | 10 | 9 | 2 | 9 | 9 | 9 | 9 | 9 | 9 | 9 | 9 | 10 | 9 | 9 |
| Morningglory | 10 | 9 | 9 | 10 | 10 | 10 | 8 | 1 | 8 | 3 | 2 | 4 | 9 | 10 | 1 | 9 | 9 | 9 | 10 |
| Nutsedge | — | 8 | 4 | 3 | 5 | 9 | — | — | 7 | 4 | 2 | 1 | — | 7 | 2 | 7 | 9 | 9 | 9 |
| Rape | 9 | 10 | 10 | 8 | 10 | 10 | 3 | 0 | 10 | 4 | 7 | 8 | 10 | 10 | 8 | 10 | 10 | 10 | 9 |
| Rice | 9 | 9 | 8 | 10 | 9 | 10 | 9 | 0 | 9 | 5 | 8 | 9 | 9 | 9 | 6 | 9 | 9 | 9 | 9 |
| Sorghum | 9 | 10 | 8 | 9 | 10 | 10 | 9 | 0 | 10 | 0 | 3 | 2 | 9 | 8 | 2 | 3 | 10 | 10 | 10 |
| Soybean | 10 | 9 | 6 | 9 | 10 | 10 | 9 | 2 | 7 | 4 | 4 | 5 | 10 | 9 | 7 | 6 | 9 | 8 | 10 |
| Sugar beet | 9 | 10 | 10 | 10 | 10 | 10 | 8 | 4 | 10 | 7 | 10 | 10 | 9 | 9 | 10 | 10 | 10 | 10 | 10 |
| Velvetleaf | 10 | 10 | 9 | 10 | 10 | 10 | 10 | 2 | 10 | 8 | 9 | 7 | 10 | 10 | 10 | 10 | 10 | 10 | 10 |
| Wheat | 6 | 9 | 7 | 8 | 9 | 9 | 4 | 0 | 9 | 1 | 2 | 2 | 5 | 7 | 4 | 2 | 9 | 9 | 9 |
| Wild buckwheat | 9 | 9 | 7 | 9 | 10 | 9 | 1 | 0 | 9 | 1 | 2 | 2 | 10 | 6 | 2 | 7 | 9 | 6 | 8 |
| Wild oat | 9 | 9 | 8 | 9 | 9 | 10 | 7 | 0 | 10 | 1 | 5 | 6 | 8 | 9 | 3 | 4 | 10 | 10 | 10 |

PREEMERGENCE

| | 1 | 2 | 3 | 4 | 5 | 6 | 9 | 10 | 16 | 19 | 20 | 21 | 23 | 24 | 25 | 26 | 27 | 30 | 31 |
|---|---|---|---|---|---|---|---|---|---|---|---|---|---|---|---|---|---|---|---|
| Barley | 0 | 0 | 0 | 0 | 3 | 3 | 0 | 0 | 0 | 0 | 0 | 0 | 0 | 0 | 0 | 0 | 0 | 0 | 3 |
| Barnyardgrass | 9 | 10 | 10 | 6 | 9 | 5 | 7 | 0 | 10 | 0 | 0 | 1 | 3 | 1 | 0 | 2 | 5 | 9 | 10 |
| Bedstraw | 1 | 8 | 3 | 10 | 7 | 7 | 0 | 0 | 2 | 0 | — | — | — | 7 | — | 0 | 9 | 9 | 9 |
| Blackgrass | 4 | 2 | 2 | 6 | 8 | 9 | 1 | 0 | 3 | 0 | 1 | 0 | 0 | 1 | 0 | 0 | 2 | 6 | 9 |
| Chickweed | 9 | 9 | 7 | 9 | 9 | 9 | 6 | 0 | 10 | — | 2 | — | 3 | 9 | — | — | 9 | 10 | 10 |
| Cocklebur | 3 | 7 | 4 | 5 | 10 | 7 | 0 | 0 | 3 | 0 | 0 | 0 | 0 | 0 | 0 | 4 | 3 | 1 | 3 |
| Corn | 0 | 0 | 2 | 0 | 2 | 0 | 0 | 0 | 0 | 0 | 0 | 0 | 0 | 0 | 0 | 0 | 0 | 0 | 0 |
| Cotton | 1 | 4 | 5 | 2 | 2 | 4 | 0 | 0 | 0 | 0 | 0 | 0 | 2 | 0 | 0 | 1 | 0 | 5 | 8 |
| Crabgrass | 9 | 9 | 10 | 9 | 10 | 10 | 6 | 0 | 10 | 0 | 1 | 3 | 10 | 9 | 1 | 2 | 10 | 10 | 10 |
| Downy brome | 7 | 7 | 1 | 8 | 9 | 8 | 0 | 0 | 7 | 0 | 0 | 0 | 0 | 1 | 0 | 0 | 8 | 9 | 10 |
| Giant foxtail | 7 | 8 | 6 | 1 | 8 | 9 | 3 | 0 | 7 | 0 | 0 | 1 | 7 | 3 | 0 | 1 | 8 | 6 | 9 |
| Lambsquarter | 10 | 10 | 10 | 9 | 9 | 10 | 9 | 0 | 9 | — | 7 | — | 10 | 9 | — | — | 10 | 10 | 10 |
| Morningglory | 2 | 3 | 7 | 3 | 8 | 4 | 3 | 0 | 0 | 0 | 0 | 0 | 0 | 1 | 0 | 1 | 3 | 4 | 6 |
| Nutsedge | — | 0 | — | 2 | 4 | 4 | — | — | 0 | 0 | 0 | 0 | 6 | 1 | 0 | 2 | — | 2 | 10 |
| Rape | 0 | 7 | 8 | 5 | 8 | 3 | 4 | 0 | 1 | 0 | 0 | 0 | 0 | 8 | 0 | 0 | 3 | 7 | 7 |
| Rice | 8 | 9 | 8 | 0 | 9 | 9 | 2 | 0 | 9 | 0 | 0 | 0 | 3 | 2 | 0 | 3 | 4 | 9 | 10 |
| Sorghum | 8 | 9 | 7 | 2 | 9 | 9 | 0 | 0 | 7 | 0 | 0 | 0 | 2 | 1 | 0 | 0 | 6 | 4 | 9 |
| Soybean | 6 | 5 | 6 | 0 | 7 | 5 | 0 | 0 | 4 | 0 | 0 | 0 | 0 | 2 | 0 | 0 | 0 | 5 | 3 |
| Sugar beet | 9 | 10 | 10 | 10 | 10 | 10 | 9 | 0 | 10 | 5 | 0 | 0 | 8 | 4 | 0 | 0 | 9 | 9 | 10 |
| Velvetleaf | 10 | 10 | 9 | 8 | 10 | 10 | 10 | 0 | 10 | 0 | 0 | 2 | 9 | 10 | 2 | 6 | 10 | 10 | 10 |
| Wheat | 1 | 0 | 0 | 0 | 6 | 7 | 0 | 0 | 0 | 0 | 0 | 0 | 0 | 0 | 0 | 0 | 1 | 0 | 7 |
| Wild buckwheat | 0 | 4 | 1 | 2 | 4 | 5 | 0 | 0 | 0 | 0 | 0 | 0 | 0 | 2 | 0 | 0 | 0 | 3 | 2 |
| Wild oat | 10 | 3 | 3 | 4 | 9 | 8 | 4 | 0 | 3 | 0 | 0 | 0 | 0 | 8 | 0 | 0 | 9 | 2 | 10 |

| Rate 100 g/ha | COMPOUND | | | | | | | | | | |
|---|---|---|---|---|---|---|---|---|---|---|---|
| | 1 | 2 | 5 | 6 | 7 | 8 | 12 | 15 | 16 | 18 | 29 |

POSTEMERGENCE

| | 1 | 2 | 5 | 6 | 7 | 8 | 12 | 15 | 16 | 18 | 29 |
|---|---|---|---|---|---|---|---|---|---|---|---|
| Barley | 5 | 8 | 9 | 9 | 2 | 8 | 4 | 1 | 1 | 1 | 0 |
| Barnyardgrass | 10 | 10 | 10 | 10 | 10 | 10 | 10 | 9 | 10 | 9 | 9 |
| Bedstraw | 9 | 8 | 9 | 9 | 9 | 8 | 8 | 8 | 10 | 9 | 7 |
| Blackgrass | 9 | 9 | 9 | 9 | 5 | 8 | 7 | 5 | 8 | 8 | 0 |
| Chickweed | 9 | 9 | 9 | 9 | 9 | 8 | 10 | 9 | 10 | 9 | 9 |
| Cocklebur | 10 | 9 | 10 | 10 | 9 | 9 | 9 | 9 | 10 | 10 | 9 |
| Corn | 1 | 9 | 7 | 2 | 2 | 0 | 2 | 3 | 8 | 6 | 2 |
| Cotton | 10 | 10 | 10 | 10 | 8 | 10 | 10 | 5 | 10 | 10 | 9 |
| Crabgrass | 9 | 9 | 9 | 10 | 9 | 9 | 9 | 9 | 10 | 9 | 9 |
| Downy brome | 7 | 8 | 9 | 8 | 3 | 8 | 8 | 1 | 6 | 6 | 0 |
| Giant foxtail | 9 | 9 | 9 | 9 | 6 | 8 | 9 | 9 | 9 | 9 | 1 |
| Lambsquarter | 9 | 9 | 9 | 9 | 9 | 8 | 9 | 8 | 10 | 9 | 9 |
| Morningglory | 10 | 9 | 9 | 9 | 9 | 9 | 10 | 3 | 8 | 9 | 0 |
| Nutsedge | 8 | 8 | — | 8 | 5 | 8 | 8 | 2 | 6 | 5 | 0 |
| Rape | 7 | 10 | 9 | 10 | 9 | 10 | 10 | 2 | 7 | 5 | 7 |
| Rice | 9 | 9 | 9 | 8 | 9 | 9 | 10 | 9 | 9 | 8 | 8 |
| Sorghum | 9 | 10 | 9 | 9 | 9 | 9 | 10 | 2 | 9 | 9 | 3 |
| Soybean | 10 | 9 | 10 | 10 | 6 | 9 | 9 | 3 | 7 | 7 | 6 |

TABLE E-continued

| | | | | | | | | | | | |
|---|---|---|---|---|---|---|---|---|---|---|---|
| Sugar beet | 9 | 10 | 10 | 10 | 10 | 10 | 10 | 8 | 10 | 10 | 10 |
| Velvetleaf | 10 | 9 | 10 | 7 | 9 | 9 | 10 | 8 | 10 | 9 | 7 |
| Wheat | 6 | 9 | 9 | 9 | 4 | 9 | 7 | 6 | 8 | 5 | 0 |
| Wild buckwheat | 7 | 8 | 8 | 9 | 4 | 2 | 8 | 2 | 10 | 9 | 7 |
| Wild oat | 9 | 9 | 9 | 9 | 5 | 9 | 10 | 6 | 9 | 9 | 4 |

PREEMERGENCE

| | | | | | | | | | | | |
|---|---|---|---|---|---|---|---|---|---|---|---|
| Barley | 0 | 0 | 0 | 0 | 0 | 0 | 0 | 0 | 0 | 0 | 0 |
| Barnyardgrass | 6 | 7 | 2 | 3 | 2 | 3 | 2 | 0 | 3 | 1 | 0 |
| Bedstraw | 0 | 3 | 0 | 0 | 0 | 2 | 0 | 4 | 9 | 1 | 0 |
| Blackgrass | 3 | 1 | 4 | 4 | 0 | 1 | 3 | 0 | 2 | 1 | 0 |
| Chickweed | 7 | 8 | 8 | 3 | 2 | 5 | 5 | 7 | 9 | 7 | 3 |
| Cocklebur | 3 | 4 | 5 | 2 | — | 8 | 3 | 0 | 7 | — | 0 |
| Corn | 0 | 0 | 0 | 0 | 0 | 0 | 0 | 0 | 0 | 0 | 0 |
| Cotton | 0 | 2 | 0 | 3 | 0 | 0 | 2 | 0 | 0 | 0 | 0 |
| Crabgrass | 5 | 9 | 6 | 5 | 3 | 7 | 9 | 9 | 9 | 9 | 1 |
| Downy brome | 3 | 7 | 3 | 7 | 0 | 3 | 2 | 0 | 4 | 0 | 0 |
| Giant foxtail | 4 | 5 | 3 | 3 | 0 | 3 | 2 | 3 | 8 | 4 | 0 |
| Lambsquarter | 10 | 10 | 9 | 9 | 8 | 9 | 9 | 9 | 10 | 9 | 8 |
| Morningglory | 2 | 2 | 3 | 3 | 0 | — | 8 | 0 | 0 | 0 | 0 |
| Nutsedge | — | 0 | — | — | 0 | 3 | 0 | 0 | 4 | 1 | 0 |
| Rape | 0 | 1 | 0 | 0 | 0 | 0 | 0 | 0 | 0 | 0 | 0 |
| Rice | 3 | 9 | 5 | 5 | 0 | 0 | 8 | 0 | 3 | 0 | 0 |
| Sorghum | 5 | 0 | 6 | 5 | 0 | 0 | 0 | 0 | 2 | 3 | 0 |
| Soybean | 3 | 0 | 0 | 0 | 5 | 0 | 5 | 0 | 0 | 0 | 0 |
| Sugar beet | 7 | 10 | 0 | 0 | 0 | 3 | 9 | 1 | 10 | 9 | 0 |
| Velvetleaf | 9 | 10 | 10 | 10 | 0 | 8 | 10 | 0 | 10 | 10 | 0 |
| Wheat | 0 | 0 | 0 | 0 | 0 | 0 | 0 | 0 | 0 | 0 | 0 |
| Wild buckwheat | 0 | 2 | 0 | 0 | 0 | 0 | 0 | 2 | 0 | 0 | 0 |
| Wild oat | 7 | 1 | 6 | 7 | 0 | 1 | 7 | 0 | 9 | 2 | 0 |

| | COMPOUND | | | | | | | | | | | | | | | | | | |
|---|---|---|---|---|---|---|---|---|---|---|---|---|---|---|---|---|---|---|---|
| Rate 50 g/ha | 1 | 2 | 3 | 4 | 5 | 6 | 7 | 8 | 9 | 10 | 16 | 19 | 20 | 21 | 23 | 24 | 25 | 26 | 27 | 30 | 31 |

POSTEMERGENCE

| | 1 | 2 | 3 | 4 | 5 | 6 | 7 | 8 | 9 | 10 | 16 | 19 | 20 | 21 | 23 | 24 | 25 | 26 | 27 | 30 | 31 |
|---|---|---|---|---|---|---|---|---|---|---|---|---|---|---|---|---|---|---|---|---|---|
| Barley | 5 | 4 | 2 | 5 | 9 | 9 | 1 | 3 | 2 | 0 | 2 | 0 | 0 | 0 | 2 | 6 | 0 | 1 | 2 | 9 | 9 |
| Barnyardgrass | 10 | 10 | 9 | 9 | 10 | 10 | 10 | 10 | 10 | 0 | 10 | 5 | 6 | 4 | 9 | 9 | 8 | 9 | 10 | 9 | 10 |
| Bedstraw | 8 | 9 | 8 | 9 | 9 | 9 | 8 | 8 | 3 | 0 | 9 | 2 | 7 | 6 | 9 | 9 | 7 | 9 | 10 | 9 | 7 |
| Blackgrass | 7 | 8 | 5 | 4 | 9 | 9 | 2 | 5 | 1 | 0 | 7 | 0 | 1 | 1 | 3 | 4 | 3 | 3 | 6 | 9 | 8 |
| Chickweed | 9 | 10 | 10 | 9 | 9 | 9 | 7 | 8 | 8 | 0 | 10 | 2 | — | 1 | 9 | 9 | 9 | — | 10 | 9 | — |
| Cocklebur | 10 | 9 | 8 | 9 | 10 | 10 | 9 | 9 | 10 | 0 | 10 | 6 | 9 | 8 | 10 | 9 | 9 | 9 | 10 | 10 | 9 |
| Corn | 0 | 9 | 1 | 1 | 3 | 1 | 2 | 0 | 1 | 0 | 6 | 0 | 0 | 0 | 3 | 1 | 0 | 1 | 5 | 2 | 2 |
| Cotton | 10 | 10 | 8 | 9 | 10 | 10 | 8 | 7 | 9 | 0 | 10 | 5 | 9 | 9 | 10 | 9 | 6 | 9 | 10 | 10 | 10 |
| Crabgrass | 9 | 9 | 9 | 8 | 9 | 9 | 7 | 9 | 9 | 0 | 9 | 3 | 2 | 2 | 9 | 8 | 3 | 1 | 8 | 9 | 9 |
| Downy brome | 7 | 7 | 6 | 6 | 9 | 9 | 1 | 6 | 3 | 0 | 7 | 0 | 0 | 0 | 1 | 4 | 0 | 2 | 4 | 9 | 9 |
| Giant foxtail | 9 | 9 | 3 | 5 | 9 | 9 | 5 | 7 | 9 | 1 | 9 | 1 | 1 | 1 | 9 | 8 | 1 | 3 | 8 | 9 | 9 |
| Lambsquarter | 8 | 9 | 9 | 9 | 9 | 9 | 8 | 7 | 8 | 0 | 9 | 8 | 8 | 7 | 9 | 8 | 8 | 9 | 9 | 9 | 9 |
| Morningglory | 9 | 9 | 9 | 10 | 10 | 9 | 8 | 8 | 8 | 1 | 8 | — | 1 | 1 | 9 | 9 | 2 | 8 | 8 | 9 | 8 |
| Nutsedge | 7 | 8 | 4 | 3 | 4 | 9 | 5 | 2 | — | — | 7 | 0 | 0 | 0 | — | 2 | 0 | 2 | 7 | 4 | 7 |
| Rape | 7 | 9 | 10 | 8 | 10 | 9 | 8 | 10 | 1 | 0 | 7 | 2 | 7 | 5 | 9 | 10 | 7 | 9 | 10 | 10 | 8 |
| Rice | 9 | 9 | 8 | 9 | 9 | 9 | 8 | 9 | 9 | 0 | 9 | 0 | 3 | 7 | 9 | 9 | 2 | 9 | 9 | 9 | 9 |
| Sorghum | 9 | 10 | 8 | 9 | 9 | 9 | 9 | 9 | 9 | 0 | 9 | 0 | 3 | 0 | 8 | 3 | 2 | 3 | 9 | 10 | 10 |
| Soybean | 10 | 9 | 5 | 9 | 10 | 9 | 7 | 8 | 8 | 0 | 6 | 4 | 4 | 2 | 9 | 9 | 4 | 4 | 9 | 9 | 9 |
| Sugar beet | 9 | 10 | 9 | 10 | 10 | 10 | 9 | 10 | 9 | 0 | 10 | 7 | 9 | 8 | 9 | 3 | 10 | 9 | 10 | 10 | 8 |
| Velvetleaf | 10 | 10 | 9 | 10 | 10 | 10 | 9 | 9 | 10 | 0 | 10 | 7 | 8 | 7 | 10 | 10 | 9 | 10 | 10 | 10 | 9 |
| Wheat | 5 | 8 | 4 | 7 | 9 | 9 | 4 | 8 | 3 | 0 | 5 | 0 | 1 | 1 | 4 | 4 | 1 | 1 | 8 | 9 | 9 |
| Wild buckwheat | 6 | 8 | 7 | 7 | 9 | 9 | 2 | 1 | 0 | 0 | 7 | 1 | 1 | 1 | 6 | 3 | 2 | 6 | 6 | 4 | 3 |
| Wild oat | 9 | 8 | 3 | 7 | 10 | 10 | 5 | 8 | 4 | 0 | 9 | 0 | 3 | 3 | 3 | 9 | 2 | 3 | 9 | 10 | 10 |

PREEMERGENCE

| | 1 | 2 | 3 | 4 | 5 | 6 | 7 | 8 | 9 | 10 | 16 | 19 | 20 | 21 | 23 | 24 | 25 | 26 | 27 | 30 | 31 |
|---|---|---|---|---|---|---|---|---|---|---|---|---|---|---|---|---|---|---|---|---|---|
| Barley | 0 | 0 | 0 | 0 | 0 | 0 | 0 | 0 | 0 | 0 | 0 | 0 | 0 | 0 | 0 | 0 | 0 | 0 | 0 | | 0 |
| Barnyardgrass | 3 | 2 | 4 | 0 | 2 | 2 | 0 | 1 | 3 | 0 | 0 | 0 | 0 | 0 | 0 | 0 | 0 | 1 | 3 | 1 | 2 |
| Bedstraw | 0 | 3 | — | 3 | 7 | 4 | 0 | 0 | 0 | 0 | 2 | — | 2 | 0 | 0 | 3 | 0 | 0 | 2 | 3 | 4 |
| Blackgrass | 0 | 0 | 1 | 0 | 2 | 6 | 0 | 0 | 0 | 0 | 0 | 0 | 0 | 0 | 0 | 0 | 0 | 0 | 0 | 2 | 9 |
| Chickweed | 1 | 8 | 4 | 7 | 8 | 7 | 0 | 5 | 0 | 0 | 9 | 0 | 0 | — | 3 | 6 | — | 0 | 8 | 10 | 6 |
| Cocklebur | 0 | 3 | 2 | 2 | 4 | 2 | 0 | 0 | 0 | 0 | 3 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 2 | 0 | 0 | 0 | 0 | 1 |
| Crabgrass | 5 | 9 | 8 | 6 | 9 | 10 | 2 | 3 | 4 | 0 | 9 | 0 | 0 | 0 | 8 | 5 | — | 1 | 6 | 10 | 10 |
| Downy brome | 0 | 0 | 0 | 4 | 2 | 4 | 0 | 0 | 0 | 0 | 0 | 0 | 0 | 0 | 0 | 0 | 0 | 0 | 2 | 3 | 6 |
| Giant foxtail | 3 | 2 | 1 | 0 | 3 | 6 | 0 | 0 | 0 | 0 | 3 | 0 | 0 | 0 | 2 | 0 | 0 | 0 | 1 | 3 | 5 |
| Lambsquarter | 9 | 9 | 9 | 8 | 9 | 9 | 0 | 8 | 8 | 0 | 9 | 0 | — | 0 | 10 | 7 | 0 | 0 | 10 | 9 | 10 |
| Morningglory | 0 | 2 | 3 | 1 | 0 | 0 | 0 | 0 | 1 | 0 | 0 | 0 | 0 | 0 | 0 | 0 | 0 | 0 | 1 | 0 | 0 |
| Nutsedge | — | 0 | — | 0 | 2 | 2 | 0 | 0 | — | — | 0 | 0 | 0 | — | — | 0 | 0 | — | 0 | 0 | 0 |
| Rape | 0 | 2 | 2 | 5 | 5 | 2 | 0 | 0 | 0 | 0 | 0 | 0 | 0 | 0 | 0 | 0 | 0 | 0 | 0 | 3 | 5 |
| Rice | 3 | 0 | 4 | 0 | 5 | 7 | 0 | 0 | 0 | 0 | 0 | 0 | 0 | 0 | 0 | 0 | 0 | 0 | 2 | 3 | 3 |
| Sorghum | 4 | 0 | 3 | 0 | 5 | 5 | 0 | 0 | 0 | 0 | 0 | 0 | 0 | 0 | 0 | 0 | 0 | 0 | 0 | 1 | 2 |

TABLE E-continued

| | | | | | | | | | | | | | | | | | | | | | |
|---|---|---|---|---|---|---|---|---|---|---|---|---|---|---|---|---|---|---|---|---|---|
| Soybean | 1 | 0 | 4 | 0 | 3 | 0 | 0 | 0 | 0 | 0 | 0 | 0 | 0 | 0 | 0 | 0 | 0 | 0 | 0 | 2 | 2 |
| Sugar beet | 7 | 10 | 9 | 10 | 10 | 9 | 0 | 0 | 4 | 0 | 7 | 0 | 0 | 0 | 0 | 0 | 0 | 0 | 7 | 8 | 9 |
| Velvetleaf | 10 | 7 | 4 | 7 | 10 | 10 | 0 | 5 | 8 | 0 | 10 | 0 | 0 | 0 | 3 | 8 | 0 | 4 | 5 | 9 | 10 |
| Wheat | 0 | 0 | 0 | 0 | 1 | 0 | 0 | 0 | 0 | 0 | 0 | 0 | 0 | 0 | 0 | 0 | 0 | 0 | 0 | 0 | 4 |
| Wild buckwheat | 0 | 0 | 0 | 0 | 1 | 3 | 0 | 0 | 0 | 0 | 0 | 0 | 0 | 0 | 0 | 0 | 0 | 0 | 0 | 0 | 0 |
| Wild oat | 8 | 1 | 0 | 3 | 7 | 4 | 0 | 0 | 0 | 0 | 2 | 0 | 0 | 0 | 0 | 5 | 0 | 0 | 7 | 1 | 8 |

| | COMPOUND | | | | COMPOUND | | |
|---|---|---|---|---|---|---|---|
| Rate 20 g/ha | 1 | 5 | 6 | Rate 20 g/ha | 1 | 5 | 6 |
| POSTEMERGENCE | | | | PREEMERGENCE | | | |
| Barley | 4 | 9 | 8 | Barley | 0 | 0 | 0 |
| Barnyardgrass | 10 | 10 | 9 | Barnyardgrass | 0 | 1 | 1 |
| Bedstraw | 8 | 8 | 8 | Bedstraw | 0 | 0 | 0 |
| Blackgrass | 7 | 9 | 6 | Blackgrass | 0 | 0 | 0 |
| Chickweed | 7 | 9 | 8 | Chickweed | 0 | 5 | 0 |
| Cocklebur | 10 | 10 | 10 | Cocklebur | 0 | 0 | 0 |
| Corn | 0 | 1 | 1 | Corn | 0 | 0 | 0 |
| Cotton | 9 | 8 | 10 | Cotton | 0 | 0 | 0 |
| Crabgrass | 9 | 8 | 9 | Crabgrass | 2 | 1 | 1 |
| Downy brome | 6 | 7 | 7 | Downy brome | 0 | 0 | 0 |
| Giant foxtail | 9 | 9 | 9 | Giant foxtail | 0 | 0 | 0 |
| Lambsquarter | 8 | 9 | 9 | Lambsquarter | 6 | 9 | 8 |
| Morningglory | 9 | 9 | 8 | Morningglory | 0 | 0 | 0 |
| Nutsedge | 8 | 4 | 4 | Nutsedge | — | — | — |
| Rape | 2 | 9 | 6 | Rape | 0 | 0 | 0 |
| Rice | 9 | 9 | 8 | Rice | 0 | 0 | 0 |
| Sorghum | 9 | 9 | 9 | Sorghum | 0 | 0 | 0 |
| Soybean | 10 | 9 | 8 | Soybean | 0 | 0 | 0 |
| Sugar beet | 9 | 10 | 7 | Sugar beet | 0 | 0 | 0 |
| Velvetleaf | 10 | 10 | 10 | Velvetleaf | 10 | 10 | 9 |
| Wheat | 5 | 9 | 9 | Wheat | 0 | 0 | 0 |
| Wild buckwheat | 4 | 7 | 7 | Wild buckwheat | 0 | 0 | 0 |
| Wild oat | 9 | 9 | 9 | Wild oat | 0 | 3 | 3 |

| | COMPOUND | | | COMPOUND | |
|---|---|---|---|---|---|
| Rate 10 g/ha | 7 | 8 | Rate 10 g/ha | 7 | 8 |
| POSTEMERGENCE | | | PREEMERGENCE | | |
| Barley | 0 | 0 | Barley | 0 | 0 |
| Barnyardgrass | 9 | 8 | Barnyardgrass | 0 | 0 |
| Bedstraw | 4 | 2 | Bedstraw | 0 | 0 |
| Blackgrass | 0 | 1 | Blackgrass | 0 | 0 |
| Chickweed | 5 | 6 | Chickweed | 0 | 0 |
| Cocklebur | 8 | 6 | Cocklebur | 0 | 0 |
| Corn | 0 | 0 | Corn | 0 | 0 |
| Cotton | 3 | 4 | Cotton | 0 | 0 |
| Crabgrass | 3 | 3 | Crabgrass | 0 | 0 |
| Downy brome | 0 | 0 | Downy brome | 0 | 0 |
| Giant foxtail | 2 | 2 | Giant foxtail | 0 | 0 |
| Lambsquarter | 7 | 3 | Lambsquarter | 0 | 0 |
| Morningglory | 7 | 2 | Morningglory | 0 | 0 |
| Nutsedge | 2 | 3 | Nutsedge | 0 | 0 |
| Rape | 0 | 1 | Rape | 0 | 0 |
| Rice | 4 | 7 | Rice | 0 | 0 |
| Sorghum | 4 | 6 | Sorghum | 0 | 0 |
| Soybean | 3 | 3 | Soybean | 0 | 0 |
| Sugar beet | 6 | 9 | Sugar beet | 0 | 0 |
| Velvetleaf | 5 | 7 | Velvetleaf | 0 | 0 |
| Wheat | 1 | 2 | Wheat | 0 | 0 |
| Wild buckwheat | 0 | 0 | Wild buckwheat | 0 | 0 |
| Wild oat | 0 | 2 | Wild oat | 0 | 0 |

Test F

Compounds evaluated in this test were formulated in a non-phytotoxic solvent mixture and applied to the surface of the water which was contained in each pot. Individual containers of barnyardgrass (*Echinochloa oryzicola*), small flower umbrella sedge (*Cyperus difformus*), common falsepimpernel (*Lindernia procumbens*), monochoria (*Monochoria vaginalis*) and bulrush (*Scirpus juicoides*) were seeded and allowed to grow until the 1.5 to 2.5 leaf stage of development. A clay loam soil was used for this propagation. Japonica rice (*Oryza sativa*) was transplanted at 0 and 2 cm depth five days before application of the test compound to the water surface.

Treated plants and untreated controls were maintained under greenhouse conditions for twenty to thirty days at which time treated plants were compared to untreated controls and visually evaluated. Plant response ratings, summarized in Table F, are based upon a 0 to 100 scale where 0 is no effect and 100 is complete control. A dash response (-) indicated that no test result was recorded.

TABLE F

| Rate 250 g/ha | COMPOUND 3 |
|---|---|
| Flood Saita soi | |
| barnyard early | 100 |
| barnyard late | 85 |
| C. difformis ea | 80 |
| C. difformis la | 90 |
| Japoni rice 0 cm | 100 |
| Japoni rice 2 cm | 100 |
| L. procumben ea | 100 |
| L. procumben la | 100 |
| M. vaginalis ea | 100 |
| M. vaginalis la | 80 |
| S. juncoides 1. | 90 |
| S. juncoides 2. | 70 |

| Rate 125 g/ha | COMPOUND 3 |
|---|---|
| Flood Saita soi | |
| barnyard early | 100 |
| barnyard late | 70 |
| C. difformis ea | 85 |
| C. difformis la | 70 |
| Japoni rice 0 cm | 100 |
| Japoni rice 2 cm | 40 |
| L. procumben ea | 100 |
| L. procumben la | 100 |
| M. vaginalis ea | 100 |
| M. vaginalis la | 80 |
| S. juncoides 1. | 85 |
| S. juncoides 2. | 50 |

| Rate 64 g/ha | COMPOUND 2 | 3 |
|---|---|---|
| Flood Saita soi | | |
| barnyard early | 90 | 70 |
| barnyard late | 65 | 40 |
| C. difformis ea | 100 | 95 |
| C. difformis la | 70 | 40 |
| Japoni rice 0 cm | 100 | 95 |
| Japoni rice 2 cm | 75 | 70 |
| L. procumben ea | 100 | 100 |
| L. procumben la | 100 | 100 |
| M. vaginalis ea | 100 | 100 |
| M. vaginalis la | 80 | 80 |
| S. juncoides 1. | 75 | 70 |
| S. juncoides 2. | 65 | 50 |

| Rate 32 g/ha | COMPOUND 1 | 2 | 3 |
|---|---|---|---|
| Flood Saita soi | | | |
| barnyard early | 85 | 45 | 20 |
| barnyard late | 50 | 45 | 20 |
| C. difformis ea | 80 | 55 | 60 |
| C. difformis la | 85 | 50 | 40 |
| Japoni rice 0 cm | 90 | 75 | 40 |
| Japoni rice 2 cm | 65 | 5 | 0 |
| L. procumben ea | 100 | 100 | 100 |
| L. procumben la | 100 | 90 | 100 |
| M. vaginalis ea | 100 | 80 | 70 |
| M. vaginalis la | 70 | 75 | 70 |
| S. juncoides 1. | 80 | 65 | 50 |
| S. juncoides 2. | 60 | 40 | 30 |

| Rate 16 g/ha | COMPOUND 1 | 2 |
|---|---|---|
| Flood Saita soi | | |
| barnyard early | 40 | 20 |
| barnyard late | 65 | 45 |
| C. difformis ea | 80 | 50 |
| C. difformis la | 75 | 50 |
| Japoni rice 0 cm | 65 | 40 |
| Japoni rice 2 cm | 25 | 0 |
| L. procumben ea | 100 | 100 |
| L. procumben la | 100 | 100 |
| M. vaginalis ea | 90 | 75 |
| M. vaginalis la | 75 | 75 |
| S. juncoides 1. | 40 | 20 |
| S. juncoides 2. | 40 | 30 |

| Rate 8 g/ha | COMPOUND 1 | 2 |
|---|---|---|
| Flood Saita soi | | |
| barnyard early | 40 | 20 |
| barnyard late | 30 | 20 |
| C. difformis ea | 55 | 20 |
| C. difformis la | 50 | 20 |
| Japoni rice 0 cm | 35 | 10 |
| Japoni rice 2 cm | 0 | 0 |
| L. procumben ea | 100 | 100 |
| L. procumben la | 100 | 100 |
| M. vaginalis ea | 70 | 60 |
| M. vaginalis la | 70 | 65 |
| S. juncoides 1. | 40 | 10 |
| S. juncoides 2. | 40 | 0 |

| Rate 4 g/ha | COMPOUND 1 |
|---|---|
| Flood Saita soi | |
| barnyard early | 30 |
| barnyard late | 40 |
| C. difformis ea | 30 |
| C. difformis la | 20 |
| Japoni rice 0 cm | 20 |
| Japoni rice 2 cm | 5 |
| L. procumben ea | 100 |
| L. procumben la | 100 |
| M. vaginalis ea | 50 |
| M. vaginalis la | 65 |
| S. juncoides 1. | 20 |
| S. juncoides 2. | 30 |

Test G

Compounds evaluated in this test were formulated in a non-phytotoxic solvent mixture which included a surfactant and applied to the soil surface before plant seedlings emerged (preemergence application) and to plants that were in the one-to four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include annual bluegrass (*Poa annua*), black nightshade (*Solanum nigra*), blackgrass (*Alopecurus myosuroides*), chickweed (*Stellaria media*), deadnettle (*Lamium amplexicaule*), downy brome (*Bromus tectorum*), field violet (*Viola arvensis*), galium (*Galium aparine*), green foxtail (*Setaria viridis*), jointed goatgrass (*Aegilops cylindrica*), kochia (*Kochia scoparia*), lambsquarters (*Chenopodium album*), littleseed canarygrass (*Phalaris minor*), rape (*Brassica napus*), redroot pigweed (*Amaranthus retroflexus*), ryegrass (*Lolium multiflorum*), sentless chamonile (*Matricaria inodora*), speedwell (*Veronica persica*), spring barely (*Hordeum vulgare* cv. 'Klages'), spring wheat (*Triticum aestivum* cv. 'ERA'), sugar beet (*Beta vulgaris* cv. 'USl'), sunflower (*Helianthus annuus* cv. 'Russian Giant'), wild buckwheat (*Polygonum* convolvulus), wild mustard (*Sinapis arvensis*), wild oat (*Avena fatua*), windgrass (*Apera spica-venti*), winter barley (*Hordeum vulgare* cv. 'Igri') and winter wheat (*Triticum aestivum* cv. 'Talent').

Wild oat was treated at two growth stages. The first stage (1) was when the plant had two to three leaves. The second stage (2) was when the plant had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table G, are based upon a 0 to 100 scale where 0 is no effect and 100 is complete control. A dash response (-) means no test result.

TABLE G

| | COMPOUND | | | | | | | | | | | | | | | | |
|---|---|---|---|---|---|---|---|---|---|---|---|---|---|---|---|---|---|
| | 10 | 2 | 5 | 6 | 8 | 9 | 10 | 12 | 1 | 2 | 4 | 5 | 6 | 7 | 8 | 9 | 10 |
| | Rate 250 g/ha | Rate 125 g/ha | | | | | | | Rate 62 g/ha | | | | | | | | |
| | POSTEMERGENCE | | | | | | | | | | | | | | | | |
| Annual Bluegras | 30 | 85 | 100 | 65 | 100 | 40 | 20 | 20 | 100 | 60 | — | 70 | 50 | 100 | 100 | 50 | 10 |
| Blackgrass (2) | 30 | 45 | 30 | 20 | 70 | 45 | 20 | 20 | 55 | 35 | — | 25 | 20 | 50 | 60 | 40 | 20 |
| Blk Nightshade | 100 | 100 | 100 | 100 | 100 | 100 | 100 | 100 | 100 | 100 | 100 | 100 | 75 | 100 | 100 | 100 | 75 |
| Chickweed | 100 | 100 | 100 | 100 | 95 | 100 | 100 | 100 | 100 | 100 | 100 | 100 | 75 | 100 | 100 | 100 | 100 |
| Deadnettle | 100 | 100 | 100 | 100 | 100 | 100 | 100 | 100 | 100 | 100 | 100 | 100 | 100 | 100 | 100 | 100 | 100 |
| Downy brome | 50 | 50 | 40 | 55 | 75 | 25 | 30 | 20 | 60 | 40 | — | 50 | 30 | 100 | 75 | 25 | 20 |
| Field violet | 100 | 100 | 60 | 70 | 100 | 100 | 100 | 75 | 100 | 100 | 100 | 50 | 70 | 100 | 100 | 70 | 70 |
| Galium (2) | 100 | 40 | 50 | 60 | 60 | 70 | 75 | 98 | 65 | 30 | 60 | 40 | 30 | 55 | 60 | 70 | 60 |
| Green foxtail | 100 | 100 | 100 | 75 | 100 | 100 | 100 | 100 | 75 | 100 | — | 65 | 60 | 100 | 100 | 100 | 100 |
| Jointed Goatgra | 30 | 40 | 30 | 40 | 100 | 30 | 20 | 30 | 40 | 30 | — | 30 | 20 | 100 | 100 | 20 | 10 |
| Kochia | 85 | 100 | 100 | 75 | 100 | 100 | 100 | 100 | 65 | 65 | 65 | 100 | 60 | 50 | 100 | 100 | 70 |
| Lambsquarters | 100 | 100 | 100 | 95 | 100 | 100 | 100 | 100 | 100 | 100 | 100 | 100 | 60 | 100 | 100 | 100 | 100 |
| LS Canarygrass | 100 | 100 | 60 | 70 | 100 | 70 | 45 | 30 | 100 | 40 | — | 40 | 50 | 100 | 100 | 50 | 40 |
| Rape | — | — | — | 100 | — | — | — | 40 | 100 | — | — | — | 70 | — | — | — | — |
| Redroot Pigweed | 100 | 100 | 100 | 65 | 100 | 100 | 100 | 100 | 100 | 70 | 100 | 100 | 30 | 100 | 100 | 100 | 100 |
| Russian Thistle | 100 | 100 | 100 | — | 80 | 100 | 100 | 100 | — | 100 | 100 | 100 | 60 | 100 | 100 | 80 | 85 |
| Ryegrass | 20 | 20 | 20 | 15 | 20 | 5 | 0 | 0 | 30 | 20 | — | 20 | 10 | 15 | 25 | 0 | 0 |
| Scentless Chamo | 95 | 100 | 100 | 100 | 100 | 100 | 75 | 100 | 100 | 100 | 60 | 100 | 65 | 100 | 100 | 100 | 70 |
| Speedwell | — | — | — | — | — | — | — | — | — | — | — | — | — | — | — | — | — |
| Spring Barley | 30 | 40 | 40 | 50 | 85 | 10 | 10 | 0 | 60 | 30 | 20 | 30 | 40 | 100 | 60 | 5 | 20 |
| Sugar beet | — | — | — | 10 | — | — | — | 100 | 100 | — | — | — | 10 | — | — | — | — |
| Sunflower | — | — | — | 70 | — | — | — | 100 | 100 | — | — | — | 40 | — | — | — | — |
| Veronica hedera | 100 | 100 | 100 | — | 100 | 100 | 100 | 100 | 100 | 100 | 100 | 100 | 20 | 100 | 100 | 100 | 100 |
| Wheat (Spring) | 30 | 40 | 30 | 40 | 100 | 40 | 20 | 20 | 30 | 30 | 25 | 20 | 30 | 100 | 85 | 30 | 10 |
| Wheat (Winter) | 20 | 60 | 40 | 20 | 95 | 20 | 15 | 20 | 40 | 30 | 30 | 30 | 15 | 100 | 100 | 20 | 10 |
| Wild buckwheat | 100 | 100 | 55 | 10 | 50 | 100 | — | 40 | 60 | 70 | 50 | 40 | 10 | 100 | 70 | 100 | 100 |
| Wild mustard | 100 | 100 | 100 | 70 | 100 | 100 | 100 | 100 | 100 | 100 | — | 100 | 75 | — | 70 | 60 | 100 |
| Wild oat (1) | 65 | 100 | 100 | 75 | 100 | 100 | 40 | 100 | 95 | 100 | — | 100 | 70 | 100 | 100 | 60 | 30 |
| Wild oat (2) | — | — | — | — | — | — | — | — | — | — | — | — | — | — | — | — | — |
| Windgrass | 45 | 50 | 55 | 45 | 95 | 60 | 20 | 30 | 100 | 30 | — | 30 | 45 | 85 | 100 | 50 | 20 |
| Winter Barley | 30 | 30 | 20 | 55 | 45 | 10 | 10 | 0 | 50 | 20 | 20 | 20 | 30 | 85 | 40 | 15 | 10 |

| | COMPOUND | | | | | | | | | | | | | |
|---|---|---|---|---|---|---|---|---|---|---|---|---|---|---|
| | 12 | 30 | 1 | 2 | 4 | 5 | 6 | 7 | 8 | 9 | 10 | 12 | 30 | 1 | 2 |
| | Rate 62 g/ha | Rate 31 g/ha | | | | | | | | | | | | | |
| | POSTEMERGENCE | | | | | | | | | | | | | PREEMERGENCE | |
| Annual Bluegras | 20 | 100 | 60 | 50 | — | 30 | 10 | 100 | 100 | 30 | 20 | 10 | 100 | 0 | 0 |
| Blackgrass (2) | 30 | 60 | 50 | 30 | — | 20 | 10 | 40 | 50 | 30 | 20 | 15 | 50 | 0 | 15 |
| Blk Nightshade | 100 | 100 | 100 | 100 | 100 | 100 | 75 | 100 | 100 | 100 | 75 | 100 | 100 | 35 | 0 |
| Chickweed | 100 | 100 | 100 | 100 | 100 | 100 | 60 | 100 | 80 | 100 | 100 | 70 | 100 | 15 | 10 |
| Deadnettle | 100 | 100 | 100 | 100 | 60 | 100 | 75 | 65 | 75 | 100 | 100 | 70 | 100 | 60 | 20 |
| Downy brome | 10 | 95 | 50 | 30 | — | 30 | 20 | 65 | 50 | 20 | 10 | 15 | 75 | 0 | 5 |
| Field violet | 60 | 70 | 100 | 65 | 60 | — | 50 | 60 | 100 | 50 | 60 | 50 | — | | |
| Galium (2) | 70 | 40 | 65 | 30 | 60 | 20 | 20 | 50 | 50 | 60 | 50 | 50 | 40 | 0 | 5 |
| Green foxtail | 100 | 100 | 70 | 70 | — | 65 | 55 | 100 | 75 | 100 | 80 | 65 | 100 | 10 | 0 |
| Jointed Goatgra | 20 | 100 | 30 | 20 | — | 15 | 10 | 45 | 75 | 10 | 0 | 20 | 50 | 0 | 0 |
| Kochia | 55 | 80 | 60 | 55 | 60 | 60 | 50 | 20 | 60 | 70 | 60 | 40 | 70 | 15 | 40 |
| Lambsquarters | 100 | 100 | 100 | 100 | 100 | 100 | 50 | 100 | 100 | 100 | 100 | 75 | 100 | 85 | 95 |
| LS Canarygrass | 20 | 100 | 100 | 30 | — | 30 | 30 | 100 | 100 | 35 | 30 | 15 | 100 | 0 | 0 |
| Rape | 40 | — | 70 | — | — | — | 60 | — | — | — | — | 20 | — | | |
| Redroot Pigweed | 100 | 100 | 100 | 50 | — | 75 | 30 | 70 | 50 | 80 | 70 | 70 | 100 | 80 | — |
| Russian Thistle | — | 100 | 100 | 75 | 100 | 75 | 20 | 100 | 70 | 80 | 70 | — | 80 | | |
| Ryegrass | 0 | 30 | 20 | 10 | — | 10 | 0 | 15 | 20 | 0 | 0 | 0 | 50 | 0 | 0 |
| Scentless Chamo | 60 | 100 | 100 | 75 | 50 | 70 | 60 | 100 | 100 | 100 | 60 | 60 | 100 | 0 | 0 |
| Speedwell | — | — | 100 | — | — | — | — | — | — | — | — | — | — | 100 | 70 |
| Spring Barley | 0 | 80 | 45 | 20 | 10 | 20 | 30 | 100 | 65 | 0 | 5 | 0 | 50 | 0 | 0 |
| Sugar beet | 100 | — | 100 | — | — | — | 0 | — | — | — | — | — | 100 | — | |

TABLE G-continued

| | | | | | | | | | | | | | | | |
|---|---|---|---|---|---|---|---|---|---|---|---|---|---|---|---|
| Sunflower | 100 | — | 100 | — | — | — | 30 | — | — | — | — | 85 | — | | |
| Veronica hedera | 100 | 100 | 100 | 70 | 100 | 100 | 10 | 100 | 60 | 70 | 60 | 75 | 100 | | |
| Wheat (Spring) | 20 | 100 | 20 | 20 | 10 | 20 | 20 | 95 | 75 | 20 | 10 | 20 | 70 | 0 | 0 |
| Wheat (Winter) | 10 | 100 | 30 | 20 | 20 | 20 | 15 | 55 | 60 | 10 | 0 | 10 | 85 | 0 | 0 |
| Wild buckwheat | 10 | 10 | 100 | 50 | 40 | 50 | 0 | 100 | 60 | 75 | 20 | 10 | 10 | 0 | 20 |
| Wild mustard | 50 | 100 | 100 | 70 | — | 80 | 70 | 55 | — | 30 | 70 | 30 | 100 | 0 | 10 |
| Wild oat (1) | 60 | 100 | 50 | 100 | — | 65 | 50 | 100 | 100 | 40 | 20 | 20 | 100 | 0 | 0 |
| Wild oat (2) | — | — | 100 | 45 | — | — | — | — | — | — | — | — | — | | |
| Windgrass | 30 | 100 | 70 | 10 | — | 20 | 20 | 55 | 80 | 10 | 10 | 20 | 60 | 0 | 0 |
| Winter Barley | 10 | 70 | 30 | 20 | 10 | 30 | 20 | 55 | 30 | 0 | 0 | 0 | 30 | 0 | 0 |

| | COMPOUND | | | | | | | | | | | | | | | |
|---|---|---|---|---|---|---|---|---|---|---|---|---|---|---|---|---|
| | 1 | 2 | 4 | 5 | 6 | 7 | 8 | 9 | 30 | 1 | 2 | 1 | 2 | 4 | 6 | 7 | 8 |
| | Rate 16 g/ha | | | | | | | | | | | Rate 8 g/ha | | | | | |
| | POSTEMERGENCE | | | | | | | | | PREEMERGENCE | | POSTEMERGENCE | | | | | |
| Annual Bluegras | 50 | 10 | — | 20 | 40 | 70 | 80 | 20 | 85 | 0 | 0 | 50 | — | — | 10 | 40 | 55 |
| Blackgrass (2) | 40 | 20 | — | 10 | 35 | 20 | 30 | 20 | 30 | 0 | 5 | 30 | 5 | — | 10 | 10 | 20 |
| Blk Nightshade | 100 | 75 | 100 | 100 | 55 | 100 | 75 | 100 | 100 | 35 | 0 | 100 | 85 | 100 | 40 | 100 | 75 |
| Chickweed | 100 | 100 | 100 | 100 | 75 | 80 | 70 | 75 | 100 | 20 | 0 | 55 | 85 | 100 | 60 | 70 | 50 |
| Deadnettle | 100 | 100 | 65 | 100 | 45 | 50 | 65 | 65 | 70 | 15 | 0 | 100 | 50 | 60 | 30 | 30 | 30 |
| Downy brome | 30 | 20 | — | 20 | 0 | 40 | 30 | 10 | 50 | 0 | 0 | 20 | 10 | — | 0 | 20 | 20 |
| Field violet | 100 | 50 | — | 30 | 45 | 30 | 60 | 50 | 60 | | | 75 | 15 | 60 | 30 | 40 | 50 |
| Galium (2) | 60 | 15 | 50 | 30 | 20 | 50 | 30 | 60 | 30 | 0 | 0 | 50 | 15 | 40 | 10 | 30 | 10 |
| Green foxtail | 65 | 50 | — | 100 | 55 | 100 | 70 | 70 | 100 | 0 | 0 | 65 | 75 | — | 55 | 60 | 65 |
| Jointed Goatgra | 20 | 10 | — | 10 | 0 | 20 | 30 | 10 | 40 | 0 | 0 | 20 | 0 | — | 0 | 10 | 10 |
| Kochia | 60 | 25 | 55 | 60 | 40 | 10 | 50 | 40 | 55 | 10 | 30 | 55 | — | 50 | 30 | 10 | 30 |
| Lambsquarters | 100 | 100 | 100 | 100 | 20 | 100 | 100 | 100 | 100 | 70 | 95 | 100 | 30 | 65 | 20 | 75 | 95 |
| LS Canarygrass | 100 | 20 | — | 20 | 40 | 50 | 100 | 30 | 100 | 0 | 0 | 100 | 5 | — | 40 | 40 | 65 |
| Rape | 50 | — | — | — | — | — | — | — | — | | | 40 | — | — | — | — | — |
| Redroot Pigweed | 100 | 65 | 60 | 60 | 20 | 60 | 30 | 80 | 100 | 75 | 65 | 60 | 25 | 50 | 10 | 50 | 30 |
| Russian Thistle | 100 | 75 | 70 | 80 | 0 | 100 | 60 | 80 | 70 | | | 100 | — | 60 | 0 | 75 | 50 |
| Ryegrass | 20 | 10 | — | 5 | 0 | 10 | 10 | 0 | 20 | 0 | 0 | 10 | 0 | — | 0 | 5 | 10 |
| Scentless Chamo | 50 | 75 | 50 | 60 | 60 | 75 | 70 | 60 | 75 | — | 0 | 65 | 25 | 50 | 50 | 60 | 60 |
| Speedwell | 100 | — | — | — | — | — | — | — | — | 60 | 60 | 65 | 35 | — | — | — | — |
| Spring Barley | 20 | 20 | 10 | 20 | 0 | 100 | 30 | 0 | 30 | 0 | 0 | 10 | 0 | 10 | 0 | 40 | 10 |
| Sugar beet | 100 | — | — | — | — | — | — | — | — | | | 100 | — | — | — | — | — |
| Sunflower | 65 | — | — | — | — | — | — | — | — | | | 65 | — | — | — | — | — |
| Veronica hedera | 100 | 75 | 70 | 100 | 30 | 65 | 60 | 75 | 70 | | | 100 | — | 50 | 30 | 60 | 60 |
| Wheat (Spring) | 10 | 20 | 10 | 20 | 10 | 65 | 30 | 10 | 70 | 0 | 0 | 10 | 0 | 10 | 10 | 30 | 15 |
| Wheat (Winter) | 20 | 10 | 10 | 15 | 0 | 50 | 30 | 5 | 50 | 0 | 0 | 10 | 0 | 10 | 0 | 30 | 20 |
| Wild buckwheat | 60 | 30 | 20 | 40 | 10 | 50 | 10 | 60 | 20 | 0 | 5 | 40 | 0 | 25 | 0 | 30 | 0 |
| Wild mustard | 100 | 65 | — | 60 | — | — | 60 | 30 | 100 | 0 | 5 | 100 | — | — | 30 | 50 | 50 |
| Wild oat (1) | 70 | 100 | — | 75 | 30 | 100 | 75 | 30 | 85 | 0 | 0 | 30 | 10 | — | 20 | 50 | 40 |
| Wild oat (2) | 85 | 45 | — | — | — | — | — | — | — | | | 75 | 15 | — | — | — | — |
| Windgrass | 50 | 10 | — | 10 | 30 | 30 | 50 | 20 | 50 | 0 | 0 | 30 | 0 | — | 30 | 40 | 50 |
| Winter Barley | 20 | 10 | 10 | 20 | 5 | 55 | 20 | 0 | 20 | 0 | 0 | 10 | 0 | 10 | 0 | 30 | 10 |

| | COMPOUND | | | | | | | | | | | |
|---|---|---|---|---|---|---|---|---|---|---|---|---|
| | 9 | 30 | 1 | 2 | 1 | 2 | 6 | 7 | 9 | 30 | 1 | 2 |
| | Rate 8 g/ha | | | | Rate 4 g/ha | | | | | | | |
| | POSTEMERGENCE | | PREEMERGENCE | | POSTEMERGENCE | | | | | | PREEMERGENCE | |
| Annual Bluegras | 10 | — | 0 | 0 | 30 | — | 10 | 20 | 10 | 10 | 0 | 0 |
| Blackgrass (2) | 10 | 20 | 0 | 0 | 40 | 5 | 10 | 10 | 0 | 10 | 0 | 0 |
| Blk Nightshade | 100 | 75 | 0 | 0 | 100 | 75 | 30 | 65 | 75 | 70 | 0 | 0 |
| Chickweed | 100 | 80 | 0 | 0 | 50 | 60 | 50 | 60 | 50 | 70 | 0 | 0 |
| Deadnettle | 100 | 55 | 5 | 0 | 100 | 45 | 20 | 20 | 10 | 30 | 0 | 0 |
| Downy brome | 0 | 40 | 0 | 0 | 20 | 0 | 0 | 10 | 0 | 20 | 0 | 0 |
| Field violet | 60 | 50 | | | 60 | 0 | 30 | 30 | 40 | 40 | | |
| Galium (2) | 60 | 20 | 0 | 0 | 30 | 15 | 0 | 20 | 10 | 10 | 0 | 0 |
| Green foxtail | 100 | 65 | 0 | 0 | 60 | 60 | 30 | 45 | 45 | 50 | 0 | 0 |
| Jointed Goatgra | 10 | 30 | 0 | 0 | 10 | 0 | 0 | 5 | 0 | 20 | 0 | 0 |
| Kochia | 20 | 35 | 0 | 0 | 30 | — | 20 | 0 | 10 | 30 | 0 | 0 |
| Lambsquarters | 100 | 70 | 50 | 65 | 60 | 25 | 15 | 70 | 65 | 50 | 35 | 25 |
| LS Canarygrass | 25 | 65 | 0 | 0 | 55 | 0 | 20 | 30 | 10 | 60 | 0 | 0 |
| Rape | — | — | | | 30 | — | — | — | — | — | | |
| Redroot Pigweed | 70 | 70 | 60 | 25 | 50 | 5 | 10 | 30 | 30 | 40 | 50 | 0 | 10 |
| Russian Thistle | 40 | 70 | | | 70 | — | 0 | 70 | 10 | 50 | | |
| Ryegrass | 0 | 20 | 0 | 0 | 5 | 0 | 0 | 0 | 0 | 10 | 0 | 0 |
| Scentless Chamo | 60 | 70 | 0 | 0 | 55 | 45 | 10 | 50 | 50 | 60 | 0 | 0 |
| Speedwell | — | — | 20 | 30 | 40 | 15 | — | — | — | — | 15 | 15 |
| Spring Barley | 10 | 20 | 0 | 0 | 5 | 0 | 0 | 10 | 0 | 5 | 0 | 0 |

TABLE G-continued

|  |  |  |  |  |  |  |  |  |  |  |  |
|---|---|---|---|---|---|---|---|---|---|---|---|
| Sugar beet | — | — |  |  | 100 | — | — | — | — | — |  |  |
| Sunflower | — | — |  |  | 50 | — | — | — | — | — |  |  |
| Veronica hedera | 100 | 60 |  |  | 100 | — | 30 | 50 | 30 | 50 |  |  |
| Wheat (Spring) | 10 | 40 | 0 | 0 | 5 | 0 | 5 | 30 | 5 | 30 | 0 | 0 |
| Wheat (Winter) | 5 | 30 | — | 0 | 5 | 0 | 0 | 20 | 0 | 10 | 0 | 0 |
| Wild buckwheat | 40 | 10 | — | 0 | 50 | 0 | 0 | 35 | 0 | 0 | 0 | 0 |
| Wild mustard | 30 | 100 | 0 | 0 | 100 | 15 | 15 | 10 | 0 | 60 | 0 | 0 |
| Wild oat (1) | 20 | 75 | 0 | 0 | 20 | 5 | 10 | 30 | 10 | 30 | 0 | 0 |
| Wild oat (2) | — | — |  |  | — | 0 | — | — | — | — |  |  |
| Windgrass | 10 | 30 | 0 | 0 | 10 | 0 | 0 | 10 | 0 | 20 | 0 | 0 |
| Winter Barley | 10 | 10 | 0 | 0 | 10 | 0 | 0 | 10 | 0 | 5 | 0 | 0 |

Test H

Seeds, tubers, or plant parts of alexandergrass (*Brachiairia plantaginea*), alfalfa (*Medicago sativa*), bermudagrass (*Cynodon dactylon*), broadleaf signal grass (*Brachiaria plantyphylla*), common purslane (*Portulaca oleracea*), common ragweed (*Ambrosia elatior*), cotton (*Gossypium hirsutum*), dallisgrass (*Paspalum dilatatum*), goosegrass (*Eleusine indica*), guineagrass (*Panicum maximum*), itchgrass (*Rottboellia exaltata*), johnson grass (*Sorghum halepense*), large crabgrass (*Digitaria sanguinalis*), peanuts (*Arachis hypogaea*), pitted morningglory (*Ipomoea lacunosa*), purple nutsedge (*Cyperus rotundus*), sandbur (*Cenchrus echinatus*), sourgrass (*Trichachne insularis*), surinam grass (*Brachiaria decumbens*) and texas panicum (*Panicum Texas*) were planted into greenhouse pots of flats containing greenhouse planting medium. Plant species were grown in separate pots or individual compartments. Preemergence applications were made within one day of planting the seed or plant part. Postemergence applications were applied when the plants were in the two to four leaf stage (three to twenty cm).

Test chemicals were formulated in a non-phytotoxic solvent mixture which included a surfactant and applied preemergence and postemergence to the plants. Untreated control plants and treated plants were placed in the greenhouse and visually evaluated for injury 13 to 21 days after herbicide application. Plant response ratings, summarized in Table H, are based on a 0 to 100 scale where 0 is no injury and 100 is complete control. A dash (-) response means no test result.

TABLE H

| Rate 1000 g/ha POSTEMERGENCE | COMPOUND 1 | Rate 1000 g/ha PREEMERGENCE | COMPOUND 1 |
|---|---|---|---|
| Alexandergrass | — | Alexandergrass | — |
| ADexandergrass | — | Bermudagrass | — |
| Bermudagrass | — | Brdlf Sgnlgrass | — |
| Brdlf Sgnlgrass | — | Cmn Purslane | — |
| Cmn Purslane | — | Cmn Ragweed | — |
| Cmn Ragweed | — | Cotton | — |
| Cotton | — | Dallisgrass | — |
| Dallisgrass | — | Goosegrass | — |
| Goosegrass | — | Guinea Grass | — |
| Guineagrass | — | Guineagrass | — |
| Itchgrass | — | Itchgrass | — |
| Johnson grass | — | Johnson grass | — |
| Large Crabgrass | — | Johnsongrass | — |
| Peanuts | — | Large Crabgrass | — |
| Pit Morninglory | — | Peanuts | — |
| Purple Nutsedge | — | Pit Morninglory | — |
| Sandbur | — | Purple Nutsedge | — |
| Sourgrass | — | Sandbur | — |
| Sugarcane | 90 | Sourgrass | — |
| Surinam grass | — | Sugarcane | 35 |
|  |  | Surinam grass | — |

| Rate 500 g/ha POSTEMERGENCE | COMPOUND 1 | Rate 500 g/ha PREEMERGENCE | COMPOUND 1 |
|---|---|---|---|
| Alexandergrass | — | Alexandergrass | — |
| ADexandergrass | — | Bermudagrass | — |
| Bermudagrass | — | Brdlf Sgnlgrass | — |
| Brdlf Sgnlgrass | — | Cmn Purslane | — |
| Cmn Purslane | — | Cmn Ragweed | — |
| Cmn Ragweed | — | Cotton | — |
| Cotton | — | Dallisgrass | — |
| Dallisgrass | — | Goosegrass | — |
| Goosegrass | — | Guinea Grass | — |
| Guineagrass | — | Guineagrass | — |
| Itchgrass | — | Itchgrass | — |
| Johnson grass | — | Johnson grass | — |
| Large Crabgrass | — | Johnsongrass | — |
| Peanuts | — | Large Crabgrass | — |

TABLE H-continued

| | | | | | | | | | | |
|---|---|---|---|---|---|---|---|---|---|---|
| Pit Morninglory | — | | Peanuts | — | | | | | | |
| Purple Nutsedge | — | | Pit Morninglory | — | | | | | | |
| Sandbur | — | | Purple Nutsedge | — | | | | | | |
| Sourgrass | — | | Sandbur | — | | | | | | |
| Sugarcane | 80 | | Sourgrass | — | | | | | | |
| Surinam grass | — | | Sugarcane | 10 | | | | | | |
| | | | Surinam grass | — | | | | | | |

| Rate 250 g/ha | | | | | COMPOUND | | | | | |
|---|---|---|---|---|---|---|---|---|---|---|
| POSTEMERGENCE | 1 | 2 | 3 | 4 | 5 | 6 | 12 | 14 | 24 | 30 |
| Alexandergrass | 100 | 90 | 95 | 95 | 90 | 70 | 75 | 75 | 90 | 85 |
| ADexandergrass | 98 | — | — | — | — | — | — | — | — | — |
| Bermudagrass | 95 | 75 | 85 | 90 | 65 | 65 | 65 | 65 | 70 | 70 |
| Brdlf Sgnlgrass | 100 | 98 | 98 | 100 | 50 | 70 | 70 | 65 | 85 | 80 |
| Cmn Purslane | 100 | 80 | 65 | 85 | 65 | 35 | 40 | 60 | 0 | 0 |
| Cmn Ragweed | 100 | 100 | 95 | 90 | 85 | 70 | 70 | 75 | 75 | — |
| Cotton | 100 | 98 | 98 | 98 | 65 | 100 | 95 | 75 | 90 | 98 |
| Dallisgrass | 100 | 90 | 95 | 90 | 65 | 65 | 80 | 80 | 90 | 90 |
| Goosegrass | 85 | 40 | 50 | 90 | 65 | 70 | 65 | 20 | 85 | 60 |
| Guineagrass | 98 | 80 | 50 | 65 | 75 | 60 | 80 | 80 | 80 | 25 |
| Itchgrass | 90 | — | — | — | 80 | 55 | 80 | 75 | 75 | 70 |
| Johnson grass | 100 | 98 | 65 | — | 75 | 60 | 75 | 70 | 50 | 85 |
| Large Crabgrass | 100 | 75 | 80 | 80 | 70 | 75 | 65 | 70 | 85 | 98 |
| Peanuts | 40 | 60 | 50 | 10 | 70 | 40 | 40 | 30 | 20 | 10 |
| Pit Morninglory | 100 | 80 | 85 | 95 | 75 | 75 | 60 | 50 | 80 | 85 |
| Purple Nutsedge | 75 | 75 | 70 | 75 | 20 | 25 | 30 | 65 | 20 | 45 |
| Sandbur | 100 | 60 | — | 50 | 75 | 65 | 75 | 35 | 80 | 70 |
| Sourgrass | 90 | 75 | 65 | 70 | 65 | 70 | 50 | 60 | 85 | 75 |
| Sugarcane | 80 | — | — | — | — | — | — | — | — | — |
| Surinam grass | 100 | 90 | 75 | 90 | 80 | 70 | 75 | 75 | 75 | 45 |

| Rate 250 g/ha PRE- | | | | | COMPOUND | | | | | |
|---|---|---|---|---|---|---|---|---|---|---|
| EMERGENCE | 1 | 2 | 3 | 4 | 5 | 6 | 12 | 14 | 16 | 24 | 30 |
| Alexandergrass | 95 | 98 | 0 | 0 | 100 | 100 | 100 | 100 | 80 | 10 | 100 |
| Bermudagrass | 98 | 100 | 98 | 98 | 100 | 100 | 100 | 100 | 100 | 95 | 100 |
| Brdlf Sgnlgrass | 95 | 100 | — | 0 | 90 | 100 | 98 | 80 | 98 | 40 | 98 |
| Cmn Purslane | 100 | 100 | 95 | 100 | 100 | 100 | 100 | 100 | 100 | 75 | 30 |
| Cmn Ragweed | 100 | 100 | 100 | 100 | — | 100 | — | — | 100 | — | 100 |
| Cotton | 100 | 10 | 15 | 0 | 30 | 20 | 50 | 90 | 10 | 0 | 98 |
| Dallisgrass | 98 | 100 | 98 | 20 | 100 | 100 | 100 | 100 | 100 | 0 | 100 |
| Goosegrass | 80 | 100 | 98 | 98 | 100 | 100 | 100 | 100 | 98 | 100 | 100 |
| Guinea Grass | — | — | — | — | — | — | — | — | — | — | — |
| Guineagrass | 95 | 95 | 20 | 0 | 95 | 100 | 80 | 95 | 80 | 10 | 65 |
| Itchgrass | 40 | 50 | 0 | 0 | 0 | 10 | 10 | 30 | 0 | 0 | 25 |
| Johnson grass | 85 | 90 | 80 | 70 | 95 | 98 | 95 | 95 | 90 | 35 | 100 |
| Johnsongrass | — | — | — | — | — | — | — | — | — | — | — |
| Large Crabgrass | 65 | 100 | 100 | 98 | 100 | 100 | 100 | 100 | 100 | 35 | 98 |
| Peanuts | 40 | 80 | 5 | 0 | 60 | 35 | 50 | 40 | 0 | 20 | 70 |
| Pit Morninglory | 80 | 95 | 20 | 35 | 80 | 95 | 85 | 80 | 90 | 70 | 90 |
| Purple Nutsedge | 65 | 20 | 5 | 10 | 0 | 30 | 30 | 60 | 10 | 5 | 30 |
| Sandbur | 100 | 80 | 30 | 50 | 98 | 85 | 98 | 65 | 85 | 0 | 90 |
| Sourgrass | 100 | 100 | 100 | 90 | 100 | 100 | 100 | 100 | 100 | 95 | 100 |
| Sugarcane | 5 | — | — | — | — | — | — | — | — | — | — |
| Surinam grass | 100 | 85 | 40 | 5 | 100 | 100 | 100 | 98 | 98 | 10 | 10 |

| Rate 125 g/ha | | | | | COMPOUND | | | |
|---|---|---|---|---|---|---|---|---|
| POSTEMERGENCE | 1 | 2 | 3 | 4 | 5 | 12 | 14 | 30 |
| Alexandergrass | 100 | 85 | 70 | 75 | 80 | 75 | 75 | 80 |
| ADexandergrass | — | — | — | — | — | — | — | — |
| Bermudagrass | 95 | 75 | 70 | 90 | 60 | 50 | 65 | 55 |
| Brdlf Sgnlgrass | 100 | 90 | 90 | 90 | 50 | 50 | 65 | 75 |
| Cmn Purslane | 100 | 75 | 65 | 75 | 50 | 30 | 60 | 0 |
| Cmn Ragweed | 100 | 98 | 80 | 95 | 80 | 65 | 80 | — |
| Cotton | 100 | 98 | 100 | 80 | 65 | 75 | 85 | 35 |
| Dallisgrass | 100 | 85 | 90 | 85 | 75 | 75 | 80 | 75 |
| Goosegrass | 85 | 40 | 30 | 50 | 65 | 20 | 20 | 40 |
| Guineagrass | 90 | 75 | 50 | 40 | 80 | 75 | 80 | 20 |
| Itchgrass | 90 | — | — | — | 80 | 75 | 70 | 55 |
| Johnson grass | 100 | 90 | 65 | 90 | 80 | 75 | 70 | 65 |

TABLE H-continued

| | | | | | | | | |
|---|---|---|---|---|---|---|---|---|
| Large Crabgrass | 95 | 75 | — | 80 | 40 | 65 | 70 | 85 |
| Peanuts | 35 | 10 | 10 | 10 | — | 35 | 30 | 10 |
| Pit Morninglory | 100 | 75 | 85 | 95 | 65 | 30 | 35 | 80 |
| Purple Nutsedge | 98 | 75 | 50 | 50 | 0 | 30 | 65 | 25 |
| Sandbur | 98 | 30 | 10 | 40 | 75 | 10 | 10 | 60 |
| Sourgrass | 80 | 75 | 50 | 30 | 65 | 50 | 60 | 75 |
| Sugarcane | — | — | — | — | — | — | — | — |
| Surinam grass | 95 | 90 | 50 | 80 | 85 | 75 | 75 | 35 |

| Rate 125 g/ha | COMPOUND | | | | | | | |
|---|---|---|---|---|---|---|---|---|
| PREEMERGENCE | 1 | 2 | 3 | 4 | 5 | 6 | 12 | 14 | 16 |
| Alexandergrass | 95 | 85 | 0 | 0 | 98 | 98 | 90 | 90 | 25 |
| Bermudagrass | 98 | 100 | 80 | 80 | 100 | 100 | 95 | 90 | 98 |
| Brdlf Sgnlgrass | 35 | 75 | 30 | 0 | 80 | 85 | 95 | 50 | 0 |
| Cmn Purslane | 100 | 80 | 90 | 100 | 100 | — | 100 | 100 | 100 |
| Cmn Ragweed | 100 | 100 | 100 | 100 | — | 100 | — | — | 100 |
| Cotton | 60 | 0 | 0 | 0 | 30 | 0 | 10 | 50 | 10 |
| Dallisgrass | 95 | 100 | 0 | 0 | 100 | 90 | 95 | 100 | 100 |
| Goosegrass | 100 | 100 | 98 | 90 | 100 | 100 | 98 | 100 | 100 |
| Guinea Grass | — | — | — | — | — | — | — | — | — |
| Guineagrass | 65 | 90 | 0 | 0 | 85 | 90 | 50 | 40 | 45 |
| Itchgrass | 10 | 40 | 0 | 0 | 0 | 0 | 10 | 30 | 0 |
| Johnson grass | 75 | 40 | 40 | 0 | 80 | 90 | 0 | 75 | 20 |
| Johnsongrass | — | — | — | — | — | — | — | — | — |
| Large Crabgrass | 100 | 100 | 90 | 100 | 100 | 100 | 100 | 100 | 98 |
| Peanuts | 40 | 40 | 0 | 0 | 60 | 30 | 50 | 10 | 0 |
| Pit Morninglory | 80 | 75 | 35 | 30 | 80 | 95 | 75 | 50 | 80 |
| Purple Nutsedge | 0 | 0 | 5 | 5 | 0 | 25 | 30 | 20 | 0 |
| Sandbur | 85 | 65 | 20 | 0 | 95 | 40 | 50 | — | 70 |
| Sourgrass | 100 | 100 | 90 | 70 | 100 | 100 | 100 | 100 | 100 |
| Sugarcane | — | — | — | — | — | — | — | — | — |
| Surinam grass | 98 | 10 | 0 | 0 | 100 | 98 | 90 | 85 | 90 |

| Rate 64 g/ha | COMPOUND | | | | | |
|---|---|---|---|---|---|---|
| POSTEMERGENCE | 1 | 2 | 3 | 4 | 5 | 30 |
| Alexandergrass | 100 | 85 | 80 | 75 | 80 | 80 |
| ADexandergrass | — | — | — | — | — | — |
| Bermudagrass | 95 | 75 | 40 | 80 | 60 | 45 |
| Brdlf Sgnlgrass | 100 | 85 | 90 | 90 | 50 | 65 |
| Cmn Purslane | 100 | 75 | 65 | 70 | 50 | 0 |
| Cmn Ragweed | 100 | 98 | 60 | 90 | 60 | — |
| Cotton | 100 | 98 | 70 | 90 | 65 | 35 |
| Dallisgrass | 100 | 75 | 70 | 70 | 80 | 70 |
| Goosegrass | 75 | 40 | 35 | 30 | 65 | 40 |
| Guineagrass | 80 | 50 | — | 50 | 65 | 0 |
| Itchgrass | 100 | — | — | — | 75 | 45 |
| Johnson grass | 100 | 75 | 65 | 75 | 80 | 50 |
| Large Crabgrass | 90 | 60 | 60 | 90 | 40 | 75 |
| Peanuts | 25 | 5 | 0 | 10 | 60 | 5 |
| Pit Morninglory | 100 | 60 | 70 | 90 | 65 | 60 |
| Purple Nutsedge | 65 | 75 | 10 | 35 | 0 | 20 |
| Sandbur | 75 | — | 0 | 20 | 40 | 40 |
| Sourgrass | 95 | 60 | 30 | 35 | 60 | 75 |
| Sugarcane | — | — | — | — | — | — |
| Surinam grass | 90 | 65 | 30 | 40 | 70 | 35 |

| Rate 64 g/ha | COMPOUND | | | | | | | |
|---|---|---|---|---|---|---|---|---|
| PREEMERGENCE | 1 | 2 | 3 | 4 | 5 | 6 | 16 | 30 |
| Alexandergrass | 90 | 60 | 0 | 0 | 30 | 0 | 0 | 20 |
| Bermudagrass | 98 | 100 | 50 | 75 | 95 | 90 | 85 | 100 |
| Brdlf Sgnlgrass | 0 | 10 | 20 | 0 | 50 | 5 | 0 | 0 |
| Cmn Purslane | 10 | 60 | 65 | 50 | 100 | — | 100 | 0 |
| Cmn Ragweed | 100 | 100 | 80 | 100 | — | 100 | 100 | 100 |
| Cotton | 20 | 0 | 0 | 0 | 30 | 0 | 0 | 40 |
| Dallisgrass | 80 | 98 | — | 0 | 100 | 90 | 85 | 70 |
| Goosegrass | 100 | 98 | 50 | 98 | 100 | 98 | 98 | 100 |
| Guinea Grass | — | — | — | — | — | — | — | — |
| Guineagrass | 5 | 85 | 0 | 0 | 10 | 50 | 0 | 0 |
| Itchgrass | 0 | 0 | — | 0 | 0 | — | 0 | 0 |
| Johnson grass | 50 | 20 | 0 | 0 | 30 | 20 | 0 | 0 |
| Johnsongrass | — | — | — | — | — | — | — | — |
| Large Crabgrass | 50 | 98 | 0 | 50 | 75 | 70 | 98 | 100 |
| Peanuts | 5 | 20 | 0 | 0 | 60 | 0 | 0 | 0 |

TABLE H-continued

| | | | | | | | | |
|---|---|---|---|---|---|---|---|---|
| Pit Morninglory | 80 | 65 | 0 | — | 75 | 80 | 40 | 40 |
| Purple Nutsedge | 0 | 0 | 0 | 0 | 0 | 5 | 0 | 0 |
| Sandbur | 40 | 50 | 0 | 0 | 65 | 0 | 50 | 80 |
| Sourgrass | 100 | 100 | 90 | 40 | 100 | 98 | 98 | 100 |
| Sugarcane | — | — | — | — | — | — | — | — |
| Surinam grass | 98 | 0 | 0 | 0 | 95 | 20 | 80 | 0 |

| Rate 32 g/ha | COMPOUND | | | | |
|---|---|---|---|---|---|
| POSTEMERGENCE | 1 | 2 | 3 | 4 | 5 |
| Alexandergrass | — | 75 | 75 | 75 | 80 |
| ADexandergrass | — | — | — | — | — |
| Bermudagrass | 90 | 60 | 40 | 70 | 50 |
| Brdlf Sgnlgrass | 95 | 80 | 40 | 98 | 30 |
| Cmn Purslane | 95 | 60 | 40 | 65 | 50 |
| Cmn Ragweed | 100 | 98 | 75 | 95 | 50 |
| Cotton | 100 | 75 | 90 | 70 | 50 |
| Dallisgrass | 95 | 75 | 40 | 35 | 80 |
| Goosegrass | 70 | 30 | 20 | 30 | 65 |
| Guineagrass | 75 | 30 | 40 | 20 | 65 |
| Itchgrass | 80 | — | — | — | 70 |
| Johnson grass | 100 | 65 | 20 | 50 | 70 |
| Large Crabgrass | 90 | 40 | 35 | 50 | 35 |
| Peanuts | 25 | 5 | 0 | 10 | 50 |
| Pit Morninglory | 100 | — | 70 | 90 | 35 |
| Purple Nutsedge | 65 | 40 | 10 | 10 | 0 |
| Sandbur | 60 | — | 0 | 20 | 50 |
| Sourgrass | 80 | 60 | 40 | 30 | 60 |
| Sugarcane | — | — | — | — | — |
| Surinam grass | 80 | 45 | 40 | 60 | 65 |

| Rate 32 g/ha | COMPOUND | | | | | | |
|---|---|---|---|---|---|---|---|
| PREEMERGENCE | 1 | 2 | 3 | 4 | 5 | 6 | 16 |
| Alexandergrass | 20 | 45 | 0 | 0 | 0 | 20 | 0 |
| Bermudagrass | 98 | 75 | 40 | 30 | 50 | 90 | 75 |
| Brdlf Sgnlgrass | 0 | 0 | 0 | 0 | 50 | 0 | 0 |
| Cmn Purslane | 50 | 40 | 40 | 30 | 100 | — | 100 |
| Cmn Ragweed | 80 | 80 | 100 | 75 | — | 100 | 100 |
| Cotton | 50 | 0 | 0 | 0 | 20 | 0 | 0 |
| Dallisgrass | 65 | 20 | 0 | 0 | 100 | 10 | 0 |
| Goosegrass | 25 | 85 | 0 | 90 | 100 | 98 | 90 |
| Guinea Grass | — | — | — | — | — | — | 0 |
| Guineagrass | 10 | 60 | 0 | 0 | 10 | 40 | — |
| Itchgrass | 0 | 0 | — | 0 | 0 | — | 0 |
| Johnson grass | 10 | 0 | 0 | 0 | 0 | 10 | — |
| Johnsongrass | — | — | — | — | — | — | 0 |
| Large Crabgrass | 40 | 75 | 0 | 30 | 70 | 65 | 75 |
| Peanuts | 0 | 20 | 0 | 0 | 10 | — | 0 |
| Pit Morninglory | 80 | 50 | — | 30 | 20 | 75 | 25 |
| Purple Nutsedge | 0 | 0 | 0 | 0 | 0 | 0 | 0 |
| Sandbur | — | 0 | 0 | 0 | 50 | 0 | 0 |
| Sourgrass | 98 | 100 | 0 | 20 | 100 | 98 | 85 |
| Sugarcane | — | — | — | — | — | — | — |
| Surinam grass | 10 | 0 | 0 | 0 | 40 | 0 | 0 |

| Rate 16 g/ha POSTEMERGENCE | COMPOUND | | | | | Rate 16 g/ha PREEMERGENCE | COMPOUND | | | | |
|---|---|---|---|---|---|---|---|---|---|---|---|
| | 1 | 2 | 3 | 4 | 5 | | 1 | 2 | 3 | 4 | 5 |
| Alexandergrass | 75 | 70 | 50 | 60 | 75 | Alexandergrass | 0 | 30 | 0 | 0 | 0 |
| ADexandergrass | — | — | — | — | — | Bermudagrass | 35 | 0 | 40 | 30 | 30 |
| Bermudagrass | 90 | 40 | 10 | 50 | 40 | Brdlf Sgnlgrass | 0 | 0 | 0 | 0 | 50 |
| Brdlf Sgnlgrass | 100 | 75 | 20 | 20 | 0 | Cmn Purslane | 0 | 0 | 40 | 0 | 80 |
| Cmn Purslane | 98 | 50 | 20 | 60 | 20 | Cmn Ragweed | 50 | 20 | 100 | 20 | — |
| Cmn Ragweed | 100 | 70 | 70 | 75 | — | Cotton | — | 0 | 0 | 0 | 0 |
| Cotton | 100 | 60 | 70 | 65 | 20 | Dallisgrass | 5 | 0 | 0 | 0 | 90 |
| Dallisgrass | 70 | 80 | 20 | 20 | 80 | Goosegrass | 0 | 20 | 0 | 0 | 90 |
| Goosegrass | 70 | 30 | 0 | 0 | 40 | Guinea Grass | — | — | — | — | — |
| Guineagrass | 50 | 30 | 10 | 5 | 50 | Guineagrass | 0 | 0 | 0 | 0 | 0 |
| Itchgrass | 60 | — | — | — | 50 | Itchgrass | 0 | 0 | — | 0 | 0 |
| Johnson grass | 90 | 35 | 0 | — | 60 | Johnson grass | 0 | 0 | 0 | 0 | 0 |
| Large Crabgrass | 75 | 30 | 5 | 50 | 35 | Johnsongrass | — | — | — | — | — |
| Peanuts | 5 | 0 | 0 | 10 | — | Large Crabgrass | 20 | 0 | 0 | 10 | 30 |
| Pit Morningiory | 90 | 30 | 10 | 80 | 35 | Peanuts | 0 | 0 | 0 | 0 | 0 |
| Purple Nutsedge | 98 | 20 | 5 | 5 | 0 | Pit Morninglory | 50 | 0 | 0 | 0 | 20 |

TABLE H-continued

| Sandbur | 75 | 20 | 0 | 20 | 20 | Purple Nutsedge | 0 | 0 | 0 | 0 | — |
|---|---|---|---|---|---|---|---|---|---|---|---|
| Sourgrass | 75 | 40 | 10 | 20 | 60 | Sandbur | — | 0 | 0 | 0 | 0 |
| Sugarcane | — | — | — | — | — | Sourgrass | 98 | 70 | 0 | 0 | 95 |
| Surinam grass | 70 | 45 | 20 | 40 | 50 | Sugarcane | — | — | — | — | — |
|  |  |  |  |  |  | Surinam grass | 20 | 0 | 0 | 0 | 10 |

| Rate 8 g/ha | COMPOUND | | | | | Rate 8 g/ha | COMPOUND | | | | |
|---|---|---|---|---|---|---|---|---|---|---|---|
| POSTEMERGENCE | 1 | 2 | 3 | 4 | 5 | PREEMERGENCE | 1 | 2 | 3 | 4 | 5 |
| Alexandergrass | — | 70 | 10 | 5 | 60 | Alexandergrass | 0 | 20 | 0 | 0 | 0 |
| ADexandergrass | — | — | — | — | — | Bermudagrass | 5 | 0 | 0 | 20 | 0 |
| Bermudagrass | 80 | 40 | 0 | 35 | 40 | Brdlf Sgnlgrass | 0 | 0 | 0 | 0 | 10 |
| Brdlf Sgnlgrass | 75 | 40 | 0 | 0 | 0 | Cmn Purslane | 0 | 0 | 30 | 0 | 0 |
| Cmn Purslane | 90 | 25 | 20 | 50 | 20 | Cmn Ragweed | 0 | 0 | 50 | 0 | — |
| Cinn Ragweed | 95 | 50 | 40 | 10 | 30 | Cotton | 0 | 0 | 0 | 0 | 0 |
| Cotton | 100 | 40 | 0 | 5 | 20 | Dallisgrass | 5 | 0 | 0 | 0 | 20 |
| Dallisgrass | 50 | 10 | 20 | 10 | 80 | Goosegrass | 0 | 0 | 0 | 0 | 0 |
| Goosegrass | 60 | 0 | 0 | 0 | 10 | Guinea Grass | — | — | — | — | — |
| Guineagrass | 40 | 20 | 0 | 5 | 20 | Guineagrass | 0 | 0 | 0 | 0 | 0 |
| Itchgrass | 30 | — | — | — | 50 | Itchgrass | 0 | 0 | 0 | 0 | 0 |
| Johnson grass | 80 | 30 | 0 | 5 | 50 | Johnson grass | 0 | 0 | 0 | 0 | 0 |
| Large Crabgrass | 75 | 25 | 5 | 35 | 35 | Johnsongrass | — | — | — | — | — |
| Peanuts | 0 | 0 | 0 | 10 | 30 | Large Crabgrass | 20 | 0 | 0 | 5 | 30 |
| Pit Morninglory | 75 | 0 | — | 75 | 20 | Peanuts | 0 | 50 | 0 | 0 | 0 |
| Purple Nutsedge | 0 | 20 | 0 | 0 | 0 | Pit Morninglory | 80 | 0 | 0 | 0 | 0 |
| Sandbur | 75 | 0 | 0 | 20 | 10 | Purple Nutsedge | 0 | — | 0 | 0 | 0 |
| Sourgrass | 65 | 20 | 0 | 0 | 30 | Sandbur | — | 0 | 0 | 0 | — |
| Sugarcane | — | — | — | — | — | Sourgrass | 80 | 50 | 0 | 0 | 50 |
| Surinam grass | 40 | 10 | 0 | 0 | 65 | Sugarcane | — | — | — | — | — |
|  |  |  |  |  |  | Surinam grass | 0 | 0 | 0 | 0 | 0 |

| Rate 4 g/ha | COMPOUND | | | | COMPOUND | | |
|---|---|---|---|---|---|---|---|
| POSTEMERGENCE | 1 | 2 | 5 | PREEMERGENCE | 1 | 2 | 5 |
| Alexandergrass | 100 | 60 | 60 | Alexandergrass | 0 | 10 | 0 |
| ADexandergrass | — | — | — | Bermudagrass | 0 | 0 | 0 |
| Bermudagrass | 75 | 0 | 20 | Brdlf Sgnlgrass | 0 | 0 | 10 |
| Brdlf Sgnlgrass | 75 | 40 | 0 | Cmn Purslane | 0 | 0 | 0 |
| Cmn Purslane | 65 | 0 | 0 | Cmn Ragweed | 0 | 0 | — |
| Cmn Ragweed | 80 | 65 | 30 | Cotton | 0 | 0 | 0 |
| Cotton | 80 | 0 | 20 | Dallisgrass | 0 | 0 | 10 |
| Dallisgrass | 20 | 0 | 65 | Goosegrass | 0 | 0 | — |
| Goosegrass | 30 | 20 | 0 | Guinea Grass | — | — | — |
| Guineagrass | 10 | 0 | 0 | Guineagrass | 0 | 0 | 0 |
| Itchgrass | 20 | — | 0 | Itchgrass | 0 | 0 | 0 |
| Johnson grass | 35 | 0 | 20 | Johnson grass | 0 | 0 | 0 |
| Large Crabgrass | 65 | 0 | 20 | Johnsongrass | — | — | — |
| Peanuts | 0 | 0 | 30 | Large Crabgrass | 20 | 0 | 30 |
| Pit Morninglory | 80 | 0 | 20 | Peanuts | 0 | 0 | 0 |
| Purple Nutsedge | 0 | 0 | 0 | Pit Morninglory | 60 | 0 | 0 |
| Sandbur | 35 | — | 0 | Purple Nutsedge | 0 | 0 | — |
| Sourgrass | 35 | 10 | 10 | Sandbur | — | 0 | 0 |
| Sugarcane | — | — | — | Sourgrass | 0 | 20 | 0 |
| Surinam grass | 50 | 0 | 30 | Sugarcane | — | — | — |
|  |  |  |  | Surinam grass | 0 | 0 | 0 |

What is claimed is:

1. A compound selected from Formula I, N-oxides and agriculturally-suitable salts thereof,

I wherein

Q is

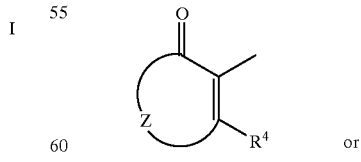

Q-1 or

-continued

Q-2
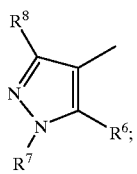

J is

J-1
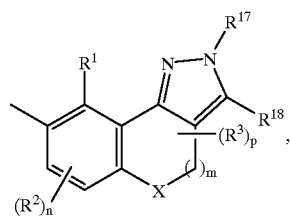

J-2
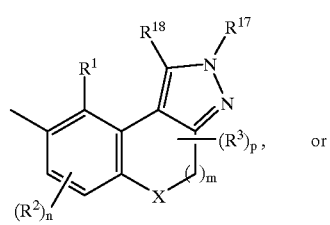

J-31
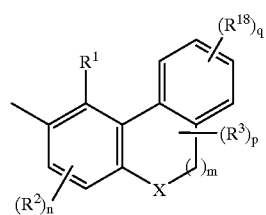

X is O, S(O)$_r$, N(C$_1$–C$_2$ alkyl) or CH$_2$ optionally substituted with 1–2 C$_1$–C$_2$ alkyl;

Z is selected from the group —CH$_2$CH$_2$CH$_2$—, —OCH$_2$CH$_2$—, —O—CH=CH—, —NR$^{13}$CH$_2$CH$_2$—, —NR$^{13}$CH=CH—, —N=CHCH$_2$—, —OCH$_2$O—, —NR$^{13}$CH$_2$NR$^{13}$—, —N=CHNR$^{13}$—, —CH$_2$OCH$_2$—, —CH$_2$NR$^{13}$CH$_2$—, —CH$_2$S(O)$_r$CH$_2$—, —CH$_2$C(O)CH$_2$—, —CH=NCH$_2$—, —CH$_2$CH$_2$—, —OCH$_2$—, —SCH$_2$—, and —NR$^{13}$CH$_2$—, each group optionally substituted with one to four R$^5$, and the directionality of the Z linkage is defined such that the moiety depicted on the left side of the linkage is bonded to the carbonyl carbon of Q-1;

R$^1$ and R$^2$ are independently H, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, aminosulfonyl, C$_1$–C$_2$ alkylaminosulfonyl, C$_2$–C$_4$ dialkylaminosulfonyl, halogen, cyano or nitro;

each R$^3$ is C$_1$–C$_2$ alkyl;

R$^4$ is OR$^{14}$, SH, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, halogen or NR$^{15}$R$^{16}$; or R$^4$ is phenylthio, phenylsulfonyl or —SCH$_2$C(O)Ph, each optionally substituted with C$_1$–C$_3$ alkyl, halogen, cyano or nitro;

each R$^5$ is independently H, C$_1$–C$_3$ alkyl, C$_3$–C$_6$ alkenyl, C$_3$–C$_6$ alkynyl, C$_1$–C$_3$ alkoxy, formyl, C$_2$–C$_6$ alkoxycarbonyl, —CH(C$_1$–C$_3$ alkoxy)$_2$, C$_1$–C$_3$ alkylthio, C$_2$–C$_4$ alkylthioalkyl, cyano or halogen; or when two R$^5$ are attached to the same carbon atom, then said R$^5$ pair can be taken together to form —OCH$_2$CH$_2$O—, —OCH$_2$CH$_2$CH$_2$O—, —SCH$_2$CH$_2$S— or —SCH$_2$CH$_2$CH$_2$S—, each group optionally substituted with 1–4 CH$_3$;

R$^6$ is OR$^{14}$, SH, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, halogen or NR$^{15}$R$^{16}$; or R$^6$ is phenylthio, phenylsulfonyl or —SCH$_2$C(O)Ph, each optionally substituted with C$_1$–C$_3$ alkyl, halogen, cyano or nitro;

R$^7$ is H, C$_1$–C$_6$ alkyl, C$_1$–C$_6$ haloalkyl, C$_3$–C$_6$ alkenyl, C$_3$–C$_6$ alkynyl or —CH$_2$CH$_2$OR$^{13}$; or R$^7$ is phenyl or benzyl, each optionally substituted on the phenyl ring with C$_1$–C$_3$ alkyl, halogen, cyano or nitro;

R$^8$ is H, C$_1$–C$_6$ alkyl, C$_1$–C$_6$ haloalkyl, C$_1$–C$_6$ alkoxy, C$_1$–C$_6$ haloalkoxy, halogen, cyano or nitro;

R$^{13}$ is H or C$_1$–C$_6$ alkyl;

R$^{14}$ is H, C$_1$–C$_6$ alkyl, C$_1$–C$_6$ haloalkyl, C$_2$–C$_6$ alkoxyalkyl, formyl, C$_2$–C$_6$ alkylcarbonyl, C$_2$–C$_6$ alkoxycarbonyl, C(O)NR$^{15}$R$^{16}$, C$_1$–C$_6$ alkylsulfonyl or C$_1$–C$_6$ haloalkylsulfonyl; or R$^{14}$ is phenyl, benzyl, benzoyl, —CH$_2$C(O)phenyl or phenylsulfonyl, each optionally substituted on the phenyl ring with C$_1$–C$_3$ alkyl, halogen, cyano or nitro;

R$^{15}$ is H or C$_1$–C$_6$ alkyl;

R$^{16}$ is C$_1$–C$_6$ alkyl or C$_1$–C$_6$ alkoxy; or

R$^{15}$ and R$^{16}$ can be taken together as —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$OCH$_2$CH$_2$—;

R$^{17}$ is H, C$_1$–C$_6$ alkyl, C$_1$–C$_6$ haloalkyl, C$_1$C$_6$ alkoxy, C$_1$–C$_6$ haloalkoxy, C$_1$–C$_6$ alkylsulfonyl, C$_1$–C$_6$ haloalkylsulfonyl, aminosulfonyl, C$_1$–C$_2$ alkylaminosulfonyl, C$_2$–C$_4$ dialkylaminosulfonyl, C$_2$–C$_6$ alkoxyalkyl, C$_2$–C$_6$ alkoxycarbonyl or C$_2$–C$_6$ alkylcarbonyl; or R$^{17}$ is phenyl or pyridyl, each optionally substituted with C$_1$–C$_3$ alkyl, halogen, cyano or nitro;

each R$^{18}$ is independently H, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio, C$_1$–C$_6$ alkylsulfinyl, C$_1$–C$_6$ haloalkylsulfinyl, C$_1$–C$_6$ alkylsulfonyl, C$_1$–C$_6$ haloalkylsulfonyl, aminosulfonyl, C$_1$–C$_2$ alkylaminosulfonyl, C$_2$–C$_4$ dialkylaminosulfonyl, NR$^{15}$R$^{16}$, C$_2$–C$_6$ alkoxyalkyl, C$_2$–C$_6$ alkoxycarbonyl, C$_2$–C$_6$ alkylcarbonyl, halogen, cyano or nitro;

m is 0, 1 or 2;

n is 1 or 2;

p is 0, 1, or 2; and r is 0, 1 or 2.

2. A compound of claim 1 wherein:

Q is Q-1.

3. A compound of claim 2 wherein:

Z is CH$_2$CH$_2$CH$_2$ optionally substituted with one to four R$^5$;

R$^1$ and R$^2$ are independently H, C$_1$–C$_3$ alkyl, C$_1$–C$_3$ alkoxy, halogen or nitro;

$R^4$ is $OR^{14}$; and $R^{14}$ is H or $C_1$–$C_4$ alkylsulfonyl; or $R^{14}$ is benzoyl or phenylsulfonyl, each optionally substituted with $C_1$–$C_3$ alkyl, halogen, cyano or nitro.

4. A compound of claim 3 wherein:

X is $S(O)_r$;

m is 1 or 2; and r is 2.

5. A compound of claim 1 wherein:

Q is Q-2.

6. A compound of claim 5 wherein:

$R^1$ and $R^2$ are independently H, $C_1$–$C_3$ alkyl, $C_1$–$C_3$ alkoxy, halogen or nitro;

$R^6$ is SH or $C_1$–$C_4$ alkylsulfonyl; or $R^6$ is benzoyl or phenylsulfonyl, each optionally substituted with $C_1$–$C_3$ alkyl, halogen, cyano, or nitro;

$R^7$ is H, $C_1$–$C_6$ alkyl, or $C_3$–$C_6$ alkenyl; and $R^8$ is H.

7. A compound of claim 6 wherein:

X is $S(O)_r$;

m is 1 or 2; and r is 2.

8. The compound of claim 1 which is selected from the group:

a) 2-[(2,4-dihydro-2,6,9-trimethyl[1]benzothiopyrano[4,3-c]pyrazol-8yl)carbonyl]-1,3-cyclohexanedione S,S-dioxide;

b) 2-[(2-ethyl-2,4-dihydro-6,9-dimethyl[1]benzothiopyrano[4,3-c]pyrazol-8yl)carbonyl]-1,3-cyclohexanedione S,S-dioxide;

c) 2-[(2,4-dihydro-2,6,9-trimethyl[1]benzothiopyrano[4,3-c]pyrazol-8yl)carbonyl]-5-methyl-1,3-cyclohexanedione S,S-dioxide;

d) (2,4-dihydro-2,6,9-trimethyl[1]benzothiopyrano[4,3-c]pyrazol-8-yl)(1-ethyl-5-hydroxy-1H-pyrazol-4-yl)methanone S,S-dioxide;

e) 2-[(3-chloro-2-ethyl-2,4-dihydro-6,9-dimethyl[1]benzothiopyrano[4,3-c]pyrazol-8-yl)carbonyl]-1,3-cyclohexanedione S,S-dioxide;

f) 2-[(4,5-dihydro-2,7,10-trimethyl-2H[1]benzothiepino[5,4-c]pyrazol-9-yl)carbonyl]-5-methyl-1,3-cyclohexanedione S,S-dioxide;

g) 2-[(2,4-dihydro-2,6,9-trimethyl[1]benzothiopyrano[4,3-c]pyrazol-8-yl)carbonyl]-1,3-cyclohexanedione S,S-dioxide monosodium salt;

h) 2-[(2-ethyl-2,4-dihydro-6,9-dimethyl[1]benzothiopyrano[4,3-c]pyrazol-8-yl)carbonyl]-1,3-cyclohexanedione S,S-dioxide monosodium salt;

i) 2-[(2,4-dihydro-2,6,9-trimethyl[1]benzothiopyrano[4,3-c]pyrazol-8-yl)carbonyl]-5-methyl-1,3-cyclohexanedione S,S-dioxide monosodium salt;

j) (2,4-dihydro-2,6,9-trimethyl[1]benzothiopyrano[4,3-c]pyrazol-8-yl)(1-ethyl-5-hydroxy-1H-pyrazol-4-yl)methanone S,S-dioxide monosodium salt;

k) 2-[(3-chloro-2-ethyl-2,4-dihydro-6,9-dimethyl[1]benzothiopyrano[4,3c]pyrazol-8-yl)carbonyl]-1,3-cyclohexanedione S,S-dioxide monosodium salt;

l) 2-[(4,5-dihydro-2,7,10-trimethyl-2H[1]benzothiepino[5,4-c]pyrazol-9-yl)carbonyl]-5-methyl-1,3-cyclohexanedione S,S-dioxide monosodium salt;

m) 2-[(2,4-dihydro-2,6,9-trimethyl[1]benzothiopyrano[4,3-c]pyrazol-8-yl)carbonyl]-1,3-cyclohexanedione S,S-dioxide monopotassium salt;

n) 2-[(2-ethyl-2,4-dihydro-6,9-dimethyl[1]benzothiopyrano[4,3-c]pyrazol-8-yl)carbonyl]-1,3-cyclohexanedione S,S-dioxide monopotassium salt;

o) 2-[(2,4-dihydro-2,6,9-trimethyl[1]benzothiopyrano[4,3-c]pyrazol-8-yl)carbonyl]-5-methyl-1,3-cyclohexanedione S,S-dioxide monopotassium salt;

p) (2,4-dihydro-2,6,9-trimethyl[1]benzothiopyrano[4,3-c]pyrazol-8-yl)(1-ethyl-5-hydroxy-1H-pyrazol-4-yl)methanone S,S-dioxide monopotassium salt;

q) 2-[(3-chloro-2-ethyl-2,4-dihydro-6,9-dimethyl[1]benzothiopyrano[4,3-c]pyrazol-8-yl)carbonyl]-1,3-cyclohexanedione S,S-dioxide monopotassium salt;

r) 2-[(4,5-dihydro-2,7,10-trimethyl-2H[1]benzothiepino[5,4-c]pyrazol-9-yl)carbonyl]-5-methyl-1,3-cyclohexanedione S,S-dioxide monopotassium salt;

s) (2,4-dihydro-2,6,9-trimethyl[1]benzothiopyrano[4,3-c]pyrazol-8-yl)[1-ethyl-5-[(methylsulfonyl)oxy]-1H-pyrazol-4-yl]methanone S,S-dioxide; and t) (2,4-dihydro-2,6,9-trimethyl[1]benzothiopyrano[4,3-c]pyrazol-8-yl)[1-ethyl-5-[(4-methylphenyl)sulfonyloxy]-1H-pyrazol-4-yl]methanone S,S-dioxide.

9. A mixture comprising a herbicidally effective amount of a compound of claim 8 with a herbicidally effective amount of one or more compounds selected from tribenuron-methyl, thifensulfuron-methyl, metsulfuron-methyl, chlorsulfuron, triasulfuron, 2,4-D, dicamba, bromoxynil, MCPA, fluroxypyr, clopyralid, fenoxaprop, diclofop, tralkoxydim, clodinafop, imazamethabenz, sulfosulfuron, difenzoquat, propanil, prosulfuron, metribuzin, glyphosate, triallate, trifluralin, paraquat, diallate, linuron, diflufenican, pendimethalin, cyanazine, neburon, terbutryn, prosulfocarb, isoproturon, chlortoluron, methabenzthiazuron, metoxuron, simazine, ioxynil, mecoprop, metosulam, fluroglycophen-ethyl, flamprop-M-isopropyl, benzoylpropethyl, ethametsulfuron-methyl, quinclorac, bentazone, rimsulfuron, nicosulfuron, primisulfuron, atrazine, terbuthylazine, imazethapyr, glyphosate-trimesium, glufosinate, fluthiacet-methyl, quizalofop-P-ethyl, flumetsulam, halosulfuron, sethoxydim, and flumiclorac-pentyl.

10. A herbicidal composition comprising a herbicidally effective amount of a compound of claim 1 and at least one of a surfactant, a solid diluent or a liquid diluent.

11. A herbicidal composition comprising a herbicidally effective amount of a mixture of claim 9 and at least one of a surfactant, a solid diluent or a liquid diluent.

12. A method for controlling the growth of undesired vegetation comprising contacting the vegetation or its environment with a herbicidally effective amount of a compound of claim 1.

13. A method for controlling the growth of undesired vegetation comprising contacting the vegetation or its environment with a herbicidally effective amount of a mixture of claim 9.

\* \* \* \* \*